United States Patent
Giuliano et al.

(10) Patent No.: US 9,546,157 B2
(45) Date of Patent: Jan. 17, 2017

(54) ASYMMETRIC PIPERIDINYL-SUBSTITUTED UREAS AS MEDICINES

(71) Applicant: Helsinn Healthcare SA, Lugano/Pazzallo (CH)

(72) Inventors: Claudio Giuliano, Como (IT); Silvina Garcia Rubio, Princeton, NJ (US); Antoine Daina, Lausanne (CH); Angelo Guainazzi, Iselin, NJ (US); Claudio Pietra, Como (IT)

(73) Assignee: Helsinn Healthcare SA, Lugano/Pazzallo (CH)

( * ) Notice: Subject to any disclaimer, the term of this patent is extended or adjusted under 35 U.S.C. 154(b) by 0 days.

(21) Appl. No.: 14/640,551

(22) Filed: Mar. 6, 2015

(65) Prior Publication Data

US 2015/0252021 A1  Sep. 10, 2015

Related U.S. Application Data

(60) Provisional application No. 61/949,664, filed on Mar. 7, 2014.

(51) Int. Cl.

| | |
|---|---|
| *A61K 31/4468* | (2006.01) |
| *C07D 211/58* | (2006.01) |
| *C07D 295/00* | (2006.01) |
| *C07D 401/14* | (2006.01) |
| *C07D 401/12* | (2006.01) |
| *C07D 417/14* | (2006.01) |
| *C07D 409/14* | (2006.01) |
| *C07D 239/26* | (2006.01) |
| *C07D 405/12* | (2006.01) |
| *C07D 403/12* | (2006.01) |
| *C07D 471/04* | (2006.01) |
| *C07D 401/06* | (2006.01) |
| *C07D 211/60* | (2006.01) |
| *C07D 211/94* | (2006.01) |
| *C07D 211/96* | (2006.01) |
| *C07D 213/00* | (2006.01) |

(52) U.S. Cl.
CPC .......... *C07D 401/14* (2013.01); *C07D 211/58* (2013.01); *C07D 211/60* (2013.01); *C07D 211/94* (2013.01); *C07D 211/96* (2013.01); *C07D 213/00* (2013.01); *C07D 239/26* (2013.01); *C07D 401/06* (2013.01); *C07D 401/12* (2013.01); *C07D 403/12* (2013.01); *C07D 405/12* (2013.01); *C07D 409/14* (2013.01); *C07D 417/14* (2013.01); *C07D 471/04* (2013.01)

(58) Field of Classification Search
CPC .. A61K 31/4468; C07D 211/58; C07D 295/00
USPC ............................... 514/329; 546/244
See application file for complete search history.

(56) References Cited

U.S. PATENT DOCUMENTS

| 6,399,619 B1 | 6/2002 | Berk |
| 2008/0064706 A1* | 3/2008 | Folmer ................. C07D 211/58 514/253.01 |
| 2008/0227780 A1 | 9/2008 | Gless |

FOREIGN PATENT DOCUMENTS

| WO | 2004064738 | 8/2004 |
| WO | 2006014136 | 2/2006 |
| WO | 2009039461 | 3/2009 |
| WO | 2011060397 | 5/2011 |
| WO | 2012113103 | 8/2012 |

OTHER PUBLICATIONS

Berlin, et al., "Reduction of hERG inhibitory activity in the 4-piperidinyl urea series of H3 antagonists", Bioorganic & Medicinal Chemistry Letters, vol. 20, No. 7, pp. 2359-2364.
Li, et al., "Studies on the structure-activity relationship of 1,3,3,4-tetra-substituted pyrrolidine embodied CCR5 receptor antagonists. Part 2: Discovery of highly potent anti-HIV agents", Bioorganic & Medicinal Chemistry Letters, vol. 20, No. 17, pp. 5334-5336.
International Search Report and Written Opinion dated Dec. 5, 2015 issued in corresponding PCT Patent Application No. PCT/US2015/019112.

* cited by examiner

*Primary Examiner* — Douglas M Willis
(74) *Attorney, Agent, or Firm* — Clark G. Sullivan

(57) ABSTRACT

Disclosed are compounds, compositions and methods for the prevention and/or treatment of diseases which are pathophysiologically mediated by the ghrelin receptor. The compounds have the general Formula I:

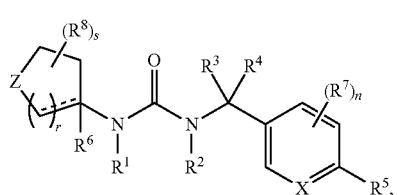

or pharmaceutically acceptable salts thereof.

38 Claims, 8 Drawing Sheets

ASYMMETRIC PIPERIDINYL-SUBSTITUTED UREAS AS MEDICINES

CROSS-REFERENCE TO RELATED APPLICATIONS

This application claims priority to U.S. Provisional Application Ser. No. 61/949,664, filed Mar. 7, 2014, which is herein incorporated by reference in its entirety.

FIELD OF THE INVENTION

The present invention relates to novel asymmetric urea compounds, medical uses thereof, particularly in the treatment of medical conditions modulated by the ghrelin receptor.

BACKGROUND

The growth hormone secretagogue receptor (GHS-R) regulates a number of physiological processes, including growth hormone (GH) release, metabolism, and appetite. Ghrelin, a circulating hormone produced predominantly by endocrine cells in the stomach, is its endogenous ligand. Ghrelin is a 28 amino acid peptide with an acyl side chain required for biological activity (Kojima et al., Nature, 402, 656-660, 1999). Ghrelin has been shown to stimulate growth hormone (GH) release and to increase food intake when administered both centrally and peripherally (Wren et al., Endocrinology, 141, 4325-4328, 2000).

Endogenous levels of ghrelin rise on fasting and fall on re-feeding in humans (Cummings et al., Diabetes, 50, 1714-1719, 2001). Ghrelin also appears to play a role in maintaining long term energy balance and appetite regulation. Chronic administration of ghrelin in rodents leads to hyperphagia and weight gain that are independent of growth hormone secretion (Tschop et al., Nature, 407, 908-913, 2000). Circulating ghrelin levels decrease in response to chronic overfeeding and increase in response to chronic negative energy balance associated with anorexia or exercise. Obese people generally have low plasma ghrelin levels (Tschop et al., Diabetes, 50, 707-709, 2001) accordingly to the physiological response of the body in reducing calories intake. Intravenous ghrelin is effective in stimulating food intake in humans. A recent study showed a 28% food intake increase from a buffet meal with a ghrelin infusion compared with saline control (Wren et al., J. Clin. Endocrinology and Metabolism, 86, 5992, 2001).

In view of the above experimental evidence, compounds that modulate ghrelin receptor activity have been proposed for preventing and/or treating disorders associated with ghrelin receptor physiology. For example, antagonists at ghrelin receptor might one day be developed to reduce appetite, reduce food intake, induce weight loss and treat obesity without affecting or reducing the circulating growth hormone levels. On the other hand, agonists at ghrelin receptor might also be developed for stimulating food intake and thus be useful in treating eating disorders, for example anorexia nervosa, or in treating cachexia resulting from cancer, AIDS or Chronic Obstructive Pulmonary Disease (COPD). Ghrelin agonists may also be useful as gastroprokinetic agents which can enhance gastrointestinal motility by increasing the frequency of contractions in the small intestine or making them stronger, but without disrupting their rhythm. Gastroprokinetic agents are used to relieve gastrointestinal symptoms such as abdominal discomfort, bloating, constipation, heart burn, nausea, and vomiting, and are used to treat a number of gastrointestinal disorders, including but not limiting to, irritable bowel syndrome, gastritis, acid reflux disease, gastroparesis, and functional dyspepsia. Furthermore, compounds that modulate ghrelin receptor activity might also be used to prevent or treat diseases related to substance abuse, for example, alcohol or drug (e.g., amphetamines, barbiturates, benzodiazepines, cocaine, methaqualone, and opioids) abuse, which refers to a maladaptive pattern of use of a substance that is not considered dependent.

A number of compounds acting on the ghrelin receptor have been reported in the literature. YIL-781, for example, is a small molecule ghrelin receptor antagonist from Bayer that reportedly improves glucose tolerance, suppresses appetite and promotes weigh loss (Esler et al., Endocrinology 148 (11):5175-5185); LY444711 is an orally active ghrelin receptor agonist from Lilly that reportedly induces adiposity by stimulating food consumption and sparing fat utilization (Bioorg. & Med. Chem. Lett., 2004, 14, 5873-5876); anamorelin is an orally available ghrelin receptor small molecule agonist from Helsinn Therapeutics that is in clinical trials for the treatment of anorexia and cachexia in cancer patients. Ghrelin receptor agonists and antagonists based on asymmetric ureas are disclosed in US 2012/0220629, which is incorporated herein by reference in its entirety. Other small molecule ghrelin receptor modulators can be found in WO 2008/092681, US 2009/0253673, WO 2008/148853, WO 2008/148856, US 2007/0270473 and US 2009/0186870.

In view of the above, it is desirable to find new compounds which modulate ghrelin receptor activity.

SUMMARY

The present invention provides compounds of Formula I:

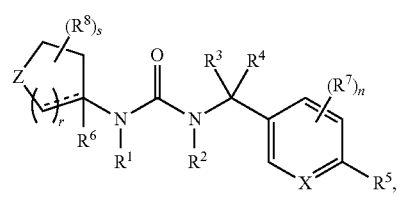

I with X, Z, $R^1$-$R^8$, r, s, and n as defined herein, and pharmaceutically acceptable salts thereof.

Compounds of Formula I, also referred to herein as asymmetric ureas, are particularly useful for preventing and/or treating diseases that are pathophysiologically related to the ghrelin receptor in a subject. Accordingly, in another embodiment the invention provides a method of treating a disease that is mediated by the ghrelin receptor, comprising administering to said subject a therapeutically effective amount of a compound of Formula I, or a pharmaceutically acceptable salt thereof.

Also disclosed are pharmaceutical compositions for preventing and/or treating diseases which are pathophysiologically related to ghrelin receptor in a subject, comprising a therapeutically effective amount of a compound of Formula I, or a pharmaceutically acceptable salt thereof, and one or more pharmaceutically acceptable excipients.

DETAILED DESCRIPTION

Figure 1:
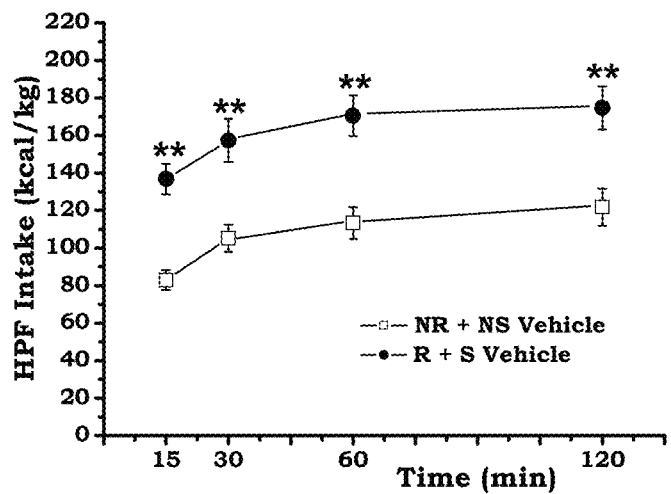
FIG. 1 shows Highly Palatable Food (HPF) intake in rats at different times after initial access to HPF. The values shown are the mean±S.E.M. of HPF intake. Statistical differences from controls (non-Restricted+non-Stressed; NR+NS): ** $P<0.01$.

Before the present compounds, compositions, articles, devices, and/or methods are disclosed and described, it is to be understood that they are not limited to specific synthetic methods or specific treatment methods unless otherwise specified, or to particular reagents unless otherwise specified, as such may, of course, vary. It is also to be understood that the terminology used herein is for the purpose of describing particular embodiments only and is not intended to be limiting.

In a first principal embodiment, the present invention provides compounds of Formula I:

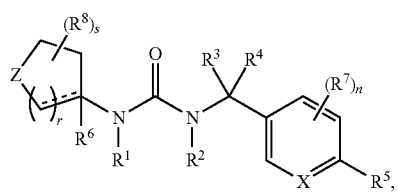

I or a pharmaceutically acceptable salt thereof, wherein:
a dashed line indicates an optional bond;
X is CH or N;
Z is $NR^9$, $CR^{10}R^{11}$, or O;

$R^1$ is H, $C_{1-6}$ alkyl, benzyl, OH, or $C_{1-6}$ alkoxy, wherein said $C_{1-6}$ alkyl, benzyl, or $C_{1-6}$ alkoxy is optionally substituted with 1-3 substituents selected from halo, OH, $C_{1-6}$ alkyl, $C_{1-6}$ alkoxy, $C_{1-6}$ hydroxyalkyl, $CO(C_{1-6}$ alkyl), CHO, $CO_2H$, $CO_2(C_{1-6}$ alkyl), and $C_{1-6}$ haloalkyl;

$R^2$ is H or $C_{1-6}$ alkyl;

$R^3$ and $R^4$ are each, independently, H, CN, halo, CHO, or $CO_2H$, or optionally substituted $C_{1-6}$ alkyl, $C_{1-6}$ hydroxyalkyl, $C_{1-6}$ alkylcycloalkyl, $C_{1-6}$ haloalkyl, $C_{1-6}$ alkoxy, $CO(C_{1-6}$ alkyl), $CO_2(C_{1-6}$ alkyl), or $CONR^{12}R^{13}$;

or $R^3$ and $R^4$ taken together with the C atom to which they are attached form a 3-6-membered ring;

$R^5$ is halo, CN, CHO, $CO_2H$, $CO(C_{1-6}$ alkyl), $CO_2(C_{1-6}$ alkyl), $NR^{14}R^{15}$, $NHCONR^{14}R^{15}$, $CONR^{14}R^{15}$, $C_{1-6}$ alkyl, $C_{1-6}$ alkoxy, $C_{1-6}$ haloalkyl, $C_{1-6}$ hydroxyalkyl, $C_{2-6}$ alkenyl, $C_{2-6}$ alkynyl, aryl, cycloalkyl, heteroaryl, or heterocycloalkyl, wherein said $CO(C_{1-6}$ alkyl), $CO_2(C_{1-6}$ alkyl), $NR^{14}R^{15}$, $NHCONR^{14}R^{15}$, $CONR^{14}R^{15}$, $C_{1-6}$ alkyl, $C_{1-6}$ alkoxy, $C_{1-6}$ haloalkyl, $C_{1-6}$ hydroxyalkyl, $C_{2-6}$ alkenyl, $C_{2-6}$ alkynyl, aryl, cycloalkyl, heteroaryl, or heterocycloalkyl is optionally substituted with 1-3 substituents selected from halo, CN, OH, $NO_2$, $Si(CH_3)_4$, CHO, and $CO_2H$, or optionally substituted $CO(C_{1-6}$ alkyl), $CO_2(C_{1-6}$ alkyl), $NR^{14}R^{15}$, $NHCONR^{14}R^{15}$, $CONR^{14}R^{15}$, CH=NOH, $C_{1-6}$ alkyl, $C_{1-6}$ alkoxy, $C_{1-6}$ haloalkyl, $C_{1-6}$ hydroxyalkyl, $C_{2-6}$ alkenyl, $C_{2-6}$ alkynyl, aryl, cycloalkyl, heteroaryl, and heterocycloalkyl;

$R^6$ is absent or H;

$R^7$ is H, CN, or halo;

or two $R^7$ can be taken together with the atoms to which they are attached form a 5-6-membered ring;

or $R^5$ and $R^7$ taken together with the atoms to which they are attached form an optionally substituted 5-6-membered ring;

$R^8$ is H or $C_{1-6}$ alkyl;

$R^9$ is H, $C_{1-6}$ alkyl, $CO(C_{1-6}$ alkyl), CHO, $CO_2H$, or $CO_2(C_{1-6}$ alkyl);

$R^{10}$ and $R^{11}$ are each, independently, H, $C_{1-6}$ alkyl, or halo;

$R^{12}$ and $R^{13}$ are each, independently, H or $C_{1-6}$ alkyl;

$R^{14}$ and $R^{15}$ are each, independently H, $C_{1-6}$ alkyl, $CO(C_{1-6}$ alkyl), CO(heteroaryl), heteroaryl, or cycloalkyl;

r is 1 or 2;
s is 0-4; and
n is 0-3.

In the first principal embodiment, as well as the second and third principal embodiments discussed below, in one subembodiment X is CH.

In the first, second and third principal embodiments, in one subembodiment, X is N.

In the first, second and third principal embodiments, in one subembodiment, Z is $NR^9$.

In the first, second and third principal embodiments, in one subembodiment, Z is $N(C_{1-6}$ alkyl).

In the first, second and third principal embodiments, in one subembodiment, Z is $NCH_3$.

In the first, second and third principal embodiments, in one subembodiment, Z is $CR^{10}R^{11}$.

In the first, second and third principal embodiments, in one subembodiment, Z is $CF_2$.

In the first, second and third principal embodiments, in one subembodiment, Z is O.

In the first, second and third principal embodiments, in one subembodiment, $R^1$ is $C_{1-6}$ alkyl.

In the first, second and third principal embodiments, in one subembodiment, $R^1$ is $CH_3$.

In the first, second and third principal embodiments, in one subembodiment, $R^1$ is benzyl.

In the first, second and third principal embodiments, in one subembodiment, said benzyl is optionally substituted with $CO_2(C_{1-6}$ alkyl) or $C_{1-6}$ hydroxyalkyl.

In the first, second and third principal embodiments, in one subembodiment, $R^1$ is OH.

In the first, second and third principal embodiments, in one subembodiment, $R^1$ is $C_{1-6}$ alkoxy.

In the first, second and third principal embodiments, in one subembodiment, said $C_{1-6}$ alkoxy is $OCH_3$, $OCH_2CH_3$ or $O(CH_2)_2CH_3$.

In the first, second and third principal embodiments, in one subembodiment, $R^2$ is H.

In the first, second and third principal embodiments, in one subembodiment, $R^3$ and $R^4$ are each, independently selected from $C_{1-6}$ alkyl, CN, $C_{1-6}$ alkylcycloalkyl, $C_{1-6}$ hydroxyalkyl, $CO_2(C_{1-6}$ alkyl), $C_{1-6}$ haloalkyl and $CONH_2$.

In the first, second and third principal embodiments, in one subembodiment, said $C_{1-6}$ alkyl is $CH_3$ or $CH_2CH_3$.

In the first, second and third principal embodiments, in one subembodiment, said $C_{1-6}$ alkylcycloalkyl is $CH_2$-cylopropyl.

In the first, second and third principal embodiments, in one subembodiment, said $C_{1-6}$ hydroxyalkyl is $CH_2OH$ optionally substituted with a substituted or unsubstituted benzyl group.

In the first, second and third principal embodiments, in one subembodiment, said $CO_2(C_{1-6}$ alkyl) is $CO_2CH_3$.

In the first, second and third principal embodiments, in one subembodiment, said $C_{1-6}$ haloalkyl is $CF_3$.

In the first, second and third principal embodiments, in one subembodiment, $R^3$ and $R^4$ taken together with the C atom to which they are attached form a 3-6-membered ring.

In the first, second and third principal embodiments, in one subembodiment, $R^3$ and $R^4$ are taken together with the C atom to which they are attached to form a cyclopropyl ring.

In the first, second and third principal embodiments, in one subembodiment, $R^3$ and $R^4$ are taken together with the C atom to which they are attached form a tetrahydropyranyl ring.

In the first, second and third principal embodiments, in one subembodiment, $R^5$ is halo, CN, CHO, $CO_2H$, $CO(C_{1-6}$ alkyl), $CO_2(C_{1-6}$ alkyl), $NR^{14}R^{15}$, $NHCONR^{14}R^{15}$, $CONR^{14}R^{15}$, $C_{1-6}$ alkyl, $C_{1-6}$ alkoxy, $C_{1-6}$ haloalkyl, $C_{1-6}$ hydroxyalkyl, $C_{2-6}$ alkenyl, $C_{2-6}$ alkynyl, aryl, cycloalkyl, heteroaryl, or heterocycloalkyl, wherein said $CO(C_{1-6}$ alkyl), $CO_2(C_{1-6}$ alkyl), $NR^{14}R^{15}$, $NHCONR^{14}R^{15}$, $CONR^{14}R^{15}$, $C_{1-6}$ alkyl, $C_{1-6}$ alkoxy, $C_{1-6}$ haloalkyl, $C_{1-6}$ hydroxyalkyl, $C_{2-6}$ alkenyl, $C_{2-6}$ alkynyl, aryl, cycloalkyl, heteroaryl, or heterocycloalkyl is optionally substituted with 1-3 substituents selected from halo, CN, OH, $NO_2$, $Si(CH_3)_4$, CHO, and $CO_2H$, or optionally substituted $CO(C_{1-6}$ alkyl), $CO_2(C_{1-6}$ alkyl), $NR^{14}R^{15}$, $NHCONR^{14}R^{15}$, $CONR^{14}R^{15}$, CH=NOH, $C_{1-6}$ alkyl, $C_{1-6}$ alkoxy, $C_{1-6}$ haloalkyl, $C_{1-6}$ hydroxyalkyl, $C_{2-6}$ alkenyl, $C_{2-6}$ alkynyl, aryl, cycloalkyl, heteroaryl, and heterocycloalkyl;

In some embodiments $R^5$ is not H;
In some embodiments, $R^5$ is not alkoxy;
In some embodiments, $R^5$ is not $OCH_3$;
In some embodiments, $R^5$ is not OH;
In some embodiments, $R^5$ is not halo;
In some embodiments, $R^5$ is not F;
In some embodiments, $R^5$ is not Cl;
In some embodiments, $R^5$ is not $SO_2CH_3$;
In some embodiments, $R^5$ is not $NH_2$;
In some embodiments, $R^5$ is not NHAc;
In some embodiments, $R^5$ is not $N(Me)_2$;
In some embodiments, $R^5$ is not alkyl;
In some embodiments, $R^5$ is not $CH_3$;
In the first, second and third principal embodiments, in one subembodiment, $R^5$ is halo;
In the first, second and third principal embodiments, in one subembodiment, $R^5$ is CN;

In the first, second and third principal embodiments, in one subembodiment, $R^5$ is CHO;

In the first, second and third principal embodiments, in one subembodiment, $R^5$ is $CO_2H$;

In the first, second and third principal embodiments, in one subembodiment, $R^5$ is $CO(C_{1-6}$ alkyl);

In the first, second and third principal embodiments, in one subembodiment, $R^5$ is $CO_2(C_{1-6}$ alkyl);

In the first, second and third principal embodiments, in one subembodiment, $R^5$ is $NR^{14}R^{15}$;

In the first, second and third principal embodiments, in one subembodiment, $R^5$ is $NHCONR^{14}R^{15}$;

In the first, second and third principal embodiments, in one subembodiment, $R^5$ is $CONR^{14}R^{15}$;

In the first, second and third principal embodiments, in one subembodiment, $R^5$ is $C_{1-6}$ alkyl;

In the first, second and third principal embodiments, in one subembodiment, $R^5$ is $C_{1-6}$ alkoxy;

In the first, second and third principal embodiments, in one subembodiment, $R^5$ is $C_{1-6}$ haloalkyl;

In the first, second and third principal embodiments, in one subembodiment, $R^5$ is $C_{1-6}$ hydroxyalkyl;

In the first, second and third principal embodiments, in one subembodiment, $R^5$ is $C_{2-6}$ alkenyl;

In the first, second and third principal embodiments, in one subembodiment, $R^5$ is $C_{2-6}$ alkynyl;

In the first, second and third principal embodiments, in one subembodiment, $R^5$ is aryl;

In the first, second and third principal embodiments, in one subembodiment, $R^5$ is cycloalkyl;

In the first, second and third principal embodiments, in one subembodiment, $R^5$ is heteroaryl;

In the first, second and third principal embodiments, in one subembodiment, $R^5$ is heterocycloalkyl;

In the first, second and third principal embodiments, in one subembodiment, $R^5$ is $C_{1-6}$ haloalkyl, heteroaryl, aryl, halo, $C_{1-6}$ alkoxy, $CO_2(C_{1-6}$ alkyl), $C_{2-6}$ alkenyl, $C_{2-6}$ alkynyl, cycloalkyl, or heterocycloalkyl, In the first, second and third principal embodiments, in one subembodiment, said cycloalkyl is cyclopropyl, cyclohexanyl or cyclohexenyl.

In the first, second and third principal embodiments, in one subembodiment, said $C_{1-6}$ haloalkyl is $CHF_2$.

In the first, second and third principal embodiments, in one subembodiment, said heteroaryl is pyridyl, pyridazinyl, pyrimidinyl, triazinyl, thiophenyl, pyrazolyl, imidazolyl, thiazolyl, oxazolyl, oxadiazolyl or furanyl, In the first, second and third principal embodiments, in one subembodiment, said aryl is phenyl.

In the first, second and third principal embodiments, in one subembodiment, said halo is Cl or I.

In the first, second and third principal embodiments, in one subembodiment, said $C_{1-6}$ alkoxy is $OCH_3$.

In the first, second and third principal embodiments, in one subembodiment, said $CO_2(C_{1-6}$ alkyl) is $CO_2CH_3$.

In the first, second and third principal embodiments, in one subembodiment, said $C_{2-6}$ alkynyl is $C_2$ alkynyl.

In the first, second and third principal embodiments, in one subembodiment, said $C_{2-6}$ alkenyl is $C_2$ alkenyl.

In the first, second and third principal embodiments, in one subembodiment, $R^6$ is absent.

In the first, second and third principal embodiments, in one subembodiment, $R^6$ is H.

In the first, second and third principal embodiments, in one subembodiment, $R^7$ is halo.

In the first, second and third principal embodiments, in one subembodiment, said halo is Cl or F.

In the first, second and third principal embodiments, in one subembodiment, 2 $R^7$ come together to form a phenyl group.

In the first, second and third principal embodiments, in one subembodiment, $R^5$ and $R^7$ come together to form a 5-membered heterocyclic ring.
In the first, second and third principal embodiments, in one subembodiment, $R^8$ is H.
In the first, second and third principal embodiments, in one subembodiment, $R^8$ is $C_{1-6}$ alkyl.
In the first, second and third principal embodiments, in one subembodiment, $R^8$ is $CH_3$.
In the first, second and third principal embodiments, in one subembodiment, $R^{10}$ is H;
In the first, second and third principal embodiments, in one subembodiment, $R^{10}$ is $C_{1-6}$ alkyl;
In the first, second and third principal embodiments, in one subembodiment, $R^{10}$ is halo;
In the first, second and third principal embodiments, in one subembodiment, $R^{11}$ is H;
In the first, second and third principal embodiments, in one subembodiment, $R^{11}$ is $C_{1-6}$ alkyl;
In the first, second and third principal embodiments, in one subembodiment, $R^{11}$ is halo;
In the first, second and third principal embodiments, in one subembodiment, $R^{12}$ is H;
In the first, second and third principal embodiments, in one subembodiment, $R^{12}$ is $C_{1-6}$ alkyl;
In the first, second and third principal embodiments, in one subembodiment, $R^{13}$ is H;
In the first, second and third principal embodiments, in one subembodiment, $R^{13}$ is $C_{1-6}$ alkyl;
In the first, second and third principal embodiments, in one subembodiment, $R^{14}$ is H;
In the first, second and third principal embodiments, in one subembodiment, $R^{14}$ is $C_{1-6}$ alkyl;
In the first, second and third principal embodiments, in one subembodiment, $R^{14}$ is $CO(C_{1-6}$ alkyl);
In the first, second and third principal embodiments, in one subembodiment, $R^{14}$ is CO(heteroaryl);
In the first, second and third principal embodiments, in one subembodiment, $R^{14}$ is heteroaryl;
In the first, second and third principal embodiments, in one subembodiment, $R^{14}$ is cycloalkyl;
In the first, second and third principal embodiments, in one subembodiment, $R^{15}$ is H;
In the first, second and third principal embodiments, in one subembodiment, $R^{15}$ is $C_{1-6}$ alkyl;
In the first, second and third principal embodiments, in one subembodiment, $R^{15}$ is $CO(C_{1-6}$ alkyl);
In the first, second and third principal embodiments, in one subembodiment, $R^{15}$ is CO(heteroaryl);
In the first, second and third principal embodiments, in one subembodiment, $R^{15}$ is heteroaryl;
In the first, second and third principal embodiments, in one subembodiment, $R^{15}$ is cycloalkyl;
In the first, second and third principal embodiments, in one subembodiment, r is 1;
In the first, second and third principal embodiments, in one subembodiment, r is 2;
In the first, second and third principal embodiments, in one subembodiment, s is 0;
In the first, second and third principal embodiments, in one subembodiment, s is 1;
In the first, second and third principal embodiments, in one subembodiment, s is 2;
In the first, second and third principal embodiments, in one subembodiment, s is 3;
In the first, second and third principal embodiments, in one subembodiment, s is 4;

In the first, second and third principal embodiments, in one subembodiment, n is 0;
In the first, second and third principal embodiments, in one subembodiment, n is 1;
In the first, second and third principal embodiments, in one subembodiment, n is 2;
In the first, second and third principal embodiments, in one subembodiment, n is 3.

In a second principal embodiment, the compounds have the structure of Formula II:

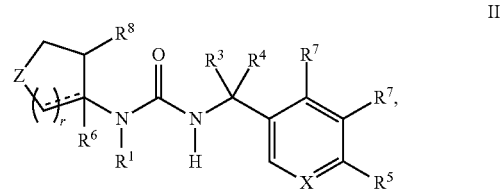

or a pharmaceutically acceptable salt thereof.

In a third principal embodiment, the compounds have the structure of Formula III:

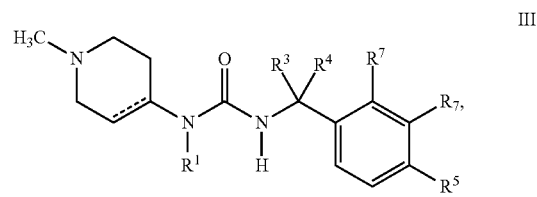

or a pharmaceutically acceptable salt thereof.

In fourth and fifth principal embodiments, the compounds have the structure of Formula IIIa or IIIb:

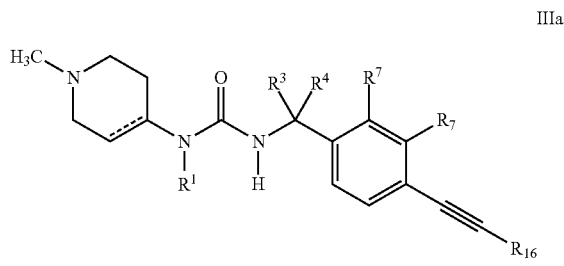

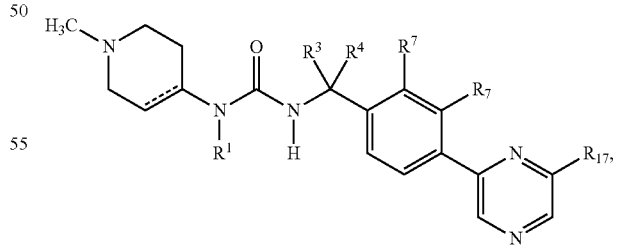

or a pharmaceutically acceptable salt thereof, wherein:
$R^{16}$ is H, cyclopropyl or thiazolyl; and
$R^{17}$ is H or halo.

In some forms, the compounds as presently disclosed are compounds of Formula I, or pharmaceutically acceptable salts thereof, wherein the compound of Formula I is a compound selected from the group consisting of:

| Compound No. | Chemical Structure | Chemical Name |
|---|---|---|
| H0494 | 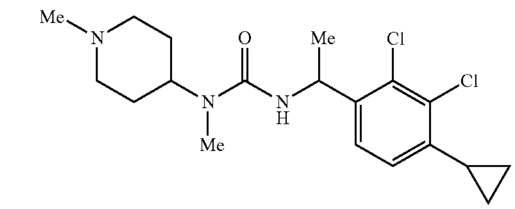 [SMILES: CC(NC(=O)N(C)C1CCN(C)CC1)c1ccc(C2CC2)c(Cl)c1Cl] | 3-(1-(2,3-dichloro-4-cyclopropylphenyl)ethyl)-1-methyl-1-(1-methylpiperidin-4-yl)urea |
| H0621 | 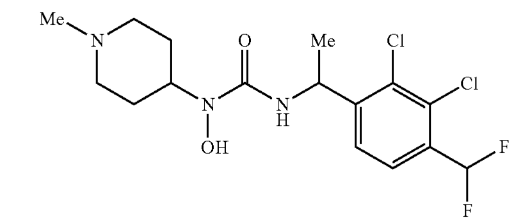 [SMILES: CC(NC(=O)N(O)C1CCN(C)CC1)c1ccc(C(F)F)c(Cl)c1Cl] | 3-(1-(2,3-dichloro-4-(difluoromethyl)phenyl)ethyl)-1-hydroxy-1-(1-methylpiperidin-4-yl)urea |
| H0496 | 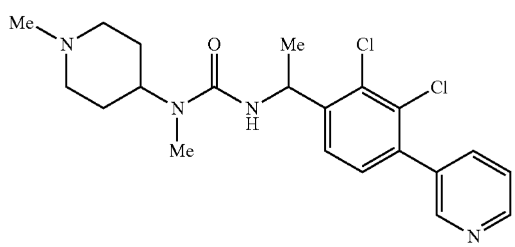 [SMILES: CC(NC(=O)N(C)C1CCN(C)CC1)c1ccc(-c2cccnc2)c(Cl)c1Cl] | 3-(1-(2,3-dichloro-4-(pyridin-3-yl)phenyl)ethyl)-1-methyl-1-(1-methylpiperidin-4-yl)urea |
| H0617 | 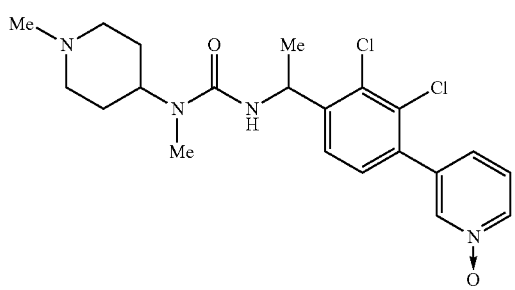 [SMILES: CC(NC(=O)N(C)C1CCN(C)CC1)c1ccc(-c2ccc[n+]([O-])c2)c(Cl)c1Cl] | 3-(1-(2,3-dichloro-4-(pyridin-3-yl)phenyl)ethyl)-1-methyl-1-(1-methylpiperidin-4-yl)urea |
| H0539 | 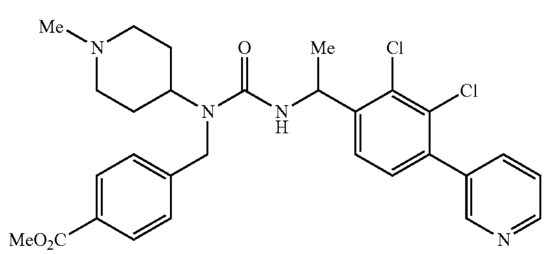 [SMILES: COC(=O)c1ccc(CN(C(=O)NC(C)c2ccc(-c3cccnc3)c(Cl)c2Cl)C2CCN(C)CC2)cc1] | methyl 4-((3-(1-(2,3-dichloro-4-(pyridin-3-yl)phenyl)ethyl)-1-(1-methylpiperidin-4-yl)ureido)methyl)benzoate |
| H0546 | 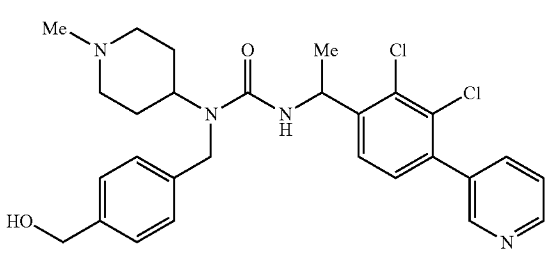 [SMILES: CC(NC(=O)N(Cc1ccc(CO)cc1)C1CCN(C)CC1)c1ccc(-c2cccnc2)c(Cl)c1Cl] | 3-(1-(2,3-dichloro-4-(pyridin-3-yl)phenyl)ethyl)-1-(4-(hydroxymethyl)benzyl)-1-(1-methylpiperidin-4-yl)urea |

-continued

| Compound No. | Chemical Structure | Chemical Name |
| --- | --- | --- |
| H0526 | 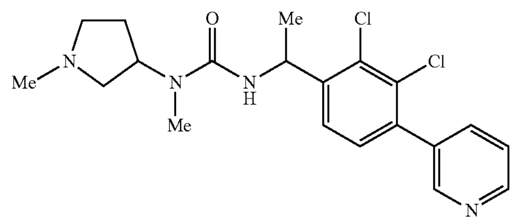 [SMILES: CC(NC(=O)N(C)C1CCN(C)C1)c1ccc(-c2cccnc2)c(Cl)c1Cl] | 3-(1-(2,3-dichloro-4-(pyridin-3-yl)phenyl)ethyl)-1-methyl-1-(1-methylpyrrolidin-3-yl)urea |
| H0527 | 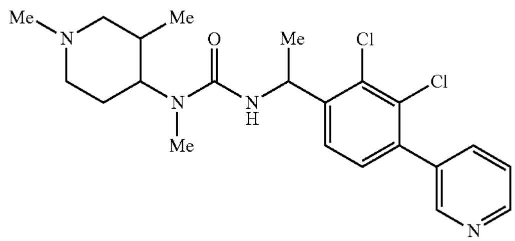 [SMILES: CC(NC(=O)N(C)C1CCN(C)CC1C)c1ccc(-c2cccnc2)c(Cl)c1Cl] | 3-(1-(2,3-dichloro-4-(pyridin-3-yl)phenyl)ethyl)-1-(1,3-dimethylpiperidin-4-yl)-1-methylurea |
| H0497 | 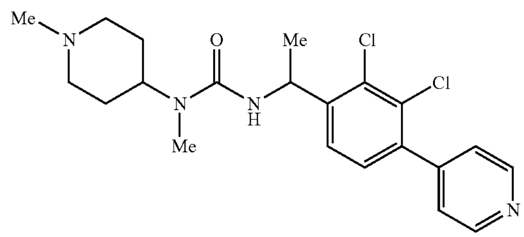 [SMILES: CC(NC(=O)N(C)C1CCN(C)CC1)c1ccc(-c2ccncc2)c(Cl)c1Cl] | 3-(1-(2,3-dichloro-4-(pyridin-4-yl)phenyl)ethyl)-1-methyl-1-(1-methylpiperidin-4-yl)urea |
| H0650 | 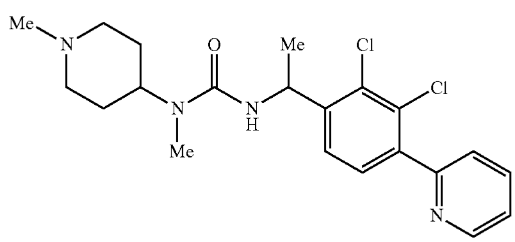 [SMILES: CC(NC(=O)N(C)C1CCN(C)CC1)c1ccc(-c2ccccn2)c(Cl)c1Cl] | 3-(1-(2,3-dichloro-4-(pyridin-2-yl)phenyl)ethyl)-1-methyl-1-(1-methylpiperidin-4-yl)urea |
| H0849 | 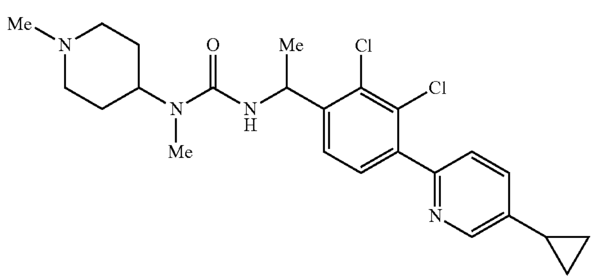 [SMILES: CC(NC(=O)N(C)C1CCN(C)CC1)c1ccc(-c2ccc(C3CC3)cn2)c(Cl)c1Cl] | 3-(1-(2,3-dichloro-4-(5-cyclopropylpyridin-2-yl)phenyl)ethyl)-1-methyl-1-(1-methylpiperidin-4-yl)urea |
| H0578 | 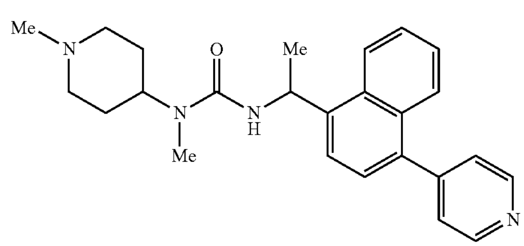 [SMILES: CC(NC(=O)N(C)C1CCN(C)CC1)c1ccc(-c2ccncc2)c2ccccc12] | 1-methyl-1-(1-methylpiperidin-4-yl)-3-(1-(4-(pyridin-4-yl)naphthalen-1-yl)ethyl)urea |

| Compound No. | Chemical Structure | Chemical Name |
|---|---|---|
| H0511 | 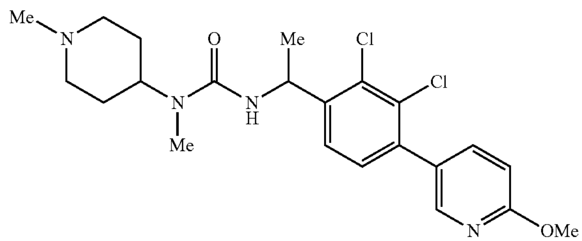 [SMILES: COc1ccc(-c2ccc(C(C)NC(=O)N(C)C3CCN(C)CC3)c(Cl)c2Cl)cn1] | 3-(1-(2,3-dichloro-4-(6-methoxypyridin-3-yl)phenyl)ethyl)-1-methyl-1-(1-methylpiepridin-4-yl)urea |
| H0820 | 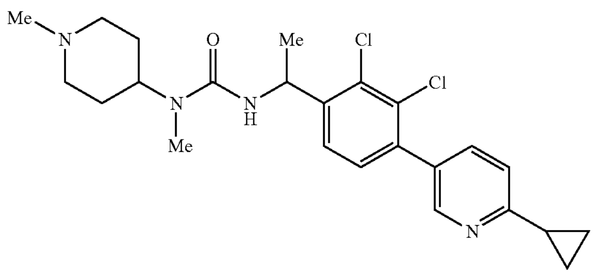 [SMILES: CC(NC(=O)N(C)C1CCN(C)CC1)c1ccc(-c2ccc(C3CC3)nc2)c(Cl)c1Cl] | 3-(1-(2,3-dichloro-4-(6-cyclopropylpyridin-3-yl)phenyl)ethyl)-1-methyl-1-(1-methylpiperidin-4-yl)urea |
| H0613 | 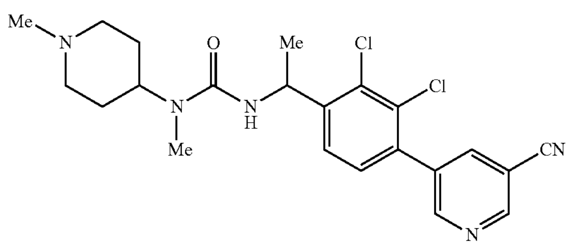 [SMILES: CC(NC(=O)N(C)C1CCN(C)CC1)c1ccc(-c2cncc(C#N)c2)c(Cl)c1Cl] | 3-(1-(2,3-dichloro-4-(5-cyanopyridin-3-yl)phenyl)ethyl)-1-methyl-1-(1-methylpiperidin-4-yl)urea |
| H0614 | 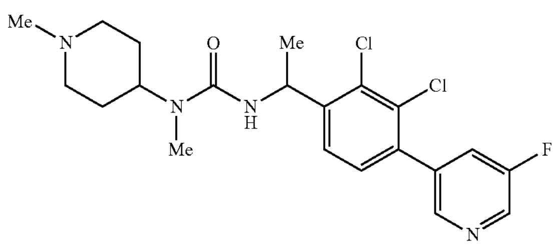 [SMILES: CC(NC(=O)N(C)C1CCN(C)CC1)c1ccc(-c2cncc(F)c2)c(Cl)c1Cl] | 3-(1-(2,3-dichloro-4-(5-fluoropyridin-3-yl)phenyl)ethyl)-1-methyl-1-(1-methylpiperidin-4-yl)urea |
| H0635 | 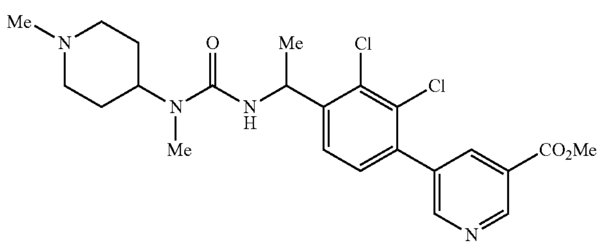 [SMILES: COC(=O)c1cncc(-c2ccc(C(C)NC(=O)N(C)C3CCN(C)CC3)c(Cl)c2Cl)c1] | methyl 5-(2,3-dichloro-4-(1-(3-methyl-3-(1-methylpiperidin-4-yl)ureido)ethyl)phenyl)nicotinate |
| H0636 | 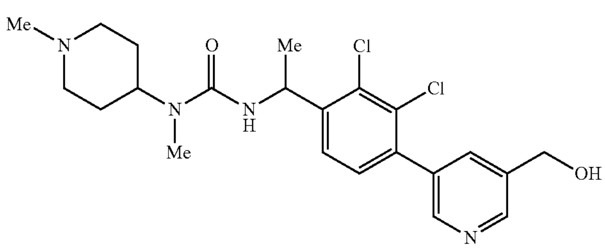 | 3-(1-(2,3-dichloro-4-(5-(hydroxymethyl)pyridin-3-yl)phenyl)ethyl)-1-methyl-1-(1-methylpiperidin-4-yl)urea |

| Compound No. | Chemical Structure | Chemical Name |
|---|---|---|
| H0637 | 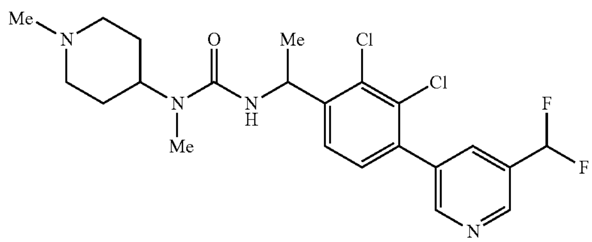 [SMILES: CC(NC(=O)N(C)C1CCN(C)CC1)c1ccc(-c2cncc(C(F)F)c2)c(Cl)c1Cl] | 3-(1-(2,3-dichloro-4-(5-(difluoromethyl)pyridin-3-yl)phenyl)ethyl)-1-methyl-1-(1-methylpiperidin-4-yl)urea |
| H0638 | 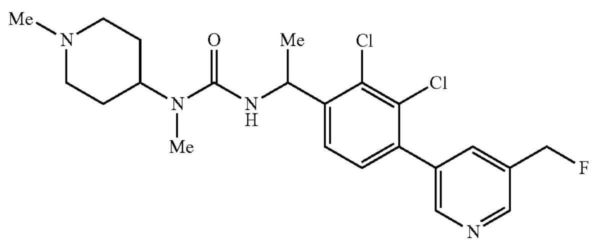 [SMILES: CC(NC(=O)N(C)C1CCN(C)CC1)c1ccc(-c2cncc(CF)c2)c(Cl)c1Cl] | 3-(1-(2,3-dichloro-4-(5-(fluoromethyl)pyridin-3-yl)phenyl)ethyl)-1-methyl-1-(1-methylpiperidin-4-yl)urea |
| H0639 | 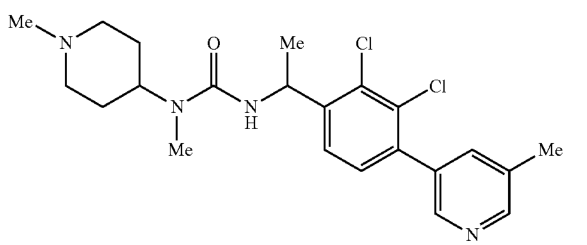 [SMILES: Cc1cncc(-c2ccc(C(C)NC(=O)N(C)C3CCN(C)CC3)c(Cl)c2Cl)c1] | 3-(1-(2,3-dichloro-4-(5-methylpyridin-3-yl)phenyl)ethyl)-1-methyl-1-(1-methylpiperidin-4-yl)urea |
| H0642 | 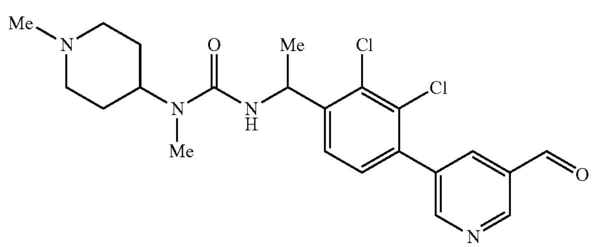 [SMILES: CC(NC(=O)N(C)C1CCN(C)CC1)c1ccc(-c2cncc(C=O)c2)c(Cl)c1Cl] | 3-(1-(2,3-dichloro-4-(5-formylpyridin-3-yl)phenyl)ethyl)-1-methyl-1-(1-methylpiperidin-4-yl)urea |
| H0704 | 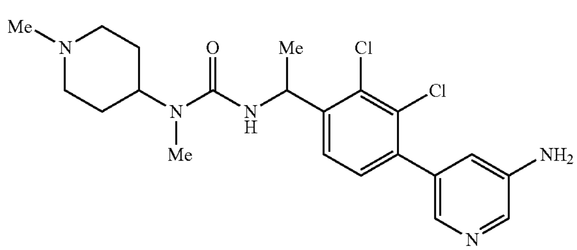 [SMILES: CC(NC(=O)N(C)C1CCN(C)CC1)c1ccc(-c2cncc(N)c2)c(Cl)c1Cl] | 3-(1-(4-(5-aminopyridin-3-yl)-2,3-dichlorophenyl)ethyl)-1-methyl-1-(1-methylpiperidin-4-yl)urea |
| H0705 | 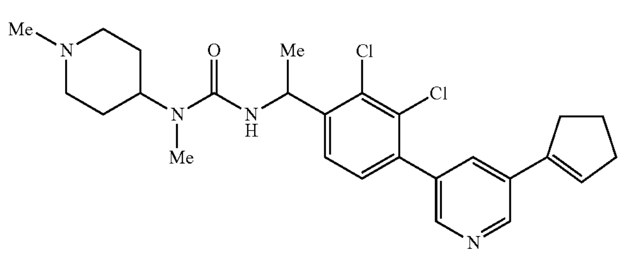 [SMILES: CC(NC(=O)N(C)C1CCN(C)CC1)c1ccc(-c2cncc(C3=CCCC3)c2)c(Cl)c1Cl] | 3-(1-(2,3-dichloro-4-(5-(cyclopent-1-en-1-yl)pyridin-3-yl)phenyl)ethyl)-1-methyl-1-(1-methylpiperidin-4-yl)urea |

-continued

| Compound No. | Chemical Structure | Chemical Name |
| --- | --- | --- |
| H0707 | 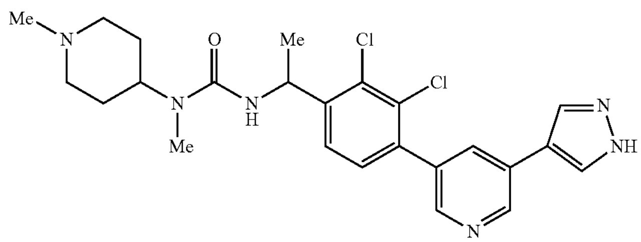 [SMILES: CC(NC(=O)N(C)C1CCN(C)CC1)c1ccc(-c2cncc(-c3cn[nH]c3)c2)c(Cl)c1Cl] | 3-(1-(4-(5-(1H-pyrazol-4-yl)pyridin-3-yl)-2,3-dichlorophenyl)ethyl)-1-methyl-1-(1-methylpiperidin-4-yl)urea |
| H0711 | 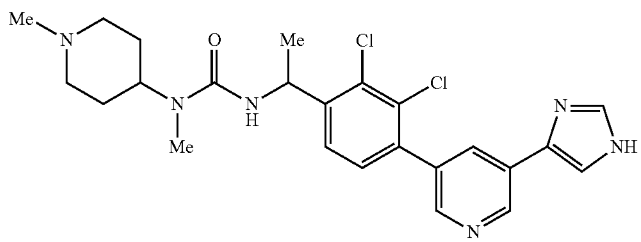 [SMILES: CC(NC(=O)N(C)C1CCN(C)CC1)c1ccc(-c2cncc(-c3c[nH]cn3)c2)c(Cl)c1Cl] | 3-(1-(4-(5-(1H-imidazol-4-yl)pyridin-3-yl)-2,3-dichlorophenyl)ethyl)-1-methyl-1-(1-methylpiperidin-4-yl)urea |
| H0716 | 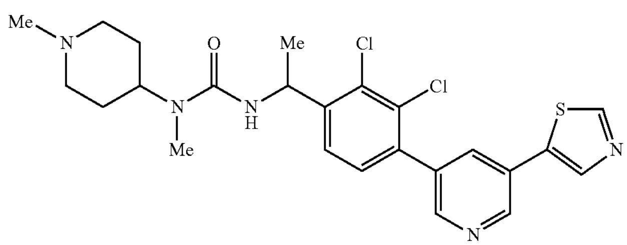 [SMILES: CC(NC(=O)N(C)C1CCN(C)CC1)c1ccc(-c2cncc(-c3cncs3)c2)c(Cl)c1Cl] | 3-(1-(2,3-dichloro-4-(5-(thiazol-5-yl)pyridin-3-yl)phenyl)ethyl)-1-methyl-1-(1-methylpiperidin-4-yl)urea |
| H0717 | 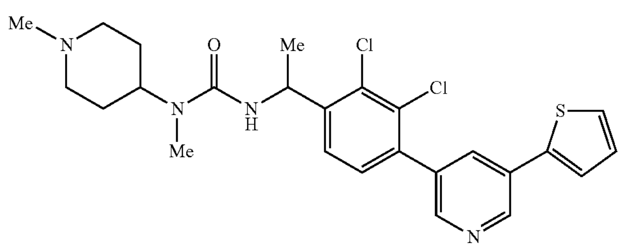 [SMILES: CC(NC(=O)N(C)C1CCN(C)CC1)c1ccc(-c2cncc(-c3cccs3)c2)c(Cl)c1Cl] | 3-(1-(2,3-dichloro-4-(5-(thiophen-2-yl)pyridin-3-yl)phenyl)ethyl)-1-methyl-1-(1-methylpiperidin-4-yl)urea |
| H0718 | 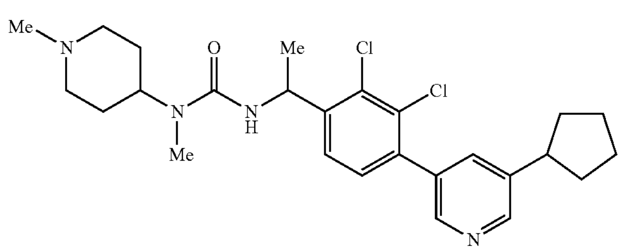 | 3-(1-(2,3-dichloro-4-(5-cyclopentylpyridin-3-yl)phenyl)ethyl)-1-methyl-1-(1-methylpiperidin-4-yl)urea |
| H0719 | 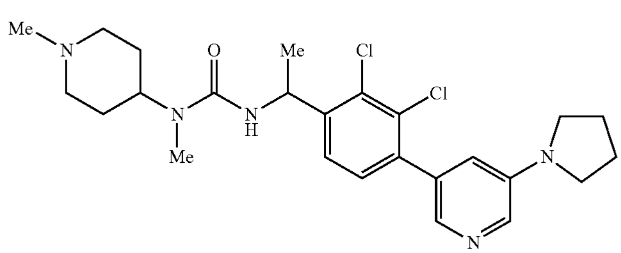 [SMILES: CC(NC(=O)N(C)C1CCN(C)CC1)c1ccc(-c2cncc(C3CCCC3)c2)c(Cl)c1Cl] | 3-(1-(2,3-dichloro-4-(5-(pyrrolidin-1-yl)pyridin-3-yl)phenyl)ethyl)-1-methyl-1-(1-methylpiperidin-4-yl)urea |

-continued

| Compound No. | Chemical Structure | Chemical Name |
|---|---|---|
| H0712 | 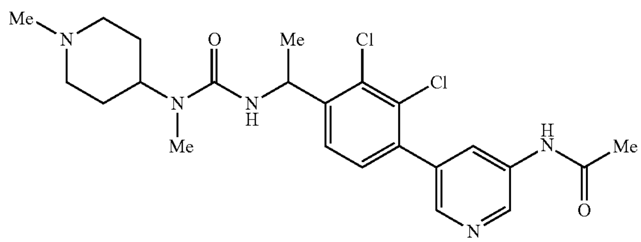 [SMILES: CC(=O)Nc1cncc(-c2ccc(C(C)NC(=O)N(C)C3CCN(C)CC3)c(Cl)c2Cl)c1] | N-(5-(2,3-dichloro-4-(1-(3-methyl-3-(1-methylpiperidin-4-yl)ureido)ethyl)phenyl)pyridin-3-yl)acetamide |
| H0708 | 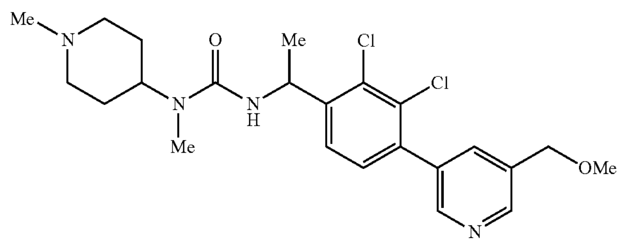 [SMILES: COCc1cncc(-c2ccc(C(C)NC(=O)N(C)C3CCN(C)CC3)c(Cl)c2Cl)c1] | 3-(1-(2,3-dichloro-4-(5-(methoxymethyl)pyridin-3-yl)phenyl)ethyl)-1-methyl-1-(1-methylpiperidin-4-yl)urea |
| H0714 | 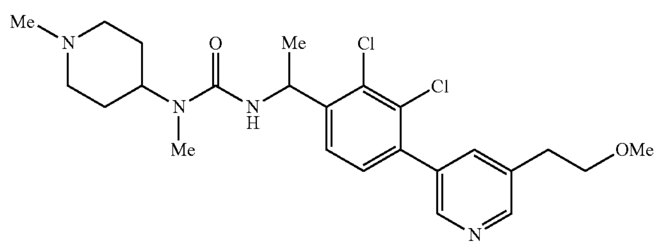 [SMILES: COCCc1cncc(-c2ccc(C(C)NC(=O)N(C)C3CCN(C)CC3)c(Cl)c2Cl)c1] | 3-(1-(2,3-dichloro-4-(5-(2-methoxyethyl)pyridin-3-yl)phenyl)ethyl)-1-methyl-1-(1-methylpiperidin-4-yl)urea |
| H0715 | 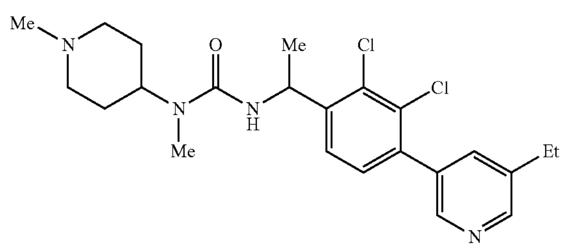 | 3-(1-(2,3-dichloro-4-(5-ethylpyridin-3-yl)phenyl)ethyl)-1-methyl-1-(1-methylpiperidin-4-yl)urea |
| H0706 | 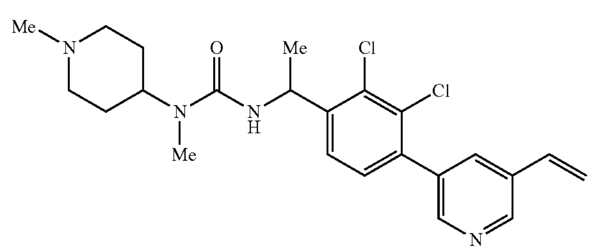 [SMILES: C=Cc1cncc(-c2ccc(C(C)NC(=O)N(C)C3CCN(C)CC3)c(Cl)c2Cl)c1] | 3-(1-(2,3-dichloro-4-(5-vinylpyridin-3-yl)phenyl)ethyl)-1-methyl-1-(1-methylpiperidin-4-yl)urea |
| H0710 | 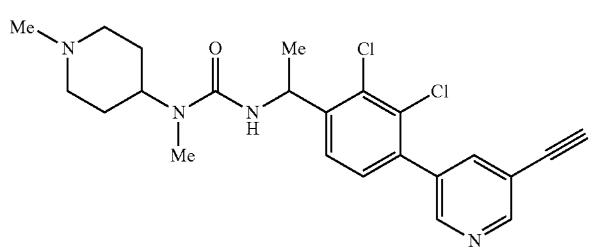 [SMILES: C#Cc1cncc(-c2ccc(C(C)NC(=O)N(C)C3CCN(C)CC3)c(Cl)c2Cl)c1] | 3-(1-(2,3-dichloro-4-(5-ethynylpyridin-3-yl)phenyl)ethyl)-1-methyl-1-(1-methylpiperidin-4-yl)urea |

-continued

| Compound No. | Chemical Structure | Chemical Name |
|---|---|---|
| H0666 | 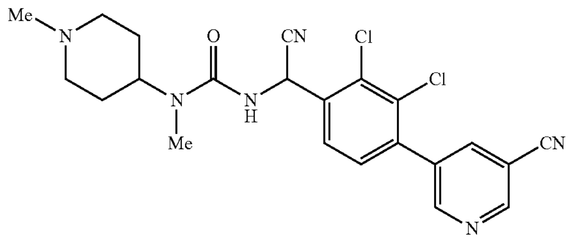 [SMILES: CN1CCC(N(C)C(=O)NC(C#N)c2ccc(-c3cncc(C#N)c3)c(Cl)c2Cl)CC1] | 3-(cyano(2,3-dichloro-4-(5-cyanopyridin-3-yl)phenyl)methyl)-1-methyl-1-(1-methylpiperidin-4-yl)urea |
| H0739 | 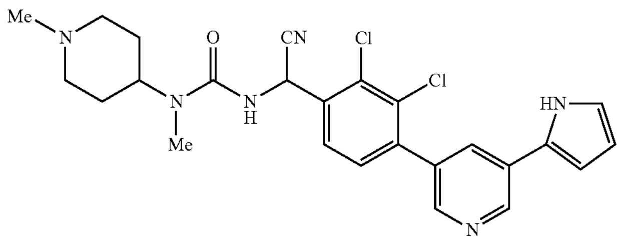 [SMILES: CN1CCC(N(C)C(=O)NC(C#N)c2ccc(-c3cncc(-c4ccc[nH]4)c3)c(Cl)c2Cl)CC1] | 3-((4-(1H-pyrrol-2-yl)pyridin-3-yl)-2,3-dichlorophenyl)(cyano)methyl)-1-methyl-1-(1-methylpiperidin-4-yl)urea |
| H0667 | 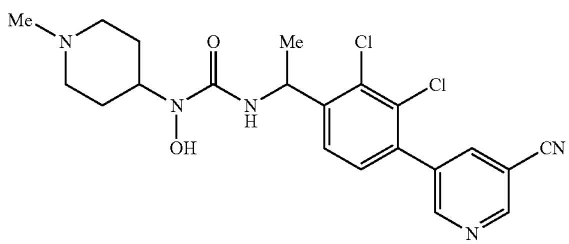 | 3-(1-(2,3-dichloro-4-(5-cyanopyridin-3-yl)phenyl)ethyl)-1-hydroxy-1-(1-methylpiperidin-4-yl)urea |
| H0821 | 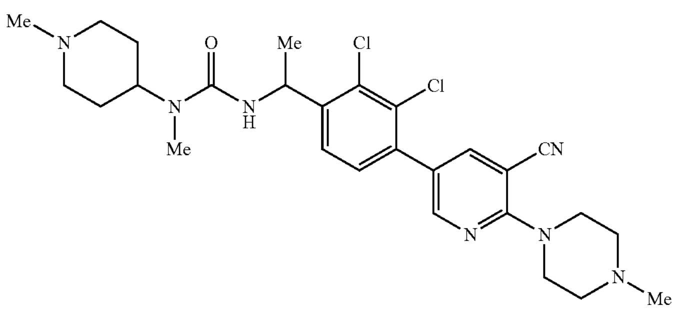 [SMILES: CC(NC(=O)N(C)C1CCN(C)CC1)c1ccc(-c2cnc(N3CCN(C)CC3)c(C#N)c2)c(Cl)c1Cl] | 3-(1-(2,3-dichloro-4-(5-cyano-6-(4-methylpiperazin-1-yl)pyridin-3-yl)phenyl)ethyl)-1-methyl-1-(1-methylpiperidin-4-yl)urea |
| H0646 | 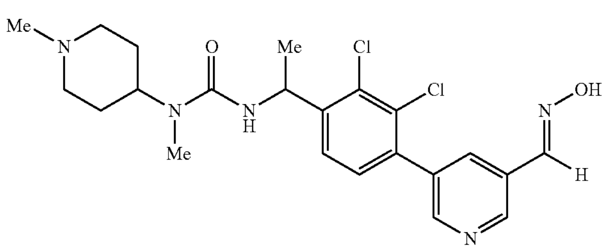 [SMILES: CC(NC(=O)N(C)C1CCN(C)CC1)c1ccc(-c2cncc(/C=N/O)c2)c(Cl)c1Cl] | (E)-3-(1-(2,3-dichloro-4-(5-((hydroxyimino)methyl)pyridin-3-yl)phenyl)ethyl)-1-methyl-1-(1-methylpiperidin-4-yl)urea |
| H0720 | 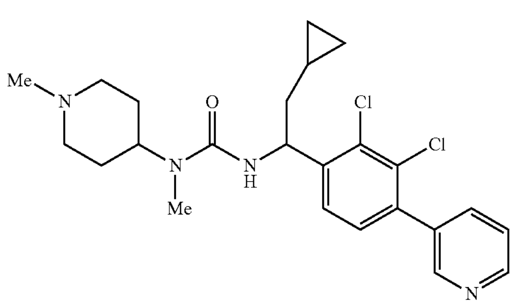 [SMILES: CN1CCC(N(C)C(=O)NC(CC2CC2)c2ccc(-c3cccnc3)c(Cl)c2Cl)CC1] | 3-(2-cyclopropyl-1-(2,3-dichloro-4-(pyridin-3-yl)phenyl)ethyl)-1-methyl-1-(1-methylpiperidin-4-yl)urea |

-continued

| Compound No. | Chemical Structure | Chemical Name |
|---|---|---|
| H0721 | 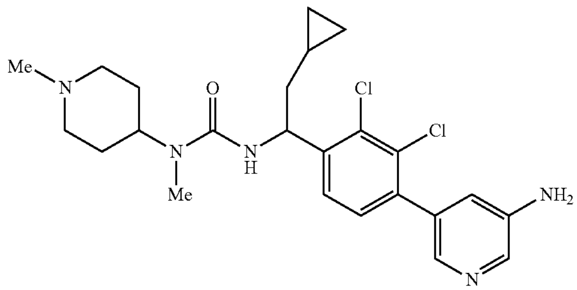 [SMILES: CN1CCC(N(C)C(=O)NC(CC2CC2)c2ccc(-c3cncc(N)c3)c(Cl)c2Cl)CC1] | 3-(1-(4-(5-aminopyridin-3-yl)-2,3-dichlorophenyl)-2-cyclopropylethyl)-1-methyl-1-(1-methylpiperidin-4-yl)urea |
| H0516 | 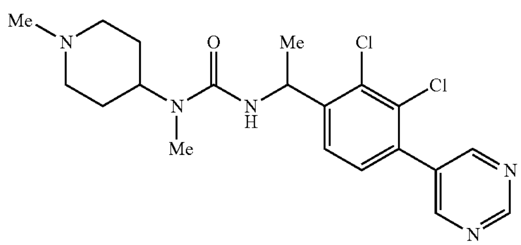 [SMILES: CC(NC(=O)N(C)C1CCN(C)CC1)c1ccc(-c2cncnc2)c(Cl)c1Cl] | 3-(1-(2,3-dichloro-4-(pyrimidin-5-yl)phenyl)ethyl)-1-methyl-1-(1-methylpiperidin-4-yl)urea |
| H0579 | 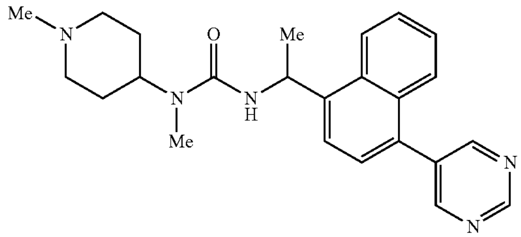 [SMILES: CC(NC(=O)N(C)C1CCN(C)CC1)c1ccc(-c2cncnc2)c2ccccc12] | 1-methyl-1-(1-methylpiperidin-4-yl)-3-(1-(4-(pyrimidin-5-yl)naphthalen-1-yl)ethyl)urea |
| H0649 | 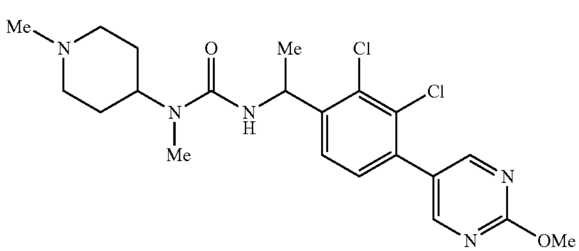 [SMILES: COc1ncc(-c2ccc(C(C)NC(=O)N(C)C3CCN(C)CC3)c(Cl)c2Cl)cn1] | 3-(1-(2,3-dichloro-4-(2-methoxypyrimidin-5-yl)phenyl)ethyl)-1-methyl-1-(1-methylpiperidin-4-yl)urea |
| H0797 | 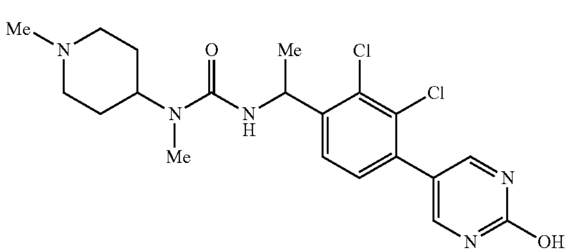 [SMILES: CC(NC(=O)N(C)C1CCN(C)CC1)c1ccc(-c2cnc(O)nc2)c(Cl)c1Cl] | 3-(1-(2,3-dichloro-4-(2-hydroxypyrimidin-5-yl)phenyl)ethyl)-1-methyl-1-(1-methylpiperidin-4-yl)urea |
| H0798 | 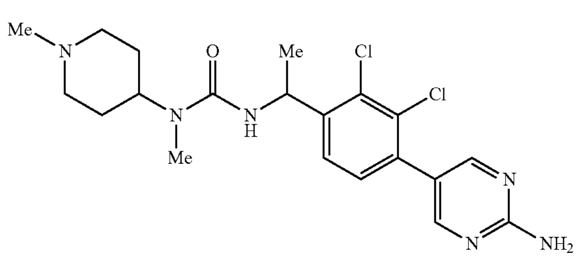 [SMILES: CC(NC(=O)N(C)C1CCN(C)CC1)c1ccc(-c2cnc(N)nc2)c(Cl)c1Cl] | 3-(1-(4-(2-aminopyrimidin-5-yl)-2,3-dichlorophenyl)ethyl)-1-methyl-1-(1-methylpiperidin-4-yl)urea |

-continued

| Compound No. | Chemical Structure | Chemical Name |
|---|---|---|
| H0799 | 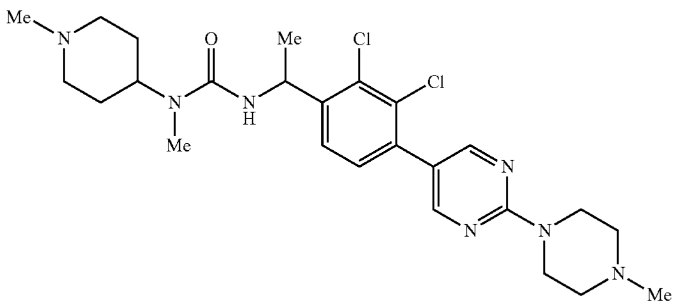 [SMILES: CC(NC(=O)N(C)C1CCN(C)CC1)c1ccc(-c2cnc(N3CCN(C)CC3)nc2)c(Cl)c1Cl] | 3-(1-(2,3-dichloro-4-(2-(4-methylpiperazin-1-yl)pyrimidin-5-yl)phenyl)ethyl)-1-methyl-1-(1-methylpiperidin-4-yl)urea |
| H0800 | 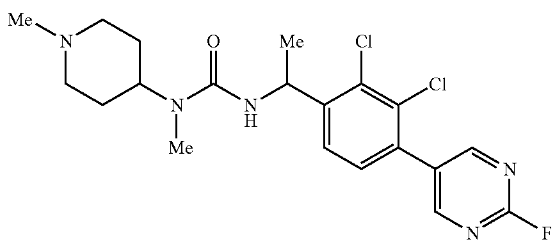 [SMILES: CC(NC(=O)N(C)C1CCN(C)CC1)c1ccc(-c2cnc(F)nc2)c(Cl)c1Cl] | 3-(1-(2,3-dichloro-4-(2-fluoropyrimidin-5-yl)phenyl)ethyl)-1-methyl-1-(1-methylpiperidin-4-yl)urea |
| H0801 | 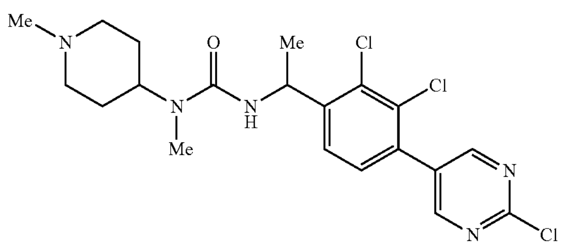 [SMILES: CC(NC(=O)N(C)C1CCN(C)CC1)c1ccc(-c2cnc(Cl)nc2)c(Cl)c1Cl] | 3-(1-(2,3-dichloro-4-(2-chloropyrimidin-5-yl)phenyl)ethyl)-1-methyl-1-(1-methylpiperidin-4-yl)urea |
| H0802 | 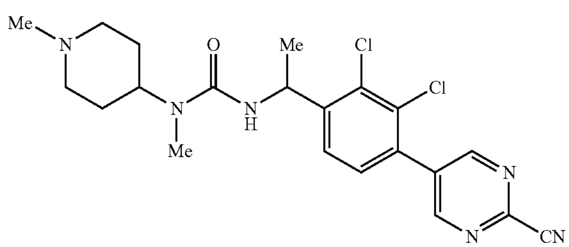 [SMILES: CC(NC(=O)N(C)C1CCN(C)CC1)c1ccc(-c2cnc(C#N)nc2)c(Cl)c1Cl] | 3-(1-(2,3-dichloro-4-(2-cyanopyrimidin-5-yl)phenyl)ethyl)-1-methyl-1-(1-methylpiperidin-4-yl)urea |
| H0803 | 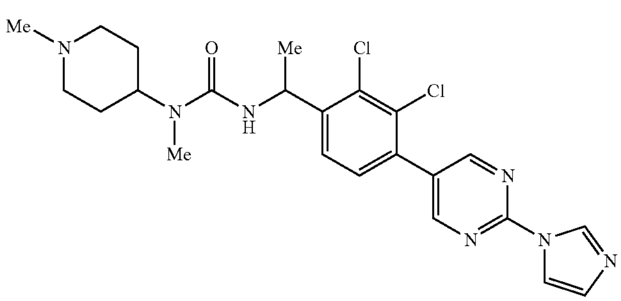 [SMILES: CC(NC(=O)N(C)C1CCN(C)CC1)c1ccc(-c2cnc(-n3ccnc3)nc2)c(Cl)c1Cl] | 3-(1-(4-(2-(1H-imidazol-1-yl)pyrimidin-5-yl)-2,3-dichlorophenyl)ethyl)-1-methyl-1-(1-methylpiperidin-4-yl)urea |

-continued

| Compound No. | Chemical Structure | Chemical Name |
|---|---|---|
| H0804 | 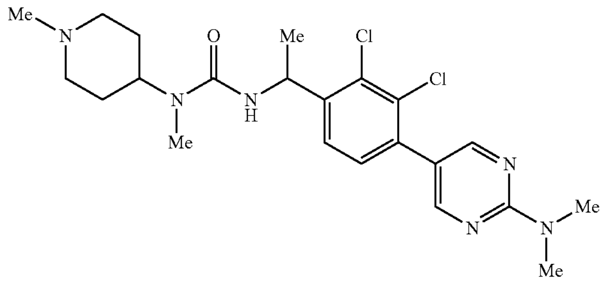 [SMILES: CC(NC(=O)N(C)C1CCN(C)CC1)c1ccc(-c2cnc(N(C)C)nc2)c(Cl)c1Cl] | 3-(1-(2,3-dichloro-4-(2-(dimethylamino)pyrimidin-5-yl)phenyl)ethyl)-1-methyl-1-(1-methylpiperidin-4-yl)urea |
| H0805 | 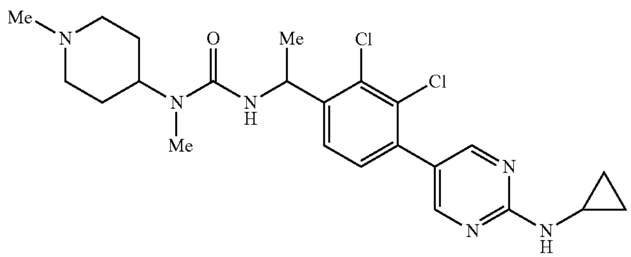 [SMILES: CC(NC(=O)N(C)C1CCN(C)CC1)c1ccc(-c2cnc(NC3CC3)nc2)c(Cl)c1Cl] | 3-(1-(2,3-dichloro-4-(2-(cyclopropylamino)pyrimidin-5-yl)phenyl)ethyl)-1-methyl-1-(1-methylpiperidin-4-yl)urea |
| H0806 | 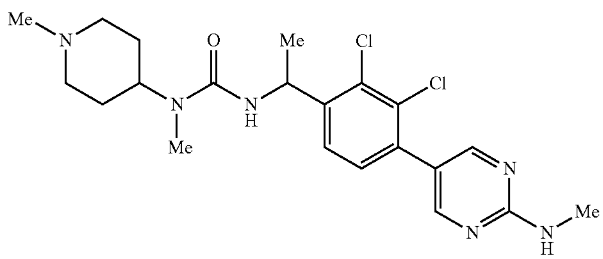 [SMILES: CNc1ncc(-c2ccc(C(C)NC(=O)N(C)C3CCN(C)CC3)c(Cl)c2Cl)cn1] | 3-(1-(2,3-dichloro-4-(2-(methylamino)pyrimidin-5-yl)phenyl)ethyl)-1-methyl-1-(1-methylpiperidin-4-yl)urea |
| H0807 | 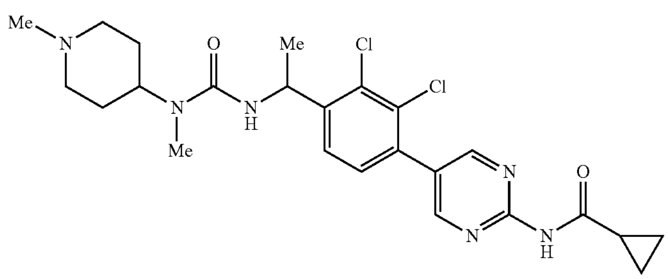 [SMILES: CC(NC(=O)N(C)C1CCN(C)CC1)c1ccc(-c2cnc(NC(=O)C3CC3)nc2)c(Cl)c1Cl] | N-(5-(2,3-dichloro-4-(1-(3-methyl-3-(1-methylpiperidin-4-yl)ureido)ethyl)phenyl)pyrimidin-2-yl)cyclopropanecarboxamide |
| H0854 | 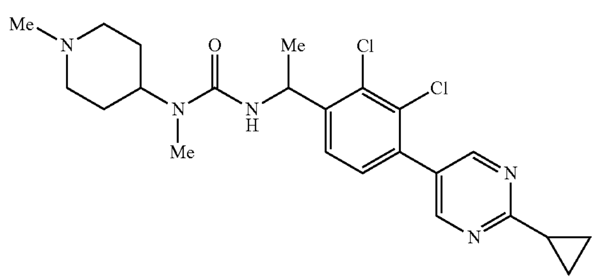 | 3-(1-(2,3-dichloro-4-(2-cyclopropylpyrimidin-5-yl)phenyl)ethyl)-1-methyl-1-(1-methylpiperidin-4-yl)urea |

-continued

| Compound No. | Chemical Structure | Chemical Name |
|---|---|---|
| H0813 | 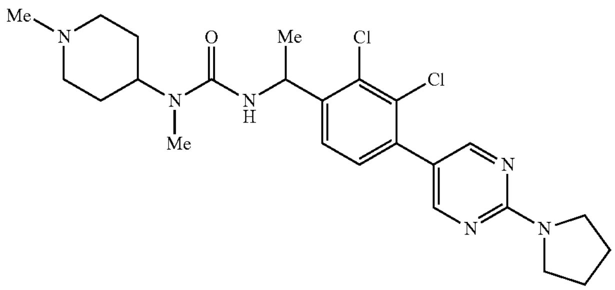 [SMILES: CC(NC(=O)N(C)C1CCN(C)CC1)c1ccc(-c2cnc(N3CCCC3)nc2)c(Cl)c1Cl] | 3-(1-(2,3-dichloro-4-(2-(pyrrolidin-1-yl)pyrimidin-5-yl)phenyl)ethyl)-1-methyl-1-(1-methylpiperazin-4-yl)urea |
| H0814 | 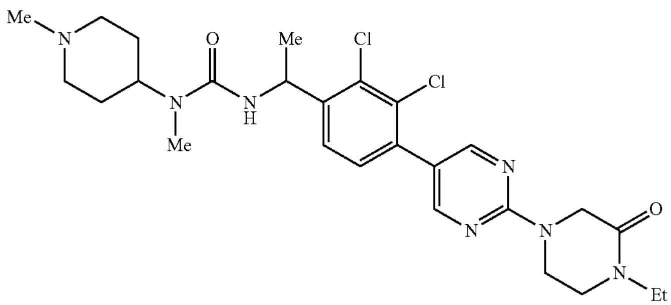 [SMILES: CCN1CCN(c2ncc(-c3ccc(C(C)NC(=O)N(C)C4CCN(C)CC4)c(Cl)c3Cl)cn2)CC1=O] | 3-(1-(2,3-dichloro-4-(2-(4-ethyl-3-oxopiperazin-1-yl)pyrimidin-5-yl)phenyl)ethyl)-1-methyl-1-(1-methylpiperidin-4-yl)urea |
| H0703 | 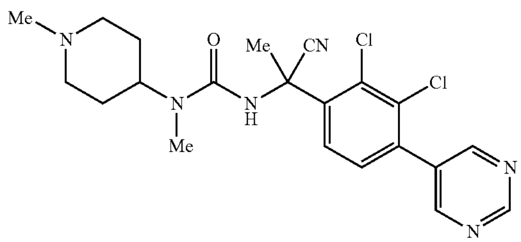 [SMILES: CN1CCC(N(C)C(=O)NC(C)(C#N)c2ccc(-c3cncnc3)c(Cl)c2Cl)CC1] | 3-(1-cyano-1-(2,3-dichloro-4-(pyrimidin-5-yl)phenyl)ethyl)-1-methyl-1-(1-methylpiperidin-4-yl)urea |
| H0709 | 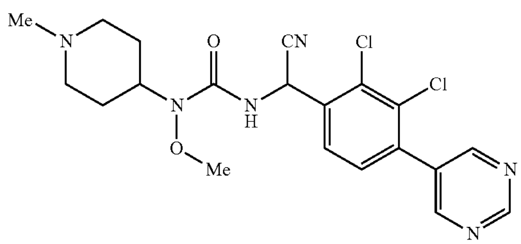 [SMILES: CON(C(=O)NC(C#N)c1ccc(-c2cncnc2)c(Cl)c1Cl)C1CCN(C)CC1] | 3-(cyano(2,3-dichloro-4-(pyrimidin-5-yl)phenyl)methyl)-1-methoxy-1-(1-methylpiperazin-4-yl)urea |
| H0584 | 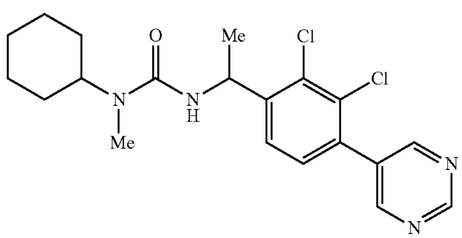 [SMILES: CC(NC(=O)N(C)C1CCCCC1)c1ccc(-c2cncnc2)c(Cl)c1Cl] | 1-cyclohexyl-3-(1-(2,3-dichloro-4-(pyrimidin-5-yl)phenyl)ethyl)-1-methylurea |
| H0586 | 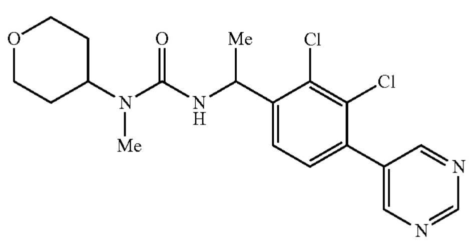 [SMILES: CC(NC(=O)N(C)C1CCOCC1)c1ccc(-c2cncnc2)c(Cl)c1Cl] | 3-(1-(2,3-dichloro-4-(pyrimidin-5-yl)phenyl)ethyl)-1-methyl-1-(tetrahydro-2H-pyran-4-yl)urea |

| Compound No. | Chemical Name |
|---|---|
| H0587 | 3-(1-(2,3-dichloro-4-(pyrimidin-5-yl)phenyl)ethyl)-1-(4,4-difluorocyclohexyl)-1-methylurea |
| H0588 | 1-(1-acetylpiperidin-4-yl)-3-(1-(2,3-dichloro-4-(pyrimidin-5-yl)phenyl)ethyl)-1-methylurea |
| H0663 | 3-(1-(2,3-dichloro-4-(2,4-dimethoxypyrimidin-5-yl)phenyl)ethyl)-1-methyl-1-(1-methylpiperidin-4-yl)urea |
| H0620 | 3-(1-(2,3-dichloro-4-(pyrimidin-5-yl)phenyl)-2-((3-(hydroxymethyl)benzyl)oxy)ethyl)-1-methyl-1-(1-methylpiperidin-4-yl)urea |
| H0624 | 3-(1-(2,3-dichloro-4-(pyrimidin-5-yl)phenyl)ethyl)-1-hydroxy-1-(1-methylpiperidin-4-yl)urea |

US 9,546,157 B2

33 34

-continued

| Compound No. | Chemical Structure | Chemical Name |
|---|---|---|
| H0662 | 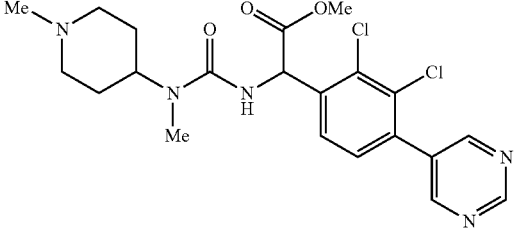 [SMILES: COC(=O)C(NC(=O)N(C)C1CCN(C)CC1)c1ccc(-c2cncnc2)c(Cl)c1Cl] | methyl 2-(2,3-dichloro-4-(pyrimidin-5-yl)phenyl)-2-(3-methyl-3-(1-methylpiperidin-4-yl)ureido)acetate |
| H0670 | 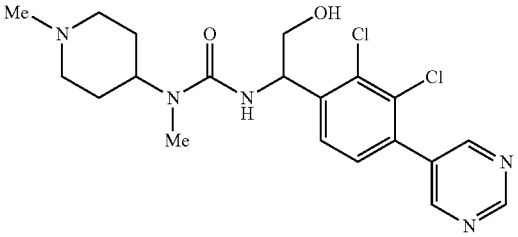 [SMILES: CN1CCC(N(C)C(=O)NC(CO)c2ccc(-c3cncnc3)c(Cl)c2Cl)CC1] | 3-(1-(2,3-dichloro-4-(pyrimidin-5-yl)phenyl)-2-hydroxyethyl)-1-methyl-1-(1-methylpiperidin-4-yl)urea |
| H0673 | 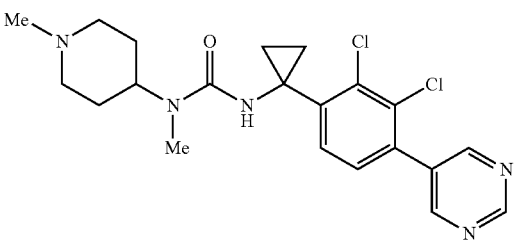 [SMILES: CN1CCC(N(C)C(=O)NC2(c3ccc(-c4cncnc4)c(Cl)c3Cl)CC2)CC1] | 3-(1-(2,3-dichloro-4-(pyrimidin-5-yl)phenyl)cyclopropyl)-1-methyl-1-(1-methylpiperidin-4-yl)urea |
| H0727 | 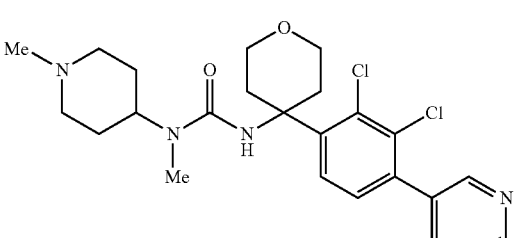 | 3-(4-(2,3-dichloro-4-(pyrimidin-5-yl)phenyl)tetrahydro-2H-pyran-4-yl)-1-methyl-1-(1-methylpiperidin-4-yl)urea |
| H0631 | 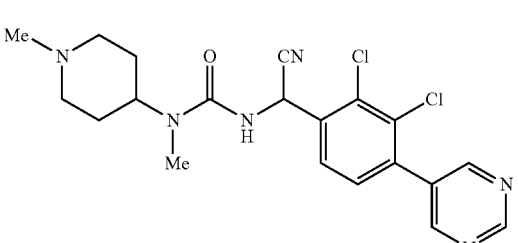 | 3-(cyano(2,3-dichloro-4-(pyrimidin-5-yl)phenyl)methyl)-1-methyl-1-(1-methylpiperidin-4-yl)urea |
| H0686 | 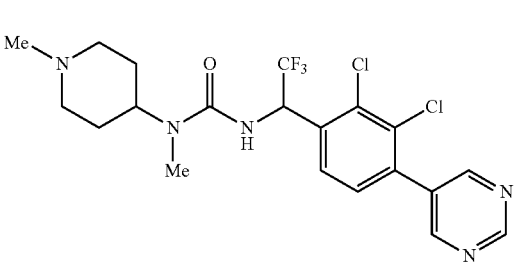 [SMILES: CN1CCC(N(C)C(=O)NC(C#N)c2ccc(-c3cncnc3)c(Cl)c2Cl)CC1] | 3-(1-(2,3-dichloro-4-(pyrimidin-5-yl)phenyl)-2,2,2-trifluoroethyl)-1-methyl-1-(1-methylpiperidin-4-yl)urea |

-continued

| Compound No. | Chemical Structure | Chemical Name |
|---|---|---|
| H0619 | 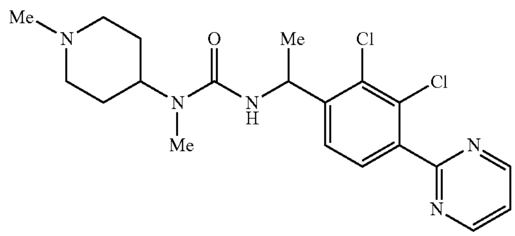 [SMILES: CC(NC(=O)N(C)C1CCN(C)CC1)c1ccc(-c2ncccn2)c(Cl)c1Cl] | 3-(1-(2,3-dichloro-4-(pyrimidin-2-yl)phenyl)ethyl)-1-methyl-1-(1-methylpiperidin-4-yl)urea |
| H0768 | 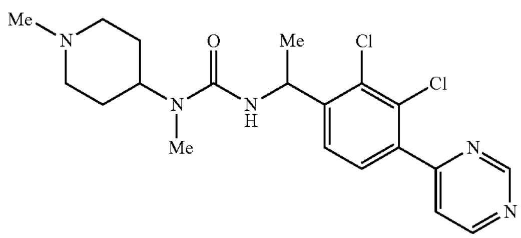 [SMILES: CC(NC(=O)N(C)C1CCN(C)CC1)c1ccc(-c2ccncn2)c(Cl)c1Cl] | 3-(1-(2,3-dichloro-4-(pyrimidin-4-yl)phenyl)ethyl)-1-methyl-1-(1-methylpiperidin-4-yl)urea |
| H0808 | 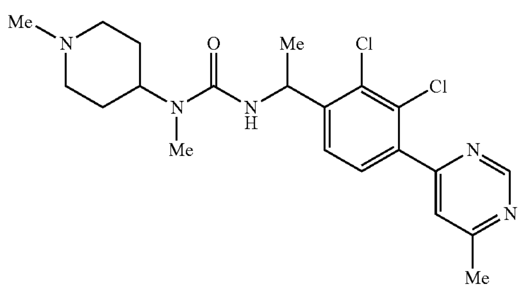 [SMILES: Cc1cc(-c2ccc(C(C)NC(=O)N(C)C3CCN(C)CC3)c(Cl)c2Cl)ncn1] | 3-(1-(2,3-dichloro-4-(6-methylpyrimidin-4-yl)phenyl)ethyl)-1-methyl-1-(1-methylpiperidin-4-yl)urea |
| H0700 | 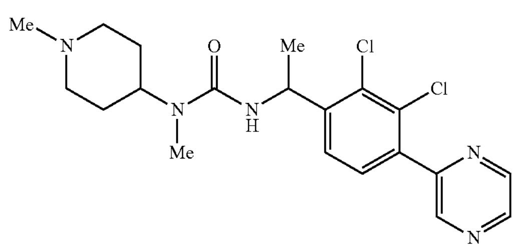 [SMILES: CC(NC(=O)N(C)C1CCN(C)CC1)c1ccc(-c2cnccn2)c(Cl)c1Cl] | 3-(1-(2,3-dichloro-4-(pyrazin-2-yl)phenyl)ethyl)-1-methyl-1-(1-methylpiperidin-4-yl)urea |
| H0816 | 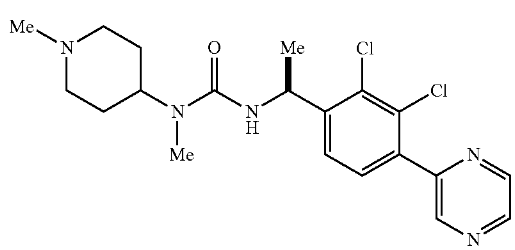 [SMILES: C[C@H](NC(=O)N(C)C1CCN(C)CC1)c1ccc(-c2cnccn2)c(Cl)c1Cl] | (S)-3-(1-(2,3-dichloro-4-(pyrazin-2-yl)phenyl)ethyl)-1-methyl-1-(1-methylpiperidin-4-yl)urea |
| H0817 | 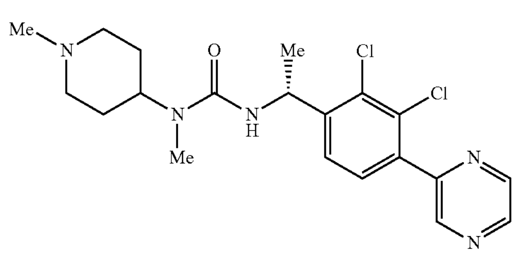 [SMILES: C[C@@H](NC(=O)N(C)C1CCN(C)CC1)c1ccc(-c2cnccn2)c(Cl)c1Cl] | (R)-3-(1-(2,3-dicholoro-4-(pyrazin-2-yl)phenyl)ethyl)-1-methyl-1-(1-methylpiperidin-4-yl)urea |

-continued

| Compound No. | Chemical Structure | Chemical Name |
|---|---|---|
| H0722 | 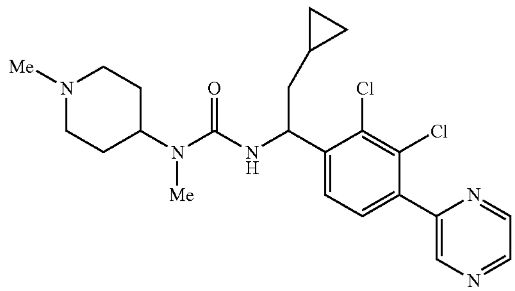 [SMILES: CN1CCC(N(C)C(=O)NC(CC2CC2)c2ccc(-c3cnccn3)c(Cl)c2Cl)CC1] | 3-(2-cyclopropyl-1-(2,3-dichloro-4-(pyrazin-2-yl)phenyl)ethyl)-1-methyl-1-(1-methylpiperidin-4-yl)urea |
| H0741 | 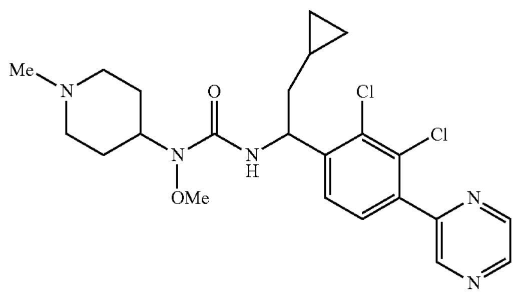 [SMILES: CON(C(=O)NC(CC1CC1)c1ccc(-c2cnccn2)c(Cl)c1Cl)C1CCN(C)CC1] | 3-(2-cyclopropyl-1-(2,3-dichloro-4-(pyrazin-2-yl)phenyl)ethyl)-1-methoxy-1-(1-methylpiperidin-4-yl)urea |
| H0752 | 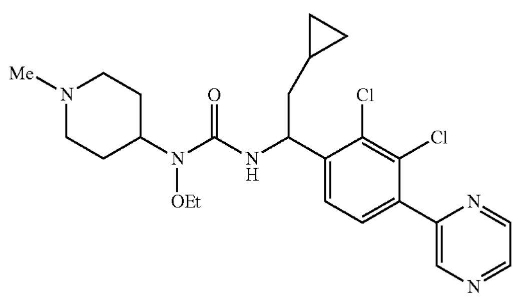 | 3-(2-cyclopropyl-1-(2,3-dichloro-4-(pyrazin-2-yl)phenyl)ethyl)-1-ethoxy-1-(1-methylpiperidin-4-yl)urea |
| H0743 | 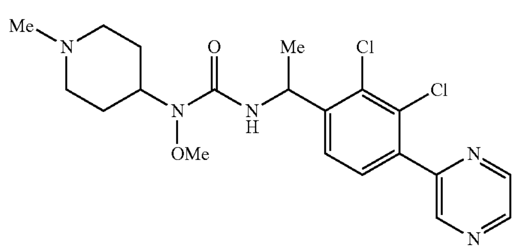 [SMILES: CON(C(=O)NC(C)c1ccc(-c2cnccn2)c(Cl)c1Cl)C1CCN(C)CC1] | 3-(1-(2,3-dichloro-4-(pyrazin-2-yl)phenyl)ethyl)-1-methoxy-1-(1-methylpiperidin-4-yl)urea |
| H0750 | 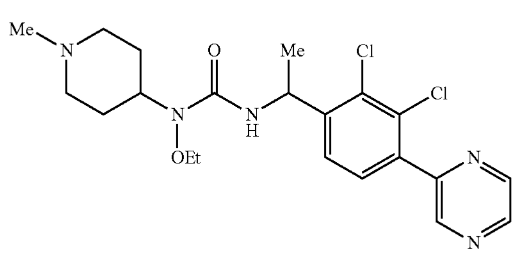 [SMILES: CCON(C(=O)NC(C)c1ccc(-c2cnccn2)c(Cl)c1Cl)C1CCN(C)CC1] | 3-(1-(2,3-dichloro-4-(pyrazin-2-yl)phenyl)ethyl)-1-ethoxy-1-(1-methylpiperidin-4-yl)urea |

-continued

| Compound No. | Chemical Structure | Chemical Name |
|---|---|---|
| H0756 | 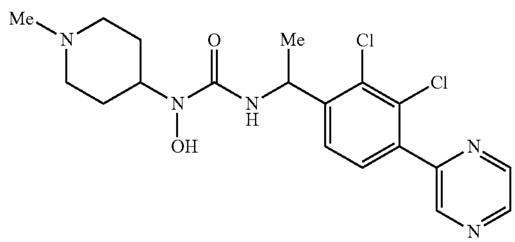 [SMILES: CC(NC(=O)N(O)C1CCN(C)CC1)c1ccc(-c2cnccn2)c(Cl)c1Cl] | 3-(1-(2,3-dichloro-4-(pyrazin-2-yl)phenyl)ethyl)-1-hydroxy-1-(1-methylpiperidin-4-yl)urea |
| H0761 | 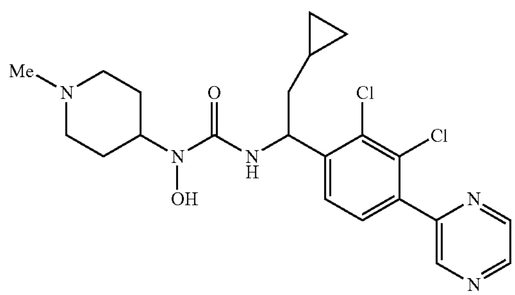 [SMILES: CN1CCC(N(O)C(=O)NC(CC2CC2)c2ccc(-c3cnccn3)c(Cl)c2Cl)CC1] | 3-(2-cyclopropyl-1-(2,3-dichloro-4-(pyrazin-2-yl)phenyl)ethyl)-1-hydroxy-1-(1-methylpiperidin-4-yl)urea |
| H0781 | 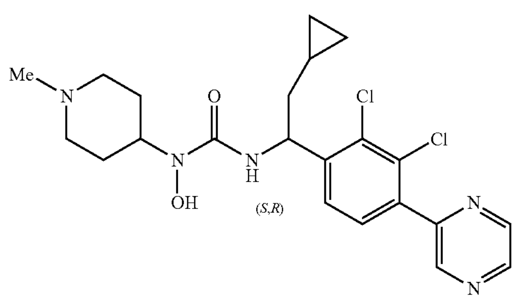 [SMILES: CN1CCC(N(O)C(=O)NC(CC2CC2)c2ccc(-c3cnccn3)c(Cl)c2Cl)CC1] | 3-(2-cyclopropyl-1-(2,3-dichloro-4-(pyrazin-2-yl)phenyl)ethyl)-1-hydroxy-1-(1-methylpiperidin-4-yl)urea (single enantiomer) |
| H0782 | 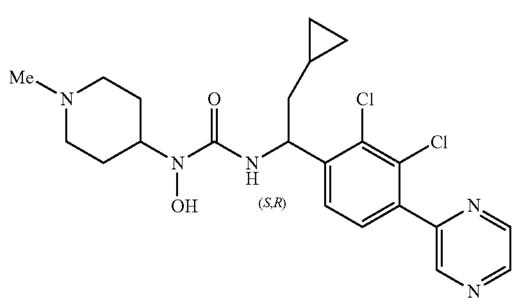 [SMILES: CN1CCC(N(O)C(=O)NC(CC2CC2)c2ccc(-c3cnccn3)c(Cl)c2Cl)CC1] | 3-(2-cyclopropyl-1-(2,3-dichloro-4-(pyrazin-2-yl)phenyl)ethyl)-1-hydroxy-1-(1-methylpiperidin-4-yl)urea (single enantiomer) |
| H0824 | 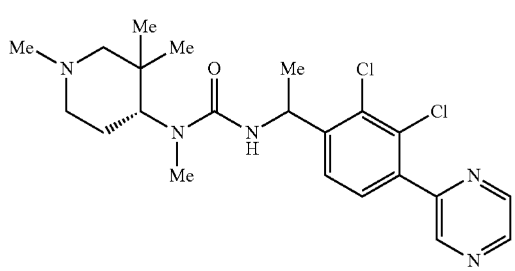 [SMILES: CC(NC(=O)N(C)[C@@H]1CCN(C)CC1(C)C)c1ccc(-c2cnccn2)c(Cl)c1Cl] | 2-(1-(2,3-dichloro-4-(pyrazin-2-yl)phenyl)ethyl)-1-methyl-1-((R)-1,3,3-trimethylpiperidin-4-yl)urea |

-continued

| Compound No. | Chemical Structure | Chemical Name |
|---|---|---|
| H0890 | 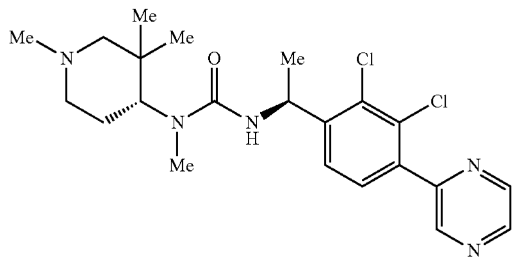 [SMILES: C[C@H](NC(=O)N(C)[C@@H]1CCN(C)CC1(C)C)c1ccc(-c2cnccn2)c(Cl)c1Cl] | 3-((S)-1-(2,3-dichloro-4-(pyrazin-2-yl)phenyl)ethyl)-1-methyl-1-((R)-1,3,3-trimethylpiperidin-4-yl)urea |
| H0858 | 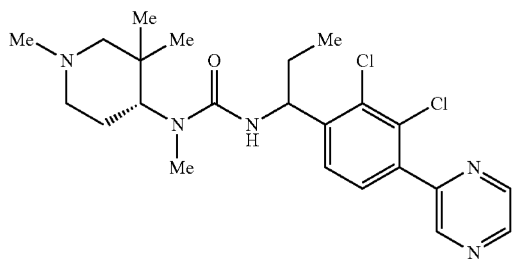 [SMILES: CCC(NC(=O)N(C)[C@@H]1CCN(C)CC1(C)C)c1ccc(-c2cnccn2)c(Cl)c1Cl] | 3-(1-(2,3-dichloro-4-(pyrazin-2-yl)phenyl)propyl)-1-methyl-1-((R)-1,3,3-trimethylpiperidin-4-yl)urea |
| H0865 | 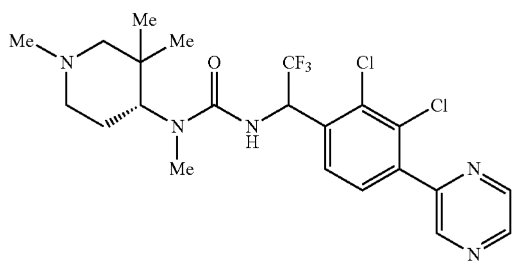 [SMILES: CN1CC[C@@H](N(C)C(=O)NC(c2ccc(-c3cnccn3)c(Cl)c2Cl)C(F)(F)F)C(C)(C)C1] | 3-(1-(2,3-dichloro-4-(pyrazin-2-yl)phenyl)-2,2,2-trifluoroethyl)-1-methyl-1-((R)-1,3,3-trimethylpiperidin-4-yl)urea |
| H0825 | 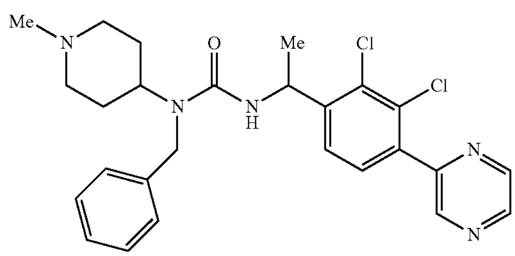 [SMILES: CC(NC(=O)N(Cc1ccccc1)C1CCN(C)CC1)c1ccc(-c2cnccn2)c(Cl)c1Cl] | 1-benzyl-3-(1-(2,3-dichloro-4-(pyrazin-2-yl)phenyl)ethyl)-1-(1-methylpiperidin-4-yl)urea |
| H0826 | 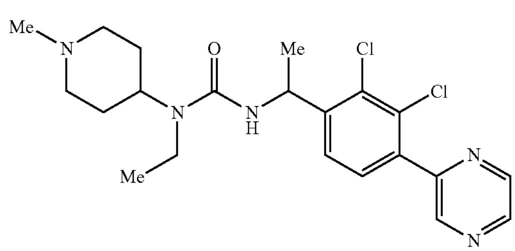 [SMILES: CCN(C(=O)NC(C)c1ccc(-c2cnccn2)c(Cl)c1Cl)C1CCN(C)CC1] | 3-(1-(2,3-dichloro-4-(pyrazin-2-yl)phenyl)ethyl)-1-ethyl-1-(1-methylpiperidin-4-yl)urea |
| H0889 | 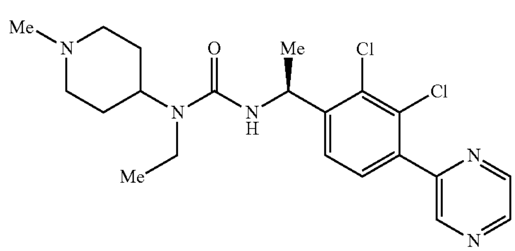 [SMILES: CCN(C(=O)N[C@@H](C)c1ccc(-c2cnccn2)c(Cl)c1Cl)C1CCN(C)CC1] | (S)-3-(1-(2,3-dichloro-4-(pyrazin-2-yl)phenyl)ethyl)-1-ethyl-1-(1-methylpiperidin-4-yl)urea |

-continued

| Compound No. | Chemical Structure | Chemical Name |
| --- | --- | --- |
| H0896 | 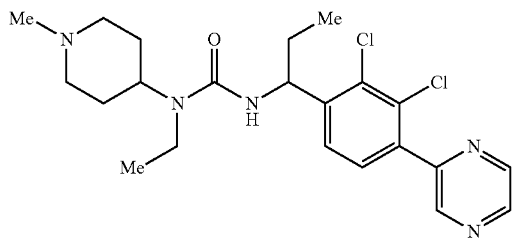 [SMILES: CCC(NC(=O)N(CC)C1CCN(C)CC1)c1ccc(-c2cnccn2)c(Cl)c1Cl] | 3-(1-(2,3-dichloro-4-(pyrazin-2-yl)phenyl)propyl)-1-ethyl-1-(1-methylpiperidin-4-yl)urea |
| H0827 | 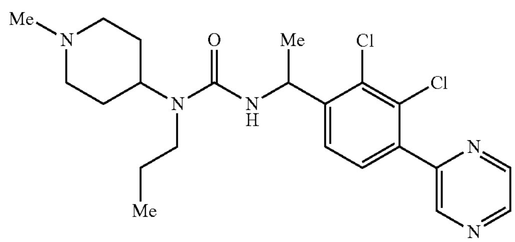 [SMILES: CCCN(C(=O)NC(C)c1ccc(-c2cnccn2)c(Cl)c1Cl)C1CCN(C)CC1] | 3-(1-(2,3-dichloro-4-(pyrazin-2-yl)phenyl)ethyl)-1-(1-methylpiperidin-4-yl)-1-propylurea |
| H0829 | 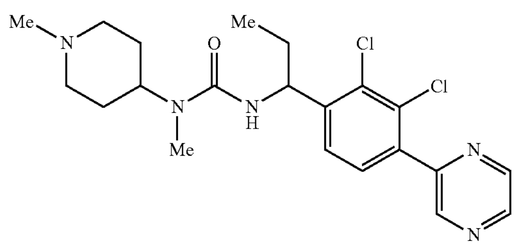 | 3-(1-(2,3-dichloro-4-(pyrazin-2-yl)phenyl)propyl)-1-methyl-1-(1-methylpiperidin-4-yl)urea |
| H0859 | 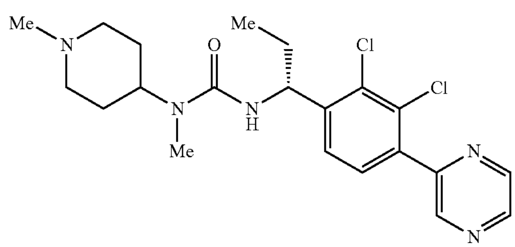 [SMILES: CC[C@@H](NC(=O)N(C)C1CCN(C)CC1)c1ccc(-c2cnccn2)c(Cl)c1Cl] | (R)-3-(1-(2,3-dichloro-4-(pyrazin-2-yl)phenyl)propyl)-1-methyl-1-methylpiperidin-4-yl)urea (single enantiomer) |
| H0860 | 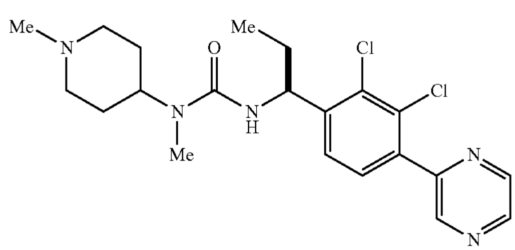 [SMILES: CC[C@H](NC(=O)N(C)C1CCN(C)CC1)c1ccc(-c2cnccn2)c(Cl)c1Cl] | (S)-3-(1-(2,3-dichloro-4-(pyrazin-2-yl)phenyl)propyl)-1-methyl-1-(1-methylpiperidin-4-yl)urea (single enantiomer) |
| H0922 | 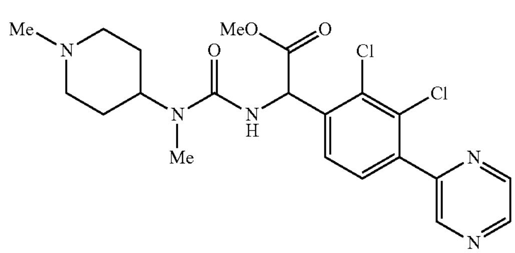 [SMILES: COC(=O)C(NC(=O)N(C)C1CCN(C)CC1)c1ccc(-c2cnccn2)c(Cl)c1Cl] | methyl 2-(2,3-dichloro-4-(pyrazin-2-yl)phenyl)-2-(3-methyl-3-(1-methylpiperidin-4-yl)ureido)acetate |

-continued

| Compound No. | Chemical Structure | Chemical Name |
|---|---|---|
| H0924 | 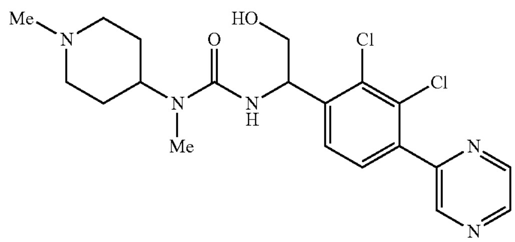 [SMILES: CN1CCC(N(C)C(=O)NC(CO)c2ccc(-c3cnccn3)c(Cl)c2Cl)CC1] | 3-(1-(2,3-dichloro-4-(pyrazin-2-yl)phenyl)-2-hydroxyethyl)-1-methyl-1-(1-methylpiperidin-4-yl)urea |
| H0830 | 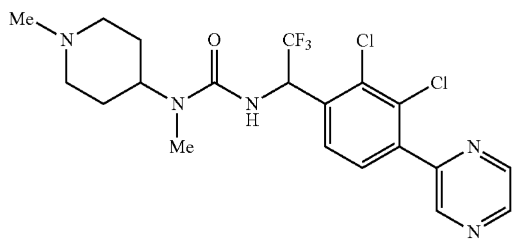 [SMILES: CN1CCC(N(C)C(=O)NC(c2ccc(-c3cnccn3)c(Cl)c2Cl)C(F)(F)F)CC1] | 3-(1-(2,3-dichloro-4-(pyrazin-2-yl)phenyl)-2,2,2-trifluoroethyl)-1-methyl-1-(1-methylpiperidin-4-yl)urea |
| H0899 | 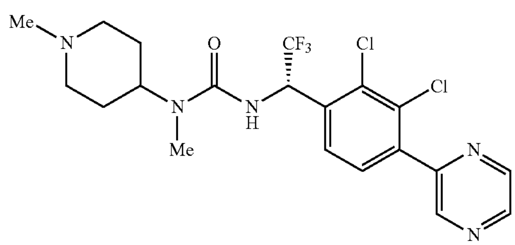 [SMILES: CN1CCC(N(C)C(=O)N[C@@H](c2ccc(-c3cnccn3)c(Cl)c2Cl)C(F)(F)F)CC1] | (S)-3-(1-(2,3-dichloro-4-(pyrazin-2-yl)phenyl)-2,2,2-trifluoroethyl)-1-methyl-1-(1-methylpiperidin-4-yl)urea |
| H0900 | 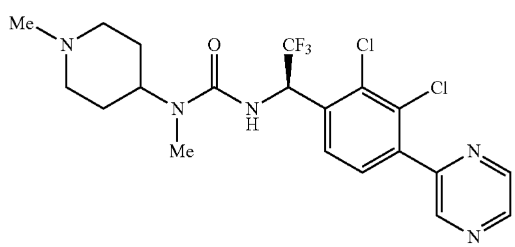 [SMILES: CN1CCC(N(C)C(=O)N[C@H](c2ccc(-c3cnccn3)c(Cl)c2Cl)C(F)(F)F)CC1] | (R)-3-(1-(2,3-dichloro-4-(pyrazin-2-yl)phenyl)-2,2,2-trifluoroethyl)-1-methyl-1-(1-methylpiperidin-4-yl)urea |
| H0909 | 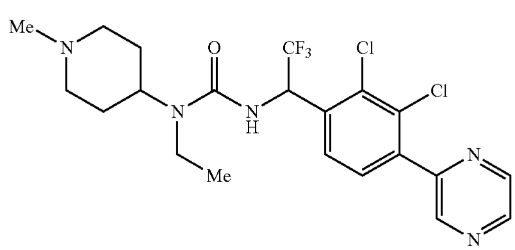 [SMILES: CCN(C(=O)NC(c1ccc(-c2cnccn2)c(Cl)c1Cl)C(F)(F)F)C1CCN(C)CC1] | 3-(1-(2,3-dichloro-4-(pyrazin-2-yl)phenyl)-2,2,2-trifluoroethyl)-1-ethyl-1-(1-methylpiperidin-4-yl)urea |
| H0856 | 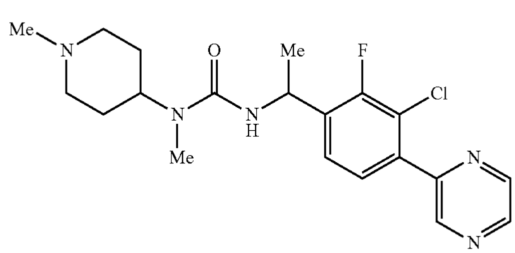 [SMILES: CC(NC(=O)N(C)C1CCN(C)CC1)c1ccc(-c2cnccn2)c(Cl)c1F] | 3-(1-(3-chloro-2-fluoro-4-(pyrazin-2-yl)phenyl)ethyl)-1-methyl-1-(1-methylpiperidin-4-yl)urea |

-continued

| Compound No. | Chemical Structure | Chemical Name |
|---|---|---|
| H0837 | 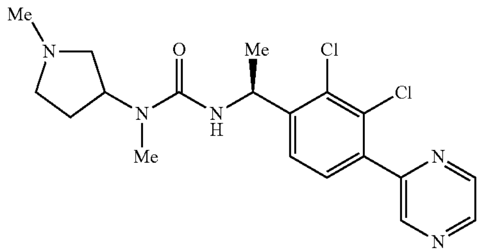 [SMILES: C[C@H](NC(=O)N(C)C1CCN(C)C1)c1ccc(-c2cnccn2)c(Cl)c1Cl] | 3-((S)-1-(2,3-dichloro-4-(pyrazin-2-yl)phenyl)ethyl)-1-methyl-1-(1-methylpyrrolidin-3-yl)urea (diasteromeric mixture) |
| H0861 | 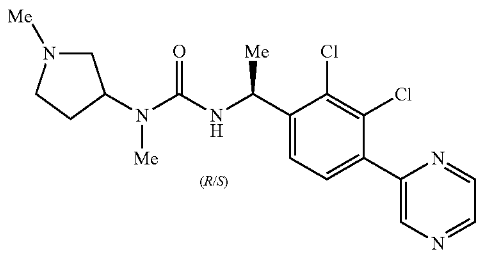 [SMILES: C[C@H](NC(=O)N(C)C1CCN(C)C1)c1ccc(-c2cnccn2)c(Cl)c1Cl] | 3-((S)-1-(2,3-dichloro-4-(pyrazin-2-yl)phenyl)ethyl)-1-methyl-1-(1-methylpyrrolidin-3-yl)urea (single diastereoisomer) |
| H0862 | 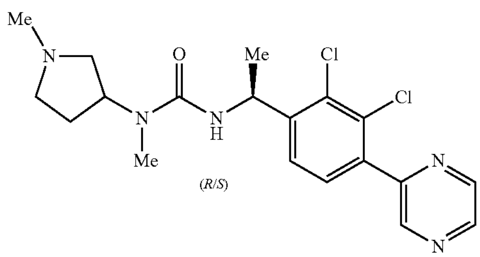 [SMILES: C[C@H](NC(=O)N(C)C1CCN(C)C1)c1ccc(-c2cnccn2)c(Cl)c1Cl] | 3-((S)-1-(2,3-dichloro-4-(pyrazin-2-yl)phenyl)ethyl)-1-methyl-1-(1-methylpyrrolidin-3-yl)urea (single diastereoisomer) |
| H0857 | 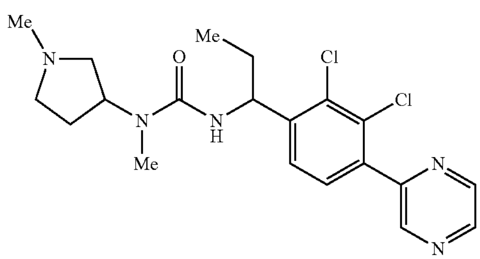 [SMILES: CCC(NC(=O)N(C)C1CCN(C)C1)c1ccc(-c2cnccn2)c(Cl)c1Cl] | 3-(1-(2,3-dichloro-4-(pyrazin-2-yl)phenyl)propyl)-1-methyl-1-(1-methylpyrrolidin-3-yl)urea |
| H0871 | 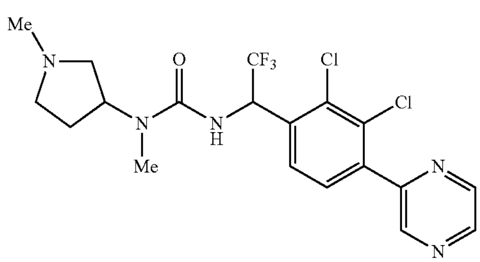 [SMILES: CN1CCC(N(C)C(=O)NC(c2ccc(-c3cnccn3)c(Cl)c2Cl)C(F)(F)F)C1] | 3-(1-(2,3-dichloro-4-(pyrazin-2-yl)phenyl)-2,2,2-trifluoroethyl)-1-methyl-1-(1-methylpyrrolidin-3-yl)urea |
| H0874 | 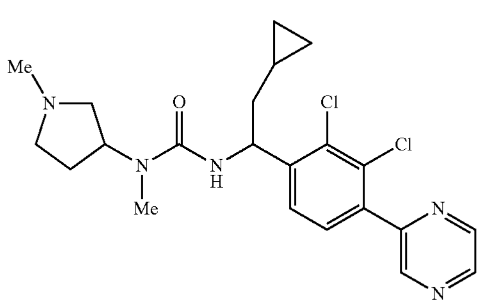 [SMILES: CN1CCC(N(C)C(=O)NC(CC2CC2)c2ccc(-c3cnccn3)c(Cl)c2Cl)C1] | 3-(2-cyclopropyl-1-(2,3-dichloro-4-(pyrazin-2-yl)phenyl)ethyl)-1-methyl-1-(1-methylpyrrolidin-3-yl)urea |

-continued

| Compound No. | Chemical Structure | Chemical Name |
|---|---|---|
| H0853 | 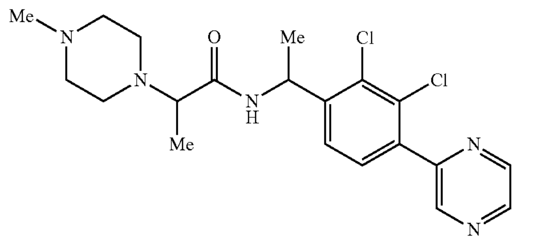 [SMILES: CC(NC(=O)C(C)N1CCN(C)CC1)c1ccc(-c2cnccn2)c(Cl)c1Cl] | N-(1-(2,3-dichloro-4-(pyrazin-2-yl)phenyl)ethyl)-2-(4-methylpiperazin-1-yl)propanamide |
| H0815 | 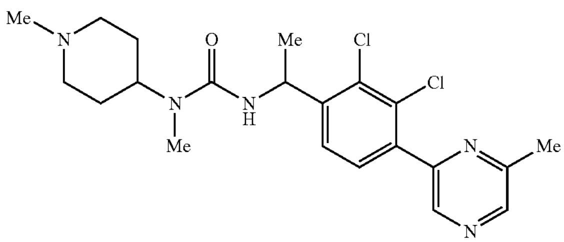 [SMILES: Cc1cncc(-c2ccc(C(C)NC(=O)N(C)C3CCN(C)CC3)c(Cl)c2Cl)n1] | 3-(1-(2,3-dichloro-4-(6-methylpyrazin-2-yl)phenyl)ethyl)-1-methyl-1-(1-methylpiperidin-4-yl)urea |
| H0831 | 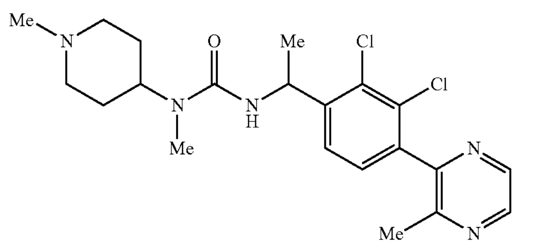 [SMILES: Cc1nccnc1-c1ccc(C(C)NC(=O)N(C)C2CCN(C)CC2)c(Cl)c1Cl] | 3-(1-(2,3-dichloro-4-(3-methylpyrazin-2-yl)phenyl)ethyl)-1-methyl-1-(1-methylpiperidin-4-yl)urea |
| H0843 | 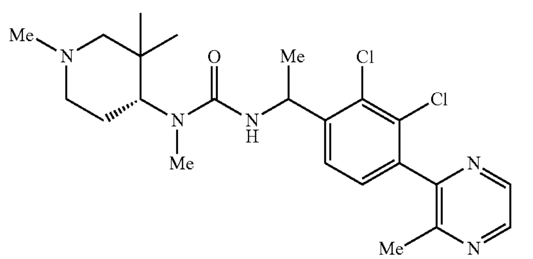 [SMILES: Cc1nccnc1-c1ccc(C(C)NC(=O)N(C)[C@@H]2CCN(C)CC2(C)C)c(Cl)c1Cl] | 3-(1-(2,3-dichloro-4-(3-methylpyrazin-2-yl)phenyl)ethyl)-1-methyl-1-((R)-1,3,3-trimethylpiperidin-4-yl)urea |
| H0844 | 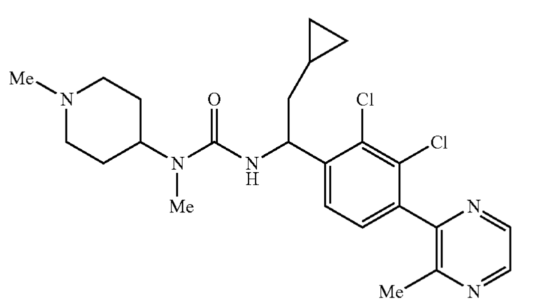 [SMILES: Cc1nccnc1-c1ccc(C(CC2CC2)NC(=O)N(C)C2CCN(C)CC2)c(Cl)c1Cl] | 3-(2-cyclopropyl-1-(2,3-dichloro-4-(3-methylpyrazin-2-yl)phenyl)ethyl)-1-methyl-1-(1-methylpiperidin-4-yl)urea |
| H0738 | 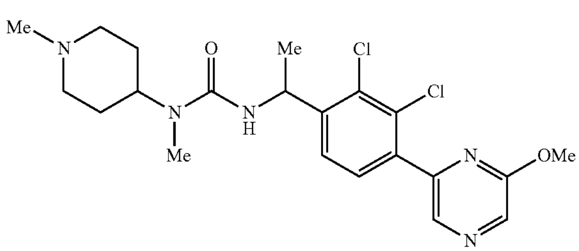 [SMILES: COc1cncc(-c2ccc(C(C)NC(=O)N(C)C3CCN(C)CC3)c(Cl)c2Cl)n1] | 3-(1-(2,3-dichloro-4-(6-methoxypyrazin-2-yl)phenyl)ethyl)-1-methyl-1-(1-methylpiperidin-4-yl)urea |

-continued

| Compound No. | Chemical Structure | Chemical Name |
|---|---|---|
| H0780 | 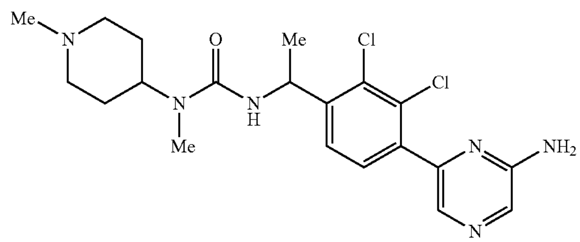 [SMILES: CC(NC(=O)N(C)C1CCN(C)CC1)c1ccc(-c2cncc(N)n2)c(Cl)c1Cl] | 3-(1-(4-(6-aminopyrazin-2-yl)-2,3-dichlorophenyl)ethyl)-1-methyl-1-(1-methylpiperidin-4-yl)urea |
| H0786 | 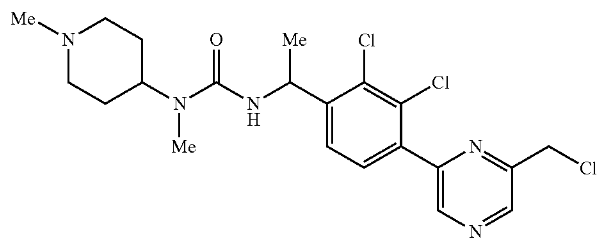 [SMILES: CC(NC(=O)N(C)C1CCN(C)CC1)c1ccc(-c2cncc(CCl)n2)c(Cl)c1Cl] | 3-(1-(2,3-dichloro-4-(6-(chloromethyl)pyrazin-2-yl)phenyl)ethyl)-1-methyl-1-(1-methylpiperidin-4-yl)urea |
| H0791 | 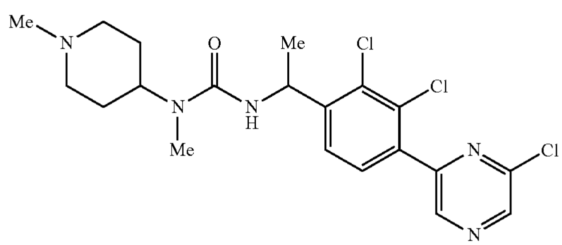 | 3-(1-(2,3-dichloro-4-(6-chloropyrazin-2-yl)phenyl)ethyl)-1-methyl-1-(1-methylpiperidin-4-yl)urea |
| H0795 | 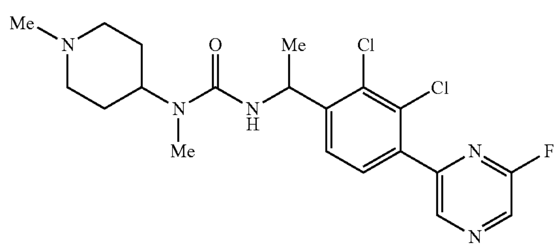 [SMILES: CC(NC(=O)N(C)C1CCN(C)CC1)c1ccc(-c2cncc(F)n2)c(Cl)c1Cl] | 3-(1-(2,3-dichloro-4-(6-fluoropyrazin-2-yl)phenyl)ethyl)-1-methyl-1-(1-methylpiperidin-4-yl)urea |
| H0847 | 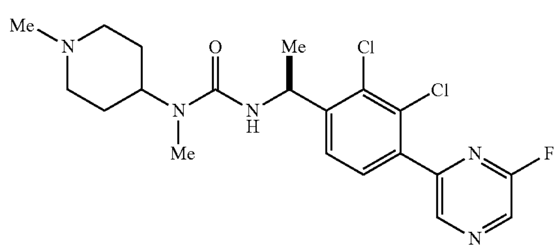 [SMILES: C[C@H](NC(=O)N(C)C1CCN(C)CC1)c1ccc(-c2cncc(F)n2)c(Cl)c1Cl] | (S)-3-(1-(2,3-dichloro-4-(6-fluoropyrazin-2-yl)phenyl)ethyl)-1-methyl-1-(1-methylpiperidin-4-yl)urea |
| H0848 | 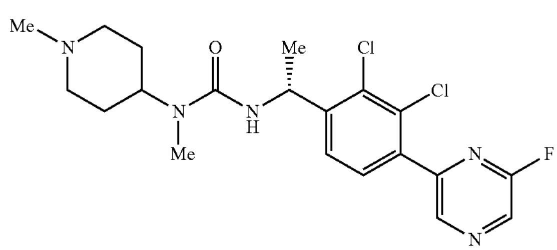 | (R)-3-(1-(2,3-dichloro-4-(6-fluoropyrazin-2-yl)phenyl)ethyl)-1-methyl-1-(1-methylpiperidin-4-yl)urea |

-continued

| Compound No. | Chemical Structure | Chemical Name |
|---|---|---|
| H0863 | 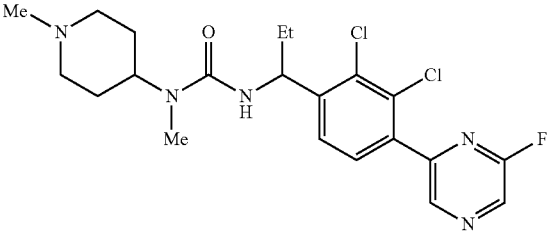 | 3-(1-(2,3-dichloro-4-(6-fluoropyrazin-2-yl)phenyl)propyl)-1-methyl-1-(1-methylpiperidin-4-yl)urea |
| H0908 | 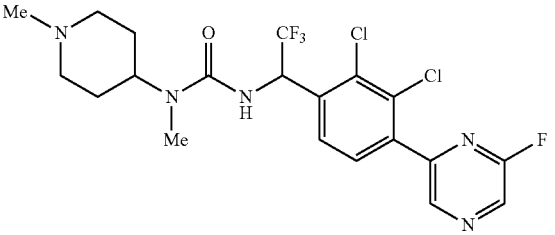 | 3-(1-(2,3-dichloro-4-(6-fluoropyrazin-2-yl)phenyl)-2,2,2-trifluoroethyl)-1-methyl-1-(1-methylpiperidin-4-yl)urea |
| H0864 | 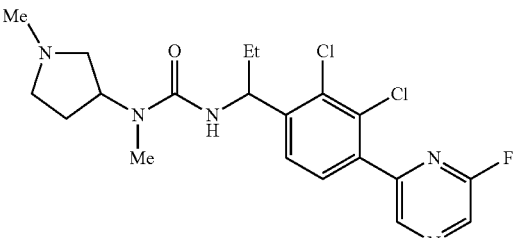 | 3-(1-(2,3-dichloro-4-(6-fluoropyrazin-2-yl)phenyl)propyl)-1-methyl-1-(1-methylpyrrolidin-3-yl)urea |
| H0872 | 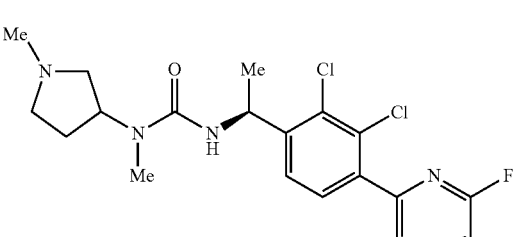 | 3-((S)-1-(2,3-dichloro-4-(6-fluoropyrazin-2-yl)phenyl)ethyl)-1-methyl-1-(1-methylpyrrolidin-3-yl)urea |
| H0840 | 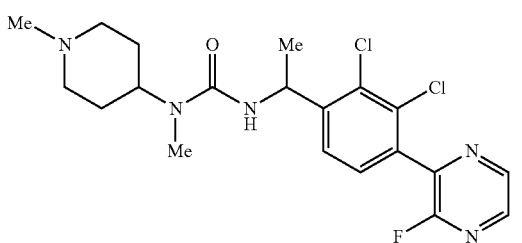 [SMILES: CC(NC(=O)N(C)C1CCN(C)CC1)c1ccc(-c2nccnc2F)c(Cl)c1Cl] | 3-(1-(2,3-dichloro-4-(3-fluoropyrazin-2-yl)phenyl)ethyl)-1-methyl-1-(1-methylpiperidin-3-yl)urea |
| H0910 | 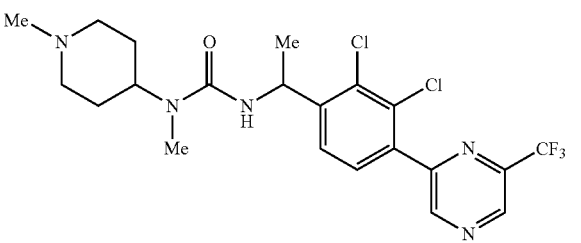 [SMILES: CC(NC(=O)N(C)C1CCN(C)CC1)c1ccc(-c2cncc(C(F)(F)F)n2)c(Cl)c1Cl] | 3-(1-(2,3-dichloro-4-(6-(trifluoromethyl)pyrazin-2-yl)phenyl)ethyl)-1-methyl-1-(1-methylpiperidin-4-yl)urea |

-continued

| Compound No. | Chemical Structure | Chemical Name |
|---|---|---|
| H0788 | 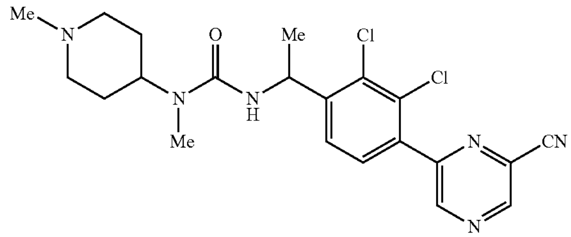 [SMILES: CC(NC(=O)N(C)C1CCN(C)CC1)c1ccc(-c2cncc(C#N)n2)c(Cl)c1Cl] | 3-(1-(2,3-dichloro-4-(6-cyanopyrazin-2-yl)phenyl)ethyl)-1-methyl-1-(1-methylpiperidin-4-yl)urea |
| H0789 | 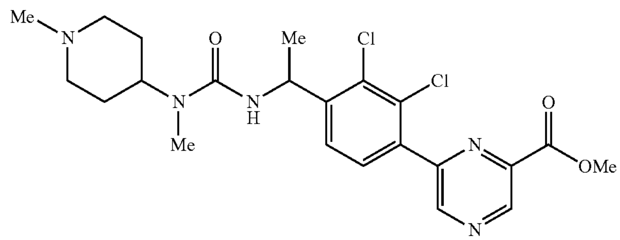 [SMILES: COC(=O)c1cncc(-c2ccc(C(C)NC(=O)N(C)C3CCN(C)CC3)c(Cl)c2Cl)n1] | methyl 6-(2,3-dichloro-4-(1-(3-methyl-3-(1-methylpiperidin-4-yl)ureido)ethyl)phenyl)pyrazine-2-carboxylate |
| H0760 | 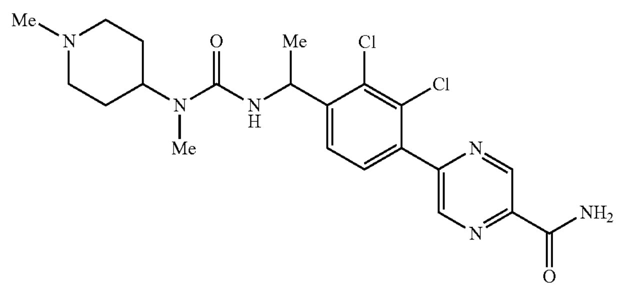 [SMILES: CC(NC(=O)N(C)C1CCN(C)CC1)c1ccc(-c2cnc(C(N)=O)cn2)c(Cl)c1Cl] | 3-(2,3-dichloro-4-(1-(3-methyl-3-(1-methylpiperidin-4-yl)ureido)ethyl)phenyl)pyrazine-2-carboxamide |
| H0769 | 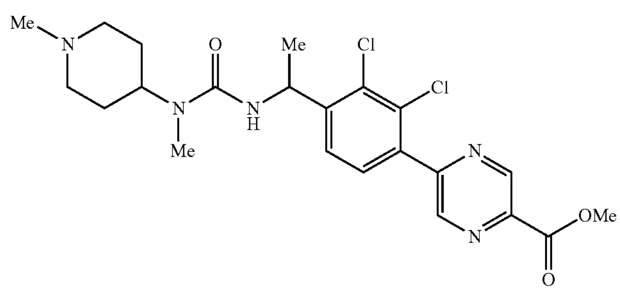 [SMILES: COC(=O)c1cnc(-c2ccc(C(C)NC(=O)N(C)C3CCN(C)CC3)c(Cl)c2Cl)cn1] | methyl 5-(2,3-dichloro-4-(1-(3-methyl-3-(1-methylpiperidin-4-yl)ureido)ethyl)phenyl)pyrazine-2-carboxylate |
| H0771 | 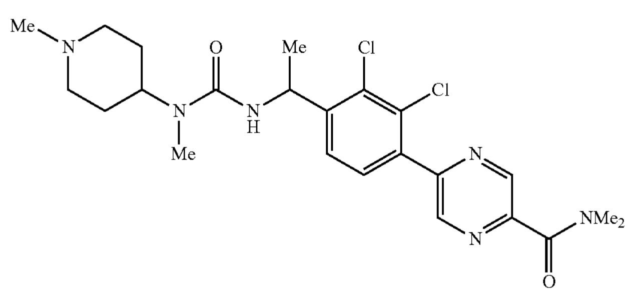 [SMILES: CC(NC(=O)N(C)C1CCN(C)CC1)c1ccc(-c2cnc(C(=O)N(C)C)cn2)c(Cl)c1Cl] | 5-(2,3-dichloro-4-(1-(3-methyl-3-(1-methylpiperidin-4-yl)ureido)ethyl)phenyl)-N,N-dimethylpyrazine-2-carboxamide |

-continued

| Compound No. | Chemical Structure | Chemical Name |
|---|---|---|
| H0770 | 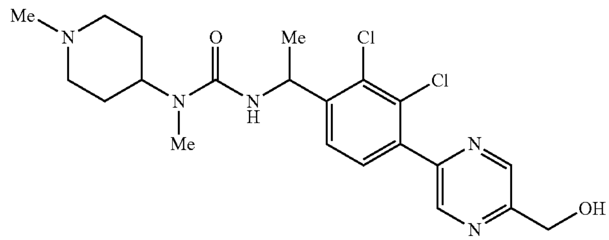 [SMILES: CC(NC(=O)N(C)C1CCN(C)CC1)c1ccc(-c2cnc(CO)cn2)c(Cl)c1Cl] | 3-(1-(2,3-dichloro-4-(5-(hydroxymethyl)pyrazin-2-yl)phenyl)ethyl)-1-methyl-1-(1-methylpiperidin-4-yl)urea |
| H0828 | 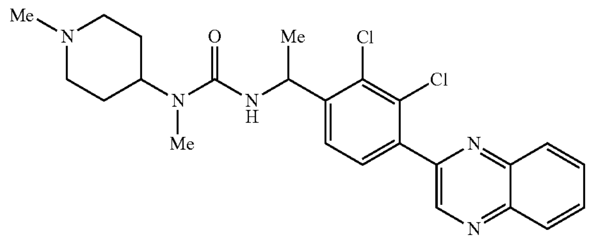 [SMILES: CC(NC(=O)N(C)C1CCN(C)CC1)c1ccc(-c2cnc3ccccc3n2)c(Cl)c1Cl] | 3-(1-(2,3-dichloro-4-(quinoxalin-2-yl)phenyl)ethyl)-1-methyl-1-(1-methylpiperidin-4-yl)urea |
| H0822 | TFA | 3-(1-(2,3-dichloro-4-(5-(4-methylpiperazin-1-yl)pyrazin-2-yl)phenyl)ethyl)-1-methyl-1-(1-methylpiperidin-4-yl)urea |
| H0850 | 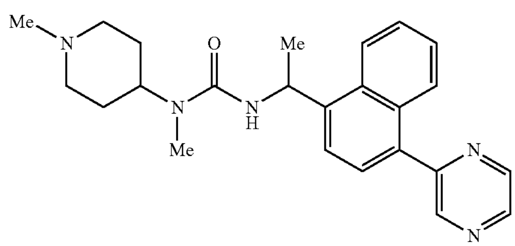 [SMILES: CC(NC(=O)N(C)C1CCN(C)CC1)c1ccc(-c2cnccn2)c2ccccc12] | 1-methyl-1-(1-methylpiperidin-4-yl)-3-(1-(4-(pyrazin-2-yl)naphthalen-1-yl)ethyl)urea |
| H0881 | 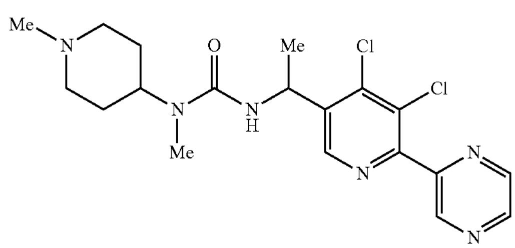 | 3-(1-(4,5-dichloro-6-(pyrazin-2-yl)pyridin-3-yl)ethyl)-1-methyl-1-(1-methylpiperidin-4-yl)urea |
| H0729 | 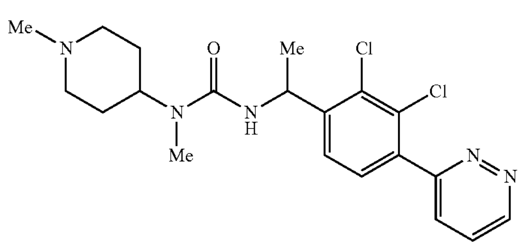 [SMILES: CC(NC(=O)N(C)C1CCN(C)CC1)c1ccc(-c2cccnn2)c(Cl)c1Cl] | 3-(1-(2,3-dichloro-4-(pyridazin-3-yl)phenyl)ethyl)-1-methyl-1-(1-methylpiperidin-4-yl)urea |

-continued

| Compound No. | Chemical Structure | Chemical Name |
|---|---|---|
| H0783 | 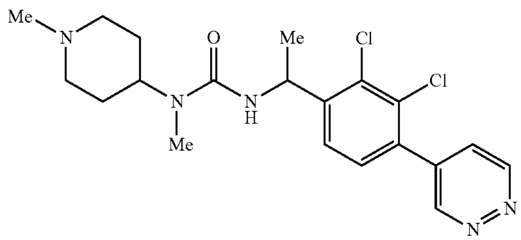 [SMILES: CC(NC(=O)N(C)C1CCN(C)CC1)c1ccc(-c2ccnnc2)c(Cl)c1Cl] | 3-(1-(2,3-dichloro-4-(pyridazin-4-yl)phenyl)ethyl)-1-methyl-1-(1-methylpiperidin-4-yl)urea |
| H0793 | 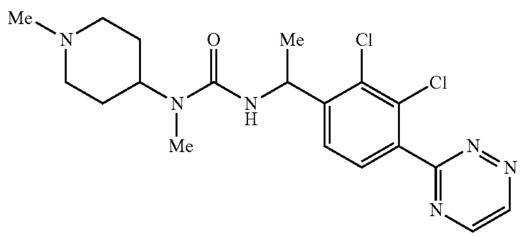 | 3-(1-(2,3-dichloro-4-(1,2,4-triazin-3-yl)phenyl)ethyl)-1-methyl-1-(1-methylpiperidin-4-yl)urea |
| H0796 | 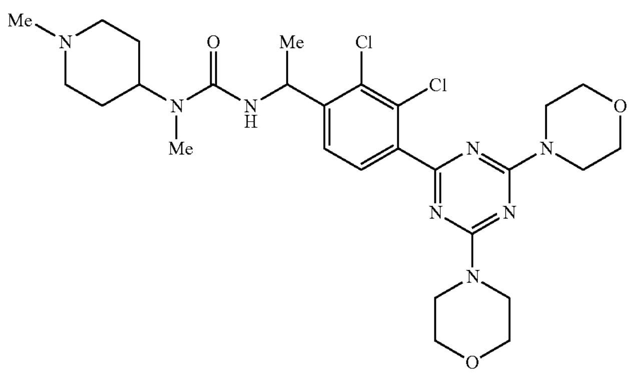 [SMILES: CC(NC(=O)N(C)C1CCN(C)CC1)c1ccc(-c2nc(N3CCOCC3)nc(N3CCOCC3)n2)c(Cl)c1Cl] | 3-(1-(2,3-dichloro-4-(4,6-dimorpholino-1,3,5-triazin-2-yl)phenyl)ethyl)-1-methyl-1-(1-methylpiperidin-4-yl)urea |
| H0498 | 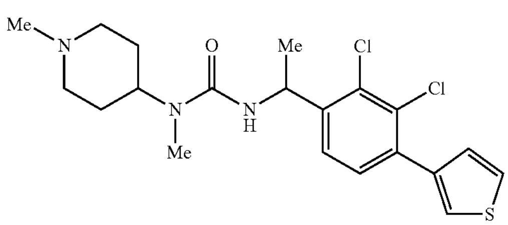 [SMILES: CC(NC(=O)N(C)C1CCN(C)CC1)c1ccc(-c2ccsc2)c(Cl)c1Cl] | 3-(1-(2,3-dichloro-4-(thiophen-3-yl)phenyl)ethyl)-1-methyl-1-(1-methylpiperidin-4-yl)urea |
| H0531 | 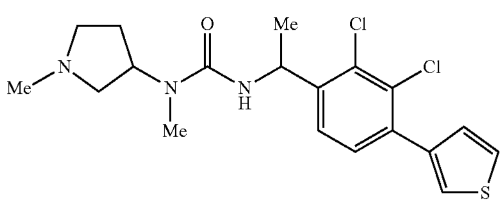 [SMILES: CC(NC(=O)N(C)C1CCN(C)C1)c1ccc(-c2ccsc2)c(Cl)c1Cl] | 3-(1-(2,3-dichloro-4-(thiophen-3-yl)phenyl)ethyl)-1-methyl-1-(1-methylpyrrolidin-3-yl)urea |

| Compound No. | Chemical Structure | Chemical Name |
|---|---|---|
| H0594 | 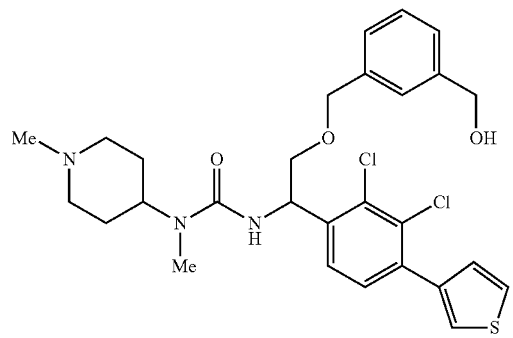 [SMILES: CN1CCC(N(C)C(=O)NC(COCc2cccc(CO)c2)c2ccc(-c3ccsc3)c(Cl)c2Cl)CC1] | 3-(1-(2,3-dichloro-4-(thiophen-3-yl)phenyl)-2-((3-(hydroxymethyl)benzyl)oxy)ethyl)-1-methyl-1-(1-methylpiperidin-4-yl)urea |
| H0644 | 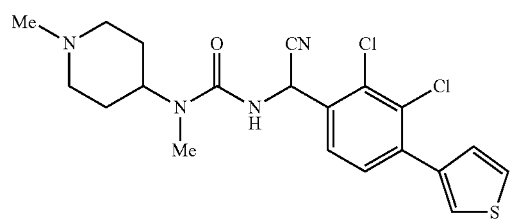 [SMILES: CN1CCC(N(C)C(=O)NC(C#N)c2ccc(-c3ccsc3)c(Cl)c2Cl)CC1] | 3-(cyano(2,3-dichloro-4-(thiophen-3-yl)phenyl)methyl)-1-methyl-1-(1-methylpiperidin-4-yl)urea |
| H0536 | 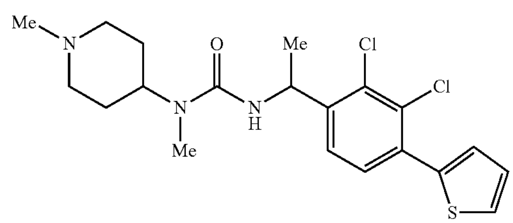 [SMILES: CC(NC(=O)N(C)C1CCN(C)CC1)c1ccc(-c2cccs2)c(Cl)c1Cl] | 3-(1-(2,3-dichloro-4-(thiophen-2-yl)phenyl)ethyl)-1-methyl-1-(1-methylpiperidin-4-yl)urea |
| H0563 | 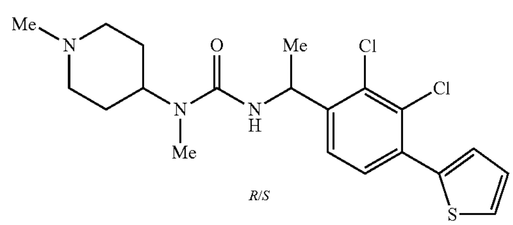 | 3-(1-(2,3-dichloro-4-(thiophen-2-yl)phenyl)ethyl)-1-methyl-1-(1-methylpiperidin-4-yl)urea (single enantiomer) |
| H0564 | 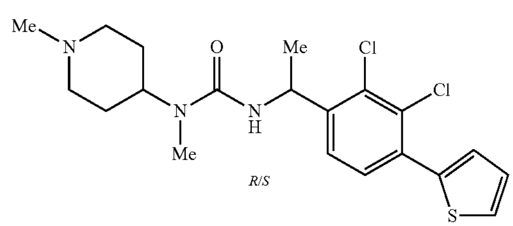 | 3-(1-(2,3-dichloro-4-(thiophen-2-yl)phenyl)ethyl)-1-methyl-1-(1-methylpiperidin-4-yl)urea (single enantiomer) |
| H0627 | 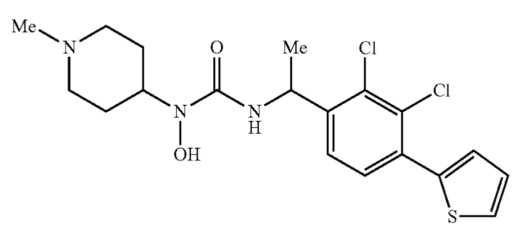 [SMILES: CC(NC(=O)N(O)C1CCN(C)CC1)c1ccc(-c2cccs2)c(Cl)c1Cl] | 3-(1-(2,3-dichloro-4-(thiophen-2-yl)phenyl)ethyl)-1-hydroxy-1-(1-methylpiperidin-4-yl)urea |

| Compound No. | Chemical Structure | Chemical Name |
|---|---|---|
| H0660 | 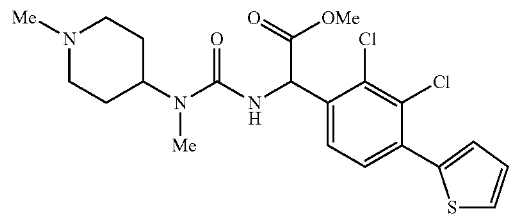 [SMILES: COC(=O)C(NC(=O)N(C)C1CCN(C)CC1)c1ccc(-c2cccs2)c(Cl)c1Cl] | methyl 2-(2,3-dichloro-4-(thiophen-2-yl)phenyl)-2-(3-methyl-3-(1-methylpiperidin-4-yl)ureido)acetate |
| H0661 | 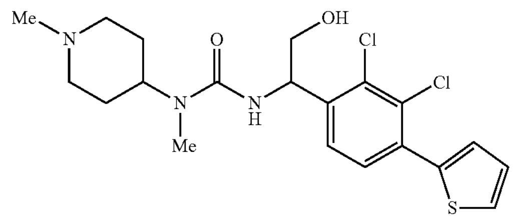 [SMILES: CN1CCC(N(C)C(=O)NC(CO)c2ccc(-c3cccs3)c(Cl)c2Cl)CC1] | 3-(1-(2,3-dichloro-4-(thiophen-2-yl)phenyl)-2-hydroxyethyl)-1-methyl-1-(1-methylpiperidin-4-yl)urea |
| H0672 | 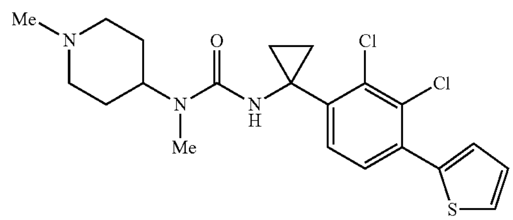 [SMILES: CN1CCC(N(C)C(=O)NC2(c3ccc(-c4cccs4)c(Cl)c3Cl)CC2)CC1] | 3-(1-(2,3-dichloro-4-(thiophen-2-yl)phenyl)cyclopropyl)-1-methyl-1-(1-methylpiperidin-4-yl)urea |
| H0651 | 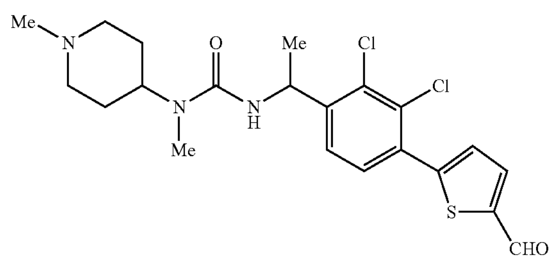 [SMILES: CC(NC(=O)N(C)C1CCN(C)CC1)c1ccc(-c2ccc(C=O)s2)c(Cl)c1Cl] | 3-(1-(2,3-dichloro-4-(5-formylthiophen-2-yl)phenyl)ethyl)-1-methyl-1-(1-methylpiperidin-4-yl)urea |
| H0653 | 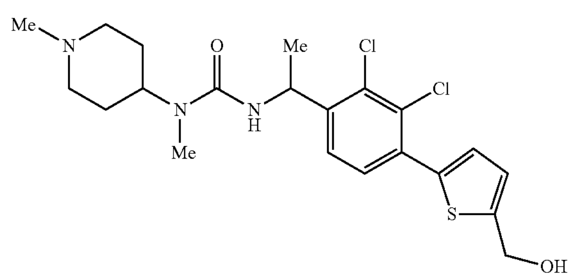 [SMILES: CC(NC(=O)N(C)C1CCN(C)CC1)c1ccc(-c2ccc(CO)s2)c(Cl)c1Cl] | 3-(1-(2,3-dichloro-4-(5-(hydroxymethyl)thiophen-2-yl)phenyl)ethyl)-1-methyl-1-(1-methylpiperidin-4-yl)urea |
| H0668 | 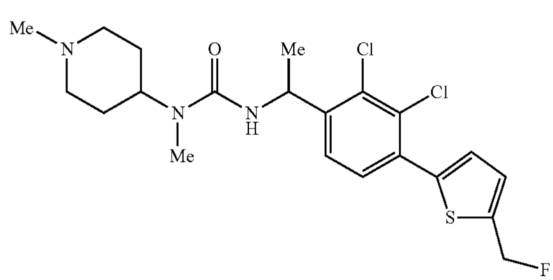 [SMILES: CC(NC(=O)N(C)C1CCN(C)CC1)c1ccc(-c2ccc(CF)s2)c(Cl)c1Cl] | 3-(1-(2,3-dichloro-4-(5-(fluoromethyl)thiophen-2-yl)phenyl)ethyl)-1-methyl-1-(1-methylpiperidin-4-yl)urea |

| Compound No. | Chemical Structure | Chemical Name |
|---|---|---|
| H0654 | 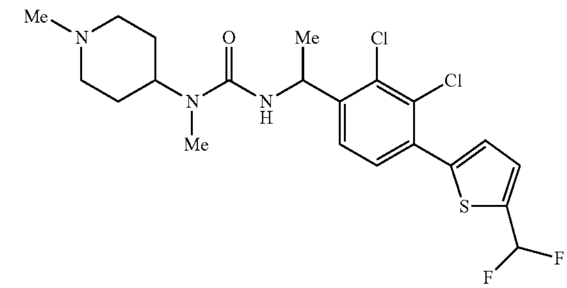 [SMILES: CC(NC(=O)N(C)C1CCN(C)CC1)c1ccc(-c2ccc(C(F)F)s2)c(Cl)c1Cl] | 3-(1-(2,3-dichloro-4-(5-(difluoromethyl)thiophen-2-yl)phenyl)ethyl)-1-methyl-1-(1-methylpiperidin-4-yl)urea |
| H0655 | 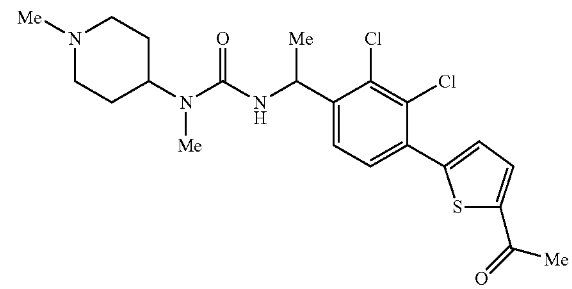 [SMILES: CC(=O)c1ccc(-c2ccc(C(C)NC(=O)N(C)C3CCN(C)CC3)c(Cl)c2Cl)s1] | 3-(1-(4-(5-acetylthiophen-2-yl)-2,3-dichlorophenyl)ethyl)-1-methyl-1-(1-methylpiperidin-4-yl)urea |
| H0691 | 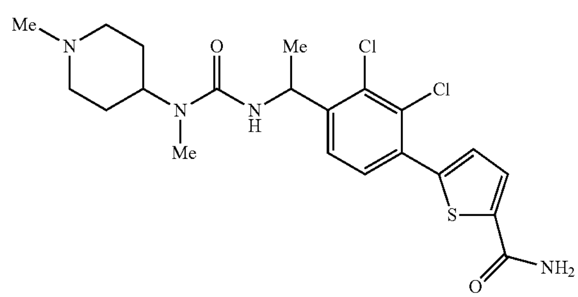 [SMILES: CC(NC(=O)N(C)C1CCN(C)CC1)c1ccc(-c2ccc(C(N)=O)s2)c(Cl)c1Cl] | 5-(2,3-dichloro-4-(1-(3-methyl-3-(1-methylpiperidin-4-yl)ureido)ethyl)phenyl)thiophene-2-carboxamide |
| H0728 | 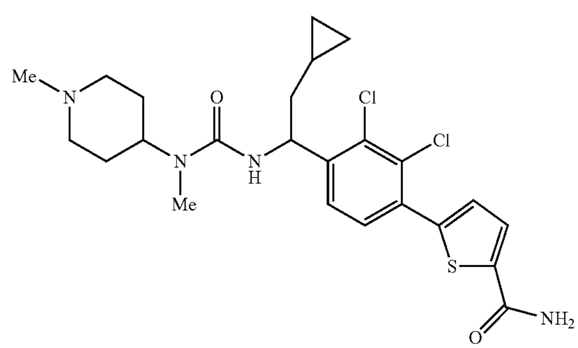 [SMILES: CN1CCC(N(C)C(=O)NC(CC2CC2)c2ccc(-c3ccc(C(N)=O)s3)c(Cl)c2Cl)CC1] | 5-(2,3-dichloro-4-(2-cyclopropyl-1-(3-methyl-3-(1-methylpiperidin-4-yl)ureido)ethyl)phenyl)thiophene-2-carboxamide |
| H0726 | 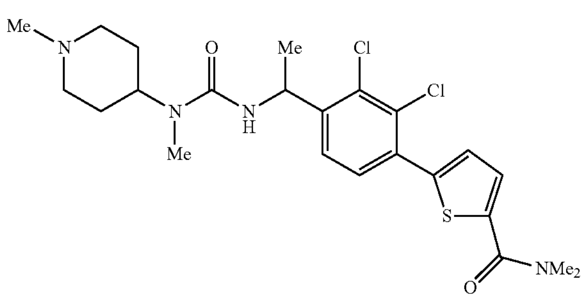 [SMILES: CC(NC(=O)N(C)C1CCN(C)CC1)c1ccc(-c2ccc(C(=O)N(C)C)s2)c(Cl)c1Cl] | 5-(2,3-dichloro-4-(1-(3-methyl-3-(1-methylpiperidin-4-yl)ureido)ethyl)phenyl)-N,N-dimethylthiophene-2-carboxamide |

| Compound No. | Chemical Structure | Chemical Name |
|---|---|---|
| H0689 | 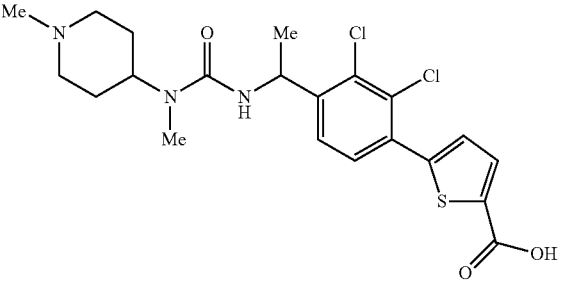 [SMILES: CC(NC(=O)N(C)C1CCN(C)CC1)c1ccc(-c2ccc(C(=O)O)s2)c(Cl)c1Cl] | 5-(2,3-dichloro-4-(1-(3-methyl-3-(1-methylpiperidin-4-yl)ureido)ethyl)phenyl)thiophene-2-carboxylic acid |
| H0692 | 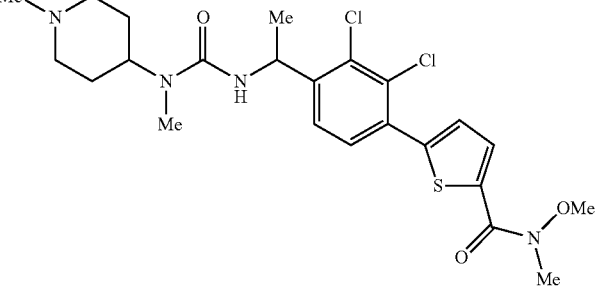 | 5-(2,3-dichloro-4-(1-(3-methyl-3-(1-methylpiperidin-4-yl)ureido)ethyl)phenyl)-N-methoxy-N-methylthiophene-2-carboxamide |
| H0656 | 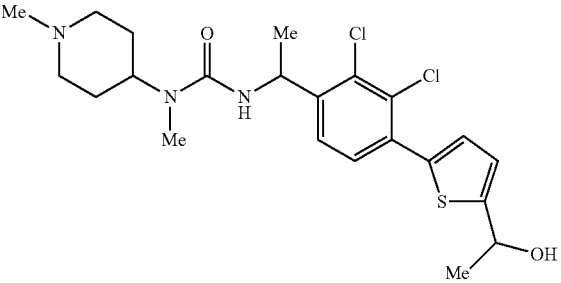 [SMILES: CC(O)c1ccc(-c2ccc(C(C)NC(=O)N(C)C3CCN(C)CC3)c(Cl)c2Cl)s1] | 3-(1-(2,3-dichloro-4-(5-(1-hydroxyethyl)thiophen-2-yl)phenyl)ethyl)-1-methyl-1-(1-methylpiperidin-4-yl)urea |
| H0652 | 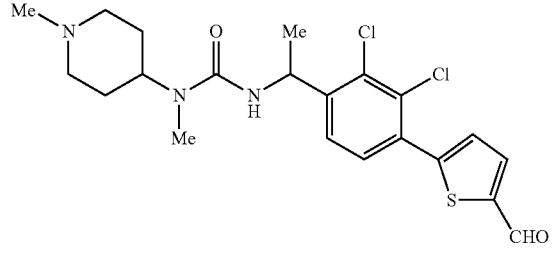 [SMILES: CC(NC(=O)N(C)C1CCN(C)CC1)c1ccc(-c2ccc(C=O)s2)c(Cl)c1Cl] | 3-(1-(2,3-dichloro-4-(5-formylthiophen-2-yl)phenyl)ethyl)-1-methyl-1-(1-methylpiperidin-4-yl)urea |
| H0713 | 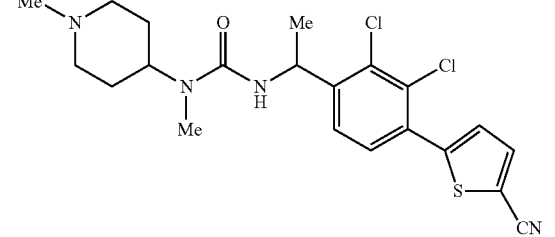 | 3-(1-(2,3-dichloro-4-(5-cyanothiophen-2-yl)phenyl)ethyl)-1-methyl-1-(1-methylpiperidin-4-yl)urea |

| Compound No. | Chemical Structure | Chemical Name |
| --- | --- | --- |
| H0688 | 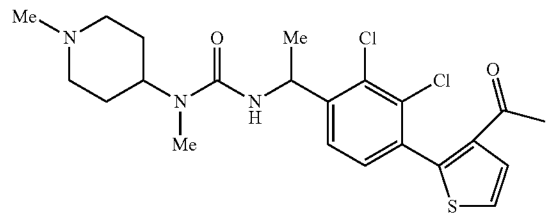 [SMILES: CC(=O)c1ccsc1-c1ccc(C(C)NC(=O)N(C)C2CCN(C)CC2)c(Cl)c1Cl] | 3-(1-(4-(3-acetylthiophen-2-yl)-2,3-dichlorophenyl)ethyl)-1-methyl-1-(1-methylpiperidin-4-yl)urea |
| H0774 | 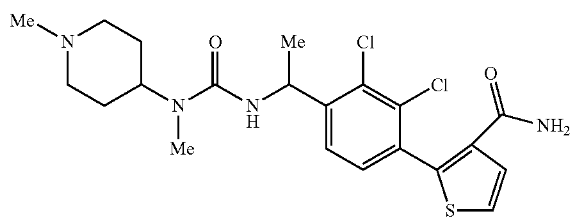 [SMILES: CC(NC(=O)N(C)C1CCN(C)CC1)c1ccc(-c2sccc2C(N)=O)c(Cl)c1Cl] | 2-(2,3-dichloro-4-(1-(3-methyl-3-(1-methylpiperidin-4-yl)ureido)ethyl)phenyl)thiophene-3-carboxamide |
| H0664 | 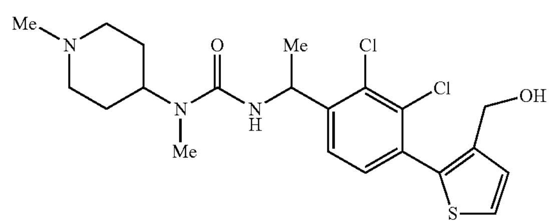 [SMILES: CC(NC(=O)N(C)C1CCN(C)CC1)c1ccc(-c2sccc2CO)c(Cl)c1Cl] | 3-(1-(2,3-dichloro-4-(3-(hydroxymethyl)thiophen-2-yl)phenyl)ethyl)-1-methyl-1-(1-methylpiperidin-4-yl)urea |
| H0535 | 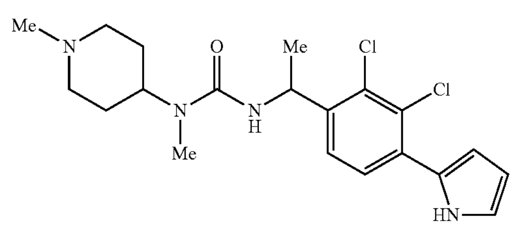 [SMILES: CC(NC(=O)N(C)C1CCN(C)CC1)c1ccc(-c2ccc[nH]2)c(Cl)c1Cl] | 3-(1-(2,3-dichloro-4-(1H-pyrrol-2-yl)phenyl)ethyl)-1-methyl-1-(1-methylpiperidin-4-yl)urea |
| H0499 | 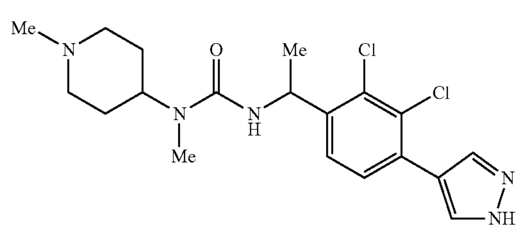 [SMILES: CC(NC(=O)N(C)C1CCN(C)CC1)c1ccc(-c2cn[nH]c2)c(Cl)c1Cl] | 3-(1-(2,3-dichloro-4-(1H-pyrazol-4-yl)phenyl)ethyl)-1-methyl-1-(1-methylpiperidin-4-yl)urea |
| H0693 | 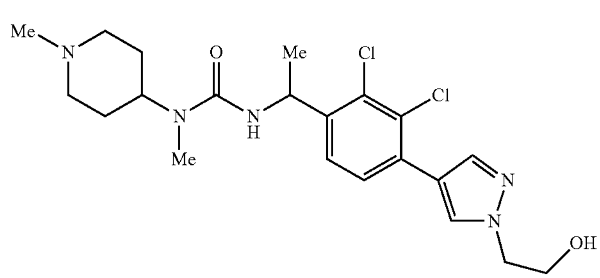 [SMILES: CC(NC(=O)N(C)C1CCN(C)CC1)c1ccc(-c2cnn(CCO)c2)c(Cl)c1Cl] | 3-(1-(2,3-dichloro-4-(1-(2-hydroxyethyl)-1H-pyrazol-4-yl)phenyl)ethyl)-1-methyl-1-(1-methylpiperidin-4-yl)urea |

-continued

| Compound No. | Chemical Structure | Chemical Name |
|---|---|---|
| H0694 | 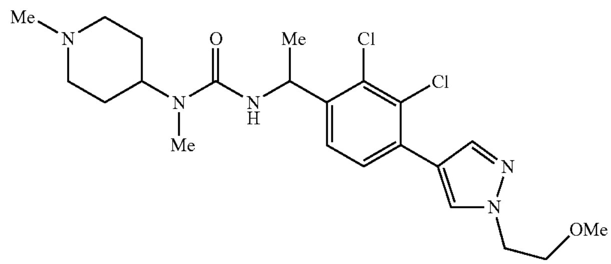 [SMILES: COCCn1cc(-c2ccc(C(C)NC(=O)N(C)C3CCN(C)CC3)c(Cl)c2Cl)cn1] | 3-(1-(2,3-dichloro-4-(1-(2-methoxyethyl)-1H-pyrazol-4-yl)phenyl)ethyl)-1-methyl-1-(1-methylpiperidin-4-yl)urea |
| H0657 | 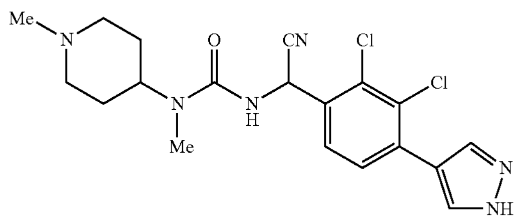 [SMILES: CN1CCC(N(C)C(=O)NC(C#N)c2ccc(-c3cn[nH]c3)c(Cl)c2Cl)CC1] | 3-(cyano(2,3-dichloro-4-(1H-pyrazol-4-yl)phenyl)methyl)-1-methyl-1-(1-methylpiperidin-4-yl)urea |
| H0553 | 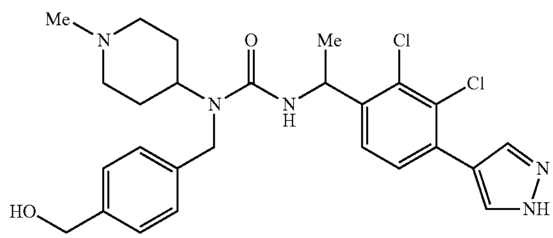 [SMILES: CC(NC(=O)N(Cc1ccc(CO)cc1)C1CCN(C)CC1)c1ccc(-c2cn[nH]c2)c(Cl)c1Cl] | 3-(1-(2,3-dichloro-4-(1H-pyrazol-4-yl)phenyl)ethyl)-1-(4-(hydroxymethyl)benzyl)-1-(1-methylpiperidin-4-yl)urea |
| H0842 | 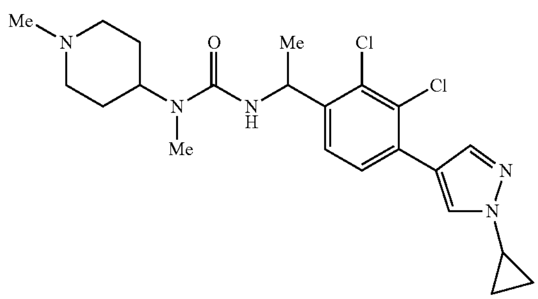 [SMILES: CC(NC(=O)N(C)C1CCN(C)CC1)c1ccc(-c2cnn(C3CC3)c2)c(Cl)c1Cl] | 3-(1-(2,3-dichloro-4-(1-cyclopropyl-1H-pyrazol-4-yl)phenyl)ethyl)-1-methyl-1-(1-methylpiperidin-4-yl)urea |
| H0542 | 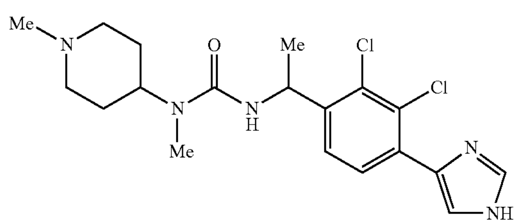 [SMILES: CC(NC(=O)N(C)C1CCN(C)CC1)c1ccc(-c2c[nH]cn2)c(Cl)c1Cl] | 3-(1-(2,3-dichloro-4-(1H-imidazol-4-yl)phenyl)ethyl)-1-methyl-1-(1-methylpiperidin-4-yl)urea |
| H0568 | 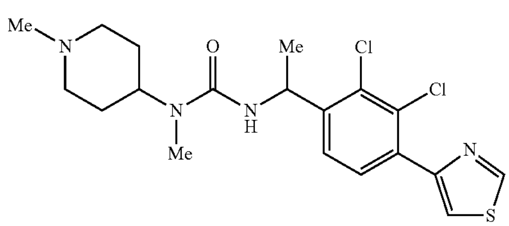 [SMILES: CC(NC(=O)N(C)C1CCN(C)CC1)c1ccc(-c2cscn2)c(Cl)c1Cl] | 3-(1-(2,3-dichloro-4-(thiazol-4-yl)phenyl)ethyl)-1-methyl-1-(1-methylpiperidin-4-yl)urea |

-continued

| Compound No. | Chemical Structure | Chemical Name |
|---|---|---|
| H0794 | 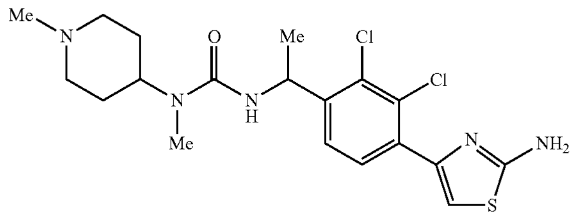 [SMILES: CC(NC(=O)N(C)C1CCN(C)CC1)c1ccc(-c2csc(N)n2)c(Cl)c1Cl] | 3-(1-(4-(2-aminothiazol-4-yl)-2,3-dichlorophenyl)ethyl)-1-methyl-1-(1-methylpiperidin-4-yl)urea |
| H0841 | 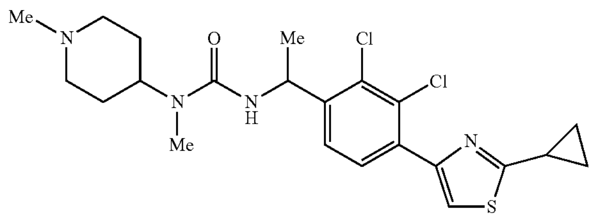 [SMILES: CC(NC(=O)N(C)C1CCN(C)CC1)c1ccc(-c2csc(C3CC3)n2)c(Cl)c1Cl] | 3-(1-(2,3-dichloro-4-(2-cyclopropylthiazol-4-yl)phenyl)ethyl)-1-methyl-1-(1-methylpiperidin-4-yl)urea |
| H0792 | 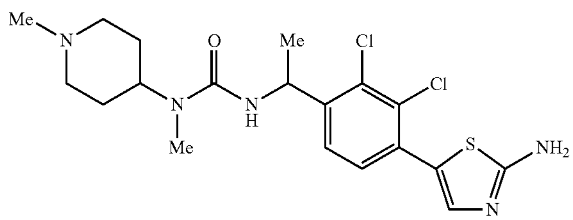 [SMILES: CC(NC(=O)N(C)C1CCN(C)CC1)c1ccc(-c2cnc(N)s2)c(Cl)c1Cl] | 3-(1-(4-(2-aminothiazol-5-yl)-2,3-dichlorophenyl)ethyl)-1-methyl-1-(1-methylpiperidin-4-yl)urea |
| H0569 | 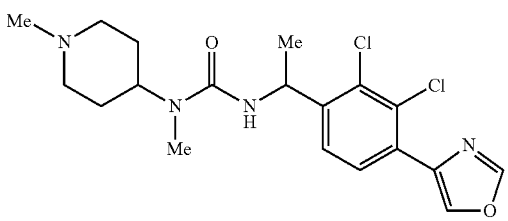 [SMILES: CC(NC(=O)N(C)C1CCN(C)CC1)c1ccc(-c2cocn2)c(Cl)c1Cl] | 3-(1-(2,3-dichloro-4-(oxazol-4-yl)phenyl)ethyl)-1-methyl-1-(1-methylpiperidin-4-yl)urea |
| H0565 | 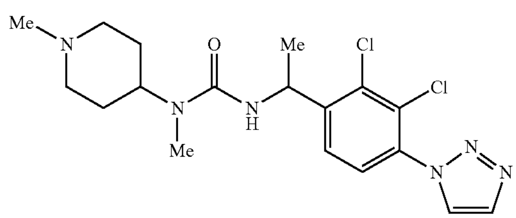 [SMILES: CC(NC(=O)N(C)C1CCN(C)CC1)c1ccc(-n2ccnn2)c(Cl)c1Cl] | 3-(1-(2,3-dichloro-4-(1H-1,2,3-triazol-1-yl)phenyl)ethyl)-1-methyl-1-(1-methylpiperidin-4-yl)urea |
| H0604 | 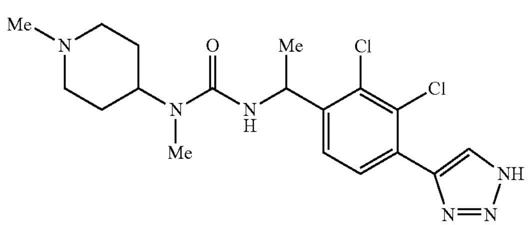 [SMILES: CC(NC(=O)N(C)C1CCN(C)CC1)c1ccc(-c2c[nH]nn2)c(Cl)c1Cl] | 3-(1-(2,3-dichloro-4-(1H-1,2,3-triazol-4-yl)phenyl)ethyl)-1-methyl-1-(1-methylpiperidin-4-yl)urea |
| H0595 | 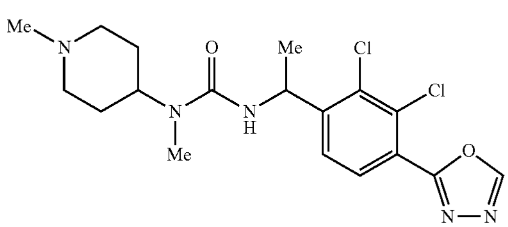 [SMILES: CC(NC(=O)N(C)C1CCN(C)CC1)c1ccc(-c2nnco2)c(Cl)c1Cl] | 3-(1-(2,3-dichloro-4-(1,3,4-oxadiazol-2-yl)phenyl)ethyl)-1-methyl-1-(1-methylpiperidin-4-yl)urea |

-continued

| Compound No. | Chemical Structure | Chemical Name |
|---|---|---|
| H0596 | 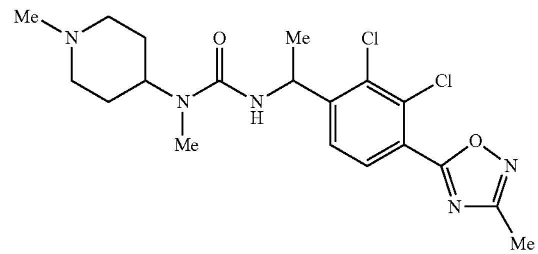 [SMILES: Cc1noc(-c2ccc(C(C)NC(=O)N(C)C3CCN(C)CC3)c(Cl)c2Cl)n1] | 3-(1-(2,3-dichloro-4-(3-methyl-1,2,4-oxadiazol-5-yl)phenyl)ethyl)-1-methyl-1-(1-methylpiperidin-4-yl)urea |
| H0851 | 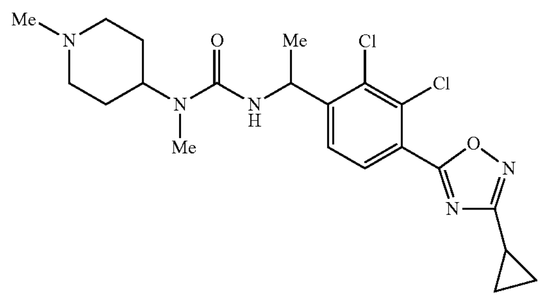 [SMILES: CC(NC(=O)N(C)C1CCN(C)CC1)c1ccc(-c2nc(C3CC3)no2)c(Cl)c1Cl] | 3-(1-(2,3-dichloro-4-(3-cyclopropyl-1,2,4-oxadiazol-5-yl)phenyl)ethyl)-1-methyl-1-(1-methylpiperidin-4-yl)urea |
| H0537 | 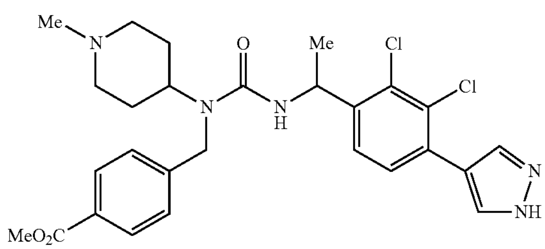 [SMILES: COC(=O)c1ccc(CN(C(=O)NC(C)c2ccc(-c3cn[nH]c3)c(Cl)c2Cl)C2CCN(C)CC2)cc1] | methyl 4-((3-(1-(2,3-dichloro-4-(1H-pyrazol-4-yl)phenyl)ethyl)-1-(1-methylpiperidin-4-yl)ureido)methyl)benzoate |
| H0529 | 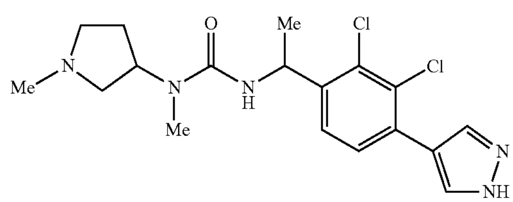 [SMILES: CC(NC(=O)N(C)C1CCN(C)C1)c1ccc(-c2cn[nH]c2)c(Cl)c1Cl] | 3-(1-(2,3-dichloro-4-(1H-pyrazol-4-yl)phenyl)ethyl)-1-methyl-1-(1-methylpyrrolidin-3-yl)urea |
| H0528 | 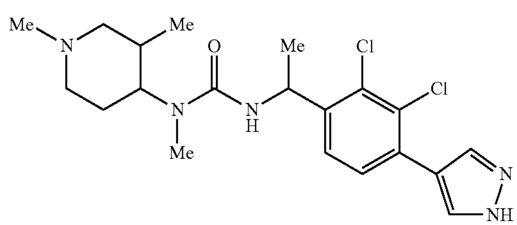 [SMILES: CC(NC(=O)N(C)C1CCN(C)CC1C)c1ccc(-c2cn[nH]c2)c(Cl)c1Cl] | 3-(1-(2,3-dichloro-4-(1H-pyrazol-4-yl)phenyl)ethyl)-1-(1,3-dimethylpiperidin-4-yl)-1-methylurea |
| H0501 | 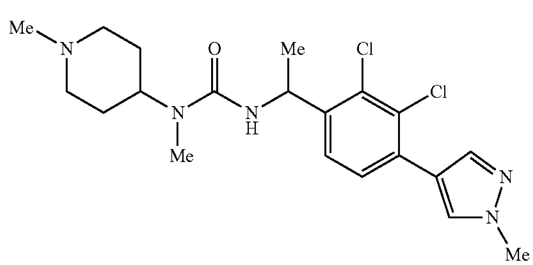 [SMILES: CC(NC(=O)N(C)C1CCN(C)CC1)c1ccc(-c2cnn(C)c2)c(Cl)c1Cl] | 3-(1-(2,3-dichloro-4-(1-methyl-1H-pyrazol-4-yl)phenyl)ethyl)-1-methyl-1-(1-methylpiperidin-4-yl)urea |

| Compound No. | Chemical Structure | Chemical Name |
|---|---|---|
| H0507 | 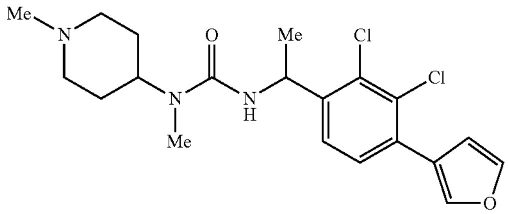 [SMILES: CC(NC(=O)N(C)C1CCN(C)CC1)c1ccc(-c2ccoc2)c(Cl)c1Cl] | 3-(1-(2,3-dichloro-4-(furan-3-yl)phenyl)ethyl)-1-methyl-1-(1-methylpiperidin-4-yl)urea |
| H0665 | 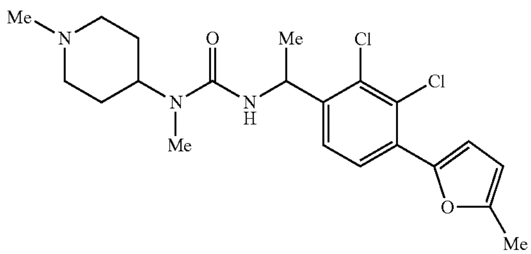 [SMILES: Cc1ccc(-c2ccc(C(C)NC(=O)N(C)C3CCN(C)CC3)c(Cl)c2Cl)o1] | 3-(1-(2,3-dichloro-4-(5-methylfuran-2-yl)phenyl)ethyl)-1-methyl-1-(1-methylpiperidin-4-yl)urea |
| H0508 | 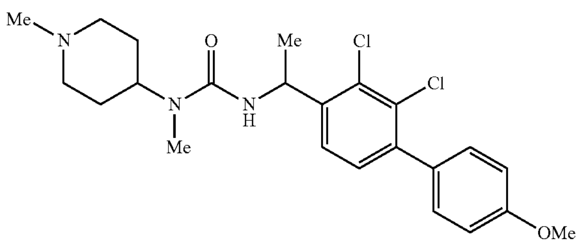 [SMILES: COc1ccc(-c2ccc(C(C)NC(=O)N(C)C3CCN(C)CC3)c(Cl)c2Cl)cc1] | 3-(1-(2,3-dichloro-4'-methoxy-[1,1'-biphenyl]-4-yl)ethyl)-1-methyl-1-(1-methylpiperidin-4-yl)urea |
| H0509 | 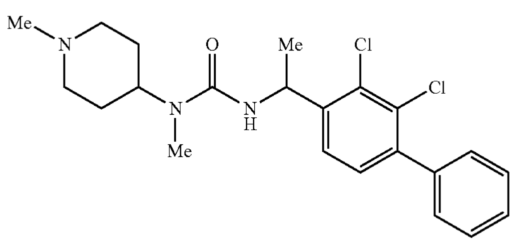 | 3-(1-(2,3-dichloro-[1,1'-biphenyl]-4-yl)ethyl)-1-methyl-1-(1-methylpiperidin-4-yl)urea |
| H0510 | 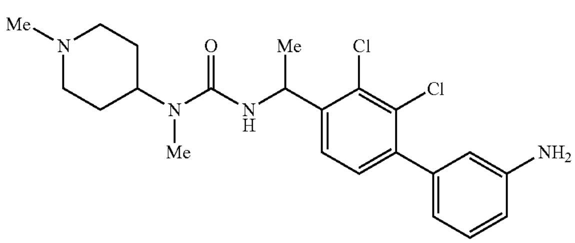 [SMILES: CC(NC(=O)N(C)C1CCN(C)CC1)c1ccc(-c2cccc(N)c2)c(Cl)c1Cl] | 3-(1-(3'-amino-2,3-dichloro-[1,1'-biphenyl]-4-yl)ethyl)-1-methyl-1-(1-methylpiperidin-4-yl)urea |
| H0606 | 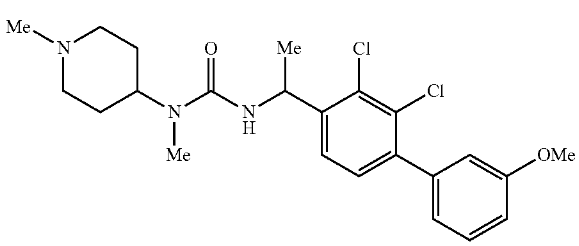 [SMILES: COc1cccc(-c2ccc(C(C)NC(=O)N(C)C3CCN(C)CC3)c(Cl)c2Cl)c1] | 3-(1-(2,3-dichloro-3'-methoxy-[1,1'-biphenyl]-4-yl)ethyl)-1-methyl-1-(1-methylpiperidin-4-yl)urea |

-continued

| Compound No. | Chemical Structure | Chemical Name |
|---|---|---|
| H0810 | 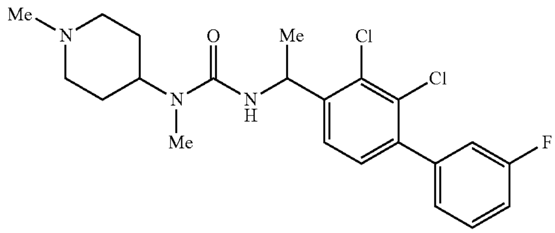 [SMILES: CC(NC(=O)N(C)C1CCN(C)CC1)c1ccc(-c2cccc(F)c2)c(Cl)c1Cl] | 3-(1-(2,3-dichloro-3'-fluoro-[1,1'-biphenyl]-4-yl)ethyl)-1-methyl-1-(1-methylpiperidin-4-yl)urea |
| H0696 | 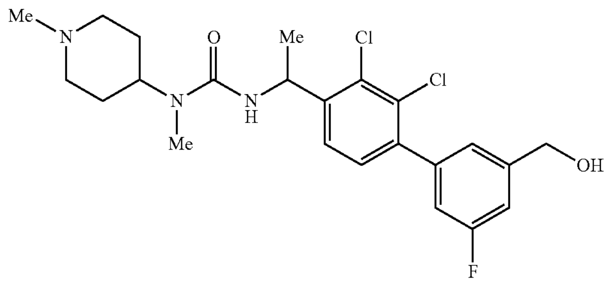 [SMILES: CC(NC(=O)N(C)C1CCN(C)CC1)c1ccc(-c2cc(F)cc(CO)c2)c(Cl)c1Cl] | 3-(1-(2,3-dichloro-3'-fluoro-5'-(hydroxymethyl)-[1,1'-biphenyl]-4-yl)ethyl)-1-methyl-1-(1-methylpiperidin-4-yl)urea |
| H0611 | 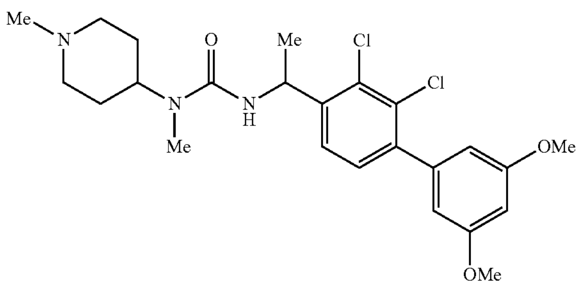 [SMILES: COc1cc(OC)cc(-c2ccc(C(C)NC(=O)N(C)C3CCN(C)CC3)c(Cl)c2Cl)c1] | 3-(1-(2,3-dichloro-3',5'-dimethoxy-[1,1'-biphenyl]-4-yl)ethyl)-1-methyl-1-(1-methylpiperidin-4-yl)urea |
| H0612 | 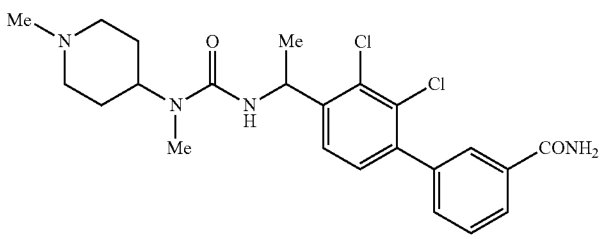 [SMILES: CC(NC(=O)N(C)C1CCN(C)CC1)c1ccc(-c2cccc(C(N)=O)c2)c(Cl)c1Cl] | 2',3'-dichloro-4'-(1-(3-methyl-3-(1-methylpiperidin-4-yl)ureido)ethyl)-[1,1'-biphenyl]-3-carboxamide |
| H0615 | 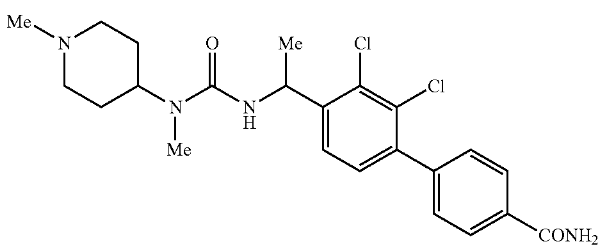 | 2',3'-dichloro-4'-(1-(3-methyl-3-(1-methylpiperidin-4-yl)ureido)ethyl)-[1,1'-biphenyl]-4-carboxamide |
| H0809 | 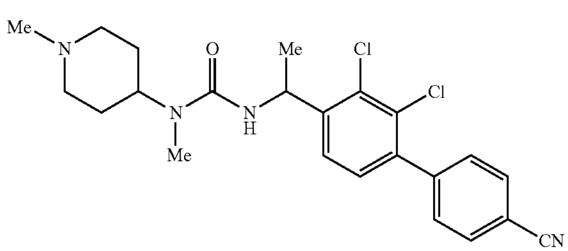 [SMILES: CC(NC(=O)N(C)C1CCN(C)CC1)c1ccc(-c2ccc(C#N)cc2)c(Cl)c1Cl] | 3-(1-(2,3-dichloro-4'-cyano-[1,1'-biphenyl]-4-yl)ethyl)-1-methyl-1-(1-methylpiperidin-4-yl)urea |

-continued

| Compound No. | Chemical Structure | Chemical Name |
|---|---|---|
| H0699 | 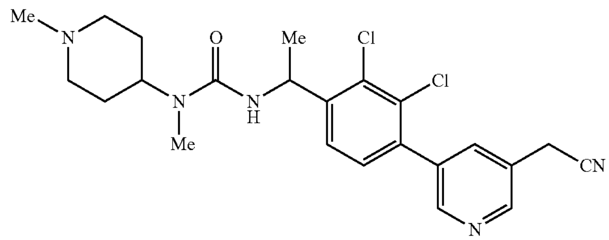 | 3-(1-(2,3-dichloro-4-(5-(cyanomethyl)pyridin-3-yl)phenyl)ethyl)-1-methyl-1-(1-methylpiperidin-4-yl)urea |
| H0607 | 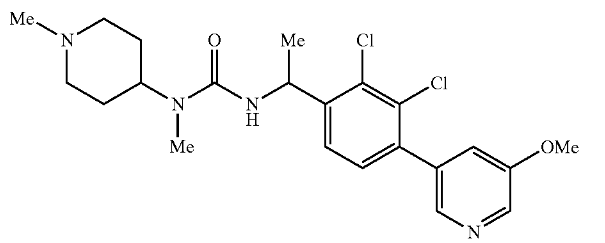 [SMILES: COc1cncc(-c2ccc(C(C)NC(=O)N(C)C3CCN(C)CC3)c(Cl)c2Cl)c1] | 3-(1-(2,3-dichloro-4-(5-methoxypyridin-3-yl)phenyl)ethyl)-1-methyl-1-(1-methylpiperidin-4-yl)urea |
| H0695 | 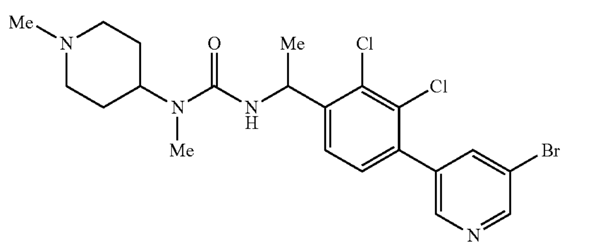 [SMILES: CC(NC(=O)N(C)C1CCN(C)CC1)c1ccc(-c2cncc(Br)c2)c(Cl)c1Cl] | 3-(1-(4-(5-bromopyridin-3-yl)-2,3-dichlorophenyl)ethyl)-1-methyl-1-(1-methylpiperidin-4-yl)urea |
| H0635 | 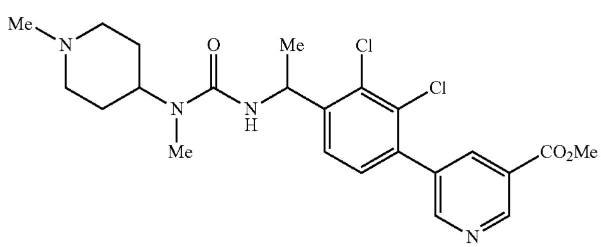 [SMILES: COC(=O)c1cncc(-c2ccc(C(C)NC(=O)N(C)C3CCN(C)CC3)c(Cl)c2Cl)c1] | methyl 5-(2,3-dichloro-4-(1-(3-methyl-3-(1-methylpiperidin-4-yl)ureido)ethyl)phenyl)nicotinate |
| H0690 | 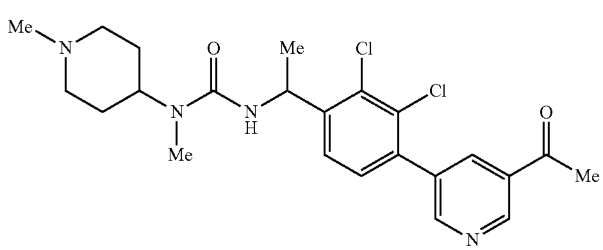 [SMILES: CC(=O)c1cncc(-c2ccc(C(C)NC(=O)N(C)C3CCN(C)CC3)c(Cl)c2Cl)c1] | 3-(1-(4-(5-acetylpyridin-3-yl)-2,3-dichlorophenyl)ethyl)-1-methyl-1-(1-methylpiperidin-4-yl)urea |
| H0735 | 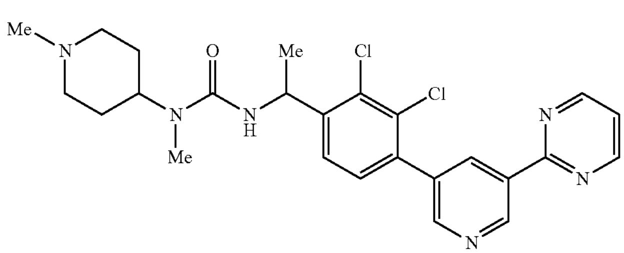 [SMILES: CC(NC(=O)N(C)C1CCN(C)CC1)c1ccc(-c2cncc(-c3ncccn3)c2)c(Cl)c1Cl] | 3-(1-(2,3-dichloro-4-(5-(pyrimidin-2-yl)pyridin-3-yl)phenyl)ethyl)-1-methyl-1-(1-methylpiperidin-4-yl)urea |

-continued

| Compound No. | Chemical Structure | Chemical Name |
|---|---|---|
| H0746 | 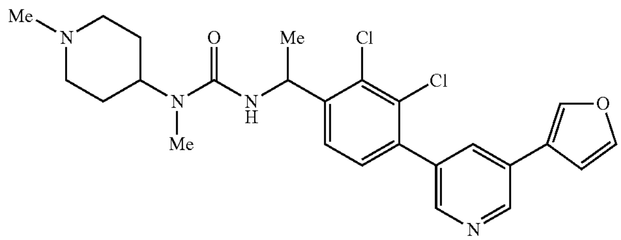 | 3-(1-(2,3-dichloro-4-(5-(furan-3-yl)pyridin-3-yl)phenyl)ethyl)-1-methyl-1-(1-methylpiperidin-4-yl)urea |
| H0747 | 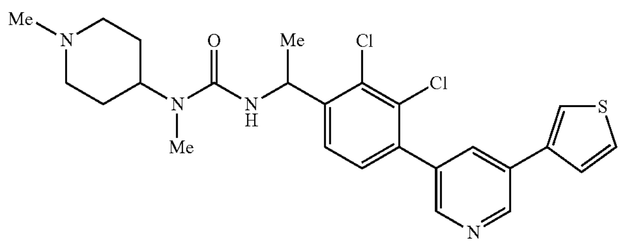 [SMILES: CC(NC(=O)N(C)C1CCN(C)CC1)c1ccc(-c2cncc(-c3ccoc3)c2)c(Cl)c1Cl] | 3-(1-(2,3-dichloro-4-(5-(thiophen-3-yl)pyridin-3-yl)phenyl)ethyl)-1-methyl-1-(1-methylpiperidin-4-yl)urea |
| H0748 | 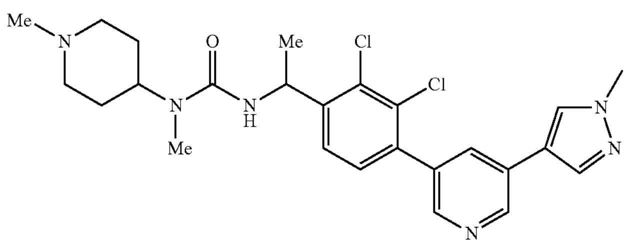 [SMILES: CC(NC(=O)N(C)C1CCN(C)CC1)c1ccc(-c2cncc(-c3cnn(C)c3)c2)c(Cl)c1Cl] | 3-(1-(2,3-dichloro-4-(5-(1-methyl-1H-pyrazol-4-yl)pyridin-3-yl)phenyl)ethyl)-1-methyl-1-(1-methylpiperidin-4-yl)urea |
| H0765 | 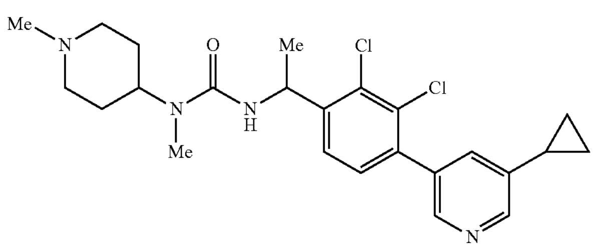 [SMILES: CC(NC(=O)N(C)C1CCN(C)CC1)c1ccc(-c2cncc(C3CC3)c2)c(Cl)c1Cl] | 3-(1-(2,3-dichloro-4-(5-cyclopropylpyridin-3-yl)phenyl)ethyl)-1-methyl-1-(1-methylpiperidin-4-yl)urea |
| H0766 | 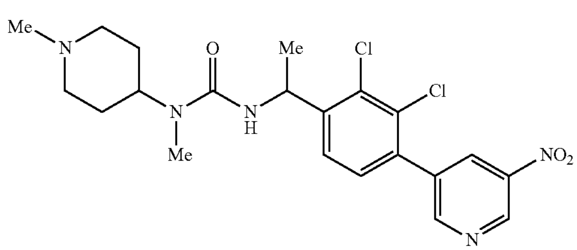 | 3-(1-(2,3-dichloro-4-(5-nitropyridin-3-yl)phenyl)ethyl)-1-methyl-1-(1-methylpiperidin-4-yl)urea |
| H0608 | 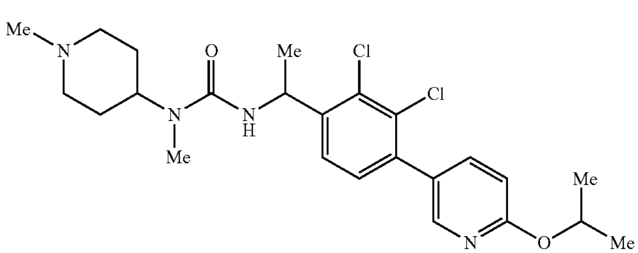 [SMILES: CC(C)Oc1ccc(-c2ccc(C(C)NC(=O)N(C)C3CCN(C)CC3)c(Cl)c2Cl)cn1] | 3-(1-(2,3-dichloro-4-(6-isopropoxypyridin-3-yl)phenyl)ethyl)-1-methyl-1-(1-methylpiperidin-4-yl)urea |

-continued

| Compound No. | Chemical Structure | Chemical Name |
|---|---|---|
| H0616 | 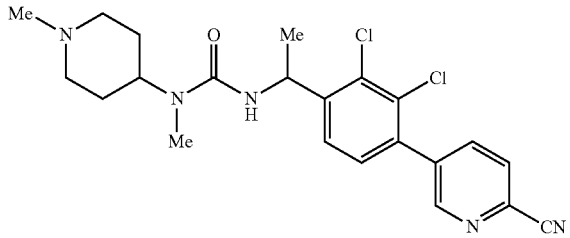 [SMILES: CC(NC(=O)N(C)C1CCN(C)CC1)c1ccc(-c2ccc(C#N)nc2)c(Cl)c1Cl] | 3-(1-(2,3-dichloro-4-(6-cyanopyridin-3-yl)phenyl)ethyl)-1-methyl-1-(1-methylpiperidin-4-yl)urea |
| H0618 | 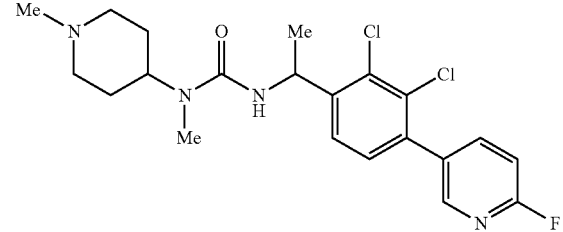 | 3-(1-(2,3-dichloro-4-(6-fluoropyridin-3-yl)phenyl)ethyl)-1-methyl-1-(1-methylpiperidin-4-yl)urea |
| H0623 | 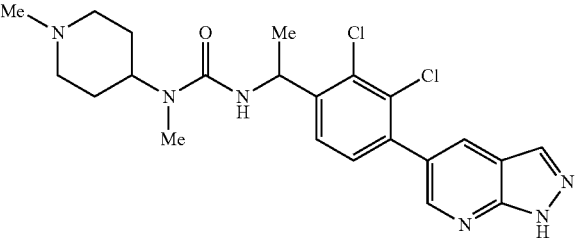 [SMILES: CC(NC(=O)N(C)C1CCN(C)CC1)c1ccc(-c2cnc3[nH]ncc3c2)c(Cl)c1Cl] | 3-(1-(2,3-dichloro-4-(1H-pyrazolo[3,4-b]pyridin-5-yl)phenyl)ethyl)-1-methyl-1-(1-methylpiperidin-4-yl)urea |
| H0610 | 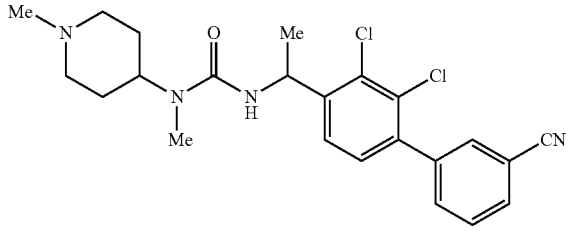 [SMILES: CC(NC(=O)N(C)C1CCN(C)CC1)c1ccc(-c2cccc(C#N)c2)c(Cl)c1Cl] | 3-(1-(2,3-dichloro-3'-cyano-[1,1'-biphenyl]-4-yl)ethyl)-1-methyl-1-(1-methylpiperidin-4-yl)urea |
| H0517 | 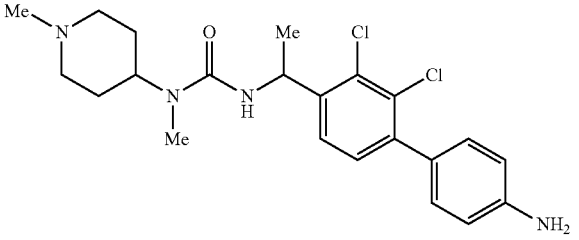 [SMILES: CC(NC(=O)N(C)C1CCN(C)CC1)c1ccc(-c2ccc(N)cc2)c(Cl)c1Cl] | 3-(1-(4'-amino-2,3-dichloro-[1,1'-biphenyl]-4-yl)ethyl)-1-methyl-1-(1-methylpiperidin-4-yl)urea |
| H0518 | 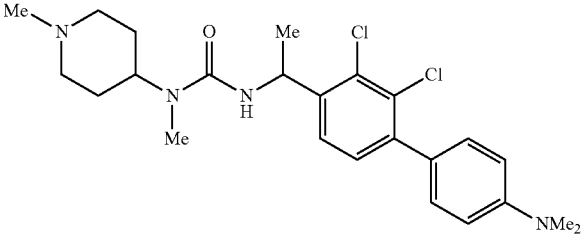 [SMILES: CC(NC(=O)N(C)C1CCN(C)CC1)c1ccc(-c2ccc(N(C)C)cc2)c(Cl)c1Cl] | 3-(1-(2,3-dichloro-4'-(dimethylamino)-[1,1'-biphenyl]-4-yl)ethyl)-1-methyl-1-(1-methylpiperidin-4-yl)urea |

-continued

| Compound No. | Chemical Structure | Chemical Name |
|---|---|---|
| H0512 | 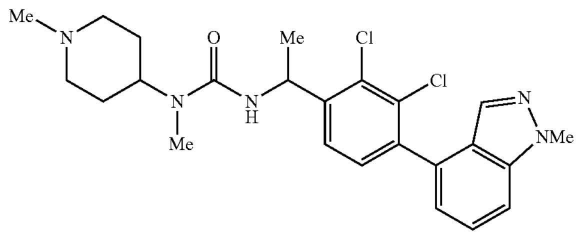 [SMILES: CC(NC(=O)N(C)C1CCN(C)CC1)c1ccc(-c2cccc3c2cnn3C)c(Cl)c1Cl] | 3-(1-(2,3-dichloro-4-(1-methyl-1H-indazol-4-yl)phenyl)ethyl)-1-methyl-1-(1-methylpiperidin-4-yl)urea |
| H0513 | 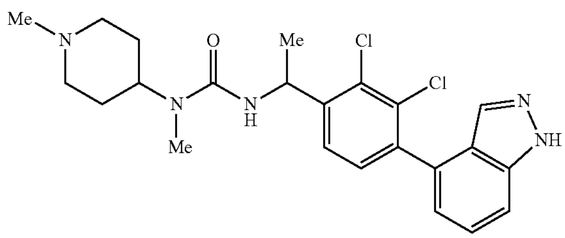 [SMILES: CC(NC(=O)N(C)C1CCN(C)CC1)c1ccc(-c2cccc3[nH]ncc23)c(Cl)c1Cl] | 3-(1-(2,3-dichloro-4-(1H-indazol-4-yl)phenyl)ethyl)-1-methyl-1-(1-methylpiperidin-4-yl)urea |
| H0514 | 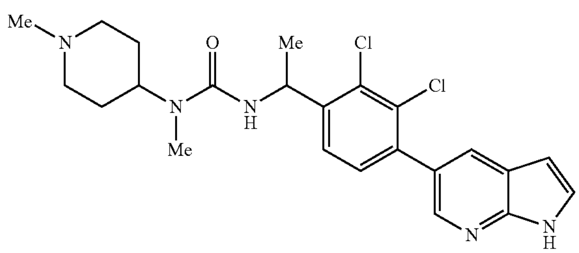 [SMILES: CC(NC(=O)N(C)C1CCN(C)CC1)c1ccc(-c2cnc3[nH]ccc3c2)c(Cl)c1Cl] | 3-(1-(2,3-dichloro-4-(1H-pyrrolo[2,2-b'pyridin-5-yl)phenyl)ethyl)-1-methyl-1-(1-methylpiperidin-4-yl)urea |
| H0515 | 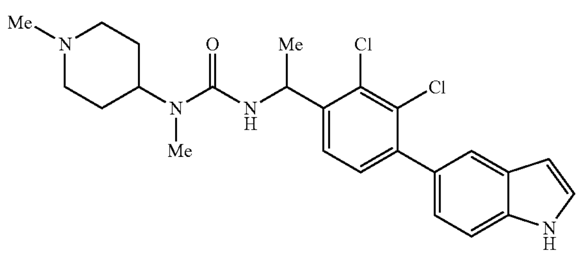 [SMILES: CC(NC(=O)N(C)C1CCN(C)CC1)c1ccc(-c2ccc3[nH]ccc3c2)c(Cl)c1Cl] | 3-(1-(2,3-dichloro-4-(1H-indol-5-yl)phenyl)ethyl)-1-methyl-1-(1-methylpiperidin-4-yl)urea |
| H0520 | 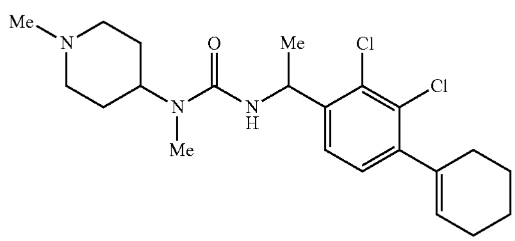 [SMILES: CC(NC(=O)N(C)C1CCN(C)CC1)c1ccc(C2=CCCCC2)c(Cl)c1Cl] | 3-(1-(2,3-dichloro-2',3',4',5'-tetrahydro-[1,1'-biphenyl]-4-yl)ethyl)-1-methyl-1-(1-methylpiperidin-4-yl)urea |
| H0787 | 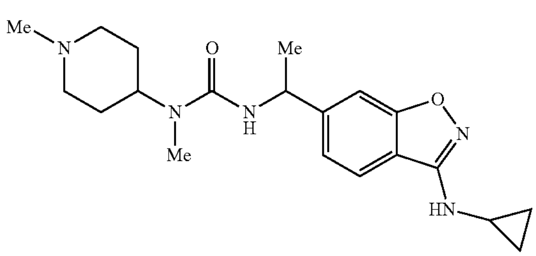 [SMILES: CC(NC(=O)N(C)C1CCN(C)CC1)c1ccc2c(NC3CC3)noc2c1] | 3-(1-(3-(cyclopropylamino)benzo[d]isoxazol-6-yl)ethyl)-1-methyl-1-(1-methylpiperidin-4-yl)urea |

| Compound No. | Chemical Name |
|---|---|
| H0582 | 3-(1-(34-chloro-2-fluoro-4-(thiophen-2-yl)phenyl)ethyl)-1-methyl-1-(1-methylpiperidin-4-yl)urea |
| H0571 | 3-(1-(3-chloro-2-fluoro-4-(1H-pyrazol-4-yl)phenyl)ethyl)-1-methyl-1-(1-methylpiperidin-4-yl)urea |
| H0605 | 3-(1-(2,3-dichloro-3',5'-difluoro[1,1'-biphenyl]-4-yl)ethyl)-1-methyl-1-(1-methylpiperidin-4-yl)urea |
| H0573 | 3-(1-(4-bromonaphthalen-1-yl)ethyl)-1-methyl-1-(1-methylpiperidin-4-yl)urea |
| H0574 | 1-methyl-1-(1-methylpiperidin-4-yl)-3-(1-(4-(thiophen-3-yl)naphthalen-1-yl)ethyl)urea |
| H0575 | 1-methyl-1-(1-methylpiperidin-4-yl)-3-(1-(4-(thiophen-2-yl)naphthalen-1-yl)ethyl)urea |
| H0576 | 3-(1-(4-(1H-pyrazol-4-yl)naphthalen-1-yl)ethyl)-1-methyl-1-(1-methylpiperidin-4-yl)urea |

-continued

| Compound No. | Chemical Structure | Chemical Name |
|---|---|---|
| H0577 | 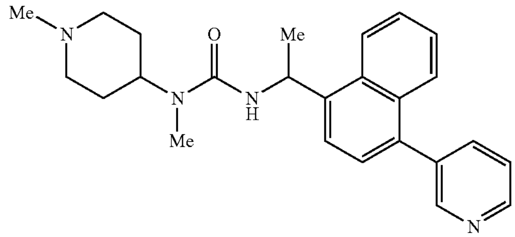 [SMILES: CC(NC(=O)N(C)C1CCN(C)CC1)c1ccc(-c2cccnc2)c2ccccc12] | 1-methyl-1-(1-methylpiperidin-4-yl)-3-(1-(4-(pyridin-3-yl)naphthalen-1-yl)ethyl)urea |
| H0591 | 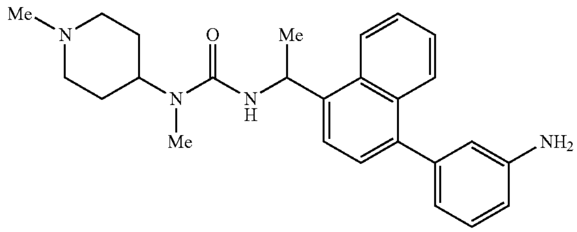 [SMILES: CC(NC(=O)N(C)C1CCN(C)CC1)c1ccc(-c2cccc(N)c2)c2ccccc12] | 3-(1-(4-(3-aminophenyl)naphthalen-1-yl)ethyl)-1-methyl-1-(1-methylpiperidin-4-yl)urea |
| H0597 | 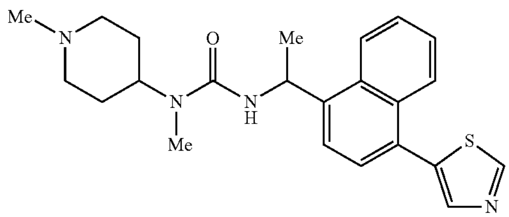 [SMILES: CC(NC(=O)N(C)C1CCN(C)CC1)c1ccc(-c2cncs2)c2ccccc12] | 1-methyl-1-(1-methylpiperidin-4-yl)-3-(1-(4-(thiazol-5-yl)naphthalen-1-yl)ethyl)urea |
| H0598 | 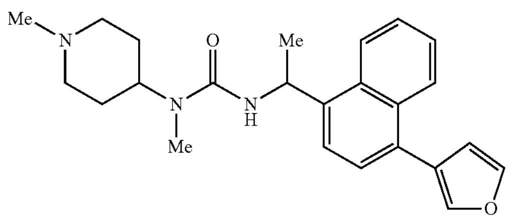 [SMILES: CC(NC(=O)N(C)C1CCN(C)CC1)c1ccc(-c2ccoc2)c2ccccc12] | 3-(1-(4-(furan-3-yl)naphthalen-1-yl)ethyl)-1-methyl-1-(1-methylpiperidin-\4-yl)urea |
| H0599 | 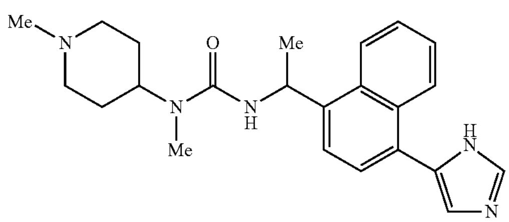 [SMILES: CC(NC(=O)N(C)C1CCN(C)CC1)c1ccc(-c2cnc[nH]2)c2ccccc12] | 3-(1-(4-(1H-imidazol-5-yl)naphthalen-1-yl)ethyl)-1-methyl-1-(1-methylpiperidin-4-yl)urea |
| H0790 | 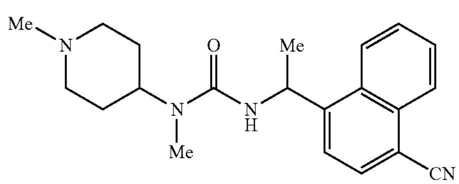 [SMILES: CC(NC(=O)N(C)C1CCN(C)CC1)c1ccc(C#N)c2ccccc12] | 3-(1-(4-cyanonaphthalen-1-yl)ethyl)-1-methyl-1-(1-methylpiperidin-4-yl)urea |
| H0381 | 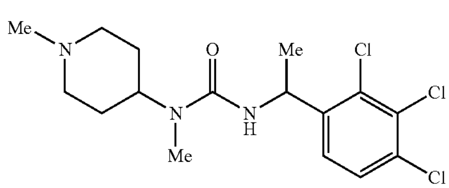 | 1-methyl-1-(1-methylpiperidin-4-yl)-3-(1-(2,3,4-trichlorophenyl)ethyl)urea |

| Compound No. | Chemical Structure | Chemical Name |
|---|---|---|
| H0519 | 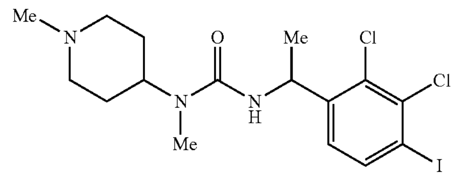 [SMILES: CC(NC(=O)N(C)C1CCN(C)CC1)c1ccc(I)c(Cl)c1Cl] | 3-(1-(2,3-dichloro-4-iodophenyl)ethyl)-1-methyl-1-(1-methylpiperidin-4-yl)urea |
| H0629 | 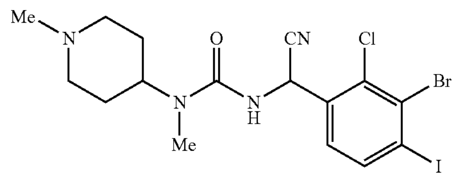 [SMILES: CN1CCC(N(C)C(=O)NC(C#N)c2ccc(I)c(Br)c2Cl)CC1] | 3-((3-bromo-2-chloro-4-iodophenyl)(cyano)methyl)-1-methyl-1-(1-methylpiperidin-4-yl)urea |
| H0658 | 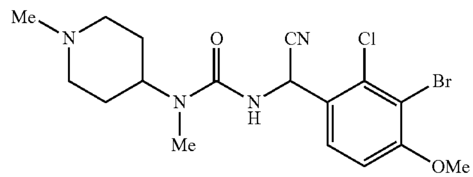 [SMILES: COc1ccc(C(C#N)NC(=O)N(C)C2CCN(C)CC2)c(Cl)c1Br] | 3-((3-bromo-2-chloro-4-methoxyphenyl)(cyano)methyl)-1-methyl-1-(1-methylpiperidin-4-yl)urea |
| H0669 | 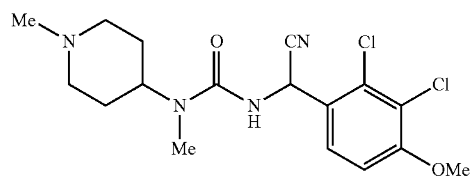 [SMILES: COc1ccc(C(C#N)NC(=O)N(C)C2CCN(C)CC2)c(Cl)c1Cl] | 3-(cyano(2,3-dichloro-4-methoxyphenyl)methyl)-1-methyl-1-(1-methylpiperidin-4-yl)urea |
| H0671 | 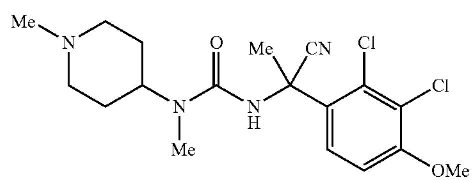 [SMILES: COc1ccc(C(C)(C#N)NC(=O)N(C)C2CCN(C)CC2)c(Cl)c1Cl] | 3-(1-cyano-1-(2,3-dichloro-4-methoxyphenyl)ethyl)-1-methyl-1-(1-methylpiperidin-4-yl)urea |
| H0659 | 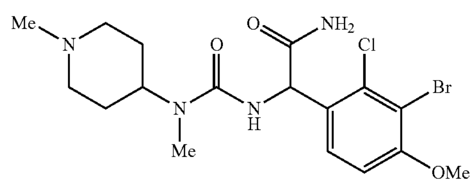 [SMILES: COc1ccc(C(NC(=O)N(C)C2CCN(C)CC2)C(N)=O)c(Cl)c1Br] | 2-(3-bromo-2-chloro-4-methoxyphenyl)-2-(3-methyl-3-(1-methylpiperidin-4-yl)ureido)acetamide |
| H0521 | 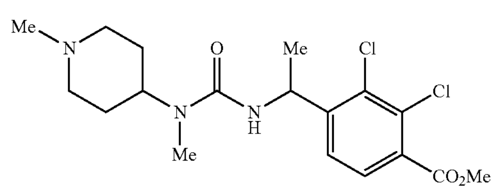 | methyl 2,3-dichloro-4-(1-(3-methyl-3-(1-methylpiperidin-4-yl)ureido)ethyl)acetamide |
| H0602 | 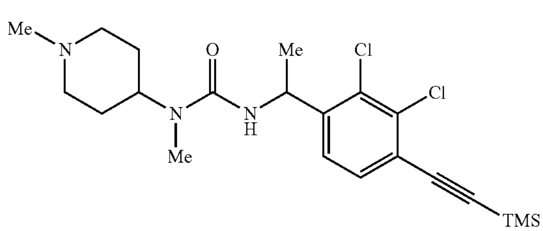 [SMILES: CC(NC(=O)N(C)C1CCN(C)CC1)c1ccc(C#C[Si](C)(C)C)c(Cl)c1Cl] | 3-(1-(2,3-dichloro-4-((trimethylsilyl)ethynyl)phenyl)ethyl)-1-methyl-1-(1-methylpiperidin-4-yl)urea |

-continued

| Compound No. | Chemical Structure | Chemical Name |
|---|---|---|
| H0603 | 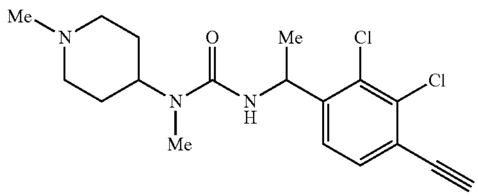 [SMILES: C#Cc1ccc(C(C)NC(=O)N(C)C2CCN(C)CC2)c(Cl)c1Cl] | 3-(1-(2,3-dichloro-4-ethynylphenyl)ethyl)-1-methyl-1-(1-methylpiperidin-4-yl)urea |
| H0677 | 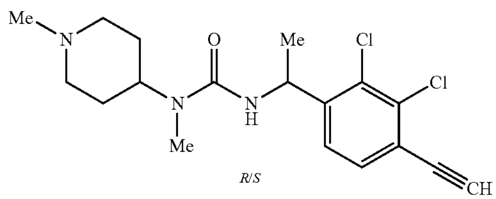 [SMILES: C#Cc1ccc(C(C)NC(=O)N(C)C2CCN(C)CC2)c(Cl)c1Cl] | 3-(1-(2,3-dichloro-4-ethynylphenyl)ethyl)-1-methyl-1-(1-methylpiperidin-4-yl)urea (single enantiomer) |
| H0678 | 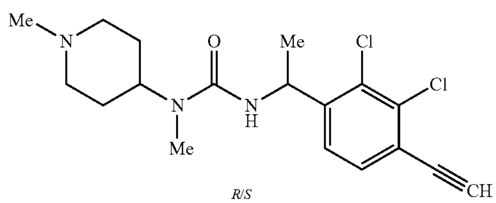 [SMILES: C#Cc1ccc(C(C)NC(=O)N(C)C2CCN(C)CC2)c(Cl)c1Cl] | 3-(1-(2,3-dichloro-4-ethynylphenyl)ethyl)-1-methyl-1-(1-methylpiperidin-4-yl)urea (single enantiomer) |
| H0832 | 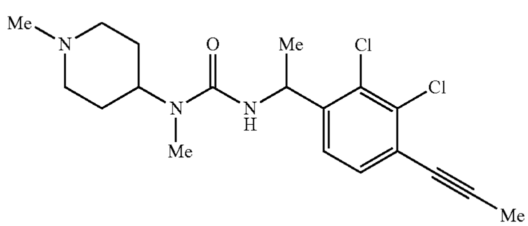 [SMILES: CC#Cc1ccc(C(C)NC(=O)N(C)C2CCN(C)CC2)c(Cl)c1Cl] | 3-(1-(2,3-dichloro-4-(prop-1-yn-1-yl)phenyl)ethyl)-1-methyl-1-(1-methylpiperidin-4-yl)urea |
| H0852 | 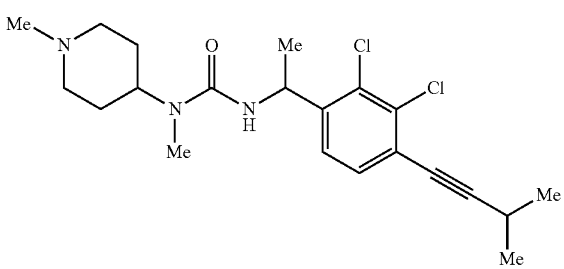 [SMILES: CC(C)C#Cc1ccc(C(C)NC(=O)N(C)C2CCN(C)CC2)c(Cl)c1Cl] | 3-(1-(2,3-dichloro-4-(3-methylbut-1-yn-1-yl)phenyl)ethyl)-1-methyl-1-(1-methylpiperidin-4-yl)urea |
| H0701 | 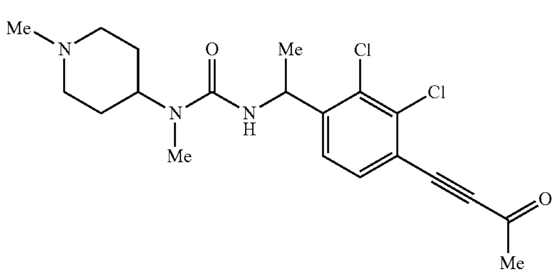 [SMILES: CC(=O)C#Cc1ccc(C(C)NC(=O)N(C)C2CCN(C)CC2)c(Cl)c1Cl] | 3-(1-(2,3-dichloro-4-(3-oxobut-1-yn-1-yl)phenyl)ethyl)-1-methyl-1-(1-methylpiperidin-4-yl)urea |

-continued

| Compound No. | Chemical Structure | Chemical Name |
|---|---|---|
| H0733 | 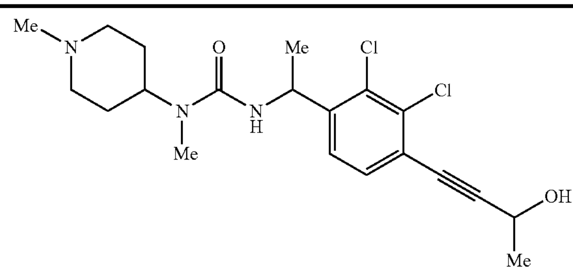 | 3-(1-(2,3-dichloro-4-(3-hydroxybut-1-yn-1-yl)phenyl)ethyl)-1-methyl-1-(1-methylpiperidin-4-yl)urea |
| H0755 | 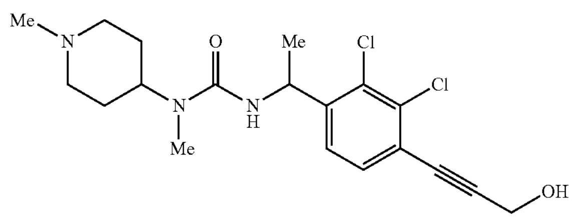 [SMILES: CC(NC(=O)N(C)C1CCN(C)CC1)c1ccc(C#CCO)c(Cl)c1Cl] | 3-(1-(2,3-dichloro-4-(3-hydroxyprop-1-yn-1-yl)phenyl)ethyl)-1-methyl-1-(1-methylpiperidin-4-yl)urea |
| H0757 | 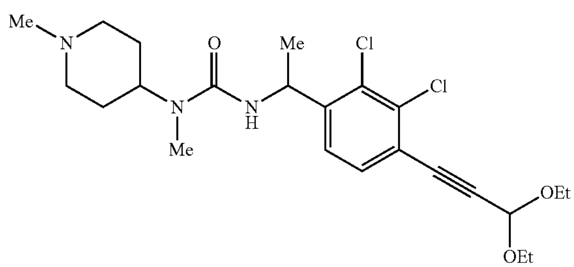 [SMILES: CCOC(C#Cc1ccc(C(C)NC(=O)N(C)C2CCN(C)CC2)c(Cl)c1Cl)OCC] | 3-(1-(2,3-dichloro-4-(3,3-diethoxyprop-1-yn-1-yl)phenyl)ethyl)-1-methyl-1-(1-methylpiperidin-4-yl)urea |
| H0734 | 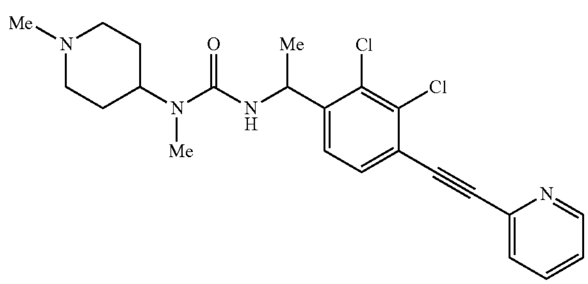 [SMILES: CC(NC(=O)N(C)C1CCN(C)CC1)c1ccc(C#Cc2ccccn2)c(Cl)c1Cl] | 3-(1-(2,3-dichloro-4-(pyridin-2-ylethynyl)phenyl)ethyl)-1-methyl-1-(1-methylpiperidin-4-yl)urea |
| H0737 | 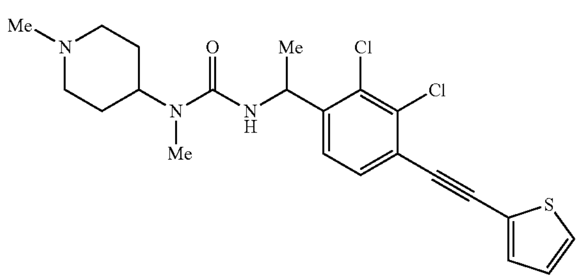 [SMILES: CC(NC(=O)N(C)C1CCN(C)CC1)c1ccc(C#Cc2cccs2)c(Cl)c1Cl] | 3-(1-(2,3-dichloro-4-(thiophen-2-ylethynyl)phenyl)ethyl)-1-methyl-1-(1-methylpiperidin-4-yl)urea |
| H0775 | 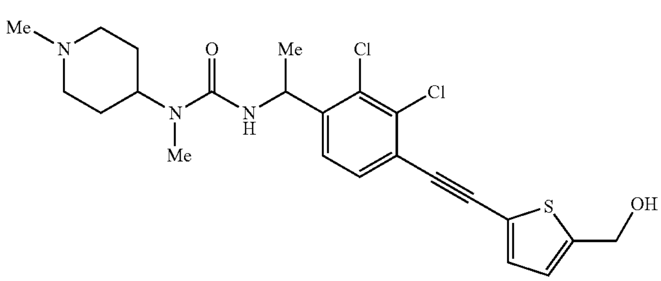 [SMILES: CC(NC(=O)N(C)C1CCN(C)CC1)c1ccc(C#Cc2ccc(CO)s2)c(Cl)c1Cl] | 3-(1-(2,3-dichloro-4-((5-(hydroxymethyl)thiophen-2-yl)ethynyl)phenyl)ethyl)-1-methyl-1-(1-methylpiperidin-4-yl)urea |

-continued

| Compound No. | Chemical Structure | Chemical Name |
|---|---|---|
| H0776 | 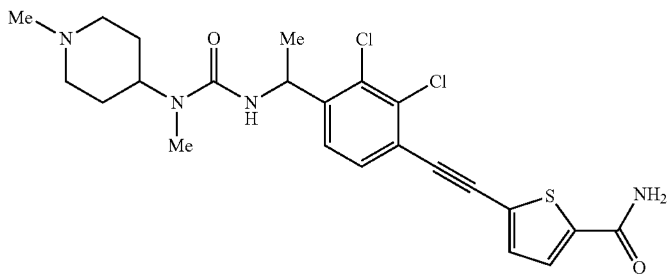 [SMILES: CC(NC(=O)N(C)C1CCN(C)CC1)c1ccc(C#Cc2ccc(C(N)=O)s2)c(Cl)c1Cl] | 5-((2,3-dichloro-4-(1-(3-methyl-3-(1-methylpiperidin-4-yl)ureido)ethyl)phenyl)ethynyl)thiophene-2-carboxamide |
| H0779 | 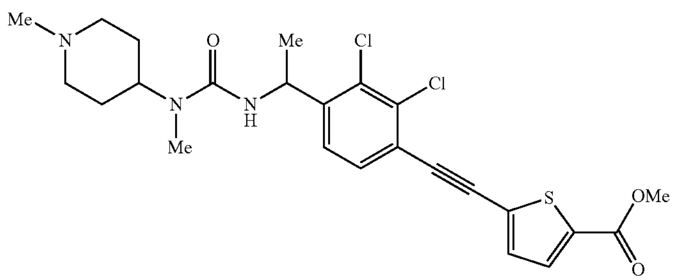 [SMILES: COC(=O)c1ccc(C#Cc2ccc(C(C)NC(=O)N(C)C3CCN(C)CC3)c(Cl)c2Cl)s1] | methyl 5-((2,3-dichloro-4-(1-(3-methyl-3-(1-methylpiperidin-4-yl)ureido)ethyl)phenyl)ethynyl)thiophene-2-carboxylate |
| H0762 | 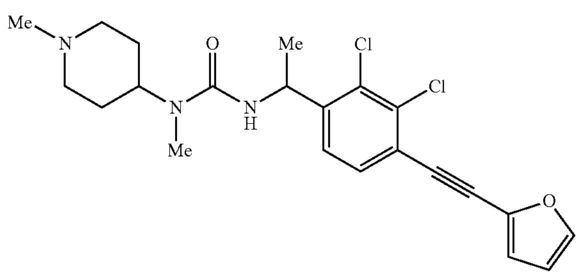 [SMILES: CC(NC(=O)N(C)C1CCN(C)CC1)c1ccc(C#Cc2ccco2)c(Cl)c1Cl] | 3-(1-(2,3-dichloro-4-(furan-2-ylethynyl)phenyl)ethyl)-1-methyl-1-(1-methylpiperidin-4-yl)urea |
| H0751 | 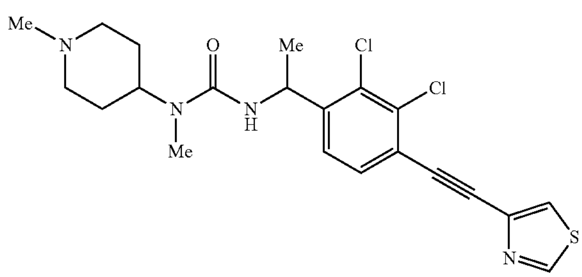 [SMILES: CC(NC(=O)N(C)C1CCN(C)CC1)c1ccc(C#Cc2cscn2)c(Cl)c1Cl] | 3-(1-(2,3-dichloro-4-(thiazol-4-ylethynyl)phenyl)ethyl)-1-methyl-1-(1-methylpiperidin-4-yl)urea |
| H0763 | 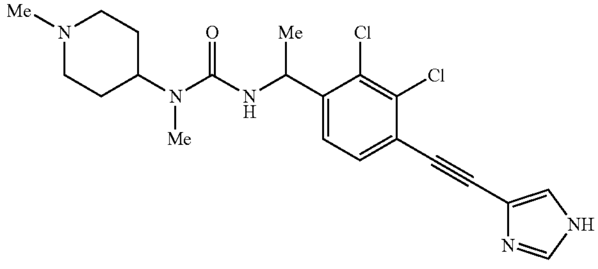 [SMILES: CC(NC(=O)N(C)C1CCN(C)CC1)c1ccc(C#Cc2c[nH]cn2)c(Cl)c1Cl] | 3-(1-(4-((1H-imidazol-4-yl)ethynyl)-2,3-dichlorophenyl)ethyl)-1-methyl-1-(1-methylpiperidin-4-yl)urea |

-continued

| Compound No. | Chemical Structure | Chemical Name |
|---|---|---|
| H0759 | 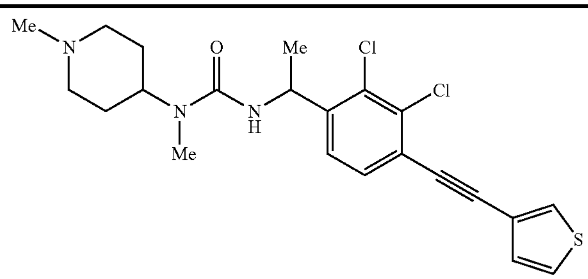 | 3-(1-(2,3-dichloro-4-(thiophen-3-ylethynyl)phenyl)ethyl)-1-methyl-1-(1-methylpiperidin-4-yl)urea |
| H0785 | 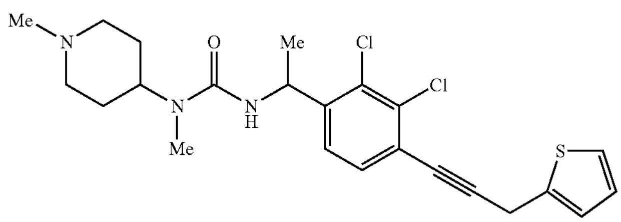 [SMILES: CC(NC(=O)N(C)C1CCN(C)CC1)c1ccc(C#CCc2cccs2)c(Cl)c1Cl] | 3-(1-(2,3-dichloro-4-(3-(thiophen-2-yl)prop-1-yn-1-yl)phenyl)ethyl)-1-methyl-1-(1-methylpiperidin-4-yl)urea |
| H0754 | 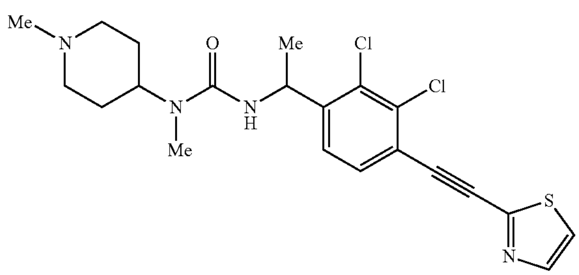 [SMILES: CC(NC(=O)N(C)C1CCN(C)CC1)c1ccc(C#Cc2nccs2)c(Cl)c1Cl] | 3-(1-(2,3-dichloro-4-(thiazol-2-ylethynyl)phenyl)ethyl)-1-methyl-1-(1-methylpiperidin-4-yl)urea |
| H0753 | 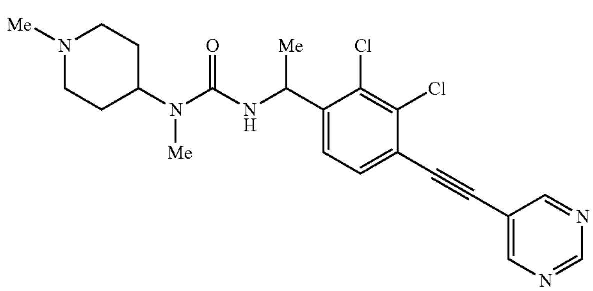 [SMILES: CC(NC(=O)N(C)C1CCN(C)CC1)c1ccc(C#Cc2cncnc2)c(Cl)c1Cl] | 3-(1-(2,3-dichloro-4-(pyrimidin-5-ylethynyl)phenyl)ethyl)-1-methyl-1-(1-methylpiperidin-4-yl)urea |
| H0609 | 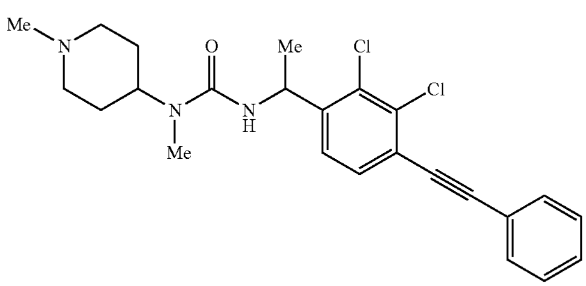 [SMILES: CC(NC(=O)N(C)C1CCN(C)CC1)c1ccc(C#Cc2ccccc2)c(Cl)c1Cl] | 3-(1-(2,3-dichloro-4-(phenylethynyl)phenyl)ethyl)-1-methyl-1-(1-methylpiperidin-4-yl)urea |
| H0764 | 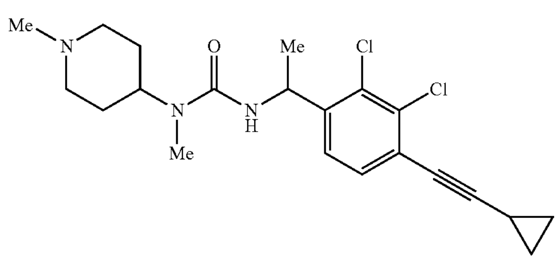 | 3-(1-(2,3-dichloro-4-(cyclopropylethynyl)phenyl)ethyl)-1-methyl-1-(1-methylpiperidin-4-yl)urea |

| Compound No. | Chemical Structure | Chemical Name |
|---|---|---|
| H0818 | 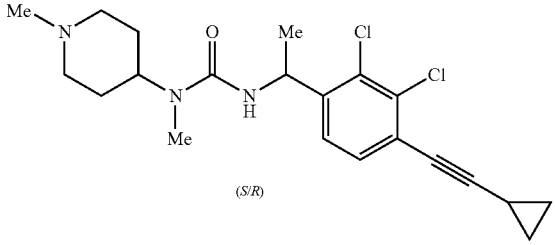 (S/R) | 3-(1-(2,3-dichloro-4-(cyclopropylethynyl)phenyl)ethyl)-1-methyl-1-(1-methylpiperidin-4-yl)urea (single enantiomer) |
| H0819 | 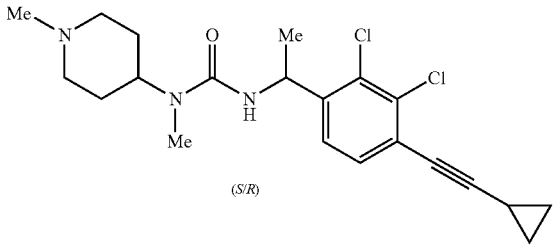 (S/R) | 3-(1-(2,3-dichloro-4-(cyclopropylethynyl)phenyl)ethyl)-1-methyl-1-(1-methylpiperidin-4-yl)urea (single enantiomer) |
| H0838 | 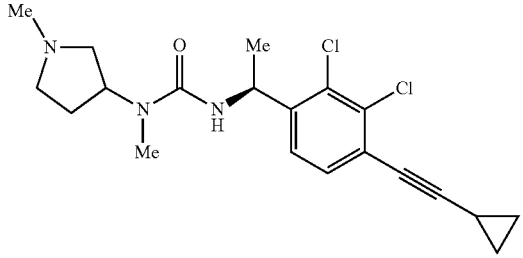 | 3-((S)-1-(2,3-dichloro-4-(cyclopropylethynyl)phenyl)ethyl)-1-methyl-1-(1-methylpyrrolidin-3-yl)urea |
| H0855 | 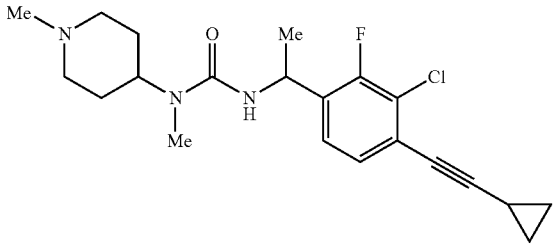 | 3-(1-(3-chloro-4-(cycloprropylethynyl)-2-fluorophenyl)ethyl)-1-methyl-1-(1-methylpiperidin-4-yl)urea |
| H0884 | 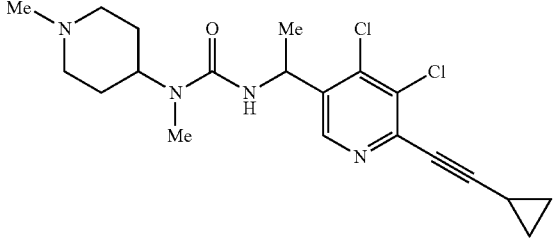 | 3-(1-(4,5-dichloro-6-(cyclopropylethynyl)pyridin-3-yl)ethyl)-1-methyl-1-(1-methylpiperidin-4-yl)urea |
| H0811 | 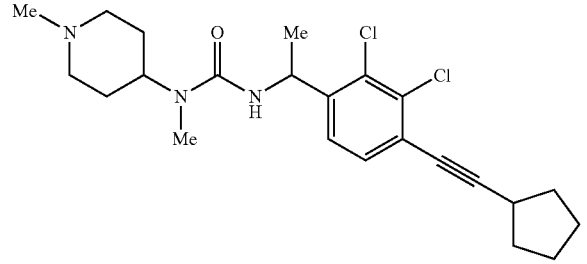 | 3-(1-(2,3-dichloro-4-(cyclopropylethynyl)phenyl)ethyl)-1-methyl-1-(1-methylpiperidin-4-yl)urea |

-continued

| Compound No. | Chemical Structure | Chemical Name |
|---|---|---|
| H0812 | 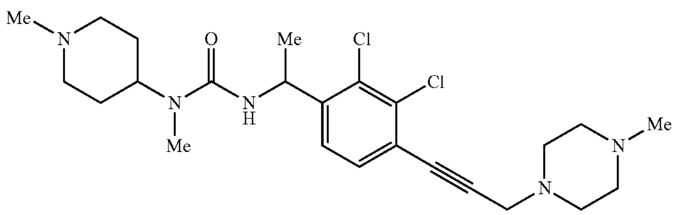 [SMILES: CC(NC(=O)N(C)C1CCN(C)CC1)c1ccc(C#CCN2CCN(C)CC2)c(Cl)c1Cl] | 3-(1-(2,3-dichloro-4-(3-(4-methylpiperazin-1-yl)prop-1-yn-1-yl)phenyl)ethyl)-1-methyl-1-(1-methylpiperidin-4-yl)urea |
| H0740 | 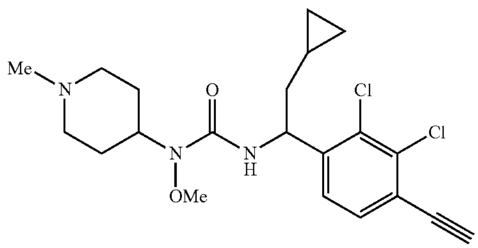 [SMILES: C#Cc1ccc(C(CC2CC2)NC(=O)N(OC)C2CCN(C)CC2)c(Cl)c1Cl] | 3-(2-cyclopropyl-1-(2,3-dichloro-4-ethynylphenyl)ethyl)-1-methoxy-1-(1-methylpiperidin-4-yl)urea |
| H0742 | 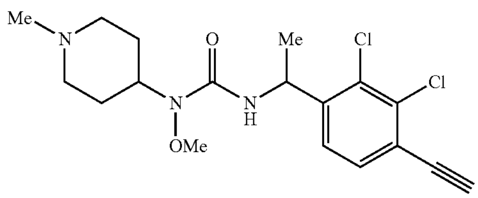 [SMILES: C#Cc1ccc(C(C)NC(=O)N(OC)C2CCN(C)CC2)c(Cl)c1Cl] | 3-(1-(2,3-dichloro-4-ethynylphenyl)ethyl)-1-methoxy-1-(1-methylpiperidin-4-yl)urea |
| H0745 | 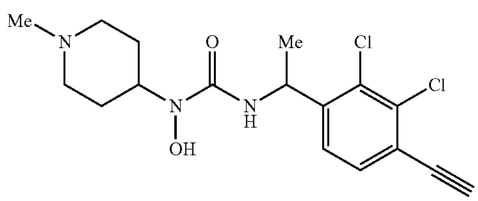 [SMILES: C#Cc1ccc(C(C)NC(=O)N(O)C2CCN(C)CC2)c(Cl)c1Cl] | 3-(1-(2,3-dichloro-4-ethynylphenyl)ethyl)-1-hydroxy-1-(1-methylpiperidin-4-yl)urea |
| H0749 | 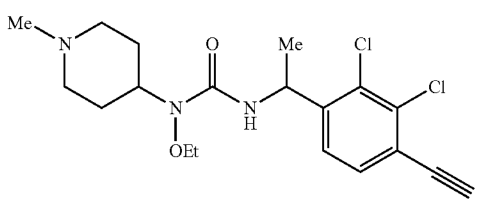 | 3-(1-(2,3-dichloro-4-ethynylphenyl)ethyl)-1-ethoxy-1-(1-methylpiperidin-4-yl)urea |
| H0744 | 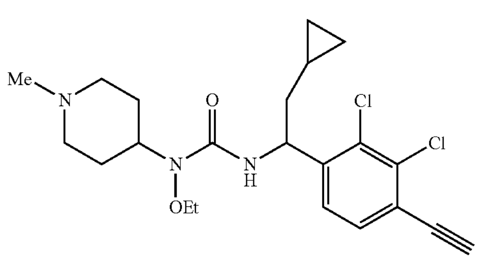 [SMILES: C#Cc1ccc(C(CC2CC2)NC(=O)N(OCC)C2CCN(C)CC2)c(Cl)c1Cl] | 3-(2-cyclopropyl-1-(2,3-dichloro-4-ethynylphenyl)ethyl)-1-ethoxy-1-(1-methylpiperidin-4-yl)urea |
| H0626 | 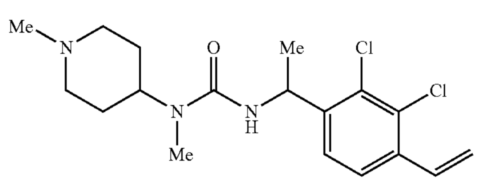 [SMILES: C=Cc1ccc(C(C)NC(=O)N(C)C2CCN(C)CC2)c(Cl)c1Cl] | 3-(1-(2,3-dichloro-4-vinylphenyl)ethyl)-1-methyl-1-(1-methylpiperidin-4-yl)urea |

-continued

| Compound No. | Chemical Structure | Chemical Name |
|---|---|---|
| H0767 | 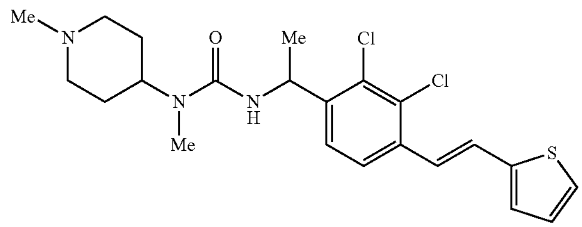 [SMILES: CC(NC(=O)N(C)C1CCN(C)CC1)c1ccc(/C=C/c2cccs2)c(Cl)c1Cl] | (E)-3-(1-(2,3-dichloro-4-(2-(thiophen-2-yl)vinyl)phenyl)ethyl)-1-methyl-1-(1-methylpiperidin-4-yl)urea |
| H0772 | 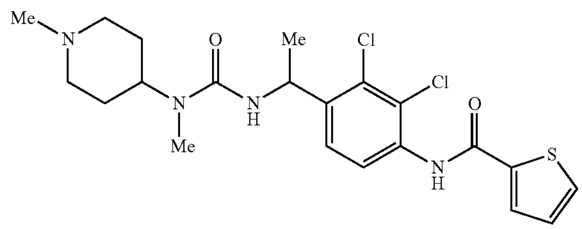 [SMILES: CC(NC(=O)N(C)C1CCN(C)CC1)c1ccc(NC(=O)c2cccs2)c(Cl)c1Cl] | N-(2,3-dichloro-4-(1-(3-methyl-3-(1-methylpiperidin-4-yl)ureido)ethyl)phenyl)thiophene-2-carboxamide |
| H0773 | 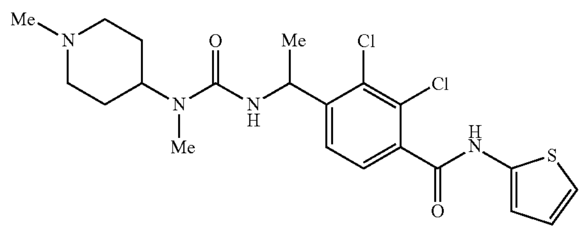 [SMILES: CC(NC(=O)N(C)C1CCN(C)CC1)c1ccc(C(=O)Nc2cccs2)c(Cl)c1Cl] | 2,3-dichloro-4-(1-(3-methyl-3-(1-methylpiperidin-4-yl)ureido)ethyl)-N-(thiophen-2-yl)benzamide |
| H0784 | 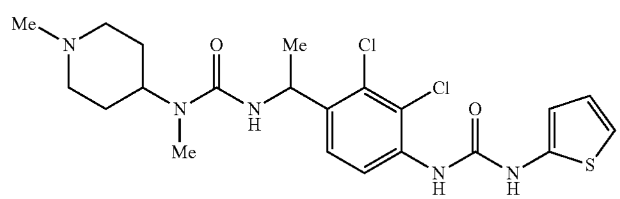 [SMILES: CC(NC(=O)N(C)C1CCN(C)CC1)c1ccc(NC(=O)Nc2cccs2)c(Cl)c1Cl] | 3-(1-(2,3-dichloro-4-(4-(thiophen-2-yl)ureido)phenyl)ethyl)-1-methyl-1-(1-methylpiperidin-4-yl)urea |
| H0777 | 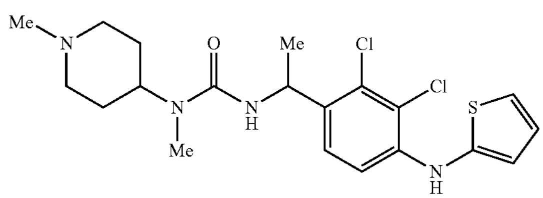 [SMILES: CC(NC(=O)N(C)C1CCN(C)CC1)c1ccc(Nc2cccs2)c(Cl)c1Cl] | 3-(1-(2,3-dichloro-4-(thiophen-2-ylamino)phenyl)ethyl)-1-methyl-1-(1-methylpiperidin-4-yl)urea |
| H0846 | 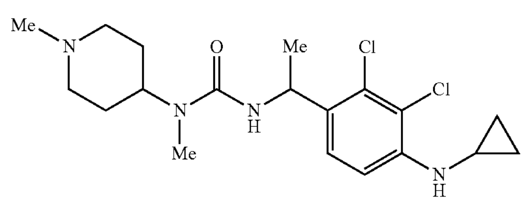 [SMILES: CC(NC(=O)N(C)C1CCN(C)CC1)c1ccc(NC2CC2)c(Cl)c1Cl] | 3-(1-(2,3-dichloro-4-(cyclopropylamino)phenyl)ethyl)-1-methyl-1-(1-methylpiperidin-4-yl)urea |
| H0875 | 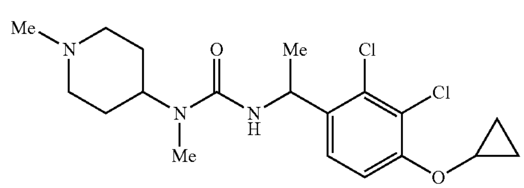 [SMILES: CC(NC(=O)N(C)C1CCN(C)CC1)c1ccc(OC2CC2)c(Cl)c1Cl] | 3-(1-(2,3-dichloro-4-cyclopropoxyphenyl)ethyl)-1-methyl-1-(1-methylpiperidin-4-yl)urea |

-continued

| Compound No. | Chemical Structure | Chemical Name |
|---|---|---|
| H0628 | 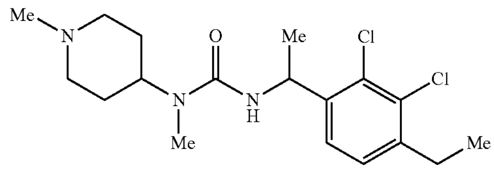 [SMILES: CCc1ccc(C(C)NC(=O)N(C)C2CCN(C)CC2)c(Cl)c1Cl] | 3-(1-(2,3-dichloro-4-ethylphenyl)ethyl)-1-methyl-1-(1-methylpiperidin-4-yl)urea |
| H0630 | 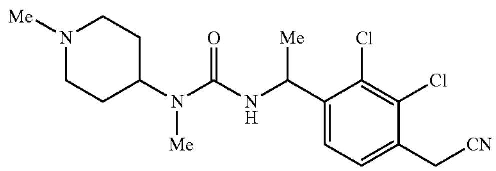 [SMILES: CC(NC(=O)N(C)C1CCN(C)CC1)c1ccc(CC#N)c(Cl)c1Cl] | 3-(1-(2,3-dichloro-4-(cyanomethyl)phenyl)ethyl)-1-methyl-1-(1-methylpiperidin-4-yl)urea |
| H0633 | 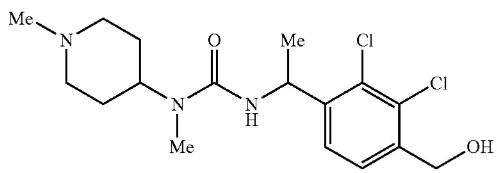 | 3-(1-(2,3-dichloro-4-(hydroxymethyl)phenyl)ethyl)-1-methyl-1-(1-methylpiperidin-4-yl)urea |
| H0634 | 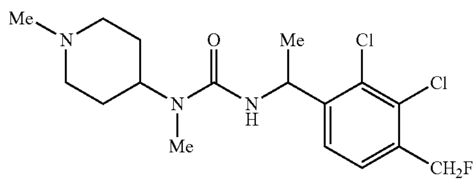 | 3-(1-(2,3-dichloro-4-(fluoromethyl)phenyl)ethyl)-1-methyl-1-(1-methylpiperidin-4-yl)urea |
| H0640 | 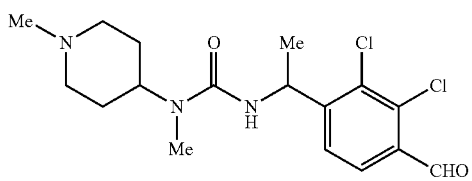 [SMILES: CC(NC(=O)N(C)C1CCN(C)CC1)c1ccc(C=O)c(Cl)c1Cl] | 3-(1-(2,3-dichloro-4-formylphenyl)ethyl)-1-methyl-1-(1-methylpiperidin-4-yl)urea |
| H0645 | 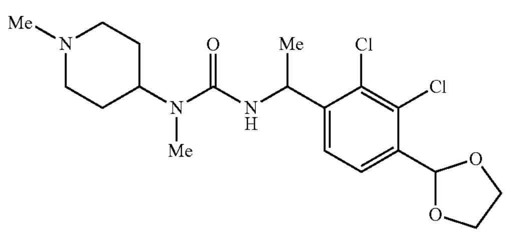 [SMILES: CC(NC(=O)N(C)C1CCN(C)CC1)c1ccc(C2OCCO2)c(Cl)c1Cl] | 3-(1-(2,3-dichloro-4-(1,3-dioxolan-2-yl)phenyl)ethyl)-1-methyl-1-(1-methylpiperidin-4-yl)urea |
| H0641 | 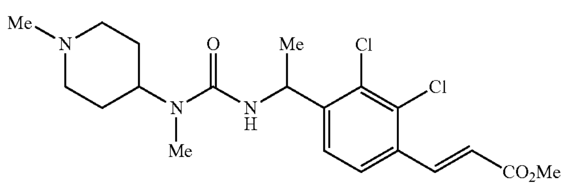 [SMILES: COC(=O)/C=C/c1ccc(C(C)NC(=O)N(C)C2CCN(C)CC2)c(Cl)c1Cl] | methyl (E)-3-(2,3-dichloro-4-(1-(3-methyl-3-(1-methylpiperidin-4-yl)ureido)ethyl)phenyl)acrylate |
| H0702 | 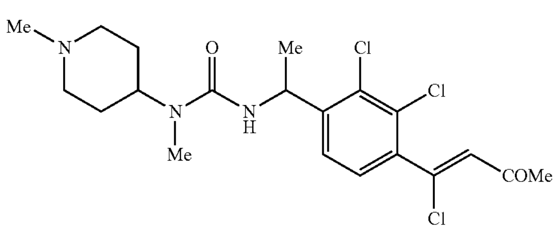 | (Z)-3-(1-(2,3-dichloro-4-(1-chloro-3-oxobut-1-en-1-yl)phenyl)ethyl)-1-methyl-1-(1-methylpiperidin-4-yl)urea |

| Compound No. | Chemical Structure | Chemical Name |
|---|---|---|
| H0643 | 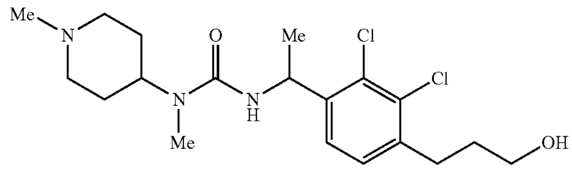 [SMILES: CC(NC(=O)N(C)C1CCN(C)CC1)c1ccc(CCCO)c(Cl)c1Cl] | 3-(1-(2,3-dichloro-4-(3-hydroxypropyl)phenyl)ethyl)-1-methyl-1-(1-methylpiperidin-4-yl)urea |
| H0522 | 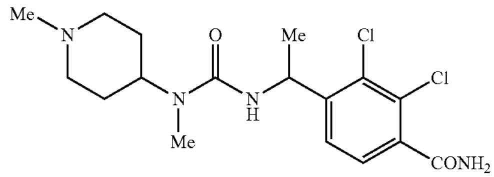 [SMILES: CC(NC(=O)N(C)C1CCN(C)CC1)c1ccc(C(N)=O)c(Cl)c1Cl] | 2,3-dichloro-4-(1-(3-methyl-3-(1-methylpiperidin-4-yl)ureido)methyl)benzamide |
| H0523 | 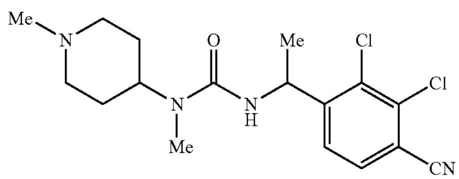 [SMILES: CC(NC(=O)N(C)C1CCN(C)CC1)c1ccc(C#N)c(Cl)c1Cl] | 3-(1-(2,3-dichloro-4-cyanophenyl)ethyl)-1-methyl-1-(1-methylpiperidin-4-yl)urea |
| H0876 | 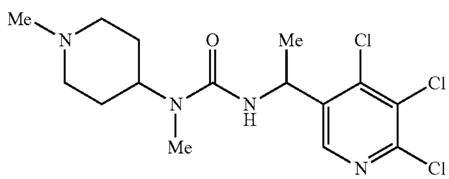 [SMILES: CC(NC(=O)N(C)C1CCN(C)CC1)c1cnc(Cl)c(Cl)c1Cl] | 1-methyl-1-(1-methylpiperidin-4-yl)-3-(1-(4,5,6-trichloropyridin-3-yl)ethyl)urea. |

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, cyclohexenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "hydroxylalkyl" refers to an alkyl group having one or more OH substituents. Example hydroxyalkyl groups include $CH_2OH$, $C_2CH_4OH$, $C_3H_6OH$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems as well as spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, pentene, hexane, and the like. In some embodiments, cycloalkyl groups can have from about 3 to about 10, or about 3 to about 7 ring-forming carbon atoms.

As used herein, "heterocyclyl" or "heterocycle" refers to a saturated or unsaturated cyclic hydrocarbon wherein one or more of the ring-forming carbon atoms of the cyclic hydrocarbon is replaced by a heteroatom such as O, S, or N. Heterocyclyl groups can be aromatic (e.g., "heteroaryl") or non-aromatic (e.g., "heterocycloalkyl"). Heterocyclyl groups can also correspond to hydrogenated and partially hydrogenated heteroaryl groups. Heterocyclyl groups can include mono- or polycyclic (e.g., having 2, 3 or 4 fused rings) ring systems. Heterocyclyl groups can be characterized as having 3-14 or 3-7 ring-forming atoms. In some embodiments, heterocyclyl groups can contain, in addition to at least one heteroatom, from about 1 to about 13, about 2 to about 10, or about 2 to about 7 carbon atoms and can be attached through a carbon atom or heteroatom. In further embodiments, the heteroatom can be oxidized (e.g., have an oxo substituent) or a nitrogen atom can be quaternized. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like, as well as any of the groups listed below for "heteroaryl" and "heterocycloalkyl." Further example heterocycles include pyrimidinyl, phenanthridinyl, phenanthrolinyl, phenazinyl, phenothiazinyl, phenoxathiinyl, phenoxazinyl, phthalazinyl, piperazinyl, piperidinyl, 3,6-dihydropyridyl, 1,2,3,6-tetrahydropyridyl, 1,2,5,6-tetrahydropyridyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzo-thiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, deca-hydroquinolinyl, 2H,6H-1,5,2dithiazinyl, dihydrofuro[2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl and isoxazolyl. Further examples of heterocycles include azetidin-1-yl, 2,5-dihydro-1H-pyrrol-1-yl, piperidin-1yl, piperazin-1-yl, pyrrolidin-1-yl, isoquinol-2-yl, pyridin-1-yl, 3,6-dihydropyridin-1-yl, 2,3-dihydroindol-1-yl, 1,3,4,9-tetrahydrocarbolin-2-yl, thieno[2,3-c]pyridin-6-yl, 3,4,10,10a-tetrahydro-1H-pyrazino[1,2-a]indol-2-yl, 1,2,4,4a,5,6-hexahydro-pyrazino[1,2-a]quinolin-3-yl, pyrazino[1,2-a]quinolin-3-yl, diazepan-1-yl, 1,4,5,6-tetrahydro-2H-benzo[f]isoquinolin-3-yl, 1,4,4a,5,6,10b-hexahydro-2H-benzo[f]isoquinolin-3-yl, 3,3a,8,8a-tetrahydro-1H-2-aza-cyclopenta[a]inden-2-yl, and 2,3,4,7-tetrahydro-1H-azepin-1-yl, azepan-1-yl.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "thioalkoxy" refers to an —S-alkyl group.

As used here, "haloalkoxy" refers to an —O-haloalkyl group. An example haloalkoxy group is OCF.

As used herein, "cycloalkyloxy" refers to —O-cycloalkyl.

As used herein, "aralkyl" refers to an alkyl group substituted by an aryl group.

As used herein, "cycloalkylalkyl" refers to an alkyl group substituted by an cycloalkyl group.

As used herein, "heterocyclylalkyl" refers to an alkyl moiety substituted by a heterocarbocyclyl group. Example heterocyclylalkyl groups include "heteroarylalkyl" (alkyl substituted by heteroaryl) and "heterocycloalkylalkyl" (alkyl substituted by heterocycloalkyl). In some embodiments, heterocyclylalkyl groups have from 3 to 24 carbon atoms in addition to at least one ring-forming heteroatom.

As used herein "oxo" refers to =O.

The compounds described herein can be asymmetric (e.g., having one or more stereocenters). The description of a compound without specifying its stereochemistry is intended to capture mixtures of stereoisomers as well as each of the individual stereoisomer encompassed within the genus.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Green and P. G. M. Wuts, Protective Groups in Organic Synthesis, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectrometry (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Pharmaceutical Compositions

Pharmaceutical compositions for preventing and/or treating a subject are further provided comprising a therapeutically effective amount of a compound of Formula I, or a pharmaceutically acceptable salt thereof, and one or more pharmaceutically acceptable excipients.

A "pharmaceutically acceptable" excipient is one that is not biologically or otherwise undesirable, i.e., the material can be administered to a subject without causing any undesirable biological effects or interacting in a deleterious manner with any of the other components of the pharmaceutical composition in which it is contained. The carrier can be selected to minimize any degradation of the active ingredient and to minimize any adverse side effects in the subject, as would be well known to one of skill in the art. The carrier can be a solid, a liquid, or both.

The disclosed compounds can be administered by any suitable route, preferably in the form of a pharmaceutical composition adapted to such a route, and in a dose effective for the treatment or prevention intended. The active compounds and compositions, for example, can be administered orally, rectally, parenterally, ocularly, inhalationaly, or topically. In particular, administration can be epicutaneous, inhalational, enema, conjunctival, eye drops, ear drops, alveolar, nasal, intranasal, vaginal, intravaginal, transvaginal, ocular, intraocular, transocular, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc.

Suitable carriers and their formulations are described in Remington: The Science and Practice of Pharmacy (19th ed.) ed. A. R. Gennaro, Mack Publishing Company, Easton, Pa., 1995. Oral administration of a solid dose form can be, for example, presented in discrete units, such as hard or soft capsules, pills, cachets, lozenges, or tablets, each containing a predetermined amount of at least one of the disclosed compound or compositions. In some forms, the oral administration can be in a powder or granule form. In some forms, the oral dose form is sub-lingual, such as, for example, a lozenge. In such solid dosage forms, the compounds of Formula I are ordinarily combined with one or more adjuvants. Such capsules or tablets can contain a controlled-release formulation. In the case of capsules, tablets, and pills, the dosage forms also can comprise buffering agents or can be prepared with enteric coatings.

In some forms, oral administration can be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also can comprise adjuvants, such as wetting, emulsifying, suspending, flavoring (e.g., sweetening), and/or perfuming agents.

In some forms, the disclosed compositions can comprise a parenteral dose form. "Parenteral administration" includes, for example, subcutaneous injections, intravenous injections, intraperitoneally, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Typically, an appropriate amount of a pharmaceutically acceptable carrier is used in the formulation to render the formulation isotonic. Examples of the pharmaceutically acceptable carrier include, but are not limited to, saline, Ringer's solution and dextrose solution. Other acceptable excipients include, but are not limited to, thickeners, diluents, buffers, preservatives, surface active agents and the like.

In some forms, the disclosed compositions can comprise a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation can include a compound which enhances absorption or penetration of the active ingredient through the skin or other affected areas. When the compounds and compositions are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes can also be used. Typical carriers include alcohol, water, mineral oil, liquid petrolatum, white petrolatum, glycerin, polyethylene glycol and propylene glycol. Penetration enhancers can be incorporated—see, for example, J Pharm Sci, 88 (10), 955-958, by Finnin and Morgan (October 1999).

Formulations suitable for topical administration to the eye include, for example, eye drops wherein the disclosed compound or composition is dissolved or suspended in suitable carrier. A typical formulation suitable for ocular or aural administration can be in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, can be incorporated together with a preservative, such as benzalkonium chloride. Such formulations can also be delivered by iontophoresis.

Other carrier materials and modes of administration known in the pharmaceutical art can also be used. The disclosed pharmaceutical compositions can be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients (3.sup.rd Ed.), American Pharmaceutical Association, Washington, 1999.

The disclosed compounds can be used, alone or in combination with other therapeutic agents, in the treatment or prevention of various conditions or disease states. The administration of two or more compounds "in combination" means that the two compounds are administered closely enough in time that the presence of one alters the biological effects of the other. The two or more compounds can be administered simultaneously, concurrently or sequentially.

Disclosed are pharmaceutical compositions comprising an effective amount of a compound of the invention or a pharmaceutically accepted salt thereof; and a pharmaceutically acceptable carrier or vehicle. These compositions may further comprise additional agents. These compositions are useful for modulating the activity of ghrelin receptor, thus to improve the prevention and treatment of ghrelin receptor associated human diseases such as obesity and/or metabolic disorders.

Methods

All of the methods of the invention may be practiced with a compound of the invention alone, or in combination with other agents.

The above-described compounds and compositions are useful for the inhibition, reduction, prevention, and/or treatment of diseases which are pathophysiologically modulated by the ghrelin receptor. Accordingly, in some forms, disclosed are methods of preventing and/or treating diseases which are pathophysiologically modulated by the ghrelin receptor, comprising administering to a subject a therapeutically effective amount of a compound of Formula I as disclosed above, or a pharmaceutically acceptable salt thereof.

Suitable subjects can include mammalian subjects. Mammals include, but are not limited to, canine, feline, bovine, caprine, equine, ovine, porcine, rodents, lagomorphs, primates, and the like, and encompass mammals in utero. In some forms, humans are the subjects. Human subjects can be of either gender and at any stage of development.

Diseases modulated by the ghrelin receptor, and potentially treatable by the methods disclosed herein, include obesity, overweight, eating disorder, diabetes, metabolic syndrome, cachexia resulting from cancer, congestive heart failure, wasting due to ageing or AIDS, chronic liver failure, chronic obstructive pulmonary disease, gastrointestinal disease, gastric disorder or substance abuse. Metabolic disorders potentially treatable by the instant methods include diabetes, Type I diabetes, Type II diabetes, inadequate glucose tolerance, insulin resistance, hyperglycemia, hyperinsulinemia, hyperlipidemia, hypertriglyceridemia, hypercholesterolemia, dyslipidemia, obesity, aging, Syndrome X, atherosclerosis, heart disease, stroke, hypertension and peripheral vascular disease. Gastric disorders potentially treatable by the instant methods include post-operative ileus (POI), diabetic gastroparesis, and opioid induced bowel dysfunction. Gastrointestinal diseases potentially treatable by the instant methods include irritable bowel syndrome, gastritis, acid reflux disease, gastroparesis, and functional dyspepsia. Substance abuse potentially treatable by the instant methods includes alcohol and drug abuse, and said drug includes amphetamines, barbiturates, benzodiazepines, cocaine, methaqualone, and opioids.

In some embodiments of the invention, the compound of Formula I is useful in the treatment of Prader-Willi Syndrome, a genetic disorder usually involving chromosome 15. Prader-Willi is characterized by obesity, hypotonia, or poor muscle tone, and significant developmental delays in children afflicted with this disorder.

In some embodiments of the invention, the compound of Formula I is useful in the treatment of an over-eating disorder. An over-eating disorder is a complex compulsion to eat. The eating may be excessive (compulsive overeating); may include normal eating punctuated with episodes of purging; or may include cycles of bingeing and purging. The most prevalent over-eating disorder is Bulimia nervosa. Another widely and rapidly spreading over-eating disorder is compulsive over-eating, also termed Binge Eating Disorder (BED). In some embodiments, the compound of Formula I is used in the treatment of BED.

In some embodiments, the compound of Formula I is useful in the treatment of Parkinson-induced constipation and gastric dysmotility. In some embodiments, the compound of Formula I is useful in the treatment of chemotherapy-induced nausea and vomiting (CINV).

In some embodiments, the compound of Formula I is useful in the treatment of inflammation, acute and chronic pain, and motion sickness.

In some embodiments, the compound of Formula I is useful in the treatment of drug and alcohol abuse. In some methods the compound of Formula I is a ghrelin receptor modulator. In some other methods the compound of Formula I is a ghrelin receptor agonist. In some methods the compound of Formula I is a ghrelin receptor antagonist. In some methods, the compound of Formula I or a pharmaceutically acceptable salt thereof, is administered by one or more routes selected from the group consisting of rectal, buccal, sublingual, intravenous, subcutaneous, intradermal, transdermal, intraperitoneal, oral, eye drops, parenteral and topical administration. In some other methods, administration is accomplished by administering an oral form of the compound of Formula I or a pharmaceutically acceptable salt thereof.

A therapeutically effective amount may vary widely depending on the severity of the disease, the age and relative health of the subject, the potency of the compound used and other factors. Therapeutically effective amounts of compounds of Formula I may range from approximately 0.01 microgram per Kg (µg/Kg) body weight per day to about 100 mg/Kg body weight per day, or from about 0.1 µg/Kg/day to about 10 mg/Kg/day, or from about 1 µg/Kg/day to about 5 mg/Kg/day, or from about 10 µg/Kg/day to about 5 mg/Kg/day, or from about 100 µg/Kg/day to about 5 mg/Kg/day, or from about 500 µg/Kg/day to about 5 mg/Kg/day.

Definitions of Terms

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

1. A, an, the

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

2. Abbreviations

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, "M" for molar, and like abbreviations).

3. About

The term "about," when used to modify the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. Whether modified by the term "about" the claims appended hereto include equivalents to these quantities.

4. Comprise

Throughout the description and claims of this specification, the word "comprise" and variations of the word, such as "comprising" and "comprises," means "including but not limited to," and is not intended to exclude, for example, other additives, components, integers or steps.

5. Ghrelin Receptor Agonist

A ghrelin receptor agonist is any molecule that binds to and activates the Ghrelin receptor in the cells.

6. Ghrelin Receptor Antagonist

A ghrelin receptor antagonist is any molecule that binds to and inhibits the activity of Ghrelin receptor.

7. Pathophysiologically Mediated by Ghrelin Receptor

Something is "pathophysiologically mediated by the ghrelin receptor" if the ghrelin receptor is involved in the functional changes in body associated with or resulting from disease or injury.

8. Obesity

Obesity is a medical condition in which excess body fat has accumulated to the extent that it may have an adverse effect on health, leading to reduced life expectancy and/or increased health problems. Obesity treatment includes inducing weight loss, reducing bodyweight, reducing food intake, reducing appetite, increasing metabolic rate, reducing fat intake, reducing carbohydrate craving; or inducing satiety. The obesity-related disorders herein are associated with, caused by, or result from obesity. Examples of obesity-related disorders include overeating, binge eating, and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. Further examples of obesity-related disorders are metabolic syndrome, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer, nicotine addiction, substance addiction and alcoholism. The compositions of the present invention are also useful for reducing the risk of secondary outcomes of obesity, such as reducing the risk of left ventricular hypertrophy.

9. Metabolic Disorder

A metabolic disorder is a disorder of metabolism, such as diabetes, Type I diabetes, Type II diabetes, inadequate glucose tolerance, insulin resistance, hyperglycemia, hyperinsulinemia, hyperlipidemia, hypertriglyceridemia, hypercholesterolemia, dyslipidemia, obesity, aging, Syndrome X, atherosclerosis, heart disease, stroke, hypertension and peripheral vascular disease.

10. Congestive Heart Failure

Congestive heart failure (CHF) is a condition in which the heart's function as a pump to deliver oxygen rich blood to the body is inadequate to meet the body's needs. Congestive heart failure can be caused by diseases that weaken the heart muscle, or diseases that cause stiffening of the heart muscles, or diseases that increase oxygen demand by the body tissue beyond the capability of the heart to deliver. Many diseases can impair the pumping action of the ventricles. For example, the muscles of the ventricles can be weakened by heart attacks or infections (myocarditis). The diminished pumping ability of the ventricles due to muscle weakening is called systolic dysfunction. After each ventricular contraction (systole) the ventricle muscles need to relax to allow blood from the atria to fill the ventricles. This relaxation of the ventricles is called diastole. Diseases such as hemochromatosis or amyloidosis can cause stiffening of the heart muscle and impair the ventricles' capacity to relax and fill; this is referred to as diastolic dysfunction. The most common cause of this is longstanding high blood pressure resulting in a thickened (hypertrophied) heart. Additionally, in some patients, although the pumping action and filling capacity of the heart may be normal, abnormally high oxygen demand by the body's tissues (for example, with hyperthyroidism) may make it difficult for the heart to supply an adequate blood flow (called high output heart failure). In some patients one or more of these factors can be present to cause congestive heart failure. Congestive heart failure can affect many organs of the body. For example, the weakened heart muscles may not be able to supply enough blood to the kidneys, which then begin to lose their normal ability to excrete salt (sodium) and water. This diminished kidney function can cause to body to retain more fluid. The lungs may become congested with fluid (pulmonary edema) and the person's ability to exercise is decreased. Fluid may likewise accumulate in the liver, thereby impairing its ability to rid the body of toxins and produce essential proteins. The intestines may become less efficient in absorbing nutrients and medicines. Over time, untreated, worsening congestive heart failure will affect virtually every organ in the body.

11. Agonism Action

Agonism action refers to the binding of a molecule to a receptor that leads to the activation of the receptor, thus triggering a cellular response similar to the cellular response for a known agonist for the receptor.

12. Antagonism Action

Antagonism action refers to the binding of a molecule to a receptor that leads to the inhibition of the receptor.

13. Modulate

To modulate, or forms thereof, means either increasing, decreasing, or maintaining a cellular activity mediated through a cellular target. It is understood that wherever one of these words is used it is also disclosed that it could be 1%, 5%, 10%, 20%, 50%, 100%, 500%, or 1000% increased from a control, or it could be 1%, 5%, 10%, 20%, 50%, or 100% decreased from a control.

14. Optional

"Optional" or "optionally" means that the subsequently described event or circumstance may or may not occur, and that the description includes instances where said event or circumstance occurs and instances where it does not.

15. Or

The word "or" or like terms as used herein means any one member of a particular list and also includes any combination of members of that list.

16. Publications

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

17. Subject

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

18. Treating

By "treating" or "treatment" is meant the medical management of a patient with the intent to cure, ameliorate, stabilize, or prevent a disease, pathological condition, or disorder. These terms include active treatment, that is, treatment directed specifically toward the improvement of a disease, pathological condition, or disorder, and also includes causal treatment, that is, treatment directed toward removal of the cause of the associated disease, pathological condition, or disorder. These terms can mean that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease. In certain situations a treatment can inadvertently cause harm. In addition, these terms include palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. These terms mean both treatment having a curing or alleviating purpose and treatment having a preventive purpose. The treatment can be made either acutely or chronically. It is understood that treatment can mean a reduction or one or more symptoms or characteristics by at least 5% 10%, 20%, 30%, 40%, 50%, 60%, 70%, 80%, 90%, 95%, 99%, 99.9%, 99.99%, 100%, relative to a control. In the context of these terms, preventing refers to the ability of a compound or composition (such as the disclosed compounds and compositions) to prevent a disease identified herein in patients diagnosed as having the disease or who are at risk of developing such disease. In this context, preventing includes the delaying the onset of the disease relative to a control. These terms do not require that the treatment in fact be effective to produce any of the intended results. It is enough that the results are intended.

19. Therapeutically Effective

The term "therapeutically effective" means that the amount of the composition used is of sufficient quantity to treat a subject as defined herein.

20. Toxicity

Toxicity is the degree to which a substance, molecule, is able to damage something, such as a cell, a tissue, an organ, or a whole organism, that has been exposed to the substance or molecule. For example, the liver, or cells in the liver, hepatocytes, can be damaged by certain substances. The methods of the present invention are preferably non-toxic.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Synthesis of Intermediate 1k

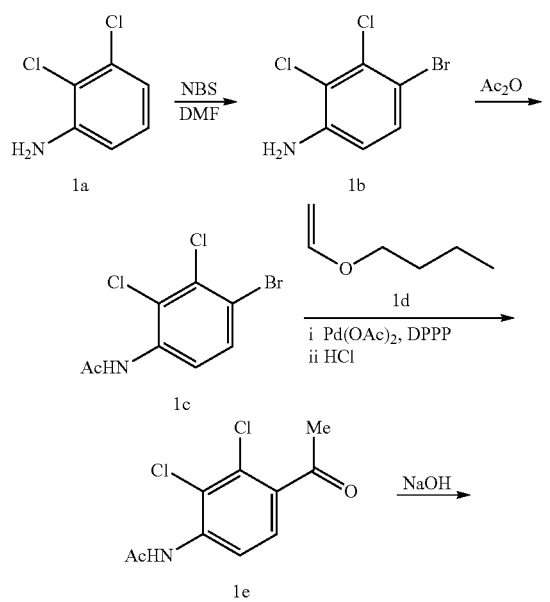

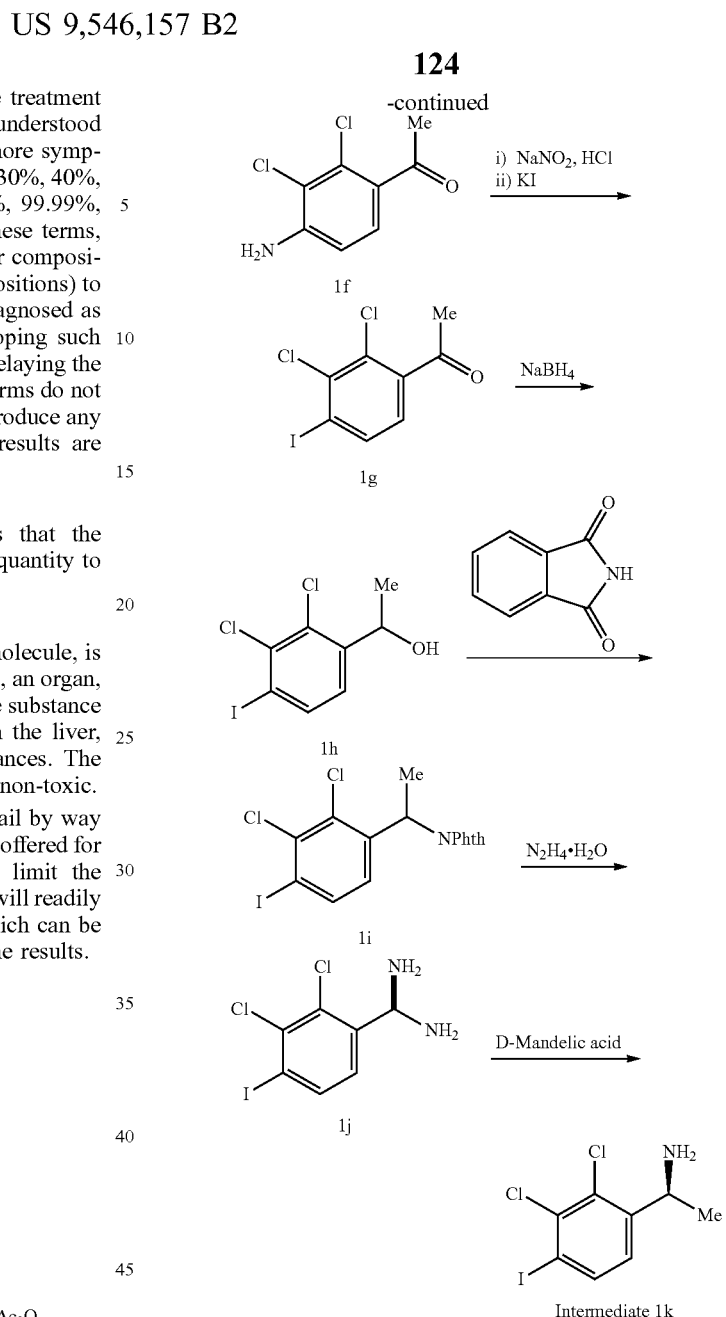

Step 1:

To a solution of 1a (100 g, 0.62 mol) in DMF (1.2 L) was added N-bromosuccinimide (110 g, 0.62 mol) at 0° C. The mixture was stirred at room temperature for 4 h, then water (800 mL) was added and the resulting mixture was extracted with EtOAc (3×500 mL). The combined organic layers were dried over anhydrous $Na_2SO_4$ and concentrated under reduced pressure. The residue was triturated with petroleum ether to provide 1b (133.7 g, 89% yield) as a brown solid. $^1$H-NMR (CDCl$_3$, 300 MHz): δ=7.30 (d, 1H), 6.59 (d, 1H), 4.22 (br, 2H). LC-MS: 241 [M+1]$^+$.

Step 2:

To a solution of 1b (133.7 g, 0.55 mol) in dry $CH_2Cl_2$ (1.5 L) was added acetic anhydride (110 g, 0.62 mol) dropwise over a period of 20 minutes at room temperature. The mixture was stirred at room temperature overnight, then diluted with $CH_2Cl_2$ (300 mL) and washed with water (150 mL) and brine (200 mL). The organic layer was separated, dried over anhydrous Na₂SO₄ and concentrated under reduced pressure. The residue was triturated with petroleum ether (300 mL) to provide compound 1c (143.0 g, 91% yield) as a white solid. ¹H-NMR (CDCl₃, 400 MHz): δ=8.26 (d, 1H), 7.63 (br, 1H), 7.54 (d, 1H), 2.26 (s, 3H). LC-MS: 280 [M−1]⁻.

Step 3:

A mixture of compound 1c (50.0 g, 0.18 mol), butyl vinyl ether (1d, 89.0 g, 0.89 mol), bis(1,3-diphenylphosphino)propane (DPPP, 22.0 g, 0.053 mol), TEA (100 mL, 0.71 mol) and Pd(OAc)₂ (6.4 g, 0.027 mol) in DMSO (1.2 L) was heated at 130° C. under N₂ overnight. After the reaction was completed, the mixture was cooled to 0° C. and 2N HCl (480 mL) was added dropwise over a period of 30 minutes. Then, the mixture was extracted with EtOAc (3×100 mL). The combined organic layers were dried over anhydrous Na₂SO₄ and concentrated under reduced pressure. The residue was purified by column chromatography (silica, EtOAc:PE=1:10) to provide 1e (19.5 g, 45% yield) as a yellow solid. ¹H-NMR (CDCl₃, 400 MHz): δ=8.46 (d, 1H), 7.82 (br, 1H), 7.51 (d, 1H), 2.63 (s, 3H), 2.29 (s, 3H). LC-MS: 244 [M−1]⁻.

Step 4:

To a solution of 1e (21.9 g, 89.4 mmol) in MeOH (350 mL) was added 2N NaOH solution (350 mL) at room temperature. The mixture was heated at 50° C. overnight, then cooled and concentrated under reduced pressure. The resulting solid was triturated with water (100 mL) for 30 min and filtered to provide 1f (18.0 g, 98% yield) as a brown solid. ¹H-NMR (CDCl₃, 400 MHz): δ=7.48 (d, 1H), 6.68 (d, 1H), 4.56 (br, 2H), 2.62 (s, 3H). LC-MS: 202[M−1]⁻.

Step 5:

To a mixture of compound 1f (18.0 g, 89.2 mmol) and ice (360 g) in conc. HCl (180 mL) was added a solution of NaNO₂ (9.2 g, 133.7 mmol) in water (20 mL) dropwise over a period of 30 minutes, and the resulting mixture stirred in an ice bath for 30 min. A solution of KI (74.0 g, 446 mmol) in water (360 mL) was added dropwise over 45 min at 0° C. The mixture was stirred for 30 min and then extracted with EtOAc (3×100 mL). The combined organic layers were dried over anhydrous Na₂SO₄ and concentrated under reduced pressure. The residue was purified by column chromatography (silica, EtOAc:PE=1:40) to provide 1g (23.9 g, 86% yield) as a yellow solid. ¹H-NMR (CDCl₃, 400 MHz): δ=7.6 (d, 1H), 7.06 (d, 1H), 2.62 (s, 3H).

Step 6:

To a solution of 1g (23.9 g, 76.1 mmol) in MeOH (100 mL)/THF (100 mL) was slowly added NaBH₄ (2.9 g, 76.1 mmol) at 0° C. The mixture was stirred at room temperature for 5 min, and then quenched with water (100 mL). The mixture was extracted with EtOAc (3×100 mL). The combined organic layers were dried over anhydrous Na₂SO₄ and concentrated under reduced pressure. The residue was purified by column chromatography (silica, EtOAc:PE=1:10) to provide 1h (22.4 g, 93% yield) as a white solid. ¹H-NMR (CDCl₃, 400 MHz): δ=7.81 (d, 1H), 7.26 (d, 1H), 5.23 (q, 1H), 2.17 (br, 1H), 1.47 (d, 3H).

Step 7:

To a mixture of 1h (22.4 g, 70.9 mmol), phthalimide (12.5 g, 85.0 mmol) and PPh₃ (22.3 g, 85.0 mmol) in dry THF (450 mL) was added DIAD (21.5 g, 106.3 mmol) at room temperature under N₂ protection. The mixture was stirred at room temperature overnight and then concentrated under reduced pressure. The residue was purified by column chromatography (silica, EtOAc:PE=1:15) to provide 1i (18.5 g, 58% yield) as a white solid. ¹H-NMR (CDCl₃, 400 MHz): δ=7.78-7.84 (m, 3H), 7.70-7.73 (m, 2H), 7.41-7.43 (d, 1H), 5.76-5.81 (q, 1H), 1.84 (d, 3H).

Step 8:

A solution of 1i (7.2 g, 16.2 mmol) and hydrazine hydrate (98%, 4.0 g, 80.9 mmol) in MeOH (150 mL) was heated under reflux for 2 h, then cooled and concentrated under reduced pressure. The residue was diluted with water (100 mL) and extracted with CH₂Cl₂ (3×100 mL). The combined organic layers were dried over anhydrous Na₂SO₄ and concentrated under reduced pressure to give 1j (3.8 g, 75% yield) as a white solid. ¹H-NMR (CDCl₃, 400 MHz): δ=7.81 (d, 1H), 7.25 (d, 1H), 4.55 (q, 1H), 1.36-1.38 (d, 3H). LC-MS: 316 [M+1]⁺.

Step 9:

To a solution of 1j (41.0 g, 0.13 mol) in methyl tert-butyl ether (750 mL) was added slowly a solution of D-mandelic acid (7.8 g, 0.052 mol) in methyl tert-butyl ether (110 mL) at 45° C. The mixture was stirred at this temperature for 30 min then cooled and filtered. White solid obtained was partitioned between 5% NaOH solution (300 mL) and methyl tert-butyl ether (300 mL). The bi-phases were separated and the aqueous phase was extracted with methyl tert-butyl ether (300 mL). The combined organic layer was concentrated to provide Intermediate 1k (12 g, 58.5% yield) as a white solid (ee %=98.0%, Chiralpak AD-H, 5 μm, 4.6*250 mm, mobile phase: Hex:EtOH:DEA=80:20:0.2), retention time=6.408 min).

Example 2

Synthesis of Compound 2b

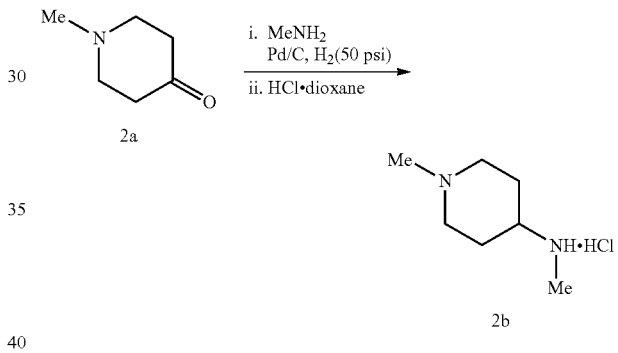

A suspension of N-methyl-4-piperidone 2a (13.3 g, 58.6 mmol), NH₂Me (30% in MeOH, 100 mL) and Pd/C (0.66 g) in MeOH (200 mL) was heated at 60° C. under H₂ atmosphere (50 psi) overnight, then cooled and filtered. The filtrate was concentrated under reduced pressure and the residue was dissolved in HCl in dioxane (3N, 100 mL) and stirred for 30 min. The precipitate was filtered and washed with EtOAc (50 mL) to provide 2b (7.7 g, 54% yield) as white powder. ¹H-NMR (DMSO, 400 MHz): δ=9.50 (br, 2H), 3.48 (d, 2H), 3.15-3.16 (m, 1H), 2.96-3.01 (m, 2H), 2.70 (s, 3H), 2.51 (s, 3H), 2.22-2.28 (m, 2H), 1.94-2.02 (m, 2H), LC-MS: 129 [M+1]⁺.

Example 3

Synthesis of Compound H0603

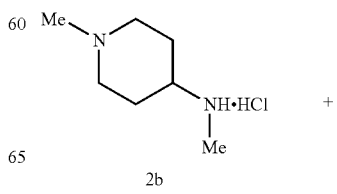

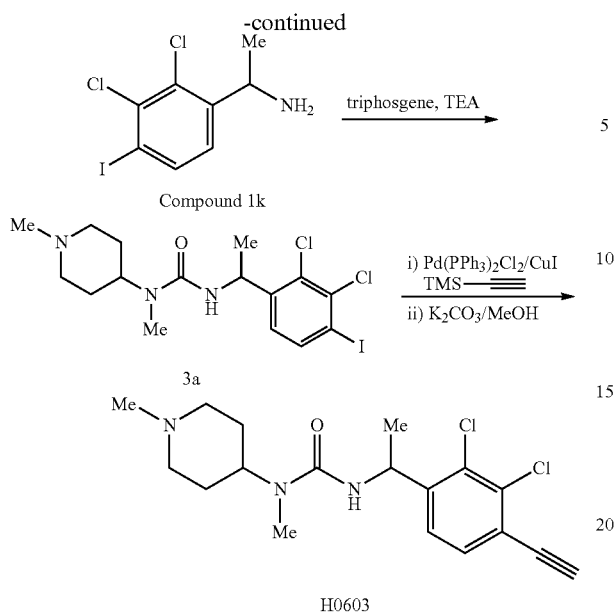

Example 4

Synthesis of Compound H0700

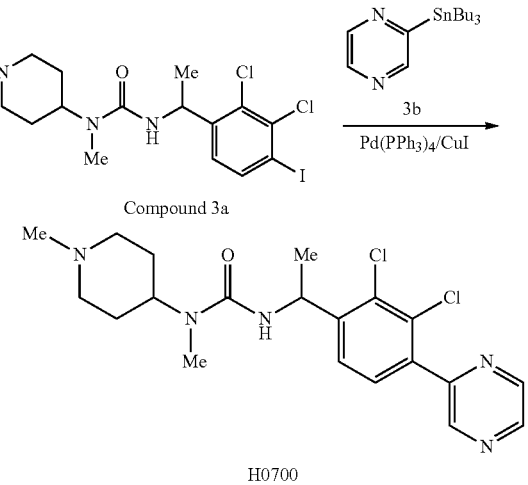

Step 1:

To a solution of 1k (1.83 g, 5.8 mmol) in $CH_2Cl_2$ (70 mL) was added TEA (5.6 mL, 40.6 mmol) and triphosgene (1.29 g, 4.4 mmol) at 0° C. The mixture was stirred for 20 min, then 2b (1.14 g, 6.97 mmol) was added. The ice bath was removed and the mixture stirred for 30 min, then concentrated under reduced pressure. The residue was partitioned between $CH_2Cl_2$ (50 mL) and saturated $NaHCO_3$ solution (50 mL). The organic phase was separated, washed with brine, dried with anhydrous $Na_2SO_4$ and concentrated under reduced pressure. The residue was triturated with a mixture of EtOAc (1 mL) and petroleum ether (20 mL) to provide compound 3a (2.31 g, 85% yield) as a white solid. $^1$H-NMR ($CDCl_3$, 400 MHz): δ=7.74 (d, 1H), 6.94 (d, 1H), 5.19-5.21 (m, 1H), 4.95 (d, 1H), 4.48-4.51 (m, 1H), 3.54-3.57 (m, 2H), 2.72-2.84 (m, 8H), 2.20-2.27 (m, 2H), 1.70-1.77 (m, 2H), 1.45 (d, 3H). LC-MS: 470 $[M+1]^+$.

Step 2:

A mixture of 3a (3 g, 6.38 mmol), Trimethylsilylacetylene (3.1 g, 31.9 mmol), $Pd(PPh_3)_2Cl_2$ (210 mg, 0.3 mmol) and CuI (85 mg, 0.45 mmol) in TEA (60 mL) was heated at 80° C. under $N_2$ overnight, then cooled, diluted with $CH_2Cl_2$ (40 mL) and filtered. The filtrate was concentrated under reduced pressure and the residue was partitioned between EtOAc (40 mL) and water (40 mL). The organic phase was separated, dried with anhydrous $Na_2SO_4$ and concentrated under reduced pressure. The residue was purified by column chromatography (silica, methanol:dichloromethane 1:30, 1% $NH_4OH$) to provide 2.4 g of light yellow solid which was dissolved in a suspension of $K_2CO_3$ (0.75 g, 5.45 mmol) in MeOH (40 mL) and stirred at room temperature for 30 min. The mixture was filtered and concentrated under reduced pressure and the residue was partitioned between EtOAc (40 mL) and water (40 mL). The organic phase was separated, dried with anhydrous $Na_2SO_4$ and concentrated under reduced pressure to provide H0603 (1.9 g, 82% yield) as a white powder. $^1$H-NMR ($CDCl_3$, 400 MHz): δ=7.43 (d, 1H), 7.21 (d, 1H), 5.27-5.31 (m, 1H), 4.81 (d, 1H), 4.09-4.17 (m, 1H), 3.38 (s, 1H), 2.86-2.91 (m, 2H), 2.80 (s, 3H), 2.27 (s, 3H), 1.98-2.09 (m, 2H), 1.61-1.65 (m, 2H), 1.48-1.52 (m, 2H), 1.46 (d, 3H). LC-MS: 368 $[M+1]^+$.

A mixture of 3a (3.0 g, 6.38 mmol), 3b (3.54 g, 9.57 mmol), CuI (243 mg, 1.27 mmol) and $Pd(PPh_3)_4$ (1.47 g, 1.27 mmol) in 1,2-dimethoxyethane (60 mL) was heated at 100° C. under $N_2$ overnight, then diluted with $CH_2Cl_2$ (100 mL) and filtered. The filtrate was washed with brine (100 mL). The organic phase was separated, dried with anhydrous $Na_2SO_4$ and concentrated under reduced pressure. The residue was purified by column chromatography (silica, MeOH:$CH_2Cl_2$ 1:30, 1% $NH_4OH$) to provide H0700 (1.3 g, 48% yield) as a white solid. $^1$H-NMR ($CDCl_3$, 400 MHz): δ=8.90 (d, 1H), 8.66-8.67 (m, 1H), 8.58 (d, 1H), 7.45 (d, 1H), 7.38 (d, 1H), 5.35-5.39 (m, 1H), 4.87 (d, 1H), 4.13-4.14 (m, 1H), 2.85-2.90 (m, 2H), 2.81 (s, 3H), 2.26 (s, 3H), 1.98-2.05 (m, 2H), 1.69-1.77 (m, 2H), 1.54-1.64 (m, 2H), 1.51 (d, 3H). LC-MS: 422 $[M+1]^+$.

Example 5

Synthesis of Compound H0722

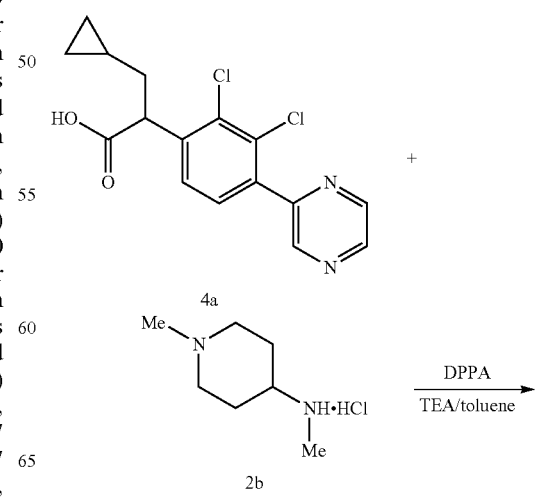

-continued

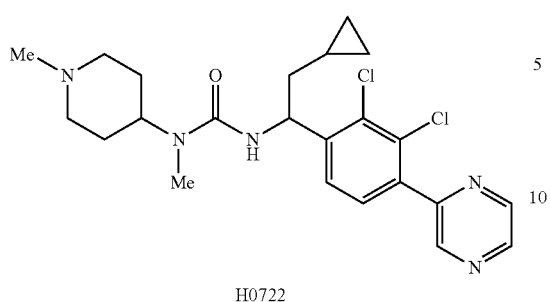

H0722

A mixture of compound 4a (1.39 g, 4.08 mmol), 2b (1.0 g, 6.1 mmol), DPPA (1.23 g, 4.5 mmol) and TEA (3 mL) in dry toluene (100 mL) was heated under reflux overnight, then cooled and concentrated under reduced pressure. The residue was partitioned between EtOAc (50 mL) and saturated Na$_2$CO$_3$ solution (50 mL). The organic phase was separated, washed with brine (50 mL), dried with anhydrous Na$_2$SO$_4$ and concentrated under reduced pressure. The residue was purified by column chromatography (silica, methanol:dichloromethane 1:40, 1% NH$_4$OH) to provide H0722 (1.03 g, 55% yield) as a white solid. $^1$H-NMR (CDCl$_3$, 400 MHz): δ=8.89 (d, 1H), 8.66-8.67 (m, 1H), 8.58 (d, 1H), 7.43 (d, 1H), 7.37 (d, 1H), 5.35-5.38 (m, 1H), 5.21 (d, 1H), 4.15-4.17 (m, 1H), 2.85-2.90 (m, 2H), 2.83 (s, 3H), 2.26 (s, 3H), 1.97-2.05 (m, 2H), 1.66-1.80 (m, 6H), 0.68-0.70 (m, 1H), 0.50-0.54 (m, 2H), 0.14-0.15 (m, 2H) LC-MS: 462 [M+1]$^+$.

Example 6

Synthesis of Compound H0751

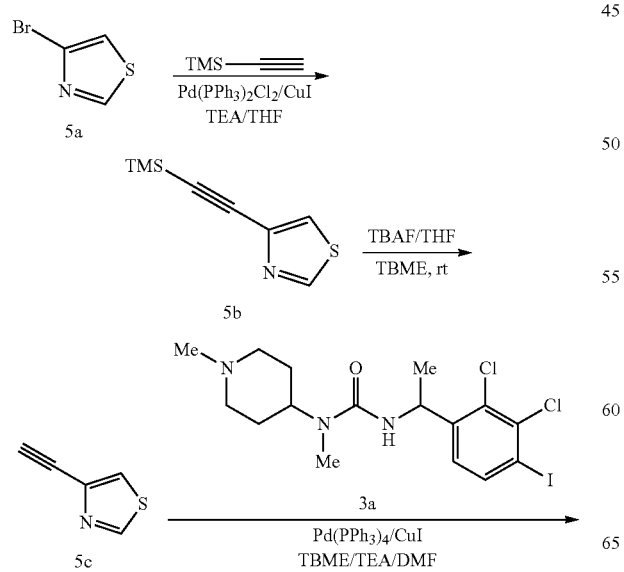

-continued

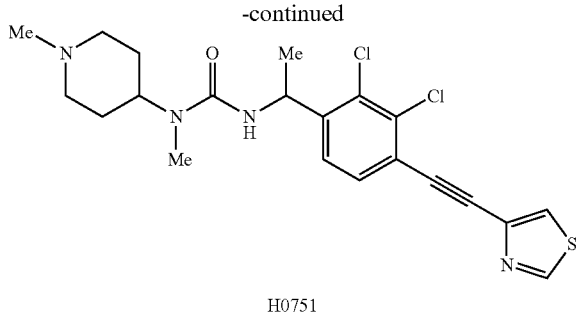

H0751

Step 1:

The mixture of 5a (5 g, 30.5 mmol), Trimethylsilylacetylene (3.6 g, 36.6 mmol), Pd(PPh$_3$)$_2$Cl$_2$ (210 mg, 0.3 mmol) and CuI (85 mg, 0.45 mmol) in TEA (150 mL) was heated at 80° C. for 3 h under N$_2$, then cooled, diluted with Et$_2$O (100 mL) and washed with brine (100 mL). The organic phase was separated, dried over anhydrous Na$_2$SO$_4$ and concentrated under reduced pressure. The residue was purified by column chromatography (silica, EtOAc/petroleum ether 1:15) to provide 5b (4.3 g, 79% yield) as a yellow oil. $^1$H-NMR (CDCl$_3$, 400 MHz): δ=8.74 (d, 1H), 7.53 (d, 1H), 0.26 (s, 9H)

Step 2:

To a solution of compound 5b (4.1 g, 22.5 mmol) in TBME (100 mL) at room temperature was added Bu$_4$NF (1 M in THF) (22.5 ml, 22.5 mmol). The mixture was stirred at room temperature for 30 min, then quenched with water (100 mL). The organic phase was separated, dried over anhydrous Na$_2$SO$_4$ and filtered to afford crude compound 7c in TBME (80 mL) which was used directly in next step without further purification.

Step 3:

A solution of crude compound 5c in TBME was added to a mixture of 3a (3 g, 6.3 mmol), Pd(PPh$_3$)$_2$Cl$_2$ (660 mg, 0.95 mmol), CuI (180 mg, 0.95 mmol) in DMF (50 ml) and TEA (10 mL). The mixture was heated at 110° C. under N$_2$ overnight in a sealed tube, then cooled, diluted with CH$_2$Cl$_2$ (100 mL) and filtered. The filtrate was washed with brine (100 mL) and the organic phase was separated, dried over anhydrous Na$_2$SO$_4$ and concentrated under reduced pressure. The residue was purified by column chromatography (silica, methanol:dichloromethane 1:30, 1% NH$_4$OH) to provide H0751 (1.18 g, 40% yield) as a yellow solid. $^1$H-NMR (CDCl$_3$, 400 MHz): δ=8.76 (d, 1H). 7.59 (d, 1H), 7.42 (d, 1H), 7.16 (d, 1H), 5.22-5.26 (m, 1H), 4.73-4.74 (d, 1H), 4.03-4.09 (m, 1H), 2.81 (br, 2H), 2.73 (s, 3H), 2.19 (s, 3H), 1.91-1.99 (m, 2H), 1.63-1.69 (m, 2H), 1.52-1.62 (m, 2H), 1.41 (d, 3H). LC-MS: 451 [M+1]$^+$.

Example 7

Synthesis of Compound H0754

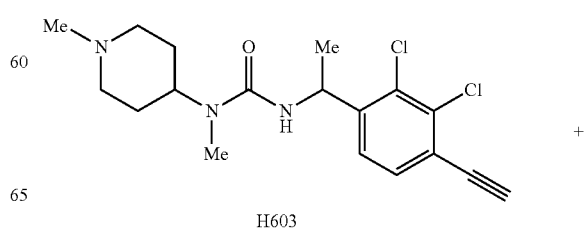

H603

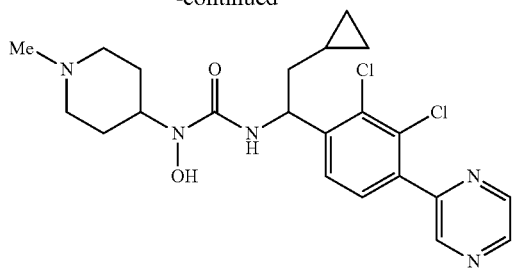

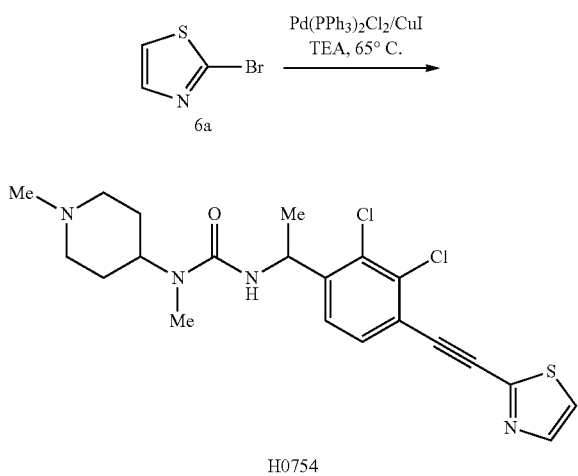

H0754

A mixture of H0603 (2.2 g, 6 mmol), 6a (2.97 g, 18 mmol), Pd(PPh₃)₂Cl₂ (0.66 g, 0.9 mmol) and CuI (264 mg, 1.38 mmol) in TEA (50 mL) was heated at 65° C. under N₂ overnight, then cooled, diluted with CH₂Cl₂ (100 mL) and filtered. The filtrate was concentrated under reduced pressure and the residue was partitioned between EtOAc (50 mL) and water (50 mL). The organic phase was separated, dried with anhydrous Na₂SO₄ and concentrated under reduced pressure. The residue was purified by column chromatography (silica, methanol:dichloromethane 1:30, 1% NH₄OH) to provide H0754 (990 mg, 37% yield) as a white solid. $^1$H-NMR (CDCl₃, 300 MHz): δ=7.91 (d, 1H), 7.54 (d, 1H), 7.46 (d, 1H), 7.22 (d, 1H), 5.32-5.26 (m, 1H), 4.99 (d, 1H), 4.47-4.60 (m, 1H), 3.40-3.62 (m, 2H), 2.88 (s, 3H), 2.76-2.91 (m, 2H), 2.82 (s, 3H), 1.70-1.90 (m, 4H), 1.51 (d, 3H). LC-MS: 451 [M+1]⁺.

Example 8

Synthesis of Compound H0761

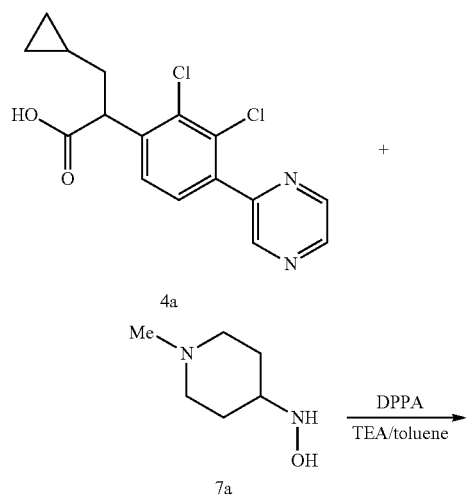

H0761

A mixture of compound 4a (2.3 g, 6.78 mmol), DPPA (1.86 g, 6.78 mmol) and TEA (10.2 mL) in dry toluene (200 mL) was stirred at 110° C. for 2 h, then cooled to room temperature and compound 7a (1.75 g, 13.56 mmol) was added. The mixture was stirred at room temperature overnight, and then concentrated under reduced pressure. The residue was partitioned between EtOAc (100 mL) and saturated Na₂CO₃ solution (100 mL). The organic phase was separated, washed with brine (100 mL), dried over anhydrous Na₂SO₄ and concentrated under reduced pressure. The residue was purified by column chromatography (silica, methanol:dichloromethane 1:30, 1% NH₄OH) to provide H0761 (1.4 g, 48.3% yield) as a white solid. $^1$H-NMR (CDCl₃, 400 MHz): δ=10.11 (s, 1H), 8.91 (d, 1H), 8.66 (m, 1H), 8.57 (d, 1H), 7.46 (d, 1H), 7.36 (d, 1H), 6.84 (d, 1H), 5.35 (m, 1H), 3.97-4.04 (m, 1H), 2.86-2.93 (m, 2H), 2.25 (s, 3H), 1.93-2.13 (m, 4H), 1.79-1.86 (m, 1H), 1.64-1.72 (m, 2H), 1.55-1.58 (d, 1H), 0.65-0.70 (m, 1H), 0.46-0.50 (m, 2H), 0.11-0.14 (m, 2H). LC-MS: 464 [M+1]⁺.

Example 9

Synthesis of Compound H0764

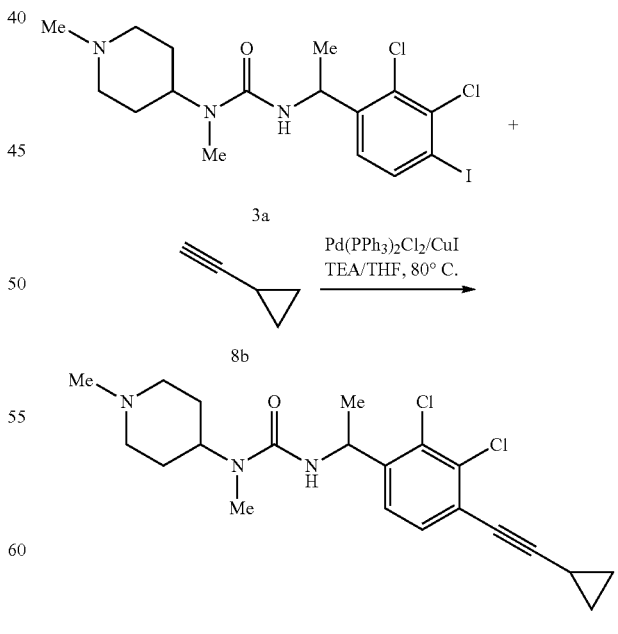

H0764

To a solution of 3a (2.0 g, 4.26 mmol) and 8b (1.4 g, 21.2 mmol) in dry THF (10 mL) and TEA (1.8 g, 17 mmol) was added Pd(PPh$_3$)$_2$Cl$_2$ (597 mg, 0.85 mmol) and CuI (220 mg, 1.16 mmol) at room temperature under N$_2$. The mixture was heated at 80° C. overnight in a sealed tube, then cooled, diluted with CH$_2$Cl$_2$ (50 mL) and filtered. The filtrate was washed with brine (50 mL) and the organic phase was separated, dried over anhydrous Na$_2$SO$_4$ and concentrated under reduced pressure. The residue was purified by column chromatography (silica, methanol:dichloromethane 1:30, 1% NH$_4$OH) to provide H0764 (990 mg, 37% yield) as a white solid. $^1$H-NMR (CDCl$_3$, 400 MHz): δ=7.27 (d, 1H), 7.12 (d, 1H), 5.24-5.29 (m, 1H), 4.78 (d, 1H), 4.07-4.14 (m, 1H), 2.74-2.88 (m, 2H), 2.76 (s, 3H), 2.24 (s, 3H), 1.96-2.04 (m, 2H), 1.40-1.73 (m, 5H), 1.38 (d, 3H), 0.70-0.90 (m, 4H). LC-MS: 408 [M+1]$^+$.

Example 10

Synthesis of Compound H0795

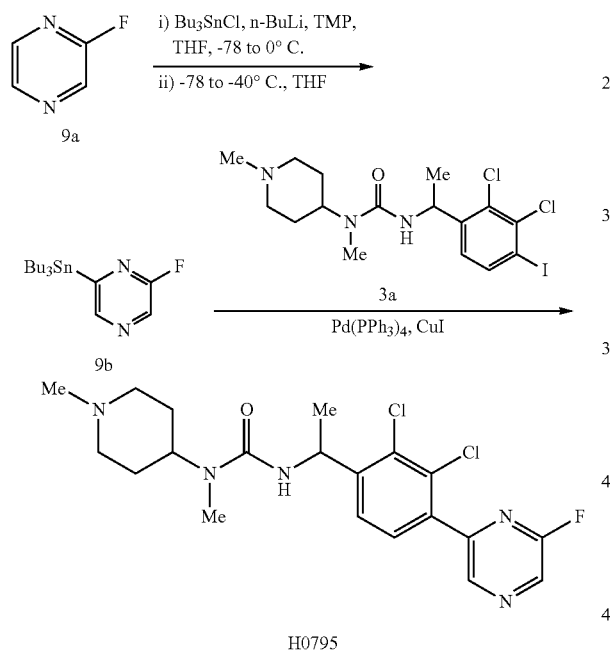

Step 1:

To a 2.5 M solution of n-butyllithium (40 mL, 0.1 mol) in anhydrous THF (250 mL) cooled to −78° C. under N$_2$ protection was added TMP (2,2,6,6-tetramethylpiperidine, 15 g, 0.106 mol) dropwise over a period of 20 minutes. The mixture was warmed to 0° C. by replacing the dry ice/acetone bath with an ice bath and stirred for 1.5 h. The mixture was cooled back to −78° C. and a solution of 9a (3 g, 0.03 mol) and tributyltin chloride (10 g, 0.03 mol) in 50 mL of dry THF was added over 10 min. The mixture was stirred at −78° C. for 6 h, then warmed to −40° C. by replacing the dry ice/acetone bath with an dry ice/acetonitrile bath. A solution of 35% HCl, ethanol and THF (1:4:5) was added. The mixture was warmed to room temperature and washed with saturated NaHCO$_3$ solution (100 mL) and extracted with EtOAc (3×100 mL). The combined organic layers were dried over anhydrous Na$_2$SO$_4$ and concentrated under reduced pressure. The residue was purified by column chromatography (silica, EtOAc:petroleum ether=1:15) to provide 9b (3.4 g, 29% yield) as light yellow oil. $^1$H-NMR (CDCl$_3$, 300 MHz): δ=8.41 (d, 1H), 8.17 (d, 1H), 1.8-0.53 (m, 27H).

Step 2:

To a solution of 3a (2.0 g, 4.4 mmol) and 9b (3.4 g, 9.35 mmol) in 1,2-dimethoxyethane (200 mL) were added Pd(PPh$_3$)$_4$ (800 mg, 0.69 mmol) and CuI (40 mg, 0.21 mmol) at room temperature under N$_2$. The mixture was then heated at 90° C. overnight, then cooled, diluted with CH$_2$Cl$_2$ (100 mL) and filtered. The filtrate was washed with brine (100 mL) and the organic phase was separated, dried over anhydrous Na$_2$SO$_4$ and concentrated under reduced pressure. The residue was purified by column chromatography (silica, MeOH:CH$_2$Cl$_2$, 1:30, 1% NH$_4$OH) to provide compound H0795 (1.0 g, 51% yield) as a white solid. $^1$H-NMR (CDCl$_3$, 400 MHz): δ=8.83 (d, 1H), 8.44 (d, 1H), 7.46 (d, 1H), 7.22 (d, 1H), 5.26-5.30 (m, 1H), 4.99 (d, 1H), 4.47-4.60 (m, 1H), 2.90-2.95 (m, 2H), 2.83 (s, 3H), 2.32 (s, 3H), 2.10-2.17 (m, 2H), 1.78-1.83 (m, 2H), 1.59-1.64 (m, 2H), 1.51 (d, 3H). LC-MS: 440 [M+1]$^+$.

Example 11

Synthesis of H0816

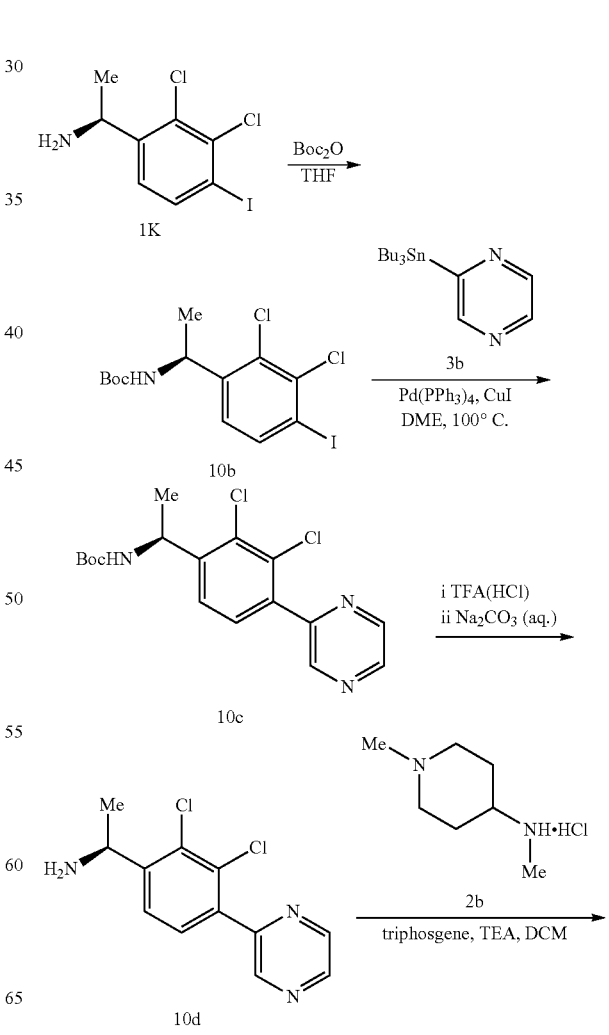

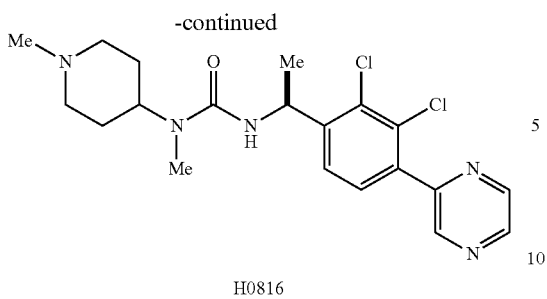

H0816

Step 1:
To a solution of 1k (12.0 g, 38.1 mmol), sat. NaHCO₃ solution (120 mL) in THF (480 mL), was added (Boc)₂O (16.6 g, 76.2 mmol) at r.t. Then the mixture was stirred at r.t. overnight. Ethyl acetate (500 mL) and water (500 mL) were added to the mixture. The organic layer was separated, washed with brine (500 mL), dried over anhydrous Na₂SO₄ and concentrated under reduced pressure. The residue was purified by column chromatography (silica, EA:PE=1:5) to provide 10b (15.4 g, 97.5% yield) as a white solid. ¹H-NMR (CDCl₃, 400 MHz): δ=7.76 (d, 1H), 6.99 (d, 1H), 5.05 (s, 1H), 4.97 (s, 1H), 1.27 (s, 12H).

Step 2:
To a solution of 10b (5.0 g, 12.0 mmol) and 3b (5.3 g, 14.4 mmol) in 1,2-dimethoxyethane (150 mL) were added Pd(PPh₃)₄ (1.39 g, 2.4 mmol), CuI (228 mg, 2.4 mmol) and LiCl (50.4 mg, 2.1 mmol) at r.t. under N₂. The mixture was then heated at 105° C. overnight, then cooled and concentrated under reduced pressure. Ethyl acetate (200 mL) and water (200 mL) were added to the above mixture which was then filtered. The organic phase was separated, dried over anhydrous Na₂SO₄ and concentrated under reduced pressure. The residue was purified by column chromatography (silica, EA:PE=1:10) to provide compound 10c (3.47 g, 78.5% yield) as yellow solid. ¹H-NMR (CDCl₃, 300 MHz): δ=8.93 (d, 1H), 8.69-8.70 (m, 1H), 8.60 (d, 1H), 7.48-7.51 (m, 1H), 7.42-7.45 (m, 1H), 5.19-5.23 (m, 1H), 5.06 (s, 1H), 1.45 (s, 12H).

Step 3:
To a solution of 10c (3.47 g, 9.5 mmol) in DCM (100 mL) cooled to 0° C. was added TFA (35 mL) dropwise. The mixture was stirred at r.t for 1 h and then concentrated under reduced pressure. DCM (100 mL) was added to the above residue and cooled to 0° C. Sat. Na₂CO₃ solution was added dropwise to the above mixture at 0° C. until pH=8. The organic layer was separated, washed with brine (200 mL), then dried over anhydrous Na₂SO₄ and concentrated under reduced pressure. The residue was purified by column chromatography (silica, MeOH:DCM=1:100) to provide 10d (1.7 g, 68.0% yield) as a yellow solid. LC-MS: 268 [M+1]⁺.

Step 4:
To a solution of 10d (1.7 g, 6.4 mmol) and TEA (17 mL) in DCM (340 mL), was added triphosgene (1.42 g, 4.8 mmol) in portions at 0° C. The solution was then warmed to r.t. and stirred for 0.5 h. 2b (1.57 g, 9.6 mmol) was added to the above mixture at r.t. The mixture was then stirred for another 0.5 h, and finally evaporated under reduced pressure. EtOAc (150 mL) was added to the residue and washed with water (100 mL) and brine (100 mL). The separated organic phase was dried over anhydrous Na₂SO₄ and concentrated. The residue was purified by column chromatography (silica, MeOH:DCM=1:10) to provide H0816 (2.04 g, 75.8% yield) as a yellow solid. ¹H-NMR (CDCl₃, 400 MHz): δ=8.82 (s, 1H), 8.60 (s, 1H), 8.51 (d, 1H), 7.36-7.38 (m, 1H), 7.29-7.31 (m, 1H), 5.28-5.31 (m, 1H), 4.79 (d, 1H), 4.04-4.10 (m, 1H), 2.78-2.83 (m, 1H), 2.74 (s, 2H), 2.19 (s, 3H), 1.91-1.99 (m, 2H), 1.61-1.70 (m, 2H), 1.47-1.57 (m, 2H), 1.44 (d, 3H). LC-MS: 422 [M+1]⁺.

Example 12

Synthesis of H0824

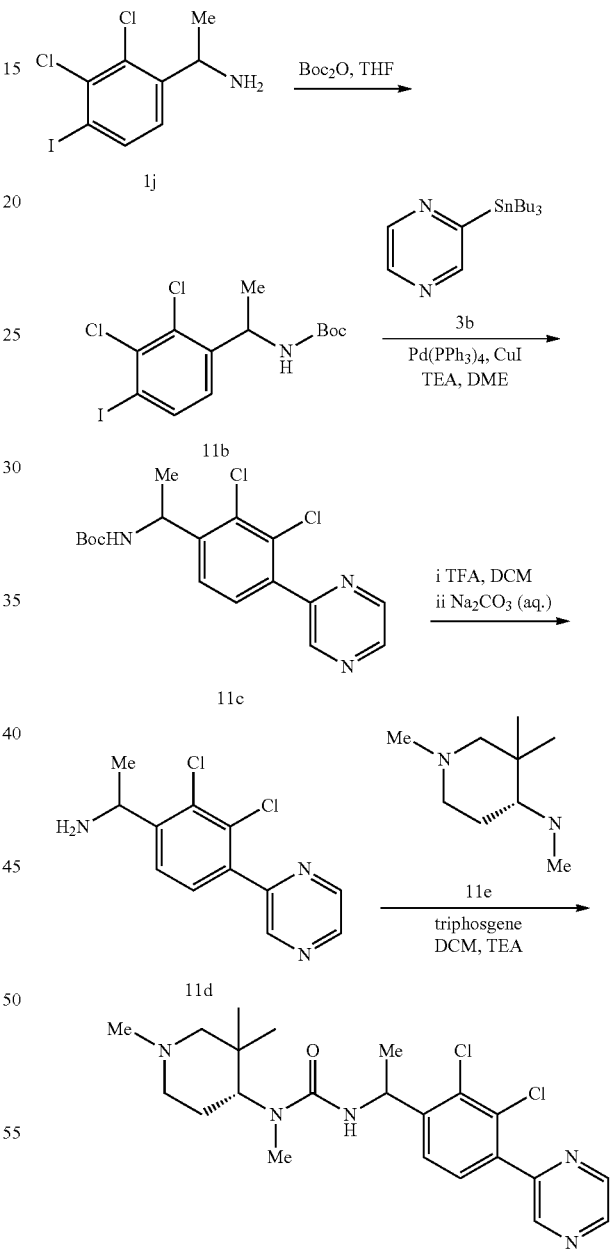

H0824

Step 1:
To a solution of 1j (2 g, 6.36 mmol) and di-tert-butyl dicarbonate (2.75 g, 12.72 mmol) in THF (30 mL) was added saturated aqueous Na₂CO₃ solution (5 mL) at 0° C. The mixture was then stirred at room temperature for 1 h, and eventually diluted with ethyl acetate (40 mL). The resulting mixture was washed with brine (10 mL), dried over anhydrous Na$_2$SO$_4$ and concentrated under reduced pressure. The residue was triturated with petroleum ether (40 mL) to provide 11b (1.86 g, 70% yield) as a white solid. $^1$H-NMR (CDCl$_3$, 400 MHz): δ=7.76 (d, 1H), 7.00 (d, 1H), 4.96-5.06 (m, 2H), 1.41-1.43 (m, 12H). LC-MS: 416 [M+1]$^+$.

Step 2:

To a solution of 1b (1.8 g, 4.5 mmol) and 3b (2.4 g, 6.5 mmol) in 1,2-dimethoxyethane (160 mL) were added Pd(PPh$_3$)$_4$ (780 mg, 0.67 mmol) and CuI (90 mg, 0.45 mmol) at room temperature under the protection of N$_2$. The mixture was then heated to 90° C. and stirred overnight at this temperature. It was subsequently cooled down and concentrated under reduced pressure. The residue was purified by silica gel column chromatography (silica, ethyl acetate:petroleum ether 1:10) to provide 11c (1.2 g, 73% yield) as a white solid. LC-MS: 368 [M+1]$^+$.

Step 3:

To a solution of 11c (600 mg, 1.63 mmol) in dichloromethane (15 mL) was added trifluoroacetic acid (5 mL) at 0° C. After the addition, the mixture was stirred at room temperature for 2 h and then concentrated under reduced pressure. The residue was partitioned between saturated aqueous NaHCO$_3$ solution (15 mL) and dichloromethane (20 mL). The organic layer was separated, dried over anhydrous Na$_2$SO$_4$ and concentrated under reduced pressure to provide 11d (350 mg, 80% yield) as a colorless oil. $^1$H-NMR (CDCl$_3$, 400 MHz): δ=8.92 (d, 1H), 8.69 (dd, 1H), 8.59 (d, 1H), 7.69 (d, 1H), 7.49 (d, 1H), 4.67-4.69 (m, 1H), 1.43 (d, 3H). LC-MS: 268 [M+1]$^+$.

Step 4:

To a solution of compound 11d (60 mg, 0.225 mmol) and TEA (0.5 mL) in dichloromethane (10 mL) was added triphosgene (46 mg, 0.158 mmol) at 0° C. The mixture was then stirred at room temperature for 15 min before the addition of 11e (53 mg, 0.337 mmol). Then stirred for another 30 min, diluted with dichloromethane (10 mL), washed with brine (10 mL), dried over anhydrous Na$_2$SO$_4$ and concentrated under reduced pressure. The residue was purified with silica gel column chromatography (silica, methanol:dichloromethane 1:40, 1% NH$_4$OH) to provide H0824 (60 mg, 57% yield) as a white solid. $^1$H-NMR (CDCl$_3$, 400 MHz): δ=8.84 (dd, 1H), 8.61 (d, 1H), 8.51 (d, 1H), 7.37 (dd, 1H), 7.30 (dd, 1H), 5.23-5.27 (m, 1H), 4.82 (dd, 1H), 4.02 (d, 1H), 2.86 (d, 2H), 2.80 (s, 3H), 2.23 (d, 3H), 1.90-2.01 (m, 2H), 1.76 (d, 1H), 1.45 (d, 3H), 1.40 (d, 1H), 1.05 (s, 3H), 0.70 (s, 3H). LC-MS: 450 [M+1]$^+$.

Example 13

Synthesis of H0890

Enantiomer of H0824

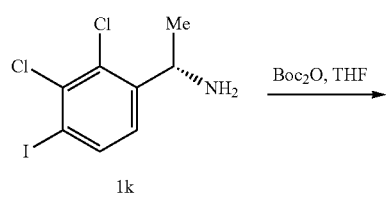

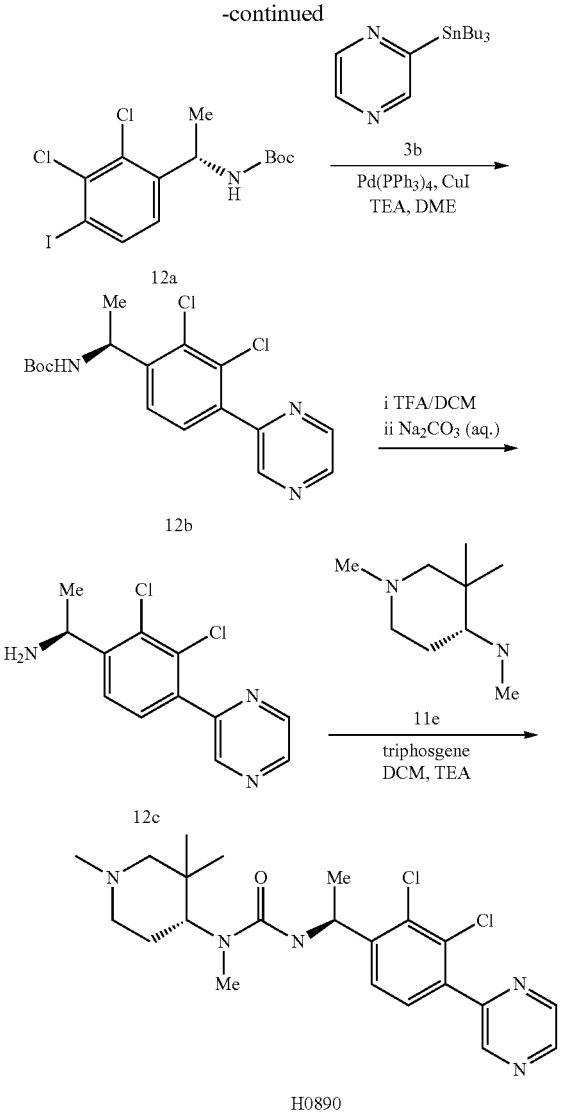

Step 1-4:

Compound H0890 was synthesized in a similar manner to H0824 (overall yield 31% from 1k). $^1$H-NMR (CDCl$_3$, 400 MHz): δ=8.91 (dd, 1H), 8.68 (d, 1H), 8.58 (d, 1H), 7.46 (dd, 1H), 7.40 (dd, 1H), 5.30-5.34 (m, 1H), 4.86 (d, 1H), 4.09 (d, 1H), 2.95 (d, 2H), 2.87 (s, 3H), 2.40 (d, 3H), 2.46-2.51 (m, 2H), 2.22 (s, 3H), 2.01-2.09 (m, 2H), 1.84 (d, 1H), 1.51 (d, 3H), 1.47 (d, 1H), 1.08 (s, 3H), 0.76 (s, 3H). LC-MS: 450 [M+1]

Example 14

Synthesis of H0826

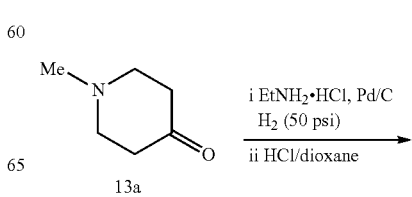

Example 15

Synthesis of H0889

Enantiomer of H0826

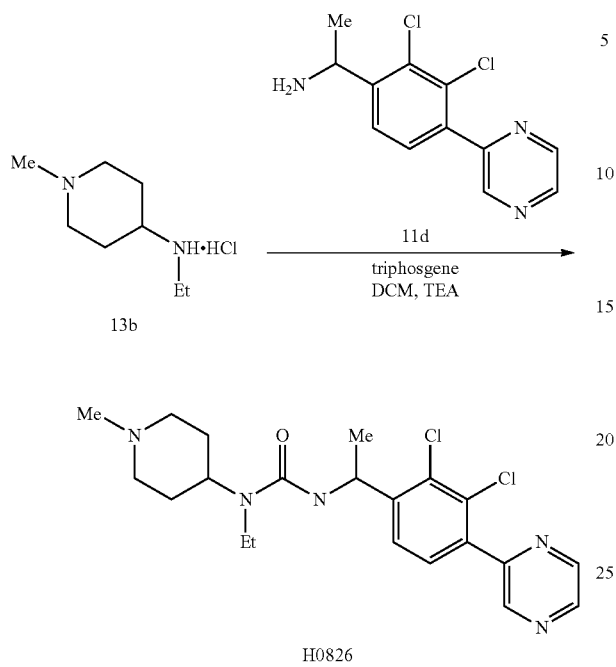

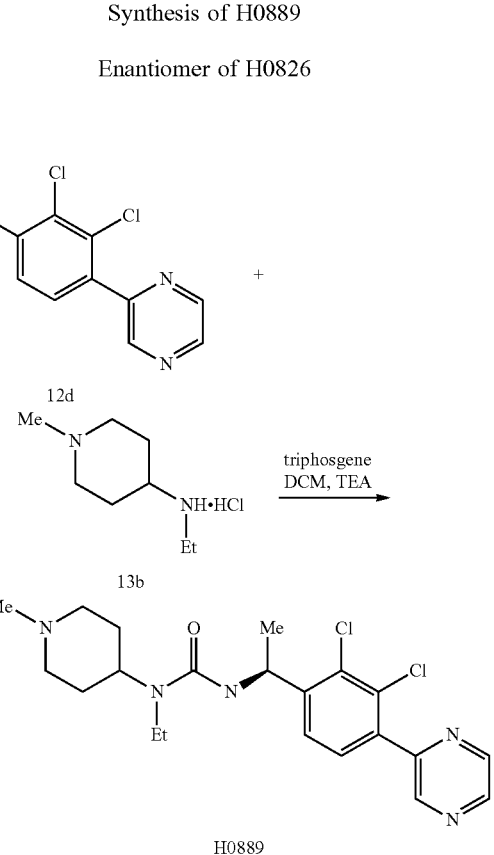

Step 1:

A mixture of 13a (3 g, 26.5 mmol), EtNH$_2$·HCl (11.2 g, 132.7 mmol), TEA (5 ml) and Pd/C (300 mg) in MeOH (50 mL) was heated at 60° C. under H$_2$ (50 psi) overnight, then cooled and filtered. The filtrate was concentrated under reduced pressure and the residue was dissolved in HCl/dioxane (4 N, 100 mL) and stirred for 30 min. The precipitate was filtered and washed with ethyl acetate (50 mL) to provide 13b (4.1 g, 87% yield) as white powder. $^1$H-NMR (DMSO-d$_6$, 400 MHz): δ=9.12 (br, 2H), 3.72 (d, 2H), 3.25-3.29 (m, 1H), 3.04 (q, 2H), 2.84-2.90 (m, 2H), 2.70 (s, 3H), 2.22-2.28 (m, 2H), 1.94-2.02 (m, 2H), 1.26 (t, 3H), LC-MS: 129 [M+1]$^+$.

Step 2:

To a solution of 11d (60 mg, 0.225 mmol) and TEA (0.5 mL) in dichloromethane (5 mL) was added triphosgene (46 mg, 0.158 mmol) at 0° C. After the addition, the mixture was stirred at room temperature for 15 min before the addition of 13b (60 mg, 0.337 mmol). The resulting mixture was stirred for another 30 min at room temperature, then diluted with dichloromethane (10 mL), washed with brine (10 mL). The organic layer was separated, dried over anhydrous Na$_2$SO$_4$ and concentrated under vacuum. The residue was purified with silica gel column chromatography (silica, methanol:dichloromethane 1:40, 1% NH$_4$OH) to provide H0826 (44 mg, 45% yield). $^1$H-NMR (CDCl$_3$, 400 MHz): δ=8.89 (d, 1H), 8.66 (dd, 1H), 8.57 (d, 1H), 7.36 (d, 1H), 5.36-5.39 (m, 1H), 4.85 (d, 1H), 4.13-4.18 (m, 1H), 3.22 (q, 2H), 2.84-2.88 (m, 2H), 2.25 (s, 3H), 1.95-2.03 (m, 2H), 1.55-1.73 (m, 4H), 1.53 (d, 3H), 1.24 (t, 3H). LC-MS: 436 [M+1]$^+$.

The synthesis of H0889 (49 mg. 30% yield) is similar to that of H0826. 1H-NMR (CDCl$_3$, 400 MHz): δ=8.90 (d, 1H), 8.67 (dd, 1H), 8.57 (d, 1H), 7.45 (d, 1H), 7.37 (d, 1H), 5.35-5.39 (m, 1H), 4.85 (d, 1H), 4.11-4.17 (m, 1H), 3.22 (q, 2H), 2.85-2.88 (m, 2H), 2.25 (s, 3H), 1.97-2.04 (m, 2H), 1.54-1.73 (m, 4H), 1.52 (d, 3H), 1.23 (t, 3H). LC-MS: 436 [M+1]$^+$.

Example 16

Synthesis of H0830

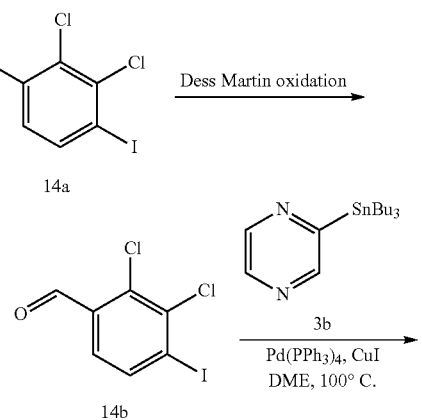

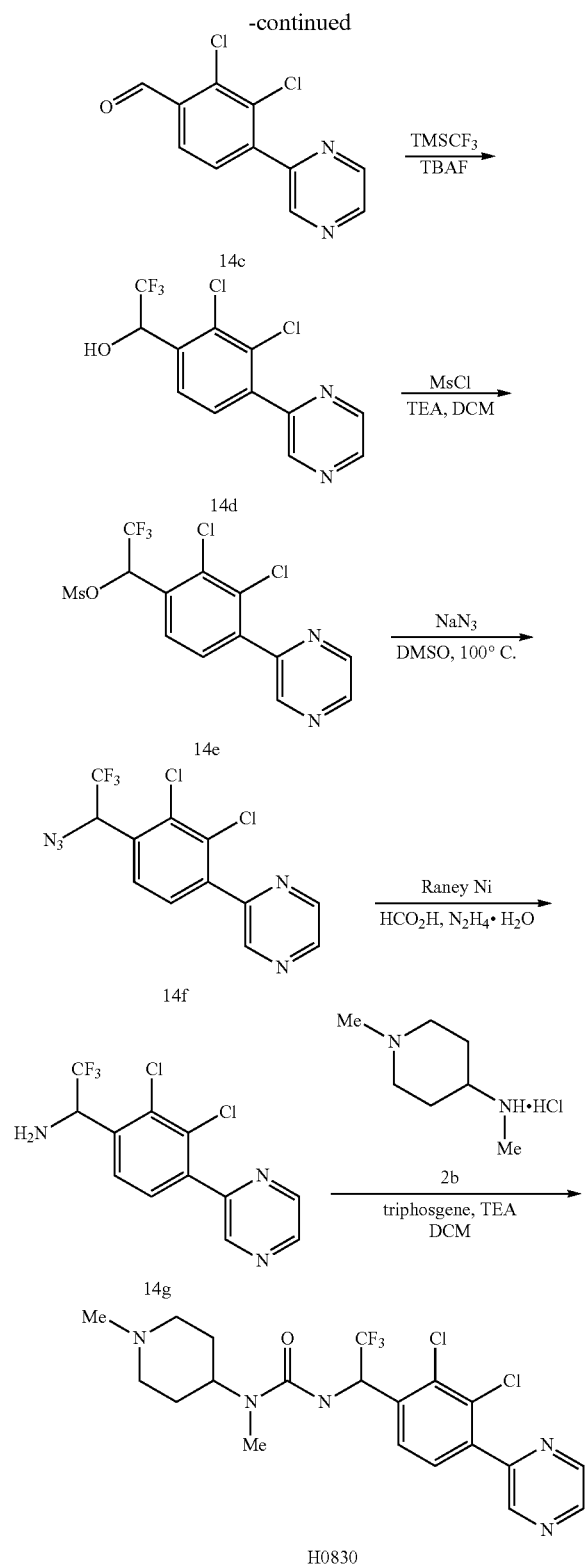

Step 1:

To a solution of 14a (3.1 g, 7.88 mol) in dichloromethane (60 mL) was added Dess-Martin periodinane (5.0 g, 11.83 mmol) at room temperature. The mixture was stirred at room temperature for 2 h, then concentrated under vacuum. The residue was purified by column chromatography (silica, ethyl acetate:petroleum ether=1:15) to provide 14b (3.05 g, 99% yield) as a light yellow solid. $^1$H-NMR (CDCl$_3$, 400 MHz): δ=10.40 (s, 1H), 7.97 (d, 1H), 7.52 (d, 1H).

Step 2:

To a solution of 14b (1.5 g, 3.8 mmol) and 3b (2.12 g, 5.7 mmol) in 1,2-dimethoxyethane (40 mL) were added Pd(PPh$_3$)$_4$ (887 mg, 0.76 mmol) and CuI (147 mg, 0.76 mmol) at room temperature under the protection of N$_2$. The mixture was heated at 90° C. overnight, and then concentrated under reduced pressure. The residue was purified with silica gel column chromatography (silica, ethyl acetate: petroleum ether=1:10) to provide 14c (826 mg, 86% yield) as a light yellow solid. $^1$H-NMR (CDCl$_3$, 400 MHz): δ=10.55 (s, 1H), 8.97 (d, 1H), 8.74 (dd, 1H), 8.66 (d, 1H), 7.98 (d, 1H), 7.64 (d, 1H). LC-MS: 253 [M+1]$^+$.

Step 3:

To a solution of 14c (980 mg, 3.5 mmol) and (trifluoromethyl)trimethylsilane (1.1 g, 7.8 mmol) in THF (20 mL) was slowly added TBAF (1 M solution in THF, 5.8 mL, 5.8 mmol) at 0° C. After the mixture was stirred at room temperature overnight, water was added (30 mL). The resulting mixture was extracted with ethyl acetate (30 mL×3). The combined organic layers were dried over anhydrous Na$_2$SO$_4$ and concentrated reduced pressure. The residue was purified by column chromatography (silica, ethyl acetate:petroleum ether=1:5) to provide 14d (640 mg, 52% yield) as a white solid. $^1$H-NMR (CDCl$_3$, 400 MHz): δ=8.92 (s, 1H), 8.72 (s, 1H), 8.66 (s, 1H), 7.75 (d, 1H), 7.53 (d, 1H), 5.70 (q, 1H), 3.68 (br, 1H). LC-MS: 323 [M+1]$^+$.

Step 4:

To a solution of 14d (750 mg, 2.33 mmol) and TEA (709 mg, 7.02 mmol) in dichloromethane (20 mL) was added methanesulfonyl chloride (320 mg, 2.8 mmol) at 0° C. After the addition was finished, the mixture was stirred at room temperature for 20 min, then diluted with dichloromethane (50 mL). The mixture was washed with saturated aqueous NaHCO$_3$ solution (40 mL), dried over anhydrous Na$_2$SO$_4$ and concentrated under vacuum to provide crude 14e (910 mg, 97% yield) as a colorless oil which was used in the next step without further purification. $^1$H-NMR (CDCl$_3$, 400 MHz): δ=8.96 (d, 1H), 8.73 (dd, 1H), 8.67 (d, 1H), 7.74 (d, 1H), 7.64 (d, 1H), 6.54 (q, 1H), 3.15 (s, 3H).

Step 5:

To a solution of compound 14e (910 mg, 2.27 mmol) in DMSO (20 mL) was added NaN$_3$ (296 mg, 4.55 mmol) at room temperature. The mixture was stirred at 100° C. overnight, then cooled and water was added (100 mL). The resulting mixture was extracted with ethyl acetate (50 mL×3). The combined organic layers were dried over anhydrous Na$_2$SO$_4$ and concentrated under vacuum. The residue was purified by column chromatography (silica, ethyl acetate:petroleum ether=1:5, v:v) to provide 14f (340 mg, 44% yield) as a yellow oil. $^1$H-NMR (CDCl$_3$, 400 MHz): δ=8.89 (d, 1H), 8.78 (dd, 1H), 8.62 (d, 1H), 7.74 (d, 1H), 7.60 (d, 1H), 6.02 (q, 1H). LC-MS: 348 [M+1]$^+$.

Step 6:

To a solution of 14f (34.7 mg, 0.1 mmol), HCOOH (46 mg, 1.0 mmol) and N$_2$H$_4$.H$_2$O (50 mg, 1.0 mmol) in EtOH (10 mL) was added Raney-Ni (50 mg). The mixture was stirred at room temperature for 1 h, then filtered and concentrated under vacuum. The residue was diluted with dichloromethane (20 mL), washed with water (15 mL), dried over anhydrous Na$_2$SO$_4$ and concentrated under vacuum to provide 14g (30 mg, 93% yield) as a colorless oil. $^1$H-NMR (CDCl$_3$, 400 MHz): δ=8.92 (d, 1H), 8.67 (d, 1H), 8.61 (d, 1H), 7.67 (d, 1H), 7.55 (d, 1H), 5.17 (q, 1H), 1.86 (br, 2H). LC-MS: 322 [M+1]$^+$.

Step 7:

To a solution of 14g (24 mg, 0.07 mmol), 2b (14.7 mg, 0.09 mmol) and TEA (0.5 mL) in dichloromethane (10 mL) was added triphosgene (46 mg, 0.158 mmol) at room temperature. The resulting mixture was stirred at 35° C. under the protection of $N_2$ for 2 h, then diluted with dichloromethane (10 mL). The mixture was washed with saturated aqueous $Na_2CO_3$ solution (10 mL) and brine (10 mL), dried over anhydrous $Na_2SO_4$ and concentrated under vacuum. The residue was purified with silica gel column chromatography (silica, methanol:dichloromethane 1:40, 1% $NH_4OH$) to provide H0830 (10 mg, 28% yield) as a white solid. 1H-NMR (CDCl$_3$, 400 MHz): δ=8.85 (d, 1H), 8.62 (dd, 1H), 8.55 (d, 1H), 7.48 (d, 1H), 7.40 (d, 1H), 6.22-6.26 (m, 1H), 5.21 (d, 1H), 4.38-4.45 (m, 1H), 3.30-3.12 (m, 2H), 2.84 (s, 3H), 2.59-2.71 (m, 5H), 1.61-1.66 (m, 2H), 1.01-1.05 (m, 2H). LC-MS: 476 [M+1]$^+$.

Example 17

Synthesis of H0847

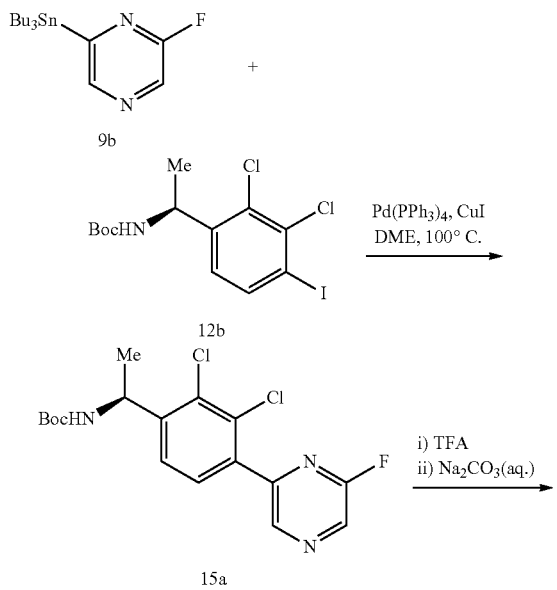

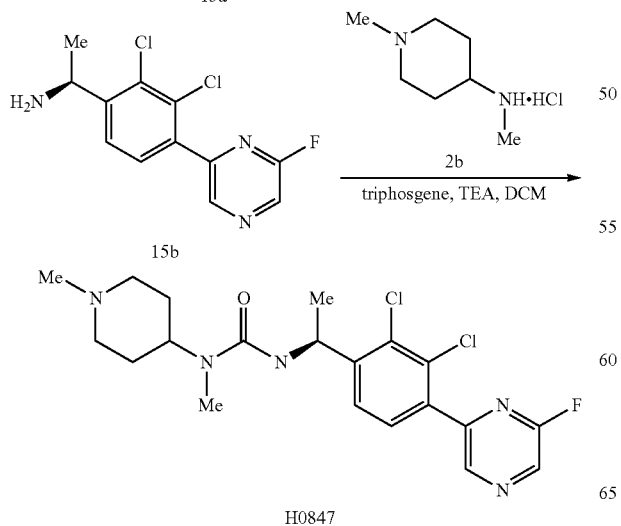

H0847

Step 1:

To a solution of 12b (10.4 g, 25 mmol) and 9b (19.4 g, 50 mmol) in 1,2-dimethoxyethane (1.2 L) were added Pd(PPh$_3$)$_4$ (4.54 g, 3.92 mmol) and CuI (227 mg, 1.19 mmol) at r.t. under $N_2$. The mixture was heated at 90° C. overnight, then cooled, diluted with CH$_2$Cl$_2$ (800 mL) and filtered. The filtrate was washed with brine (600 mL) and the organic phase was separated, dried over anhydrous $Na_2SO_4$ and concentrated under reduced pressure. The residue was purified by column chromatography (silica, EtOAc:Petroleum, 1:3) to provide crude compound 15a (10.3 g, ca. 100% yield) as yellow solid. LC-MS: 386 [M+1]$^+$.

Step 2:

To a solution of 15a (10.3 g, 26 mmol) in DCM (500 mL) cooled to 0° C. was added TFA (100 mL) dropwise. After the addition was completed, the mixture was stirred for 3 h, then basified with saturated $Na_2CO_3$ solution (400 mL) and extracted with DCM (3×100 mL). The combined organic layers were dried over anhydrous $Na_2SO_4$ and concentrated under reduced pressure. The residue was purified by column chromatography (silica, MeOH:CH$_2$Cl$_2$:NH$_4$OH, 1:20:0.01) to provide 15b (4.1 g, 57% yield) as a red solid. LC-MS: 440 [M+1]$^{+1}$ Step 3:

To a solution of 15b (2.0 g, 7.1 mmol) and TEA (80 mL) in CH$_2$Cl$_2$ (220 mL) was added triphosgene (1.52 g, 5.1 mmol) portion wise at 0° C. After the addition was completed, the solution was stirred for 45 min. 2b (2.7 g, 7.1 mmol) was then added to the above solution. The resulting solution was stirred for 2 h, then diluted with CH$_2$Cl$_2$ (100 mL) and washed with aqueous Na$_2$CO$_3$ solution (100 mL) and brine (100 mL). The organic layer was dried over anhydrous Na$_2$SO$_4$ and concentrated. The residue was purified with silica gel column chromatography (silica:CH$_2$Cl$_2$:CH$_3$OH=10/1) to provide H0847 (2.0 g, 65% yield) as white solid. $^1$H-NMR (CDCl$_3$, 400 MHz): δ=8.77 (d, 1H), 8.38 (d, 1H), 7.40 (d, 1H), 7.31 (d, 1H), 5.26-5.30 (m, 1H), 4.78 (d, 1H), 4.10-4.00 (m, 1H), 2.79-2.84 (m, 2H), 2.75 (s, 3H), 2.20 (s, 3H), 1.94-2.05 (m, 2H), 1.57-1.69 (m, 2H), 1.47-1.64 (m, 2H), 1.41 (d, 3H). LC-MS: 440 [M+1]$^+$. ee %=98.5%. (Chiralpak, 5 μm, 4.6*250 mm, Phase:Hex:EtOH:DEA=90:10:0.2), retention time=12.829 min).

Example 18

Synthesis of H0829 and H0860

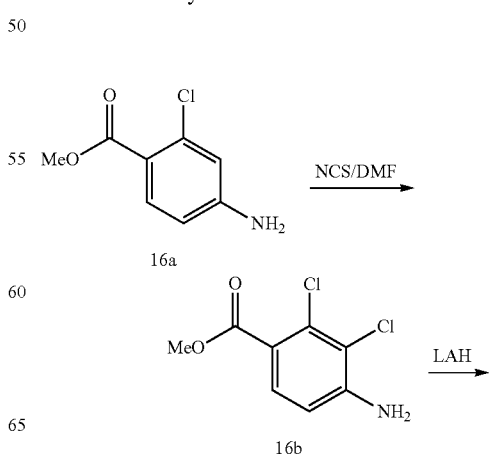

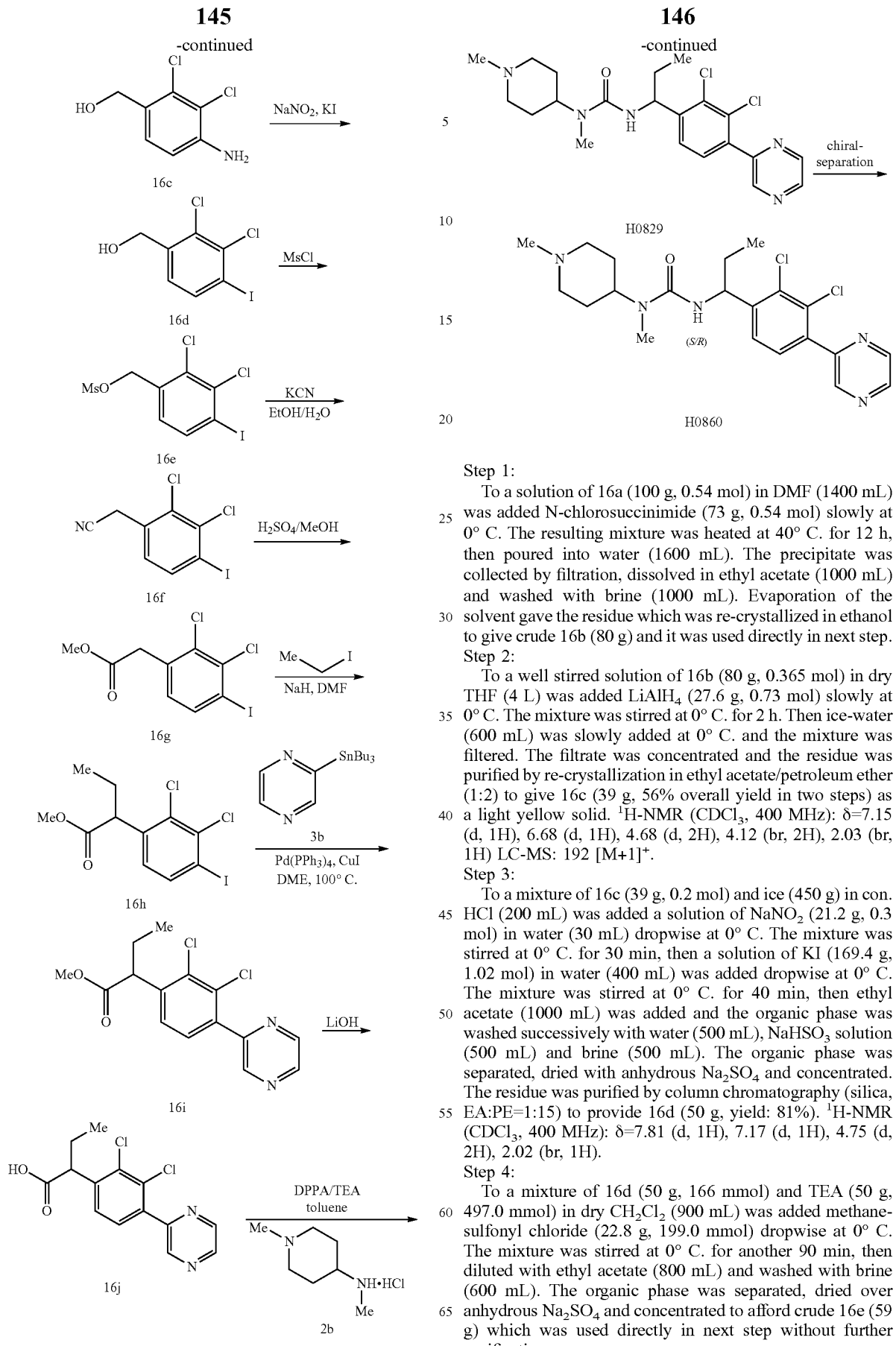

Step 1:

To a solution of 16a (100 g, 0.54 mol) in DMF (1400 mL) was added N-chlorosuccinimide (73 g, 0.54 mol) slowly at 0° C. The resulting mixture was heated at 40° C. for 12 h, then poured into water (1600 mL). The precipitate was collected by filtration, dissolved in ethyl acetate (1000 mL) and washed with brine (1000 mL). Evaporation of the solvent gave the residue which was re-crystallized in ethanol to give crude 16b (80 g) and it was used directly in next step.

Step 2:

To a well stirred solution of 16b (80 g, 0.365 mol) in dry THF (4 L) was added LiAlH$_4$ (27.6 g, 0.73 mol) slowly at 0° C. The mixture was stirred at 0° C. for 2 h. Then ice-water (600 mL) was slowly added at 0° C. and the mixture was filtered. The filtrate was concentrated and the residue was purified by re-crystallization in ethyl acetate/petroleum ether (1:2) to give 16c (39 g, 56% overall yield in two steps) as a light yellow solid. $^1$H-NMR (CDCl$_3$, 400 MHz): δ=7.15 (d, 1H), 6.68 (d, 1H), 4.68 (d, 2H), 4.12 (br, 2H), 2.03 (br, 1H) LC-MS: 192 [M+1]$^+$.

Step 3:

To a mixture of 16c (39 g, 0.2 mol) and ice (450 g) in con. HCl (200 mL) was added a solution of NaNO$_2$ (21.2 g, 0.3 mol) in water (30 mL) dropwise at 0° C. The mixture was stirred at 0° C. for 30 min, then a solution of KI (169.4 g, 1.02 mol) in water (400 mL) was added dropwise at 0° C. The mixture was stirred at 0° C. for 40 min, then ethyl acetate (1000 mL) was added and the organic phase was washed successively with water (500 mL), NaHSO$_3$ solution (500 mL) and brine (500 mL). The organic phase was separated, dried with anhydrous Na$_2$SO$_4$ and concentrated. The residue was purified by column chromatography (silica, EA:PE=1:15) to provide 16d (50 g, yield: 81%). $^1$H-NMR (CDCl$_3$, 400 MHz): δ=7.81 (d, 1H), 7.17 (d, 1H), 4.75 (d, 2H), 2.02 (br, 1H).

Step 4:

To a mixture of 16d (50 g, 166 mmol) and TEA (50 g, 497.0 mmol) in dry CH$_2$Cl$_2$ (900 mL) was added methanesulfonyl chloride (22.8 g, 199.0 mmol) dropwise at 0° C. The mixture was stirred at 0° C. for another 90 min, then diluted with ethyl acetate (800 mL) and washed with brine (600 mL). The organic phase was separated, dried over anhydrous Na$_2$SO$_4$ and concentrated to afford crude 16e (59 g) which was used directly in next step without further purification.

Step 5:

To a solution of crude 16e (59 g, 160 mmol) in EtOH (1200 mL) was added a solution of NaCN (11.4 g, 230.0 mmol) in H₂O (250 mL). The resulting mixture was heated under reflux overnight, then cooled and concentrated. The residue was partitioned between ethyl acetate (500 mL) and water (500 mL). The organic phase was separated, washed with brine, dried over anhydrous Na₂SO₄ and concentrated to afford crude 16f (40 g) as a brown solid which was used directly in next step without further purification.

Step 6:

To a solution of 16f (40 g, 129 mmol) in MeOH (360 mL) was added conc. H₂SO₄ (114 mL) dropwise at 0° C. The mixture was then heated under reflux overnight, then cooled and concentrated. Aqueous Na₂CO₃ solution (50 mL) was added to the residue at 0° C. and the mixture was adjusted to pH=9-10 with the addition of Na₂CO₃ powder. The mixture was extracted with ethyl acetate (3×300 mL) and the combined organic layers were dried over anhydrous Na₂SO₄ and concentrated. The residue was purified by column chromatography (silica, EA:PE=1:20) to 16g (22 g, yield: 70.5%) as a yellow solid. ¹H-NMR (CDCl₃, 400 MHz): δ=7.75 (d, 1H), 6.93 (d, 1H), 3.78 (s, 2H), 3.72 (s, 3H).

Step 7:

To a solution of 16g (22 g, 32 mmol) in DMF (150 mL) was slowly added NaH (60%, 2.8 g, 2.2 mmol) at 0° C. The mixture was stirred at r.t. for 30 min and then EtI (10 g, 64 mmol) was added. The mixture was stirred at r.t. for another 1.5 h, then poured into ice water (600 mL). The resulting mixture was extracted with ethyl acetate (3×400 mL). The combined organic layers were dried over anhydrous Na₂SO₄ and concentrated under vacuum. The residue was purified by column chromatography (silica, ethyl acetate:petroleum ether=1:50) to provide 16h (20 g, 84% yield). ¹H NMR (CDCl₃, 400 MHz): δ=7.76 (d, 1H), 7.00 (d, 1H), 4.06 (t, 1H), 3.67 (s, 3H), 2.05-2.12 (m, 1H), 1.75-1.82 (m, 1H), 0.91 (t, 3H).

Step 8:

To a solution of 16h (22 g, 53.7 mmol) and 3b (25.9 g, 69.9 mmol) in 1,2-dimethoxyethane (660 mL) were added Pd(PPh₃)₄ (15.5 g, 13.4 mmol), LiCl (0.46 g, 13.4 mmol) and CuI (2.06 g, 10.8 mmol) at r.t. under the protection of N₂. The mixture was then heated at 105° C. overnight, cooled and concentrated under vacuum. The residue was purified with silica gel column chromatography (silica, ethyl acetate:petroleum ether=1:8) to provide 16i (12 mg, 69% yield) as a yellow solid.

Step 9:

The mixture of 16i (12 g, 37.0 mmol) and LiOH.H₂O (9.3 g, 22.2 mmol) in MeOH (480 mL) and H₂O (120 mL) was stirred at r.t. overnight, then concentrated under vacuum. The residue was acidified with 1N HCl to pH=2 which was extracted with dichloromethane (3×200 mL). The combined organic layers were dried over anhydrous Na₂SO₄ and concentrated to provide 16j (10.8 g, 94% yield) as a white solid. LC-MS: 310 [M−1]⁻.

Step 10:

The mixture of 16j (10.8 g, 34.8 mmol), 2b (8.6 g, 52 mmol), DPPA (11.5 mg, 41.8 mmol) and TEA (48 mL) in toluene (400 mL) was stirred at 125° C. overnight, then cooled and concentrated under vacuum. The residue was partitioned between saturated aqueous Na₂CO₃ solution (150 mL) and dichloromethane (300 mL). The organic phase was separated, washed with brine (200 mL), dried with anhydrous Na₂SO₄ and concentrated under vacuum. The residue was purified by column chromatography (silica, MeOH:dichloromethane 1:50, 1% NH₄OH) to provide H0829 (6 g, 41% yield) as a white solid. 1H-NMR (CDCl3, 400 MHz): δ=8.91 (d, 1H), 8.68 (d, 1H), 8.59 (d, 1H), 7.45 (d, 1H), 7.34 (d, 1H), 5.17-5.22 (m, 1H), 4.93 (d, 1H), 4.11-4.17 (m, 1H), 2.85-2.92 (m, 2H), 2.82 (s, 3H), 2.27 (s, 3H), 1.58-2.05 (m, 8H), 1.00 (t, 3H). LC-MS: 436 [M+1]+.

Step 11:

H0860 (2.0, 66.7%) was obtained through the chiral separation of H0829 (Chiralpak, 5 μm, 4.6*250 mm, Hex: EtOH:DEA=80:20:0.2, retention time: 10.76 min). 1H-NMR (CDCl3, 400 MHz): δ=8.89 (d, 1H), 8.66 (d, 1H), 8.57 (d, 1H), 7.43 (d, 1H), 7.32 (d, 1H), 5.16-5.21 (m, 1H), 4.92 (d, 1H), 4.11-4.17 (m, 1H), 2.87-2.90 (m, 2H), 2.81 (s, 3H), 2.26 (s, 3H), 1.48-2.01 (m, 8H), 0.97 (t, 3H). LC-MS: 436 [M+1]+.

Example 19

Synthesis of H0837 and H0862

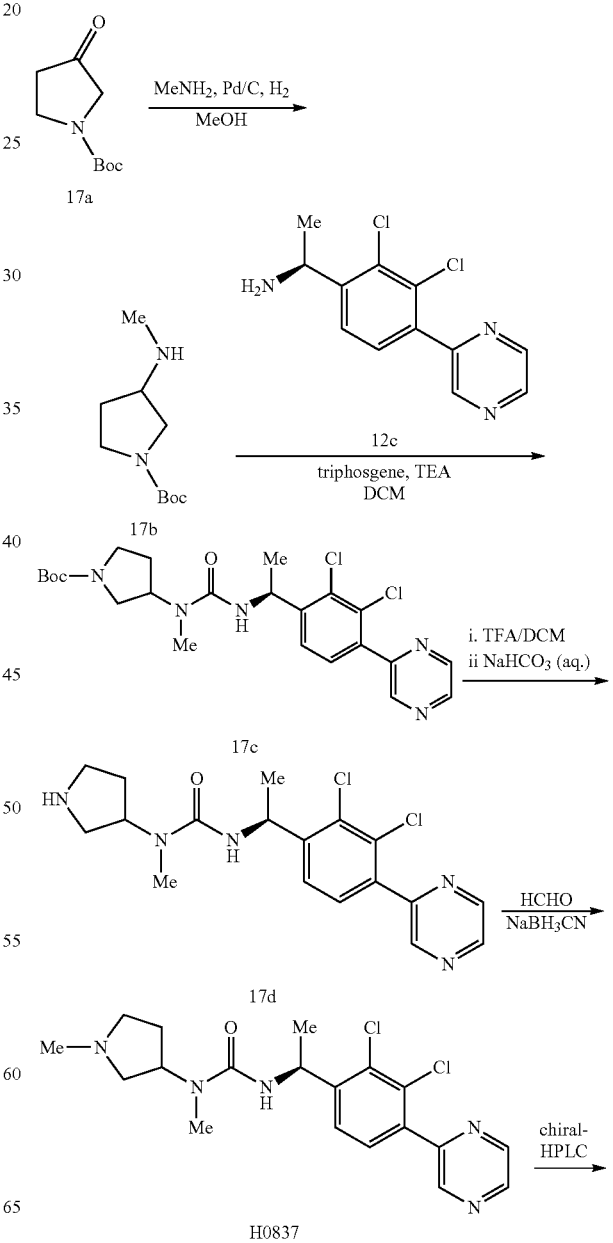

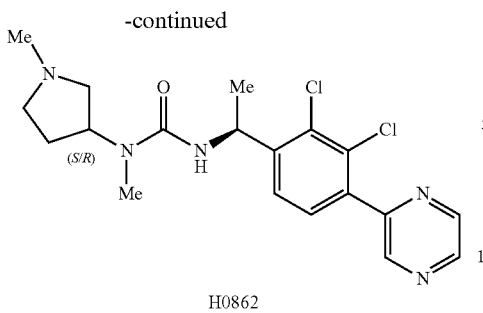

H0862

Step 1

The mixture of 17a (5 g, 27.0 mmol), 30% of methyl amine in methanol (50 mL) and 5% Pd/C (500 mg) in methanol (50 mL) was heated at 60° C. under H$_2$ (50 psi) overnight, then cooled and filtered. The filtrate was concentrated under vacuum and the residue was purified by silica gel column chromatography (methanol:dichloromethane=1: 40) to provide 17b (2.8 g, 52% yield). $^1$H-NMR (CDCl$_3$, 400 MHz): δ=9.99 (s, 1H), 3.79-3.83 (m, 1H), 3.61-3.72 (m, 3H), 3.40 (d, 1H), 2.71 (s, 3H), 2.33-2.36 (m, 2H), 1.75 (s, 9H), LC-MS: 201 [M+1]$^+$ Step 2:

To a solution of 12c (300 mg, 1.12 mmol) and TEA (3.6 g, 40.3 mmol) in dichloromethane (20 mL) was added triphosgene (283 mg, 0.95 mmol) at 0° C. After the addition was finished, the mixture was stirred at room temperature for 30 min before the addition of 17b (270 mg, 1.35 mmol). The resulting mixture was stirred at room temperature for 1 h, then concentrated under vacuum. The residue was partitioned between dichloromethane (50 mL) and saturated NaHCO$_3$ solution (50 mL). The organic phase was separated, washed with brine, dried with anhydrous Na$_2$SO$_4$ and concentrate under vacuum. The residue was purified with silica gel column chromatography (silica, methanol:dichloromethane 1:40, 1% NH$_4$OH) to provide 17c (330 mg, 60% yield) as a yellow solid. $^1$H-NMR (CDCl$_3$, 400 MHz): δ=8.82 (s, 1H), 8.63 (d, 1H), 8.51 (dd, 1H), 7.38 (d, 1H), 7.33 (d, 1H), 5.23-5.26 (m, 1H), 4.99 (d, 1H), 4.80-4.83 (m, 1H), 3.31-3.32 (m, 2H), 3.03-3.23 (m, 2H), 2.80 (s, 3H), 1.97-2.03 (m, 1H), 1.76-1.84 (m, 1H), 1.64 (s, 9H), 1.45 (d, 3H). LC-MS: 494 [M+1]$^+$.

Step 3:

To a solution of 17c (330 mg, 0.67 mmol) in dichloromethane (15 mL) was added trifluoroacetic acid (5 mL) dropwise at 0° C. The mixture was stirred at room temperature for 1 h, then concentrated under vacuum. The residue was partitioned between aqueous NaHCO$_3$ solution and dichloromethane. The organic layer were dried over anhydrous Na$_2$SO$_4$ and concentrated to provide 17d (252 mg, 96% yield) as a yellow solid. LC-MS: 394 [M+1]$^+$.

Step 4:

To a mixture of 17d (252 mg, 0.64 mmol) and 37% aqueous HCHO solution (250 mg, 3.1 mmol) in MeOH (15 mL) were added NaOAc (600 mg, 7.3 mmol), AcOH (1 mL, 50 mmol) and NaBH$_3$CN (121 mg, 1.9 mmol) at room temperature. The mixture was stirred at room temperature overnight, and then concentrated under reduced pressure. The residue was partitioned between dichloromethane (50 mL) and saturated NaHCO$_3$ solution (50 mL). The organic phase was separated, washed with brine, dried under anhydrous Na$_2$SO$_4$ and concentrated under reduced pressure. The residue was purified with silica gel column chromatography (silica, methanol:dichloromethane 1:50, 1% NH$_4$OH) to provide H0837 (200 mg, 77% yield) as a white solid. $^1$H-NMR (CDCl$_3$, 400 MHz): δ=8.82 (d, 1H), 8.60 (dd, 1H), 8.50 (d, 1H), 7.97 (br, 1H), 7.38 (d, 1H), 7.28-7.31 (m, 1H), 5.26-5.31 (m, 1H), 4.08-4.10 (m, 1H), 3.03-3.06 (m, 1H), 2.95-2.99 (m, 2H), 2.90 (s, 3H), 2.19-2.35 (m, 5H), 1.94-1.98 (m, 2H), 1.37-1.40 (m, 3H). LC-MS: 408 [M+1]$^+$.

Step 5:

H0862 was obtained through the chiral separation of H0837 (Chiralcel OJ-H, 5 μm, 4.6×250 mm, Hex:EtOH: DEA=90:10:0.3, retention time: 11.34 min). $^1$H-NMR (CDCl$_3$, 400 MHz): δ=8.82 (d, 1H), 8.60 (dd, 1H), 8.51 (d, 1H), 7.98 (br, 1H), 7.37 (d, 1H), 7.30 (d, 1H), 5.28-5.31 (m, 1H), 4.07-4.10 (m, 1H), 3.06-3.10 (m, 1H), 2.99-3.06 (m, 1H), 2.90 (s, 3H), 2.20-2.35 (m, 5H), 1.96-2.05 (m, 2H), 1.38 (d, 3H). LC-MS: 408 [M+1]$^+$.

Example 20

Synthesis of H0900

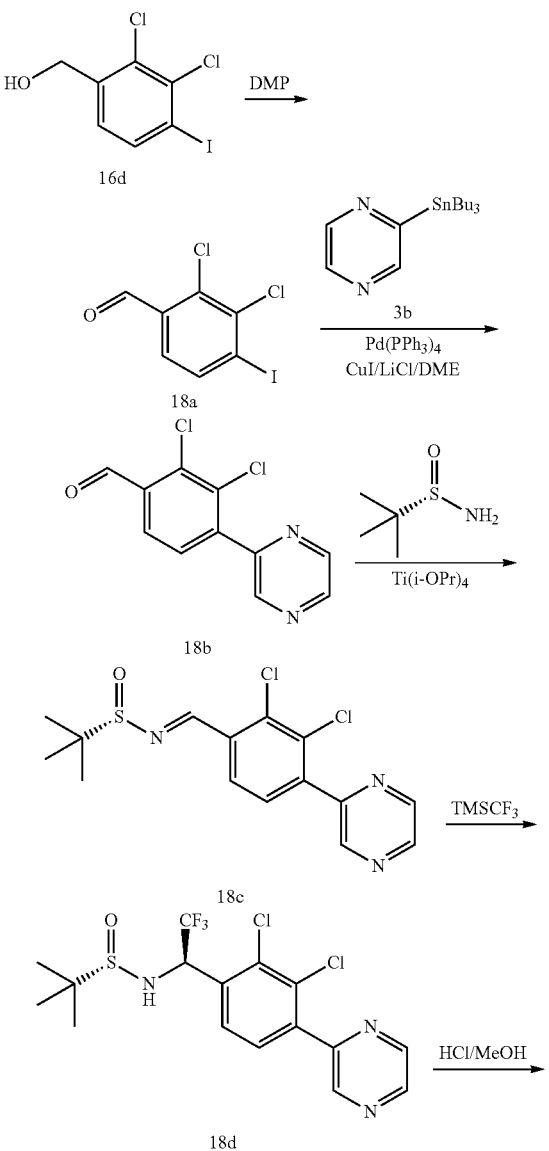

-continued

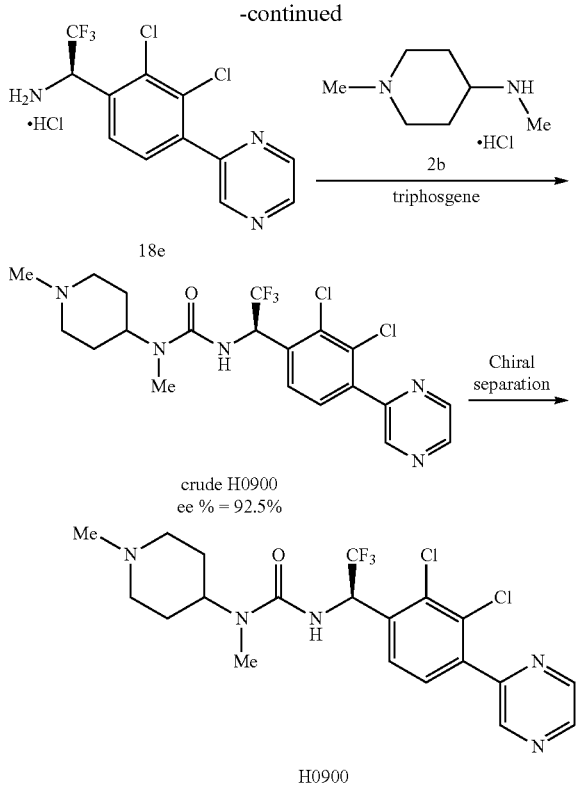

Step 1:

To a mixture of 16d (32 g, 120 mmol) in dry $CH_2Cl_2$ (800 mL) was added Dess-Martin peroxide reagent (76 g, 180 mmol) portion-wise at 0° C. The mixture was stirred at room temperature for 1 h, then diluted with DCM (800 mL), washed with aqueous $NaHCO_3$ solution (300 mL) and brine (300 mL). The organic phase was separated, dried over anhydrous $Na_2SO_4$ and concentrated under reduced pressure to afford crude 18a (31.4 g) which was used directly in the next step without further purification.

Step 2:

To a solution of 18a (12 g, 40 mmol) and 3b (22.2 g, 60 mmol) in DME (560 mL) were added $Pd(PPh_3)_4$ (9.25 g, 8 mmol) and CuI (1.52 g, 8 mmol) at room temperature. The mixture was stirred at 90° C. overnight, then concentrated under reduced pressure. The residue was purified with silica gel column chromatography (silica, EA:PE=1:5) to provide 18b (8.0 g, 79.3%) as a white solid. LC-MS: 253 $[M+1]^+$.

Step 3:

To a solution of 18b (7 g, 27.7 mmol) and (S)-tert-butylsulfinamide (7.27 g, 30.56 mmol) in dry THF (200 mL) was added $Ti(i-OPr)_4$ (15.7 g, 55.4 mmol) dropwise at room temperature. The mixture was stirred at 80° C. overnight, and then cooled. Ethyl acetate (40 mL) was added, the resulting mixture was filtered and the filtrate was concentrated under reduced pressure. The residue was purified with silica gel column chromatography (silica, EA:PE=1:5) to provide 18c (6.8 g, 69%) as a yellow solid. $^1$H-NMR ($CDCl_3$, 400 MHz): δ=9.10 (s, 1H), 8.97 (s, 1H), 8.72 (s, 1H), 8.64 (d, 1H), 8.12 (d, 1H), 7.59 (d, 1H), 1.30 (s, 9H). LC-MS: 356 $[M+1]^+$.

Step 4:

To a stirred solution of 18c (6.8 g, 19 mmol) and Tetrabutylammonium difluorotriphenylsilicate (15.8 g, 29 mmol) in dry THF (250 mL) was added a solution of $TMSCF_3$ (11 g, 77 mmol) in anhydrous THF (50 mL) at −65° C. The mixture was then stirred at −65° C. for 2 h, and at that point aqueous $NH_4Cl$ solution (250 mL) was added. The mixture was diluted with ethyl acetate (250 mL), washed with brine (250 mL), dried over anhydrous $Na_2SO_4$ and concentrated under reduced pressure. The residue was purified with silica gel column chromatography (silica, EA:PE=1:2) to provide 18d (4.3 g, 52%) as a yellow solid. LC-MS: 426 $[M+1]^+$.

Step 5:

To a stirred solution of 18d (4.3 g, 10.1 mmol) in MeOH (40 mL) was added a solution of HCl/MeOH (4N, 40 mL) at room temperature. The mixture was stirred for 1 h, then concentrated under reduced pressure. The residue was triturated with ethyl acetate (40 mL) to afford crude 18e (4.3 g) which was directly in the next step without further purification. LC-MS: 322 $[M+1]^+$.

Step 6:

To a solution of 18e (2.7 g, 7.1 mmol), 2b (3.4 g, 21.3 mmol) and TEA (80 mL) in DCM (220 mL) was added thiphosgene (3.15 g, 10.6 mmol) in DCM (40 mL) dropwise at 0° C. The solution was warmed to ambient temperature and stirred for 1 h, then diluted with DCM (100 mL) and washed with aqueous $Na_2CO_3$ solution (100 mL) and brine (100 mL). The organic layer was separated, dried over anhydrous $Na_2SO_4$ and concentrated. The residue was purified with silica gel column chromatography (silica, DCM:$CH_3OH$=10:1) to provide crude H0900 (2.13 g, ee %=92.5%) which was further purified through chiral separation to afford H0900 (1.6 g, 49% yield) as a white solid. (ee %=98.5%, Chiralpak IC Sum, 4.6*250 mm, Phase:Hex:EtOH:DEA=90:10:0.2), retention time=12.829 min. $^1$H-NMR ($CDCl_3$, 400 MHz): δ=8.86 (d, 1H), 8.63 (dd, 1H), 8.55 (d, 1H), 7.47 (d, 1H), 7.40 (d, 1H), 6.28 (m, 1H), 5.18 (d, 1H), 4.12 (m, 1H), 2.88 (t, 2H), 2.77 (s, 3H), 2.22 (s, 3H), 2.05 (m, 2H), 2.48 (m, 2H), 1.52 (m, 2H), 1.73-1.49 (m, 4H). LC-MS: 476 $[M+1]^+$.

Example A

Calcium FLIPR Assay

The intracellular calcium assay was carried out in a 384-well format FLIPR™ (Molecular Device) HEK293/GHSR1a cell line. Cells were seeded 24 hr prior to the experiments at an optimal density per well. Preincubation with selected calcium dye lasted for 30-60 min at room temperature or 37° C. Test compounds, dissolved in DMSO, were added at the appropriate time and incubated for 15 min followed by the addition of ghrelin with FlexStation or FLIPR. Relative fluorescence was monitored by the FLIPR™ Molecular Device. $EC_{50}$ and $IC_{50}$ values were estimated from dose-response data using GraphPad Prism software. To check for GHSR-1a agonism the compound was added at t=20 sec. and the calcium response was followed for 2 minutes. To check for GHSR-1a antagonism the compound and Ghrelin (10 nM) were added to the cells at t=20 sec. and the calcium response was measured for 2 minutes. The potency of the antagonist was calculated by its ability to reduce the ghrelin response. Dose-response curves were made for relevant antagonists.

Example B

Evaluation of GHSR1a Antagonists on Food Intake Test in Mouse

Male C57BL/6J mice, 18-22 g body weight, were fasted overnight (16 h before compound administration) and placed in a regular light dark cycle (6:00-18:00 light/18:00-6:00 dark). After 1 wk acclimation, animals were sorted into two groups (n=6 each, 2 per cage) based on body weight. Animals in group one were be treated with vehicle and animals in group 2 were treated with the test agent (n=6 for each group). The cumulative food intake was evaluated at 1, 2, 4, 8 and 24 hrs after drug or vehicle treatment. Food intake was measured by subtracting uneaten food from the initial premeasured food.

The following table presents representative compounds of Formula I with biological data including the ghrelin antagonist/agonist activity in vitro (Example A) and mouse food intake results (Example B). The data clearly demonstrates that compounds of Formula I are ghrelin receptor modulators and are useful in preventing and/or treating diseases associated with ghrelin receptor, for example, obesity.

TABLE 1

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0494 | 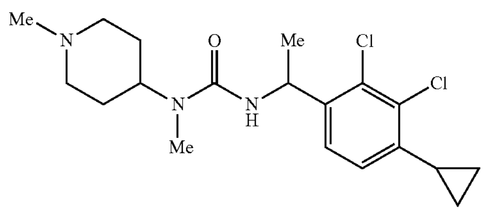 [SMILES: CC(NC(=O)N(C)C1CCN(C)CC1)c1ccc(C2CC2)c(Cl)c1Cl] | $IC_{50}$ = 52 nM<br>$EC_{50}$ = 66 nM<br>$E_{max}$ = 2996 | Medium H<br>High M | No Effect |
| H0621 | 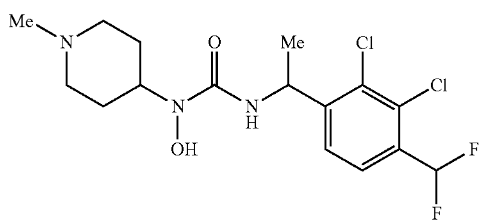 [SMILES: CC(NC(=O)N(O)C1CCN(C)CC1)c1ccc(C(F)F)c(Cl)c1Cl] | $IC_{50}$ > 30 μM<br>$EC_{50}$ = 2 nM<br>$E_{max}$ = 3896 | High H<br>High M | No Effect |
| H0496 | 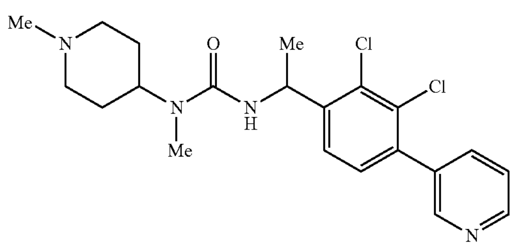 [SMILES: CC(NC(=O)N(C)C1CCN(C)CC1)c1ccc(-c2cccnc2)c(Cl)c1Cl] | $IC_{50}$ = 10 nM<br>$EC_{50}$ > 30 μM | Medium H<br>High M | NSE (10 mg/kg) |
| H0617 | 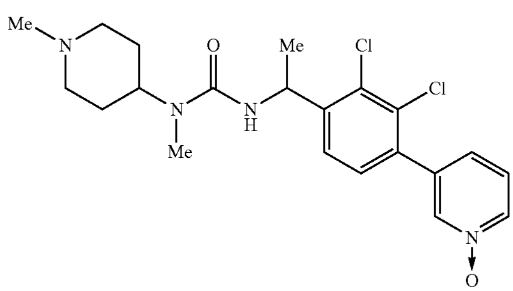 [SMILES: CC(NC(=O)N(C)C1CCN(C)CC1)c1ccc(-c2ccc[n+]([O-])c2)c(Cl)c1Cl] | $IC_{50}$ = 3.4 μM<br>$EC_{50}$ > 30 μM | Not done | Not Done |
| H0539 | 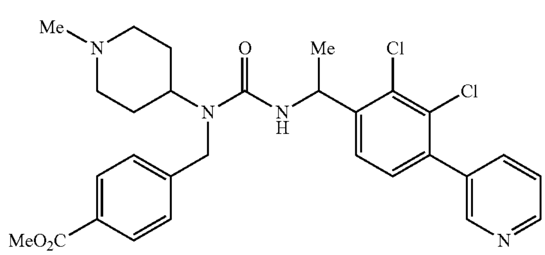 [SMILES: COC(=O)c1ccc(CN(C(=O)NC(C)c2ccc(-c3cccnc3)c(Cl)c2Cl)C2CCN(C)CC2)cc1] | $IC_{50}$ = 9 nM<br>$EC_{50}$ > 30 μM | Not done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0546 | 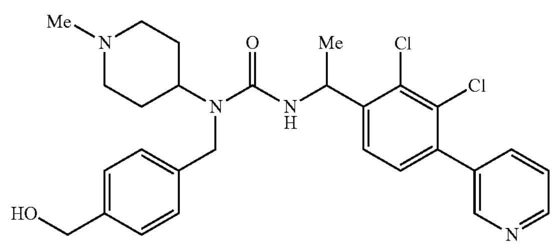 [SMILES: CC(NC(=O)N(Cc1ccc(CO)cc1)C1CCN(C)CC1)c1ccc(-c2cccnc2)c(Cl)c1Cl] | $IC_{50}$ = 8 nM<br>$EC_{50}$ > 30 µM | Medium H<br>Medium M | Not Done |
| H0526 | 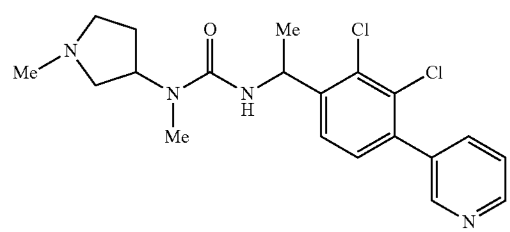 [SMILES: CC(NC(=O)N(C)C1CCN(C)C1)c1ccc(-c2cccnc2)c(Cl)c1Cl] | $IC_{50}$ = 57 nM<br>$EC_{50}$ > 30 µM | Not done | Not Done |
| H0527 | 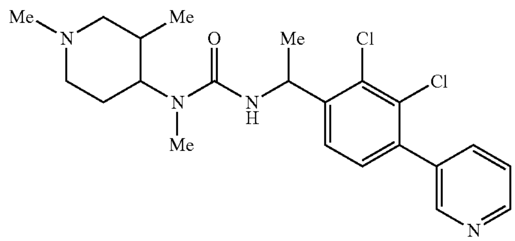 [SMILES: CC(NC(=O)N(C)C1CCN(C)CC1C)c1ccc(-c2cccnc2)c(Cl)c1Cl] | $IC_{50}$ = 19 nM<br>$EC_{50}$ > 30 µM | Medium H<br>Medium M | Not done |
| H0497 | 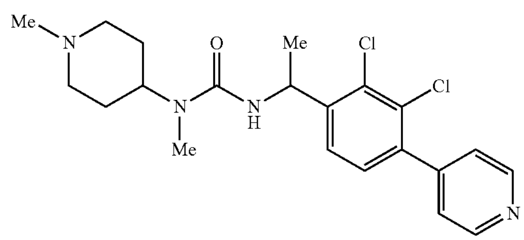 | $IC_{50}$ = 24 nM<br>$EC_{50}$ > 30 µM | Medium H<br>Medium M | NSE (30 mg/kg) |
| H0650 | 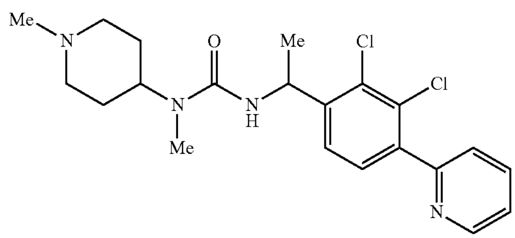 | $IC_{50}$ = 4 nM<br>$EC_{50}$ = 9 nM<br>$E_{max}$ = 2150 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0849 | 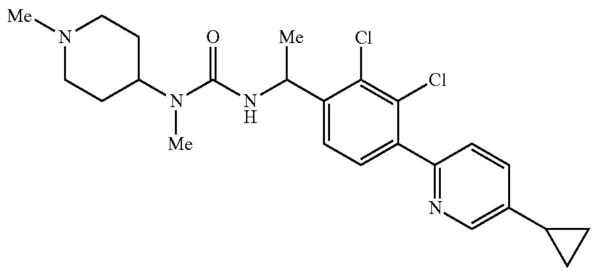 [SMILES: CC(NC(=O)N(C)C1CCN(C)CC1)c1ccc(-c2ccc(C3CC3)cn2)c(Cl)c1Cl] | $IC_{50}$ = 37 nM<br>$EC_{50}$ = 51 nM<br>$E_{max}$ = 1383 | Not Done | Not Done |
| H0578 | 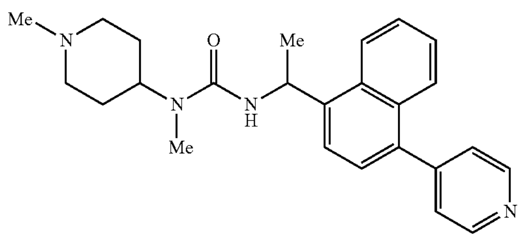 [SMILES: CC(NC(=O)N(C)C1CCN(C)CC1)c1ccc(-c2ccncc2)c2ccccc12] | $IC_{50}$ = 490 nM<br>$EC_{50}$ > 30 μM | Not Done | Not Done |
| H0511 | 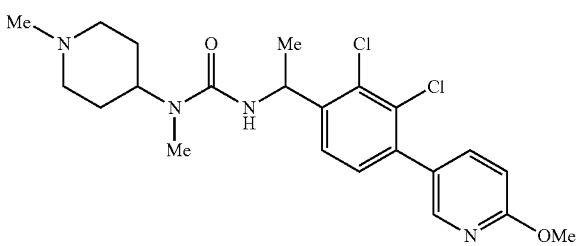 | $IC_{50}$ = 98 nM<br>$EC_{50}$ > 30 μM | Medium H<br>Medium M | 94% at 1 h Inhibition up to 24 h (30 mg/kg)) |
| H0820 | 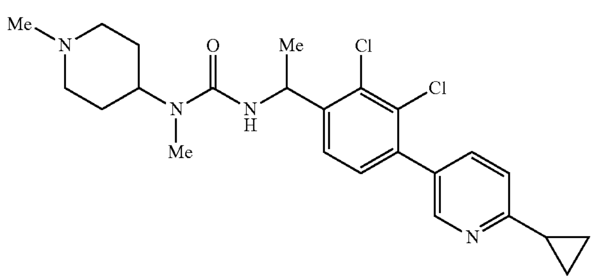 [SMILES: CC(NC(=O)N(C)C1CCN(C)CC1)c1ccc(-c2ccc(C3CC3)nc2)c(Cl)c1Cl] | $IC_{50}$ = 5.7 nM<br>$EC_{50}$ = 9 nM<br>$E_{max}$ = 3955 | Not Done | Not Done |
| H0613 | 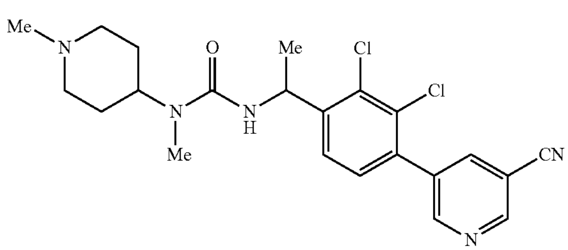 | $IC_{50}$ = 20 nM<br>$EC_{50}$ > 30 μM | High H<br>High M | NSE (10 mg/kg) PO: inhibition at 1 h, up to 2 h IP + ANAM 30 mpk PO: inhibition at 1 h up to 24 h |

TABLE 1-continued

| Compound No. | Chemical Structure | Activity | Metabolic Stability (H = Human; M = Mouse) | Mouse Food Intake (% Inhibition; Doses as mg/kg i.p.)* |
| --- | --- | --- | --- | --- |
| H0614 | 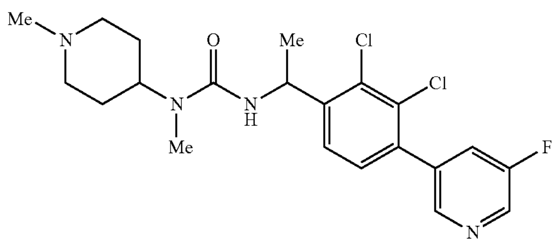 | $IC_{50}$ = 12 nM<br>$EC_{50}$ > 30 μM | High H<br>High M | No IP done,<br>PO: NSE |
| H0635 | 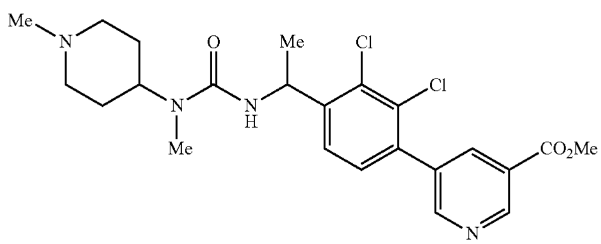 [SMILES: COC(=O)c1cncc(-c2ccc(C(C)NC(=O)N(C)C3CCN(C)CC3)c(Cl)c2Cl)c1] | $IC_{50}$ = 1090 nM<br>$EC_{50}$ > 30 μM | Not Done | Not Done |
| H0636 | 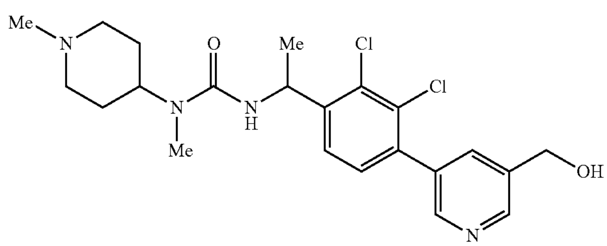 | $IC_{50}$ = 90 nM<br>$EC_{50}$ > 30 μM | High H<br>Medium M | Not Done |
| H0637 | 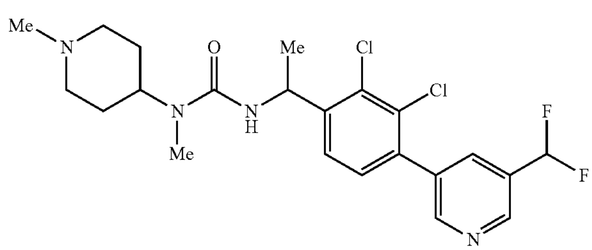 [SMILES: CC(NC(=O)N(C)C1CCN(C)CC1)c1ccc(-c2cncc(C(F)F)c2)c(Cl)c1Cl] | $IC_{50}$ = 85 nM<br>$EC_{50}$ > 30 μM | Medium H<br>Medium M | Not Done |
| H0638 | 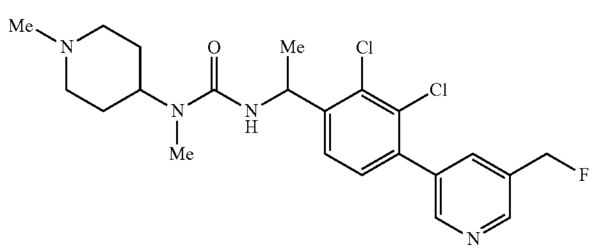 [SMILES: CC(NC(=O)N(C)C1CCN(C)CC1)c1ccc(-c2cncc(CF)c2)c(Cl)c1Cl] | $IC_{50}$ = 57 nM<br>$EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0639 | [Structure: 1-methylpiperidin-4-yl N-methyl urea linked to CH(Me)NH-(2,3-dichloro-4-(5-methylpyridin-3-yl)phenyl)] | IC$_{50}$ = 48 nM<br>EC$_{50}$ > 30 μM | Medium H<br>Medium M | NSE (10 mg/kg) |
| H0642 | [Structure: 1-methylpiperidin-4-yl N-methyl urea linked to CH(Me)NH-(2,3-dichloro-4-(5-formylpyridin-3-yl)phenyl)] | IC$_{50}$ = 78 nM<br>EC$_{50}$ > 30 μM | Very low H<br>Very Low M | Not Done |
| H0704 | [Structure: 1-methylpiperidin-4-yl N-methyl urea linked to CH(Me)NH-(2,3-dichloro-4-(5-aminopyridin-3-yl)phenyl)] | IC$_{50}$ = 19 nM<br>EC$_{50}$ > 30 μM | High H<br>Medium M | 32% inhibition at 2 h (10 mg/kg) |
| H0705 | [Structure: 1-methylpiperidin-4-yl N-methyl urea linked to CH(Me)NH-(2,3-dichloro-4-(5-(cyclopent-1-en-1-yl)pyridin-3-yl)phenyl)] | IC$_{50}$ = 53 nM<br>EC$_{50}$ > 30 μM | High H<br>High M | Not Done |
| H0707 | [Structure: 1-methylpiperidin-4-yl N-methyl urea linked to CH(Me)NH-(2,3-dichloro-4-(5-(1H-pyrazol-4-yl)pyridin-3-yl)phenyl)] | IC$_{50}$ = 185 nM<br>EC$_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0711 | 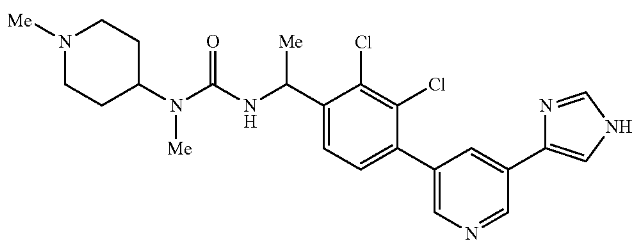 [SMILES: CC(NC(=O)N(C)C1CCN(C)CC1)c1ccc(-c2cncc(-c3c[nH]cn3)c2)c(Cl)c1Cl] | $IC_{50}$ = 1.85 μM $EC_{50}$ > 30 μM | Not Done | Not Done |
| H0716 | 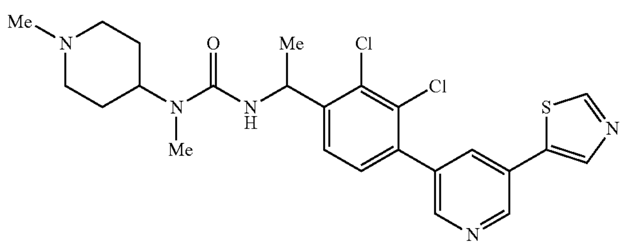 [SMILES: CC(NC(=O)N(C)C1CCN(C)CC1)c1ccc(-c2cncc(-c3cncs3)c2)c(Cl)c1Cl] | $IC_{50}$ = 15 nM $EC_{50}$ > 30 μM | Low H Medium M | Not Done |
| H0717 | 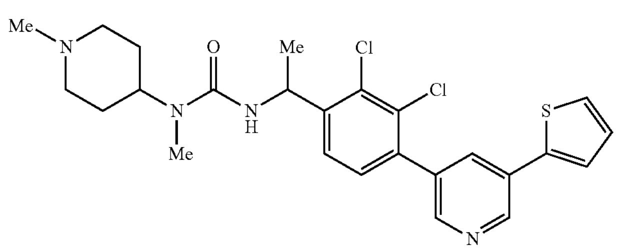 [SMILES: CC(NC(=O)N(C)C1CCN(C)CC1)c1ccc(-c2cncc(-c3cccs3)c2)c(Cl)c1Cl] | $IC_{50}$ = 396 nM $EC_{50}$ > 30 μM | Not Done | Not Done |
| H0718 | 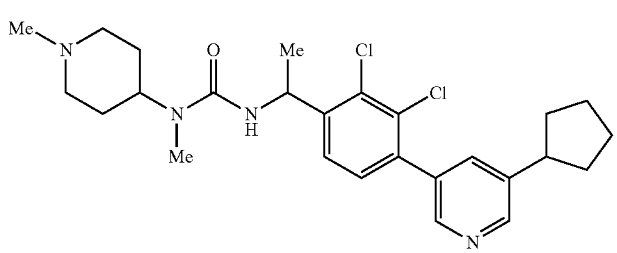 [SMILES: CC(NC(=O)N(C)C1CCN(C)CC1)c1ccc(-c2cncc(C3CCCC3)c2)c(Cl)c1Cl] | $IC_{50}$ = 499 nM $EC_{50}$ > 30 μM | Not Done | Not Done |
| H0719 | 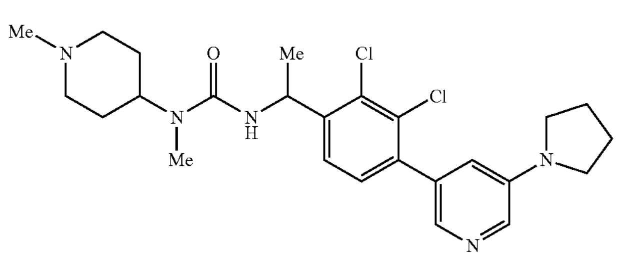 [SMILES: CC(NC(=O)N(C)C1CCN(C)CC1)c1ccc(-c2cncc(N3CCCC3)c2)c(Cl)c1Cl] | $IC_{50}$ = 780 nM $EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0712 | 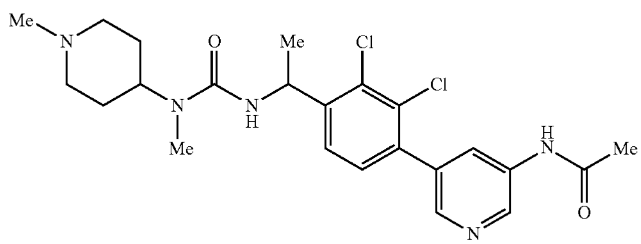 [SMILES: CC(=O)Nc1cncc(-c2ccc(C(C)NC(=O)N(C)C3CCN(C)CC3)c(Cl)c2Cl)c1] | $IC_{50}$ = 420 nM<br>$EC_{50}$ = 220 nM<br>$E_{max}$ = 1962 | Not Done | Not Done |
| H0708 | 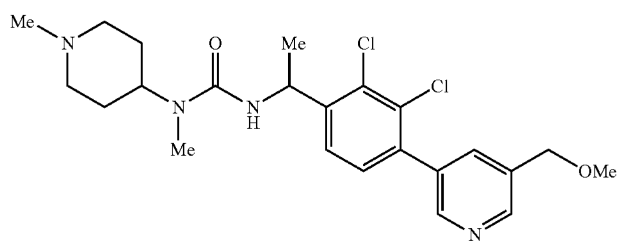 [SMILES: COCc1cncc(-c2ccc(C(C)NC(=O)N(C)C3CCN(C)CC3)c(Cl)c2Cl)c1] | $IC_{50}$ = 1.37 μM<br>$EC_{50}$ > 30 μM | Not Done | Not Done |
| H0714 | 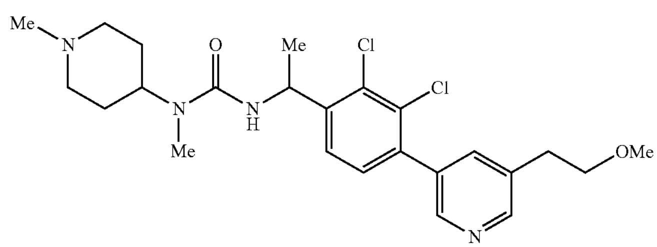 [SMILES: COCCc1cncc(-c2ccc(C(C)NC(=O)N(C)C3CCN(C)CC3)c(Cl)c2Cl)c1] | $IC_{50}$ = 453 nM<br>$EC_{50}$ > 30 μM | Not Done | Not Done |
| H0715 | 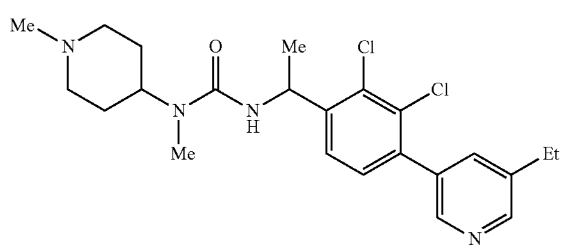 | $IC_{50}$ = 57 nM<br>$EC_{50}$ = 42 nM<br>$E_{max}$ = 2479 | Not Done | Not Done |
| H0706 | 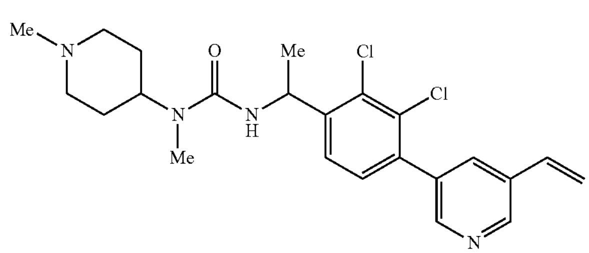 [SMILES: C=Cc1cncc(-c2ccc(C(C)NC(=O)N(C)C3CCN(C)CC3)c(Cl)c2Cl)c1] | $IC_{50}$ = 116 nM<br>$EC_{50}$ = 91 nM<br>$E_{max}$ = 2111 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0710 | 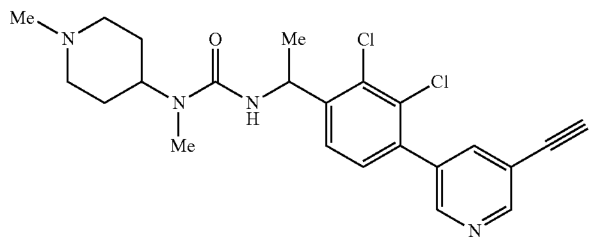 [SMILES: C#Cc1cncc(-c2ccc(C(C)NC(=O)N(C)C3CCN(C)CC3)c(Cl)c2Cl)c1] | $IC_{50}$ = 275 nM<br>$EC_{50}$ = 395 nM<br>$E_{max}$ – 1621 | Not Done | Not Done |
| H0666 | 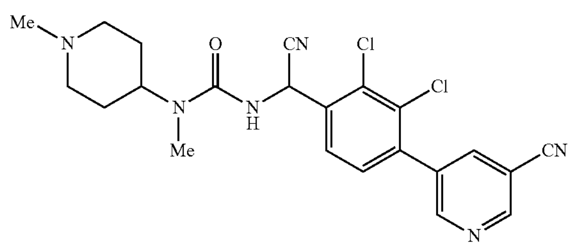 | $IC_{50}$ = 8 nM<br>$EC_{50}$ = 21 nM<br>$E_{max}$ = 4927 | Not Done | Not Done |
| H0739 | 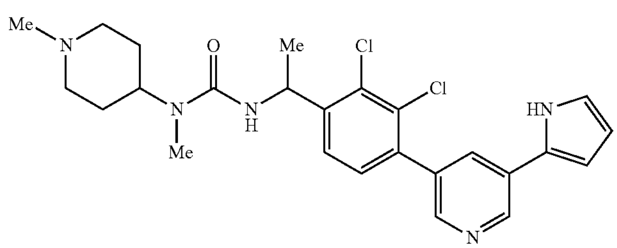 | $IC_{50}$ = 39 nM<br>$EC_{50}$ > 30 μM | Not Done | Not Done |
| H0667 | 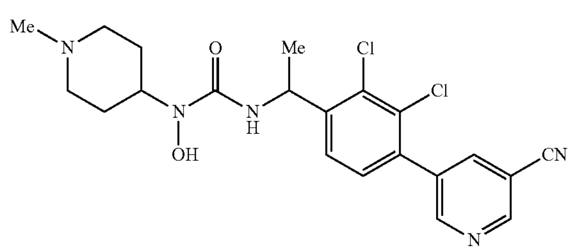 | $IC_{50}$ < 1 nM<br>$EC_{50}$ = 3 nM<br>$E_{max}$ = 4887 | High H<br>High M | 76% inhibition at 1 h; activity up to 4 h (10 mg/kg) |
| H0821 | 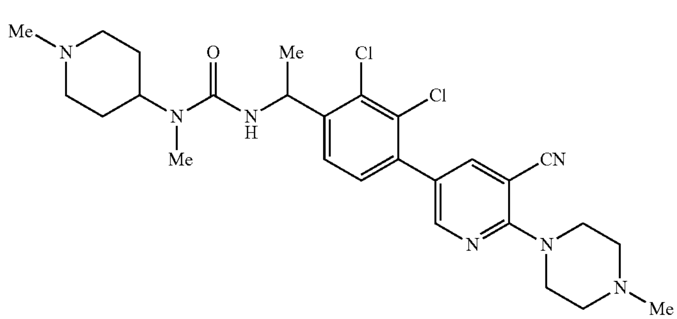 [SMILES: CC(NC(=O)N(C)C1CCN(C)CC1)c1ccc(-c2cnc(N3CCN(C)CC3)c(C#N)c2)c(Cl)c1Cl] | $IC_{50}$ = 2.3 μM<br>$EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0646 | 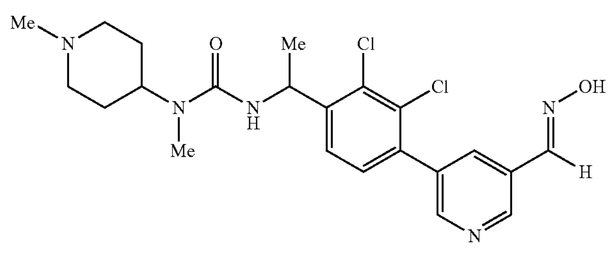 [SMILES: CC(NC(=O)N(C)C1CCN(C)CC1)c1ccc(-c2cncc(/C=N/O)c2)c(Cl)c1Cl] | IC$_{50}$ = 541 nM<br>EC$_{50}$ > 30 μM | Not Done | Not Done |
| H0720 | 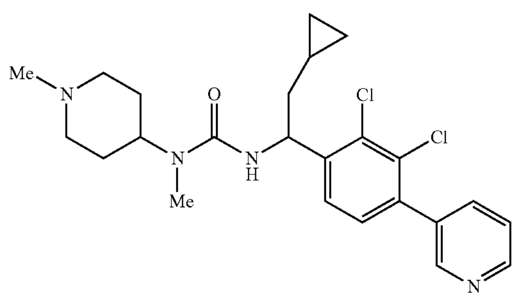 [SMILES: CN1CCC(N(C)C(=O)NC(CC2CC2)c2ccc(-c3cccnc3)c(Cl)c2Cl)CC1] | IC$_{50}$ = 8 nM<br>EC$_{50}$ > 30 μM | Medium H<br>High M | Not Done |
| H0721 | 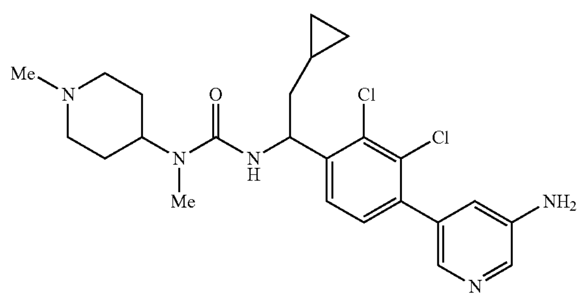 [SMILES: CN1CCC(N(C)C(=O)NC(CC2CC2)c2ccc(-c3cncc(N)c3)c(Cl)c2Cl)CC1] | IC$_{50}$ = 20 nM<br>EC$_{50}$ > 30 μM | Medium H<br>High M | Not Done |
| H0516 | 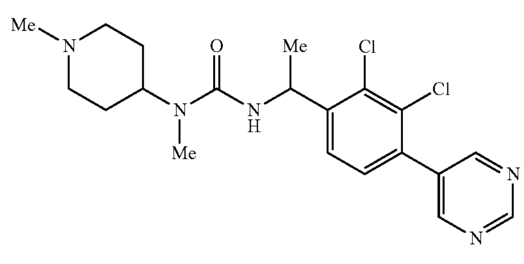 | IC$_{50}$ = 41 nM<br>EC$_{50}$ > 30 μM | High H<br>High M | 88% inhibition at 1 hour. Activity up to 24 h (30 mg/kg) PO: no effect |
| H0579 | 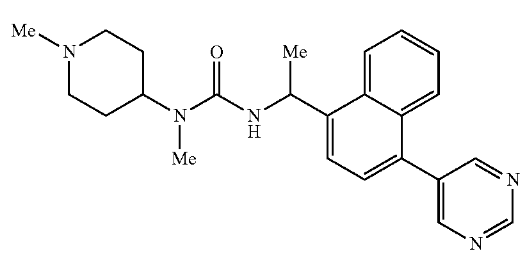 [SMILES: CC(NC(=O)N(C)C1CCN(C)CC1)c1ccc(-c2cncnc2)c2ccccc12] | IC$_{50}$ = 1 μM<br>EC$_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0649 | 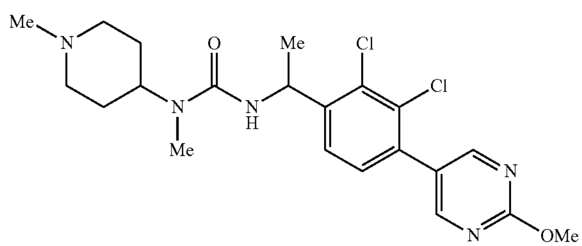 [SMILES: COc1ncc(-c2ccc(C(C)NC(=O)N(C)C3CCN(C)CC3)c(Cl)c2Cl)cn1] | $IC_{50}$ = 18 nM<br>$EC_{50}$ = 64 nM<br>$E_{max}$ = 1400 | High H<br>High M | 48% inhibition at 1 and 2 h (10 mg/kg) |
| H0797 | 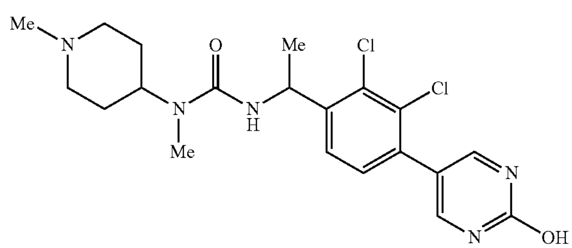 | $IC_{50}$ = 594 nM<br>$EC_{50}$ = 1.8 μM<br>$E_{max}$ = 2879 | Not Done | Not Done |
| H0798 | 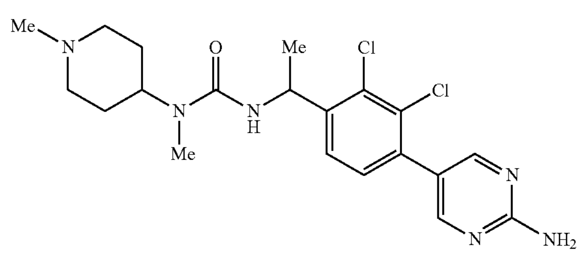 | $IC_{50}$ = 162 nM<br>$EC_{50}$ > 30 μM | Not Done | Not Done |
| H0799 | 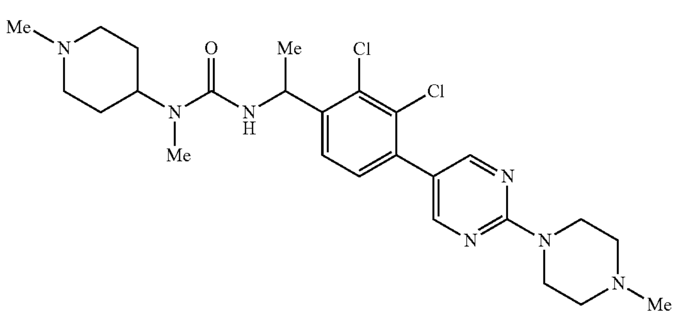 [SMILES: CC(NC(=O)N(C)C1CCN(C)CC1)c1ccc(-c2cnc(N3CCN(C)CC3)nc2)c(Cl)c1Cl] | $IC_{50}$ = 5.4 nM<br>$EC_{50}$ = 14 nM<br>$E_{max}$ = 5031 | Not Done | Not Done |
| H0800 | 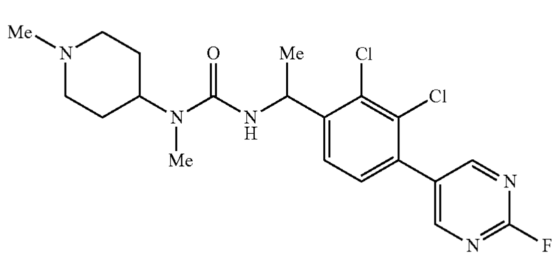 | $IC_{50}$ = 1.3 μM<br>$EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0801 | 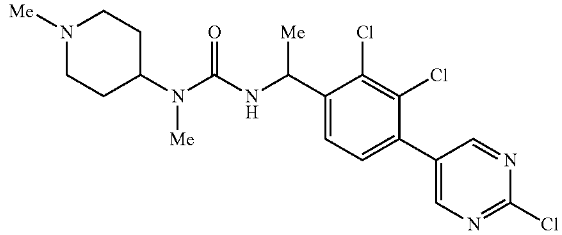 [SMILES: CC(NC(=O)N(C)C1CCN(C)CC1)c1ccc(-c2cnc(Cl)nc2)c(Cl)c1Cl] | $IC_{50}$ = 20 nM<br>$EC_{50}$ = 45 nM<br>$E_{max}$ = 3915 | Not Done | Not Done |
| H0802 | 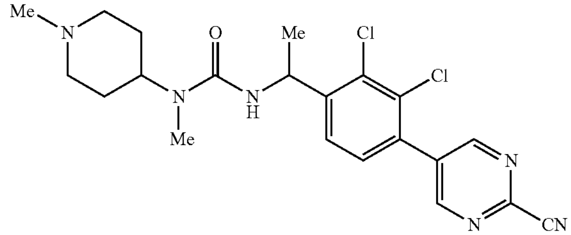 | $IC_{50}$ = 99 nM<br>$EC_{50}$ = 153 nM<br>$E_{max}$ = 4149 | Not Done | Not Done |
| H0803 | 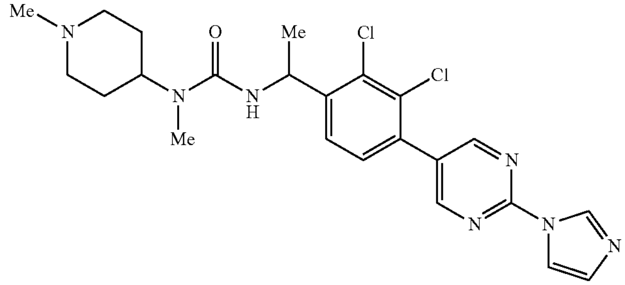 [SMILES: CC(NC(=O)N(C)C1CCN(C)CC1)c1ccc(-c2cnc(-n3ccnc3)nc2)c(Cl)c1Cl] | $IC_{50}$ = 171 nM<br>$EC_{50}$ = 149 nM<br>$E_{max}$ = 2364 | Not Done | Not Done |
| H0804 | 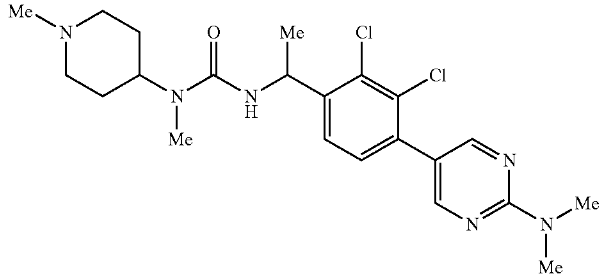 [SMILES: CC(NC(=O)N(C)C1CCN(C)CC1)c1ccc(-c2cnc(N(C)C)nc2)c(Cl)c1Cl] | $IC_{50}$ = 375 nM<br>$EC_{50}$ = 263 nM<br>$E_{max}$ = 2740 | Not Done | Not Done |
| H0805 | 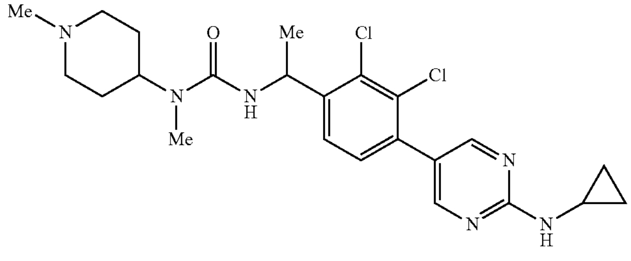 [SMILES: CC(NC(=O)N(C)C1CCN(C)CC1)c1ccc(-c2cnc(NC3CC3)nc2)c(Cl)c1Cl] | $IC_{50}$ = 4 nM<br>$EC_{50}$ = 9 nM<br>$E_{max}$ = 5433 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0806 | 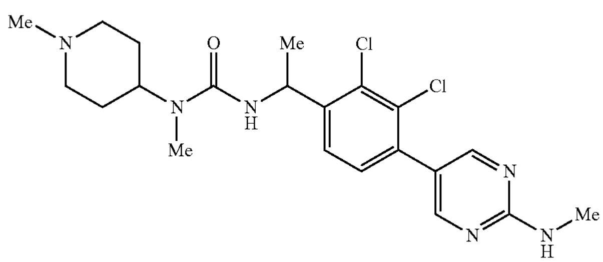 [SMILES: CNc1ncc(-c2ccc(C(C)NC(=O)N(C)C3CCN(C)CC3)c(Cl)c2Cl)cn1] | $IC_{50}$ = 1.2 nM<br>$EC_{50}$ = 6.8 nM<br>$E_{max}$ = 5751 | Not Done | Not Done |
| H0807 | 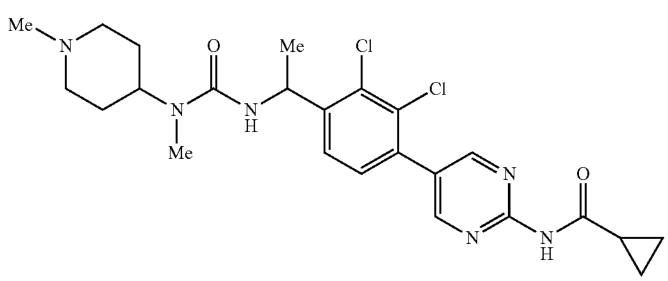 [SMILES: CC(NC(=O)N(C)C1CCN(C)CC1)c1ccc(-c2cnc(NC(=O)C3CC3)nc2)c(Cl)c1Cl] | $IC_{50}$ = 14 nM<br>$EC_{50}$ = 24 nM<br>$E_{max}$ = 3669 | Not Done | Not Done |
| H0854 | 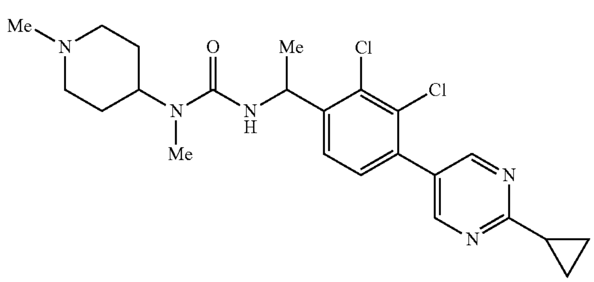 [SMILES: CC(NC(=O)N(C)C1CCN(C)CC1)c1ccc(-c2cnc(C3CC3)nc2)c(Cl)c1Cl] | $IC_{50}$ = 65 nM<br>$EC_{50}$ = 24 nM<br>$E_{max}$ = 3246 | Not Done | Not Done |
| H0813 | 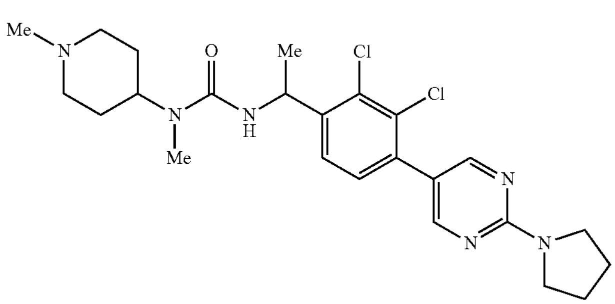 [SMILES: CC(NC(=O)N(C)C1CCN(C)CC1)c1ccc(-c2cnc(N3CCCC3)nc2)c(Cl)c1Cl] | $IC_{50}$ = 644 nM<br>$EC_{50}$ = 528 nM<br>$E_{max}$ = 1605 | Not Done | Not Done |
| H0814 | 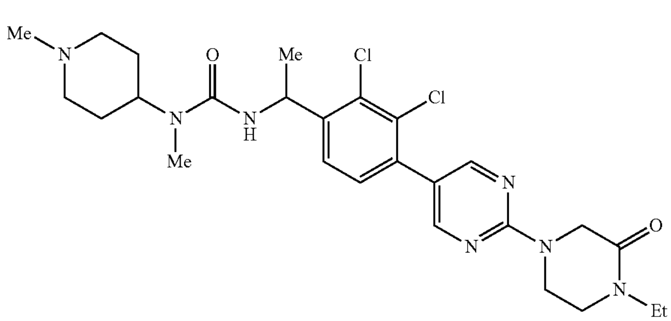 [SMILES: CCN1CCN(c2ncc(-c3ccc(C(C)NC(=O)N(C)C4CCN(C)CC4)c(Cl)c3Cl)cn2)CC1=O] | $IC_{50}$ = 926 nM<br>$EC_{50}$ = 15 nM<br>$E_{max}$ = 1097 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0703 | 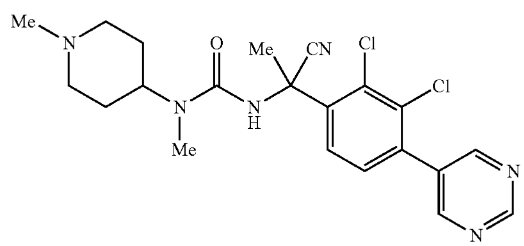 [SMILES: CN1CCC(N(C)C(=O)NC(C)(C#N)c2ccc(-c3cncnc3)c(Cl)c2Cl)CC1] | $IC_{50} = 695$ nM<br>$EC_{50} > 30$ μM | Not Done | Not Done |
| H0709 | 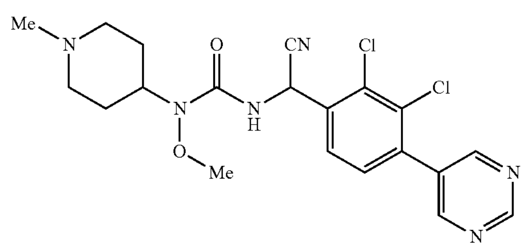 [SMILES: CON(C(=O)NC(C#N)c1ccc(-c2cncnc2)c(Cl)c1Cl)C1CCN(C)CC1] | $IC_{50} = 676$ nM<br>$EC_{50} > 30$ μM | Not Done | Not Done |
| H0584 | 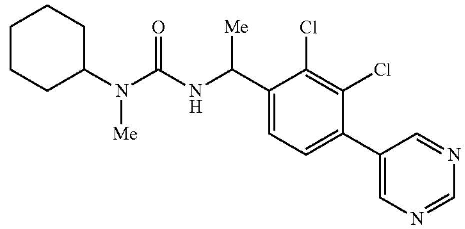 [SMILES: CC(NC(=O)N(C)C1CCCCC1)c1ccc(-c2cncnc2)c(Cl)c1Cl] | $IC_{50} = 1.1$ μM<br>$EC_{50} > 30$ μM | Not Done | Not Done |
| H0586 | 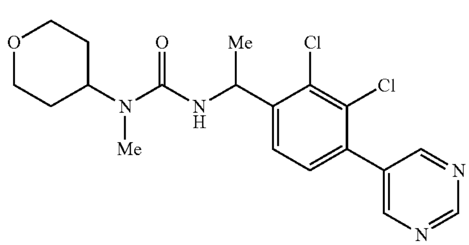 [SMILES: CC(NC(=O)N(C)C1CCOCC1)c1ccc(-c2cncnc2)c(Cl)c1Cl] | $IC_{50} = 4.2$ μM<br>$EC_{50} = 63$ μM | Not Done | Not Done |
| H0587 | 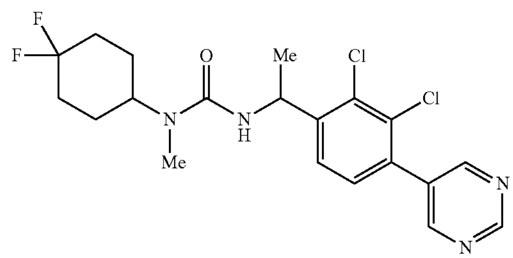 [SMILES: CC(NC(=O)N(C)C1CCC(F)(F)CC1)c1ccc(-c2cncnc2)c(Cl)c1Cl] | $IC_{50} > 30$ μM<br>$EC_{50} > 30$ μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0588 | 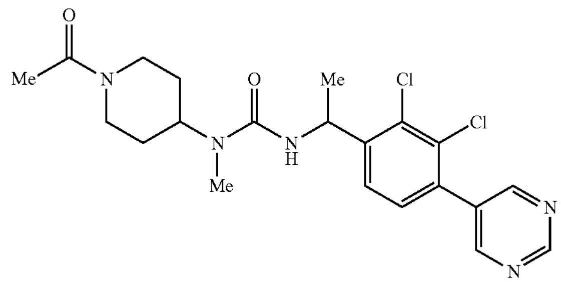 [SMILES: CC(=O)N1CCC(N(C)C(=O)NC(C)c2ccc(-c3cncnc3)c(Cl)c2Cl)CC1] | IC$_{50}$ > 30 μM<br>EC$_{50}$ > 30 μM | Not Done | Not Done |
| H0663 | 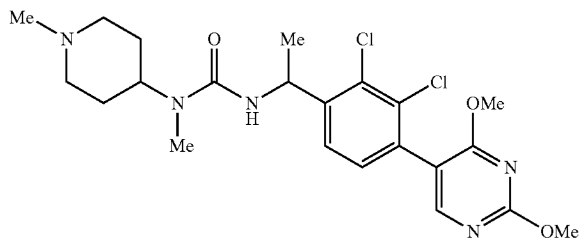 [SMILES: COc1ncc(-c2ccc(C(C)NC(=O)N(C)C3CCN(C)CC3)c(Cl)c2Cl)c(OC)n1] | IC$_{50}$ = 274 nM<br>EC$_{50}$ > 30 μM | Not Done | Not Done |
| H0620 | 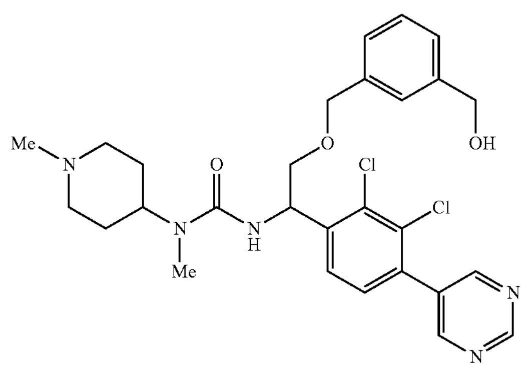 [SMILES: CN1CCC(N(C)C(=O)NC(COCc2cccc(CO)c2)c2ccc(-c3cncnc3)c(Cl)c2Cl)CC1] | IC$_{50}$ = 32 nM<br>EC$_{50}$ > 30 μM | Poor H<br>Poor M | Not Done |
| H0624 | 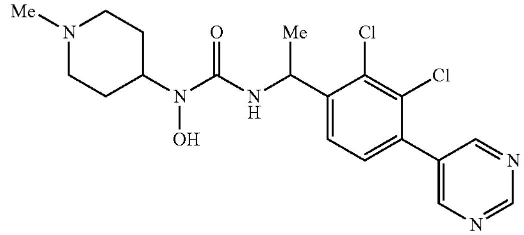 | IC$_{50}$ = 253 nM<br>EC$_{50}$ > 30 μM | Not Done | Not Done |
| H0662 | 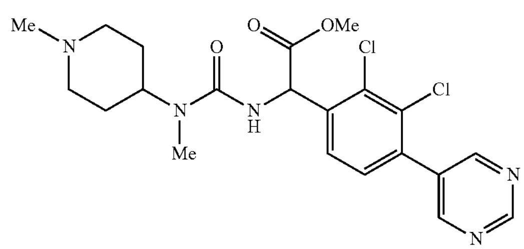 [SMILES: COC(=O)C(NC(=O)N(C)C1CCN(C)CC1)c1ccc(-c2cncnc2)c(Cl)c1Cl] | IC$_{50}$ => 1 μM<br>EC$_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0670 | 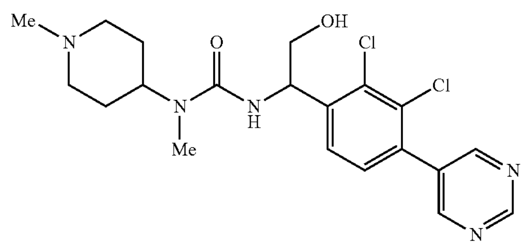 [SMILES: CN1CCC(N(C)C(=O)NC(CO)c2ccc(-c3cncnc3)c(Cl)c2Cl)CC1] | $IC_{50} = 523$ μM $EC_{50} > 30$ μM | Not Done | Not Done |
| H0673 | 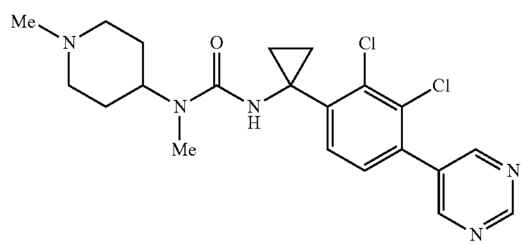 [SMILES: CN1CCC(N(C)C(=O)NC2(c3ccc(-c4cncnc4)c(Cl)c3Cl)CC2)CC1] | $IC_{50} > 1$ μM $EC_{50} > 30$ μM | Not Done | Not Done |
| H0727 | 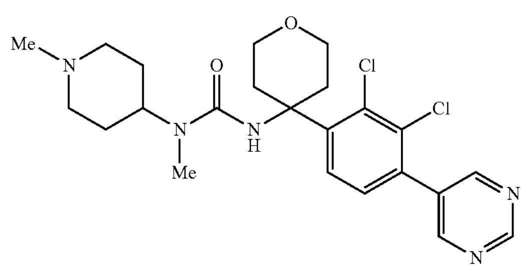 [SMILES: CN1CCC(N(C)C(=O)NC2(c3ccc(-c4cncnc4)c(Cl)c3Cl)CCOCC2)CC1] | $IC_{50} = 3.6$ μM $EC_{50} > 30$ μM | Not Done | Not Done |
| H0631 | 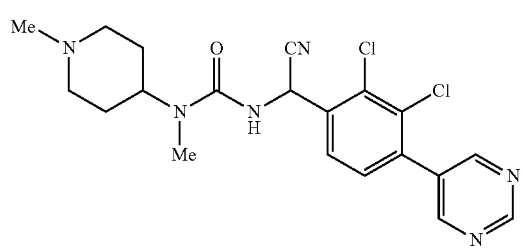 | $IC_{50} = 719$ nM $EC_{50} > 30$ μM | Not Done | Not Done |
| H0686 | 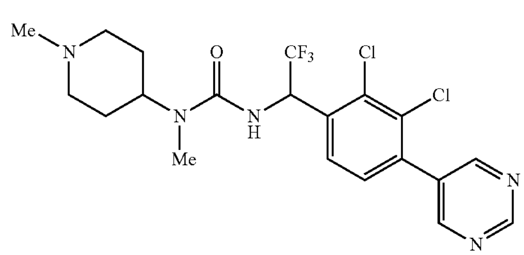 | $IC_{50} = 14$ nM $EC_{50} > 30$ μM | Medium H High M | 61% inhibition at 2 h and 4 h (10 mg/kg) PO: NSE |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0619 | 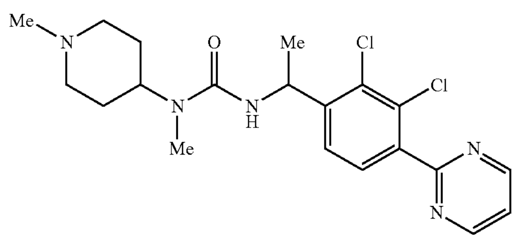 | $IC_{50}$ = 13 nM<br>$EC_{50}$ = 39 nM | High H<br>High M | 34% inhibition at 1 and 2 h (10 mgkg) |
| H0768 | 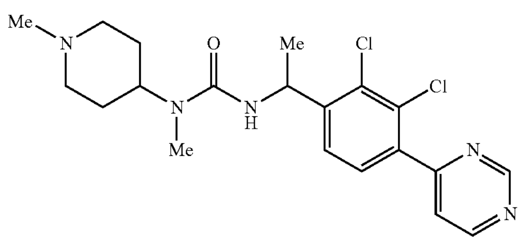 | $IC_{50}$ = 279 nM<br>$EC_{50}$ > 30 μM | Not Done | Not Done |
| H0808 | 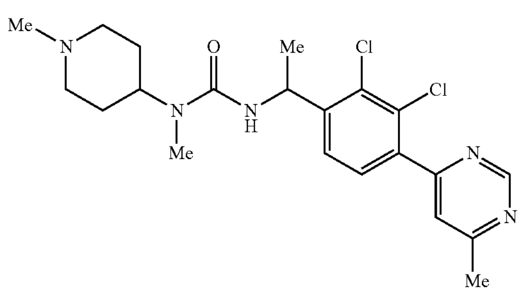 [SMILES: Cc1cc(-c2ccc(C(C)NC(=O)N(C)C3CCN(C)CC3)c(Cl)c2Cl)ncn1] | $IC_{50}$ = 674 nM<br>$EC_{50}$ = 90 nM<br>$E_{max}$ = 1494 | Not Done | Not Done |
| H0700 | 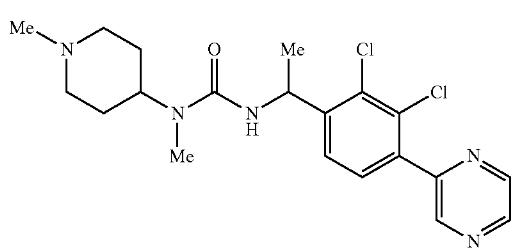 | $IC_{50}$ = 7 nM<br>$EC_{50}$ > 30 μM | High H<br>High M | 41% inhibition at 2 h; activity up to 4 h (10 mg/kg) 71% inhibition at 1 h, activity up to 2 h (Fed, 10 mg/kg) PO SC: inhib at 1, 2 H) |
| H0816 | 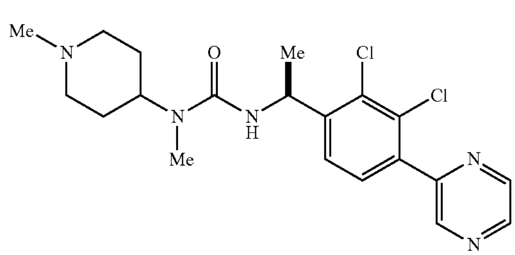 [SMILES: C[C@H](NC(=O)N(C)C1CCN(C)CC1)c1ccc(-c2cnccn2)c(Cl)c1Cl] | $IC_{50}$ = 5.1 nM<br>$EC_{50}$ > 30 μM | Not Done | 12% inhib 30 mg/kg PO fasted mice |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0817 | [Me-N-piperidine-N(Me)-C(O)-NH-CH(Me)-(2,3-dichloro-4-pyrazinyl-phenyl)] | IC$_{50}$ = 94 nM<br>EC$_{50}$ > 30 μM | Not Done | 30 mg/kg PO fasted mice NSE |
| H0722 | [Me-N-piperidine-N(Me)-C(O)-NH-CH(CH2-cyclopropyl)-(2,3-dichloro-4-pyrazinyl-phenyl)] | IC$_{50}$ = 13 nM<br>EC$_{50}$ > 30 μM | High H<br>High M | 90% inhibition at 1 h; activity up to 24 h (10 mg/kg) PO: NSE (30 mg/kg) |
| H0741 | [Me-N-piperidine-N(OMe)-C(O)-NH-CH(CH2-cyclopropyl)-(2,3-dichloro-4-pyrazinyl-phenyl)] | IC$_{50}$ = 15 nM<br>EC$_{50}$ > 30 μM | Not Done | Not Done |
| H0752 | [Me-N-piperidine-N(OEt)-C(O)-NH-CH(CH2-cyclopropyl)-(2,3-dichloro-4-pyrazinyl-phenyl)] | IC$_{50}$ = 100 nM<br>EC$_{50}$ > 30 μM | Not Done | Not Done |
| H0743 | [Me-N-piperidine-N(OMe)-C(O)-NH-CH(Me)-(2,3-dichloro-4-pyrazinyl-phenyl)] | IC$_{50}$ = 94 nM<br>EC$_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0750 | 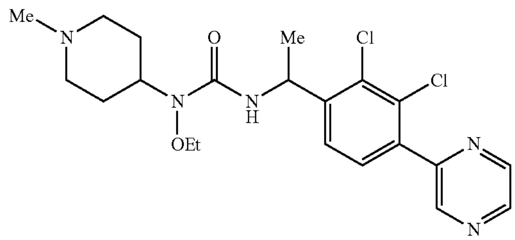 | $IC_{50}$ = 177 nM<br>$EC_{50}$ > 30 μM | Not Done | Not Done |
| H0756 | 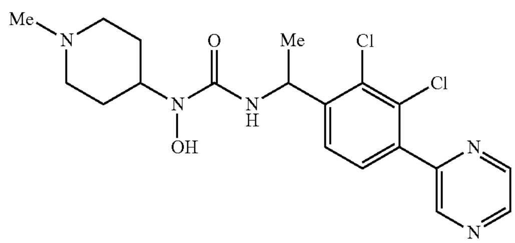 | $IC_{50}$ = 13 nM<br>$EC_{50}$ = 13 nM<br>$E_{max}$ = 1729 | Not Done | Not Done |
| H0761 | 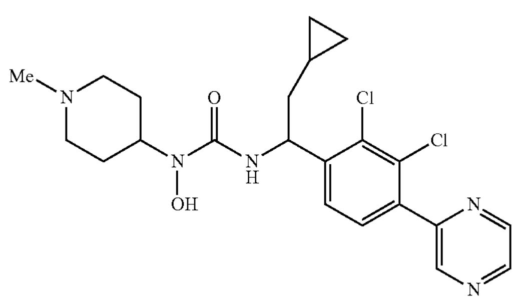 | $IC_{50}$ = 0.2 nM<br>$EC_{50}$ = 3 nM<br>$E_{max}$ = 2907 | High H<br>High M | 63% inhibition at 1 h; activity up to 8 h (10 mg/kg) PO: NSE No activity in fed mice PO: 215% FI increase in fed mice. No activity in fasted mice |
| H0781 | (S,R)<br>(single enantiomer) | $IC_{50}$ = 95 nM<br>$EC_{50}$ = 420 nM<br>$E_{max}$ = 4210 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0782 | 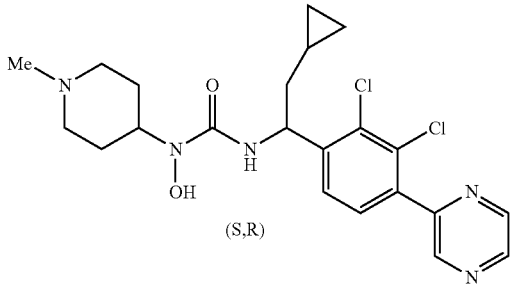 (S,R) (single enantiomer) | $IC_{50}$ = 5 nM $EC_{50}$ = 6 nM $E_{max}$ = 1923 | Not Done | 93% inhibition at 1 h, activity up to 24 h (10 mg/kg) |
| H0824 | 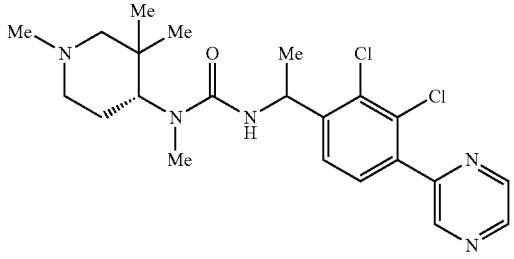 | $IC_{50}$ = 3 nM $EC_{50}$ > 30 µM | High H Medium M | PO 30 mg/kg + ANA mice: NSE |
| H0890 | 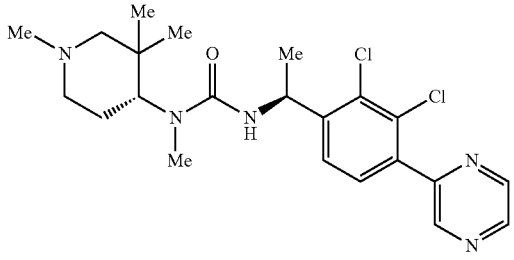 [SMILES: C[C@H](NC(=O)N(C)[C@@H]1CCN(C)CC1(C)C)c1ccc(-c2cnccn2)c(Cl)c1Cl] | $IC_{50}$ = 1.6 nM $EC_{50}$ > 30 µM | High H High M | Not Done |
| H0858 | 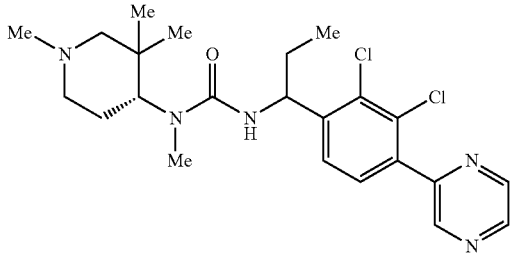 [SMILES: CCC(NC(=O)N(C)[C@@H]1CCN(C)CC1(C)C)c1ccc(-c2cnccn2)c(Cl)c1Cl] | $IC_{50}$ = 8 nM $EC_{50}$ > 30 µM | Medium H Medium M | Not Done |
| H0865 | 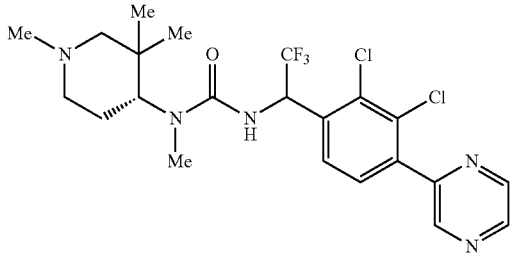 | $IC_{50}$ = 6 nM $EC_{50}$ > 30 µM | Medium H Low M Medium R | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
| --- | --- | --- | --- | --- |
| H0825 | 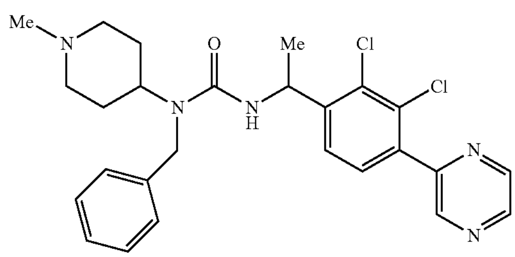 [SMILES: CC(NC(=O)N(Cc1ccccc1)C1CCN(C)CC1)c1ccc(-c2cnccn2)c(Cl)c1Cl] | $IC_{50}$ = 10 nM<br>$EC_{50}$ > 30 μM | Medium H<br>Medium M<br>Medium R | Not Done |
| H0826 | 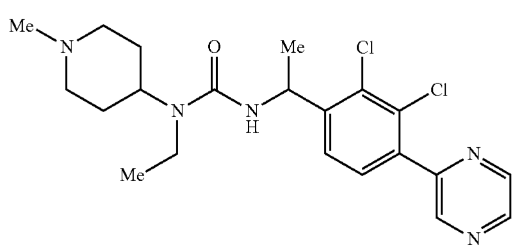 [SMILES: CCN(C(=O)NC(C)c1ccc(-c2cnccn2)c(Cl)c1Cl)C1CCN(C)CC1] | $IC_{50}$ = 5 nM<br>$EC_{50}$ > 30 μM | High H<br>High M<br>High R<br>Medium D | Not Done |
| H0889 | 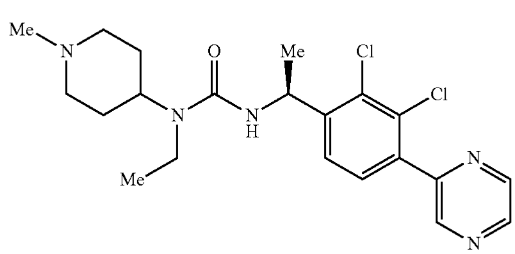 [SMILES: CCN(C(=O)N[C@@H](C)c1ccc(-c2cnccn2)c(Cl)c1Cl)C1CCN(C)CC1] | $IC_{50}$ = 6 nM<br>$EC_{50}$ > 30 μM | High H<br>High M | Not Done |
| H0896 | 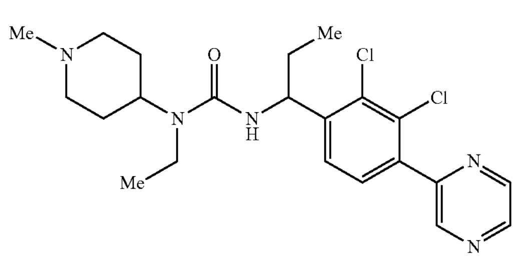 [SMILES: CCC(NC(=O)N(CC)C1CCN(C)CC1)c1ccc(-c2cnccn2)c(Cl)c1Cl] | $IC_{50}$ = 7 nM<br>$EC_{50}$ > 30 μM | Not Done | Not Done |
| H0827 | 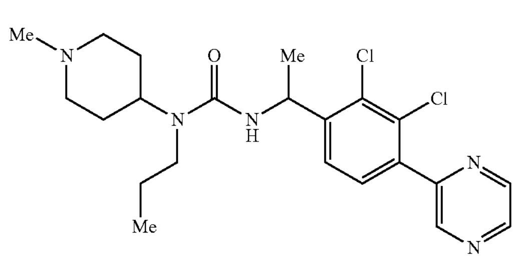 [SMILES: CCCN(C(=O)NC(C)c1ccc(-c2cnccn2)c(Cl)c1Cl)C1CCN(C)CC1] | $IC_{50}$ = 35 nM<br>$EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0829 | 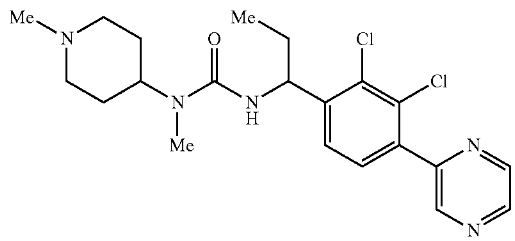 | IC$_{50}$ = 3 nM<br>EC$_{50}$ > 30 μM | High H<br>High M | PO 10 mg/kg + ANA 30 mg/kg mice: NSE |
| H0859 | 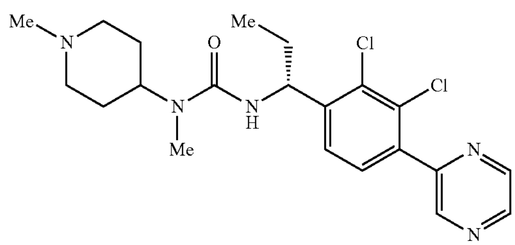 | IC$_{50}$ = 2.2 μM<br>EC$_{50}$ > 30 μM | Not Done | Not Done |
| H0860 | 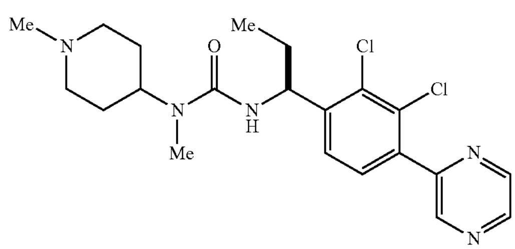 [SMILES: CC[C@H](NC(=O)N(C)C1CCN(C)CC1)c1ccc(-c2cnccn2)c(Cl)c1Cl] | IC$_{50}$ = 3 nM<br>EC$_{50}$ > 30 μM | High H<br>High M | 68% inhib 1 h PO 10 mg/kg + ANA 30 mg/kg mice |
| H0922 | 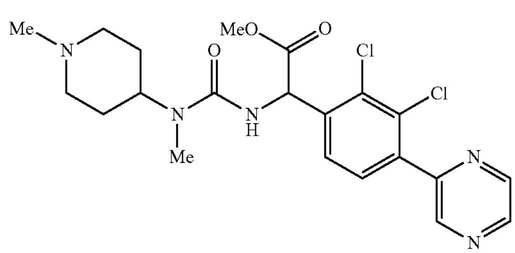 [SMILES: COC(=O)C(NC(=O)N(C)C1CCN(C)CC1)c1ccc(-c2cnccn2)c(Cl)c1Cl] | IC$_{50}$ = 2.8 μM<br>EC$_{50}$ > 30 μM | Not Done | Not Done |
| H0924 | 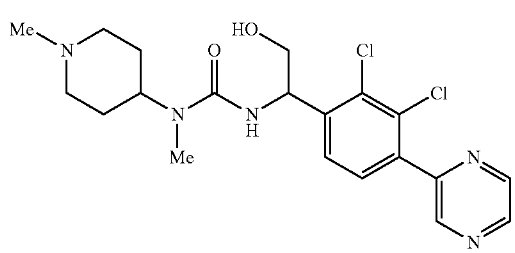 | IC$_{50}$ = 300 nM<br>EC$_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0830 | (structure) | $IC_{50}$ = 3 nM<br>$EC_{50}$ > 30 μM | High H<br>High M<br>High R<br>Medium D | Not Done<br>TBD |
| H0899 | (structure) | $IC_{50}$ = 1.6 μM<br>$EC_{50}$ > 30 μM | Medium H<br>High M | Not Done |
| H0900 | (structure) | $IC_{50}$ = 3 nM<br>$EC_{50}$ > 30 μM | Medium H<br>High M | 60% inhib 1 h PO 10 mg/kg + ANA 30 mg/kg fed mice<br>91% inhib 1 h PO 30 mg/kg + ANA 30 mg/kg fed mice<br>26% inhib 1 h PO 30 mg/kg fasted mice<br>90% inhib 1 h PO 30 mg/kg fed mice |
| H0909 | (structure) | $IC_{50}$ = 12 nM<br>$EC_{50}$ > 30 μM | Medium H<br>High M | Not Done |
| H0856 | (structure) | $IC_{50}$ = 339 nM<br>$EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0837 | 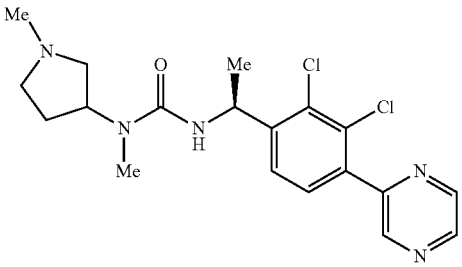<br>(diasteromeric mixture) | $IC_{50}$ = 2 nM<br>$EC_{50}$ > 30 µM | High H<br>High M<br>High R<br>High D | 180% increase 2 h mice 30 mg/kg PO<br>PO 10 mg/kg + ANA 30 mg/kg mice: NSE |
| H0861 | 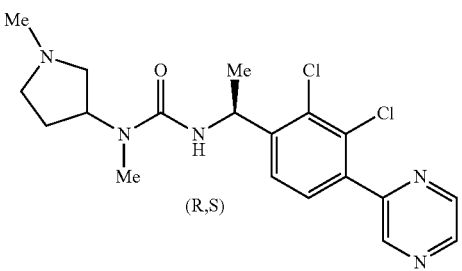<br>(R,S)<br>(single diastereoisomer) | $IC_{50}$ = 189 nM<br>$EC_{50}$ > 30 µM | Not Done | Not Done |
| H0862 | 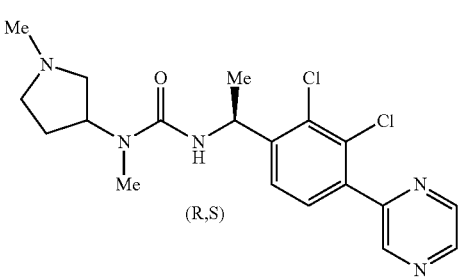<br>(R,S)<br>(single diastereoisomer) | $IC_{50}$ = 3 nM<br>$EC_{50}$ > 30 µM | High H<br>medium M | PO (10 mg/kg) + ANA: no activity in mice |
| H0857 | 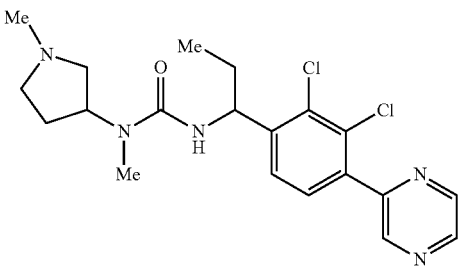 [SMILES: CCC(NC(=O)N(C)C1CCN(C)C1)c1ccc(-c2cnccn2)c(Cl)c1Cl] | $IC_{50}$ = 10 nM<br>$EC_{50}$ > 30 µM | Medium H<br>Low M | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0871 | 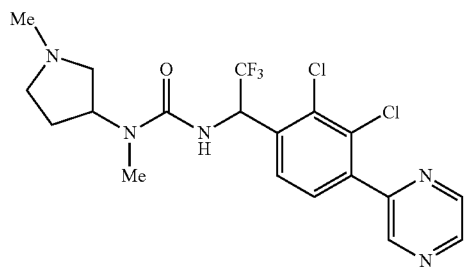 [SMILES: CN1CCC(N(C)C(=O)NC(c2ccc(-c3cnccn3)c(Cl)c2Cl)C(F)(F)F)C1] | $IC_{50}$ = 9 nM<br>$EC_{50}$ > 30 μM | Not Done | Not Done |
| H0874 | 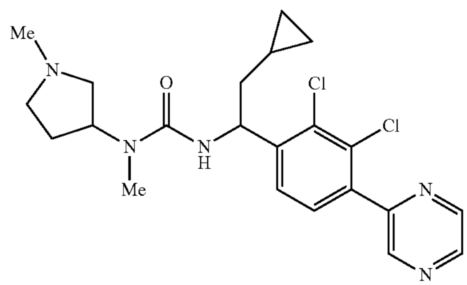 [SMILES: CN1CCC(N(C)C(=O)NC(CC2CC2)c2ccc(-c3cnccn3)c(Cl)c2Cl)C1] | $IC_{50}$ = 115 nM<br>$EC_{50}$ > 30 μM | Not Done | Not Done |
| H0853 | 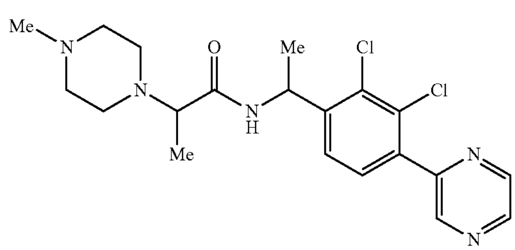 | $IC_{50}$ = 1.5 μM<br>$EC_{50}$ > 30 μM | Not Done | Not Done |
| H0815 | 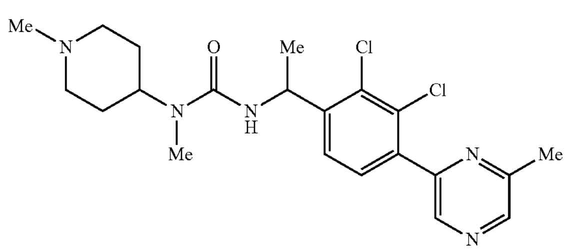 [SMILES: Cc1cncc(-c2ccc(C(C)NC(=O)N(C)C3CCN(C)CC3)c(Cl)c2Cl)n1] | $IC_{50}$ = 176 nM<br>$EC_{50}$ > 30 μM | Not Done | Not Done |
| H0831 | 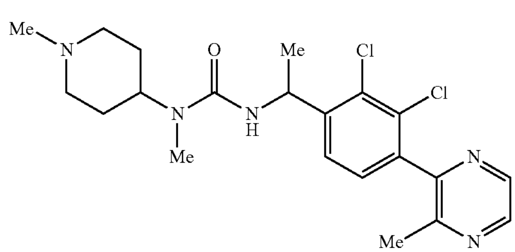 [SMILES: Cc1nccnc1-c1ccc(C(C)NC(=O)N(C)C2CCN(C)CC2)c(Cl)c1Cl] | $IC_{50}$ = 1.2 μM<br>$EC_{50}$ > 30 μM | | |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0843 | 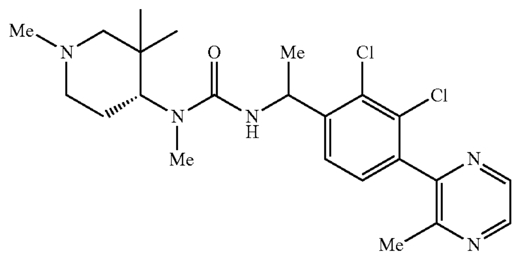 [SMILES: Cc1nccnc1-c1ccc(C(C)NC(=O)N(C)[C@@H]2CCN(C)CC2(C)C)c(Cl)c1Cl] | $IC_{50}$ = 35 nM<br>$EC_{50}$ = 51 nM<br>$E_{max}$ = 1910 | Not Done | Not Done |
| H0844 | 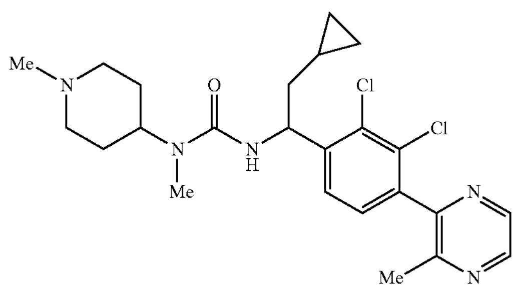 [SMILES: Cc1nccnc1-c1ccc(C(CC2CC2)NC(=O)N(C)C2CCN(C)CC2)c(Cl)c1Cl] | $IC_{50}$ = 705 nM<br>$EC_{50}$ > 30 µM | | |
| H0738 | 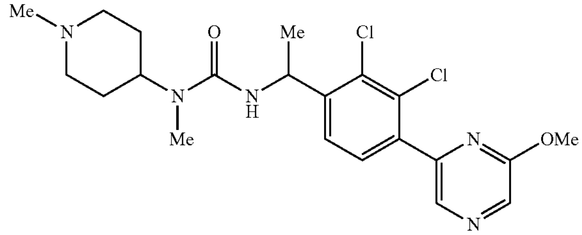 | $IC_{50}$ = 696 nM<br>$EC_{50}$ > 30 µM | Not Done | Not Done |
| H0780 | 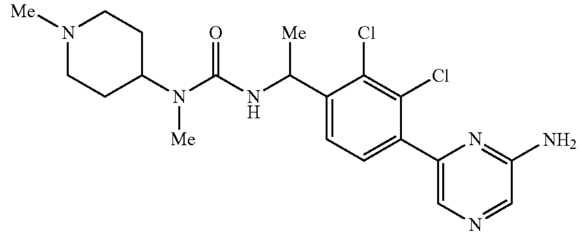 | $IC_{50}$ = 63 nM<br>$EC_{50}$ > 30 µM | Not Done | Not Done |
| H0786 | 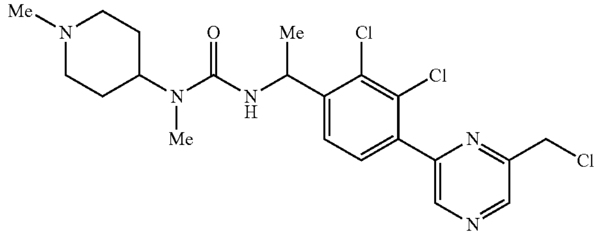 [SMILES: CC(NC(=O)N(C)C1CCN(C)CC1)c1ccc(-c2cncc(CCl)n2)c(Cl)c1Cl] | $IC_{50}$ = 855 nM<br>$EC_{50}$ = 242 nM<br>$E_{max}$ = 980 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0791 | 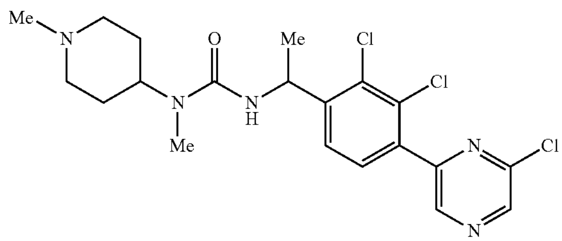 [SMILES: CC(NC(=O)N(C)C1CCN(C)CC1)c1ccc(-c2cncc(Cl)n2)c(Cl)c1Cl] | $IC_{50}$ = 75 nM<br>$EC_{50}$ > 30 μM | Not Done | Not Done |
| H0795 | 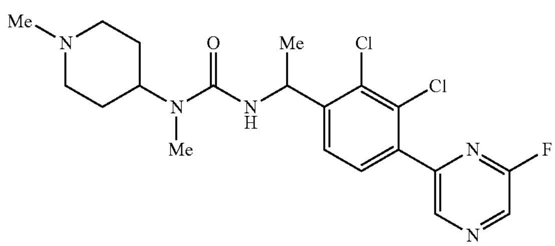 | $IC_{50}$ = 4 nM<br>$EC_{50}$ > 30 μM | High H<br>High M | PO: NSE<br>PO + ANA: inhib in mice, no activity in rat |
| H0847 | (S enantiomer) | $IC_{50}$ = 2 nM<br>$EC_{50}$ > 30 μM | High H<br>High M | PO 10 mg/kg + ANA 30 mg/kg mice: NSE |
| H0848 | (R enantiomer) | $IC_{50}$ = 432 nM<br>$EC_{50}$ > 30 μM | Medium H<br>High M | PO 10 mg/kg + ANA 30 mg/kg mice: NSE |
| H0863 | 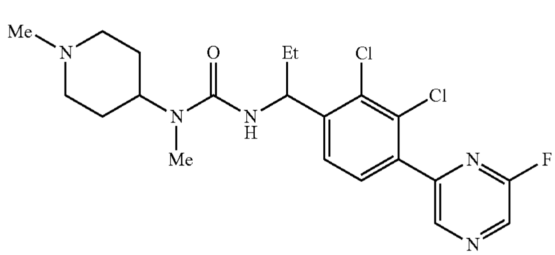 | $IC_{50}$ = 3 nM<br>$EC_{50}$ > 30 μM | Medium H<br>High M | Not done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0908 | 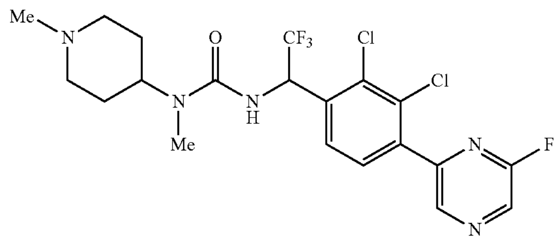 | $IC_{50}$ = 8 nM<br>$EC_{50}$ > 30 μM | Medium H<br>High M | Not Done |
| H0864 | 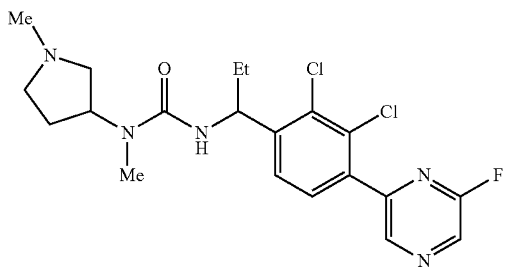 [SMILES: CCC(NC(=O)N(C)C1CCN(C)C1)c1ccc(-c2cncc(F)n2)c(Cl)c1Cl] | $IC_{50}$ = 718 nM<br>$EC_{50}$ > 30 μM | Not done | Not Done |
| H0872 | 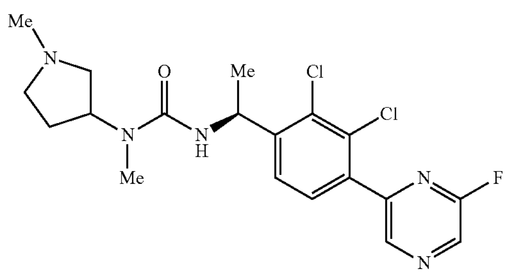 [SMILES: C[C@H](NC(=O)N(C)C1CCN(C)C1)c1ccc(-c2cncc(F)n2)c(Cl)c1Cl] | $IC_{50}$ = 6 nM<br>$EC_{50}$ > 30 μM | High H<br>medium M | Not Done |
| H0840 | 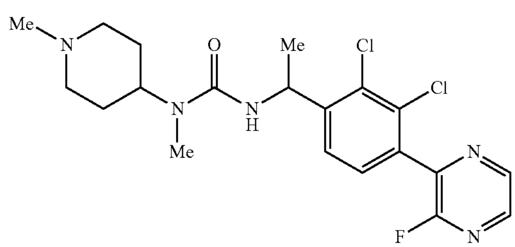 [SMILES: CC(NC(=O)N(C)C1CCN(C)CC1)c1ccc(-c2nccnc2F)c(Cl)c1Cl] | $IC_{50}$ = 47 nM<br>$EC_{50}$ > 30 μM | Not Done | PO 10 mg/kg + ANA 30 mg/kg mice: NSE |
| H0910 | 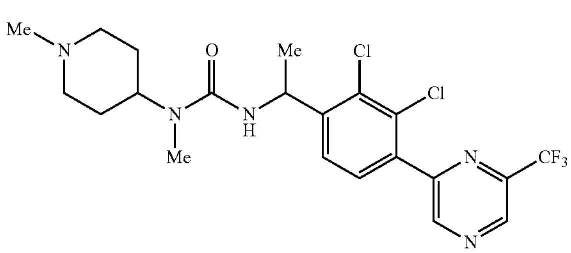 [SMILES: CC(NC(=O)N(C)C1CCN(C)CC1)c1ccc(-c2cncc(C(F)(F)F)n2)c(Cl)c1Cl] | $IC_{50}$ = 125 nM<br>$EC_{50}$ = 19 nM<br>$E_{max}$ = 1359 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0788 | 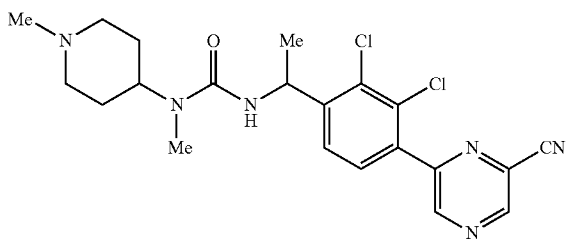 | $IC_{50}$ = 88 nM<br>$EC_{50}$ = 20 nM<br>$E_{max}$ = 1230 | Not Done | Not Done |
| H0789 | 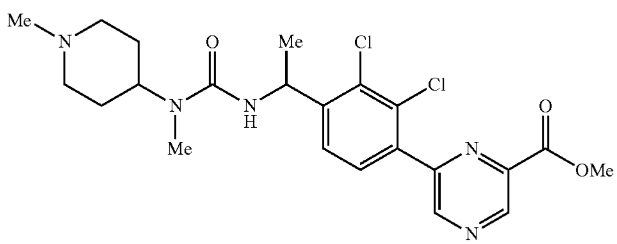 [SMILES: COC(=O)c1cncc(-c2ccc(C(C)NC(=O)N(C)C3CCN(C)CC3)c(Cl)c2Cl)n1] | $IC_{50}$ = 284 nM<br>$EC_{50}$ = 26 nM<br>$E_{max}$ = 1137 | Not Done | Not Done |
| H0760 | 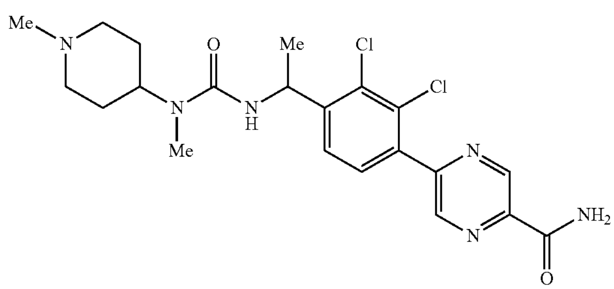 [SMILES: CC(NC(=O)N(C)C1CCN(C)CC1)c1ccc(-c2cnc(C(N)=O)cn2)c(Cl)c1Cl] | $IC_{50}$ = 6.2 μM<br>$EC_{50}$ > 30 μM | Not Done | Not Done |
| H0769 | 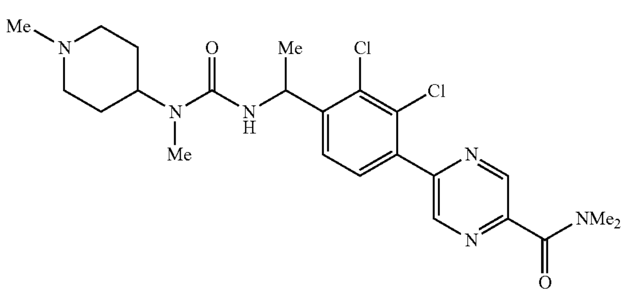 [SMILES: CC(NC(=O)N(C)C1CCN(C)CC1)c1ccc(-c2cnc(C(=O)N(C)C)cn2)c(Cl)c1Cl] | $IC_{50}$ = 318 nM<br>$EC_{50}$ > 30 μM | Not Done | Not Done |
| H0771 | 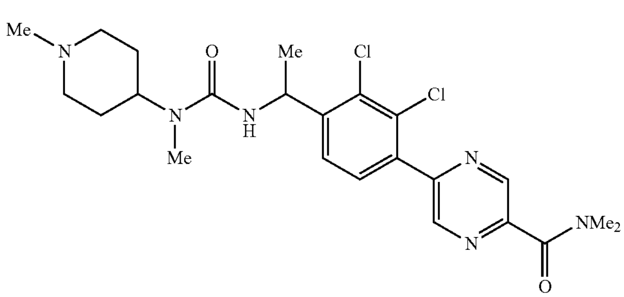 [SMILES: CC(NC(=O)N(C)C1CCN(C)CC1)c1ccc(-c2cnc(C(=O)N(C)C)cn2)c(Cl)c1Cl] | $IC_{50}$ = 9 nM<br>$EC_{50}$ = 9 nM<br>$E_{max}$ = 4662 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0770 | 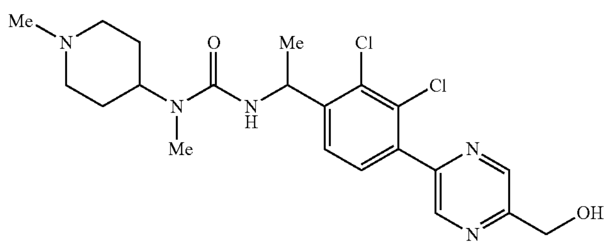 [SMILES: CC(NC(=O)N(C)C1CCN(C)CC1)c1ccc(-c2cnc(CO)cn2)c(Cl)c1Cl] | $IC_{50}$ = 700 nM<br>$EC_{50}$ = 294 nM<br>$E_{max}$ = 1783 | Not Done | Not Done |
| H0828 | 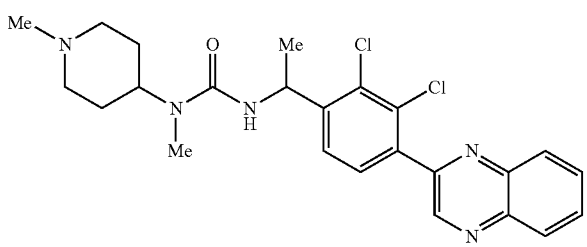 [SMILES: CC(NC(=O)N(C)C1CCN(C)CC1)c1ccc(-c2cnc3ccccc3n2)c(Cl)c1Cl] | $IC_{50}$ = 376 nM<br>$EC_{50}$ > 30 µM | Not Done | Not Done |
| H0822 | TFA | $IC_{50}$ = 1.2 µM<br>$EC_{50}$ > 30 µM | Not Done | Not Done |
| H0850 | 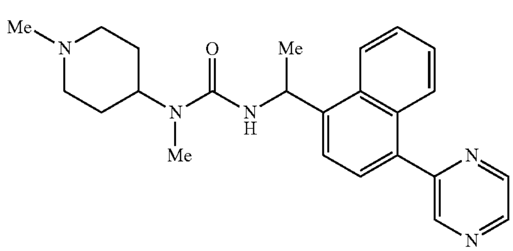 [SMILES: CC(NC(=O)N(C)C1CCN(C)CC1)c1ccc(-c2cnccn2)c2ccccc12] | $IC_{50}$ = 1.2 µM<br>$EC_{50}$ > 30 µM | Not Done | Not Done |
| H0881 | 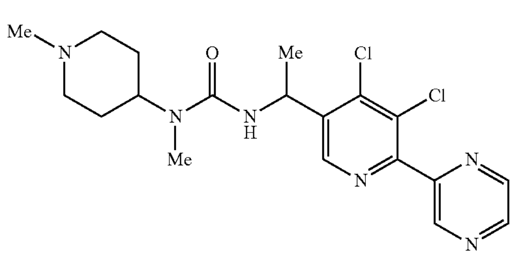 | $IC_{50}$ = 810 nM<br>$EC_{50}$ > 30 µM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0729 | 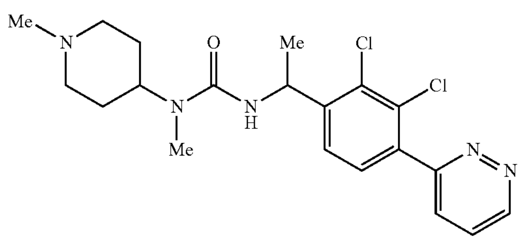 | $IC_{50}$ = 100 nM<br>$EC_{50}$ = 95 nM<br>$E_{max}$ = 2818 | Not Done | Not Done |
| H0783 | 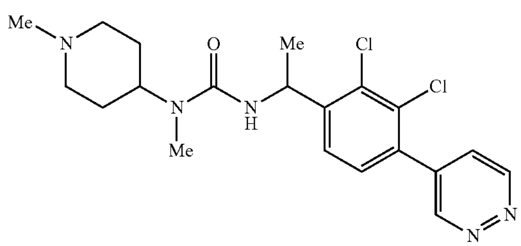 [SMILES: CC(NC(=O)N(C)C1CCN(C)CC1)c1ccc(-c2ccnnc2)c(Cl)c1Cl] | $IC_{50}$ = 681 nM<br>$EC_{50}$ = 30 nM | Not Done | Not Done |
| H0793 | 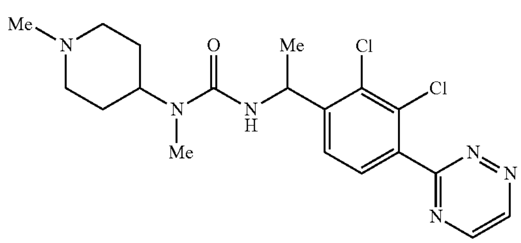 | $IC_{50}$ = 21 nM<br>$EC_{50}$ = 22 nM<br>$E_{max}$ = 3501 | Not Done | Not Done |
| H0796 | 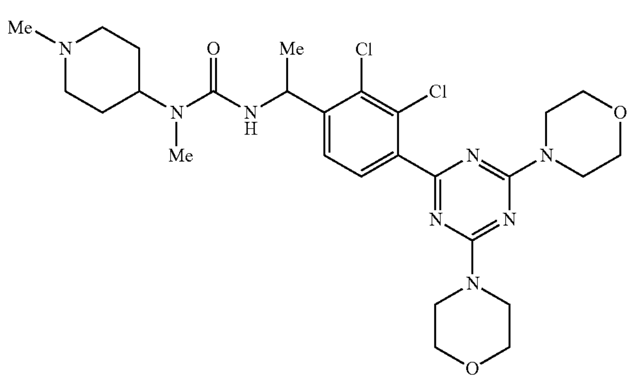 [SMILES: CC(NC(=O)N(C)C1CCN(C)CC1)c1ccc(-c2nc(N3CCOCC3)nc(N3CCOCC3)n2)c(Cl)c1Cl] | $IC_{50}$ = 826 nM<br>$EC_{50}$ = 3 μM<br>$E_{max}$ = 1671 | Not Done | Not Done |
| H0498 | 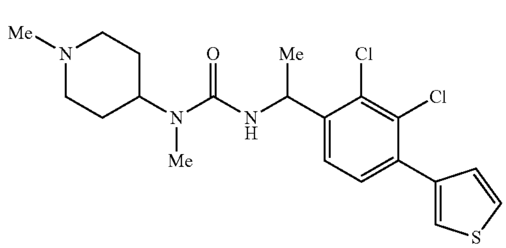 | $IC_{50}$ = 29 nM<br>$EC_{50}$ > 30 μM | Medium H<br>High M | 76% inhibition at 1 h, activity up to 24 h (30 mg/kg) |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0531 | 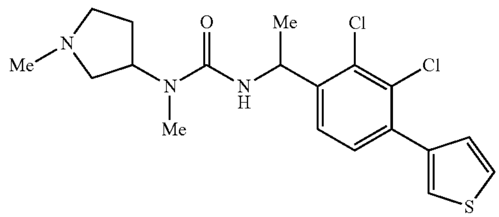 [SMILES: CC(NC(=O)N(C)C1CCN(C)C1)c1ccc(-c2ccsc2)c(Cl)c1Cl] | $IC_{50}$ = 4 nM<br>$EC_{50}$ = 5 nM | Medium H<br>Poor M | Not Done |
| H0594 | 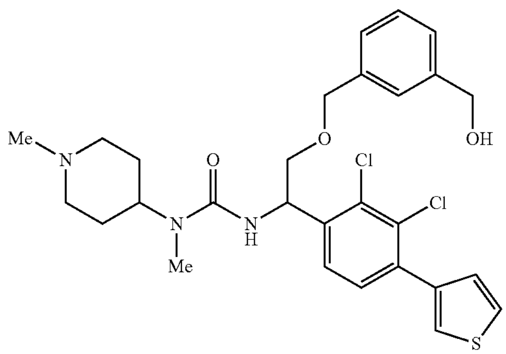 [SMILES: CN1CCC(N(C)C(=O)NC(COCc2cccc(CO)c2)c2ccc(-c3ccsc3)c(Cl)c2Cl)CC1] | $IC_{50}$ = 54 nM<br>$EC_{50}$ > 30 µM | Poor H<br>Medium M | Not Done |
| H0644 | 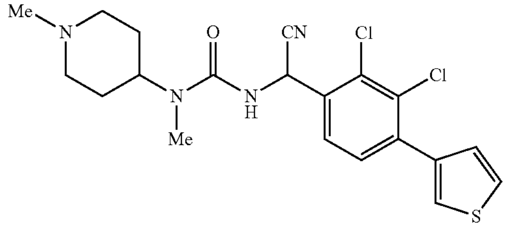 [SMILES: CN1CCC(N(C)C(=O)NC(C#N)c2ccc(-c3ccsc3)c(Cl)c2Cl)CC1] | $IC_{50}$ = 6 nM<br>$EC_{50}$ = 28 nM<br>$E_{max}$ = 2822 | Medium H<br>Medium M | Not Done |
| H0536 | (racemic mixture) | $IC_{50}$ = 3 nM<br>$EC_{50}$ > 30 µM | Medium H<br>Medium M | 76% inhibition at 1 h, activity up to 24 h (30 mg/kg) |
| H0563 | (single enantiomer) | $IC_{50}$ = 1 nM<br>$EC_{50}$ = 3 nM<br>$E_{max}$ = 2100 | Medium H<br>Medium M | 65% inhibition at 1 h (10 mg/kg) |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0564 | 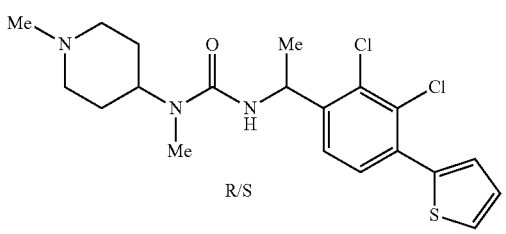<br>R/S<br>(single enantiomer) | $IC_{50}$ = 75 nM<br>$EC_{50}$ = 124 nM<br>$E_{max}$ = 1987 | Not Done | Not Done |
| H0627 | 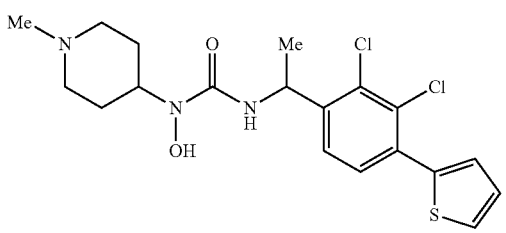 [SMILES: CC(NC(=O)N(O)C1CCN(C)CC1)c1ccc(-c2cccs2)c(Cl)c1Cl] | $IC_{50}$ = 4 nM<br>$EC_{50}$ = 1 nM<br>$E_{max}$ = 5289 | High H<br>High M | Not Done |
| H0660 | 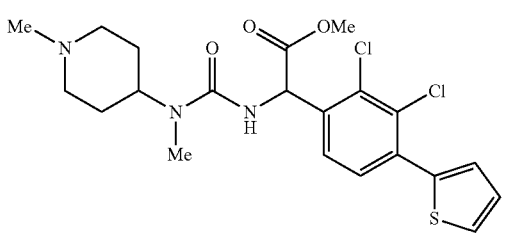 [SMILES: COC(=O)C(NC(=O)N(C)C1CCN(C)CC1)c1ccc(-c2cccs2)c(Cl)c1Cl] | $IC_{50}$ = 69 nM<br>$EC_{50}$ = 180 nM<br>$E_{max}$ = 2100 | Not Done | Not Done |
| H0661 | 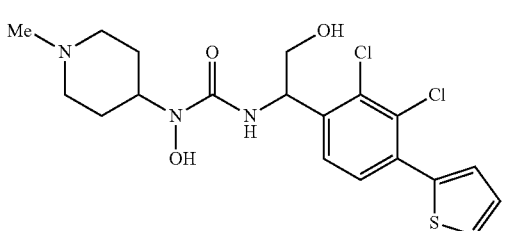 | $IC_{50}$ = 2 nM<br>$EC_{50}$ = 6 nM<br>$E_{max}$ = 2280 | Not Done | Not Done |
| H0672 | 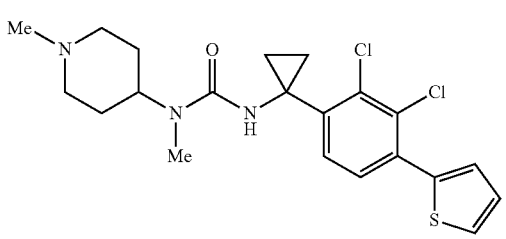 [SMILES: CN1CCC(N(C)C(=O)NC2(c3ccc(-c4cccs4)c(Cl)c3Cl)CC2)CC1] | $IC_{50}$ > 1 nM<br>$EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0651 | 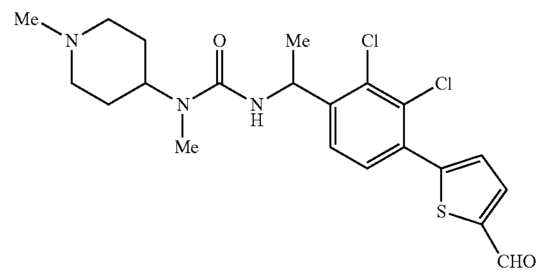 [SMILES: CC(NC(=O)N(C)C1CCN(C)CC1)c1ccc(-c2ccc(C=O)s2)c(Cl)c1Cl] | $IC_{50}$ = 4 nM<br>$EC_{50}$ = 11 nM<br>$E_{max}$ = 2300 | Not Done | Not Done |
| H0653 | 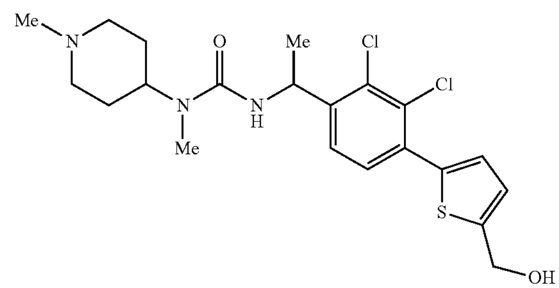 [SMILES: CC(NC(=O)N(C)C1CCN(C)CC1)c1ccc(-c2ccc(CO)s2)c(Cl)c1Cl] | $IC_{50}$ = 4 nM<br>$EC_{50}$ = 9 nM<br>$E_{max}$ = 1815 | Medium H<br>Medium M | Not Done |
| H0668 | 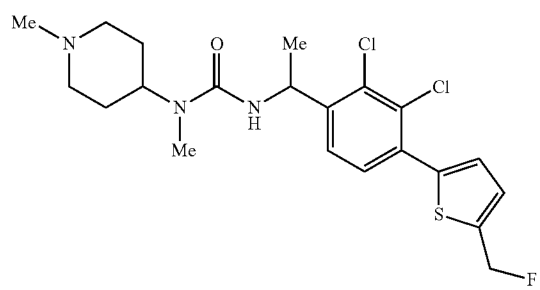 [SMILES: CC(NC(=O)N(C)C1CCN(C)CC1)c1ccc(-c2ccc(CF)s2)c(Cl)c1Cl] | $IC_{50}$ = 8 nM<br>$EC_{50}$ = 10 nM<br>$E_{max}$ = 2168 | Not Done | Not Done |
| H0654 | 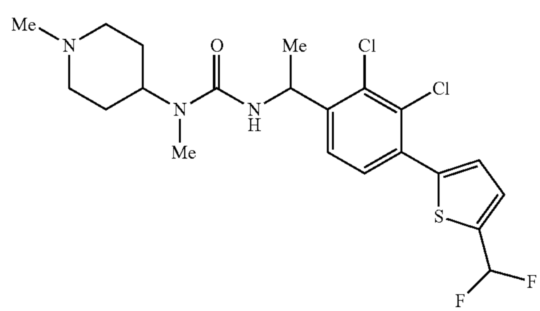 [SMILES: CC(NC(=O)N(C)C1CCN(C)CC1)c1ccc(-c2ccc(C(F)F)s2)c(Cl)c1Cl] | $IC_{50}$ = 6 nM<br>$EC_{50}$ = 10 nM<br>$E_{max}$ = 2200 | High H<br>Medium M | Not Done |
| H0655 | 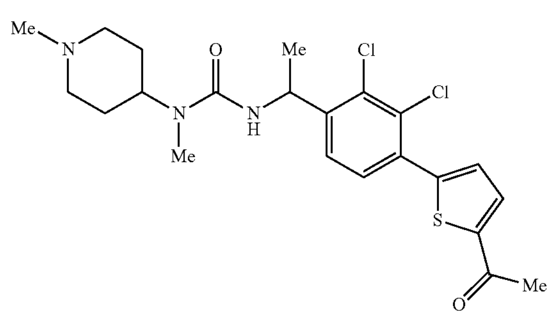 [SMILES: CC(=O)c1ccc(-c2ccc(C(C)NC(=O)N(C)C3CCN(C)CC3)c(Cl)c2Cl)s1] | $IC_{50}$ = 12 nM<br>$EC_{50}$ > 30 μM | Medium H<br>Medium M | 70% Inhibition at 1 h; activity up to 4 h (10 mg/kg) |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0691 | 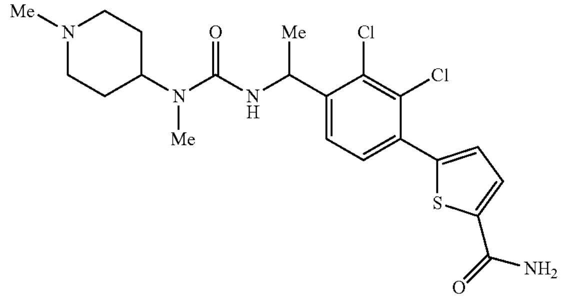 [SMILES: CC(NC(=O)N(C)C1CCN(C)CC1)c1ccc(-c2ccc(C(N)=O)s2)c(Cl)c1Cl] | $IC_{50}$ = 5 nM $EC_{50}$ > 30 μM | High H High M | 62% Inhibition at 2 h; activity up to 24 h (10 mg/kg) PO: not active |
| H0728 | 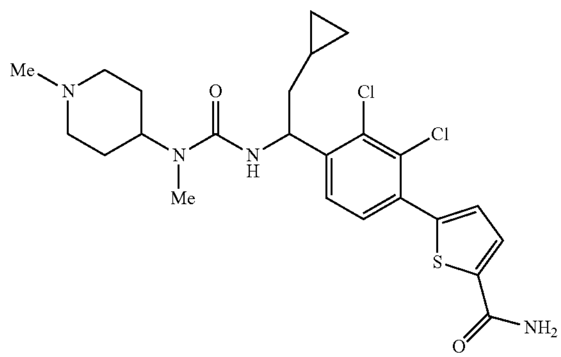 [SMILES: CN1CCC(N(C)C(=O)NC(CC2CC2)c2ccc(-c3ccc(C(N)=O)s3)c(Cl)c2Cl)CC1] | $IC_{50}$ = 5 nM $EC_{50}$ > 30 μM | Medium H Medium M | Not Done |
| H0726 | 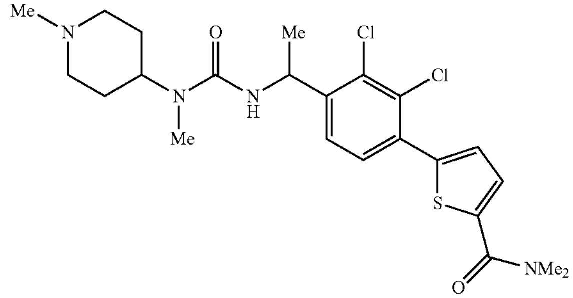 [SMILES: CC(NC(=O)N(C)C1CCN(C)CC1)c1ccc(-c2ccc(C(=O)N(C)C)s2)c(Cl)c1Cl] | $IC_{50}$ = 456 nM $EC_{50}$ > 30 μM | Not Done | Not Done |
| H0689 | 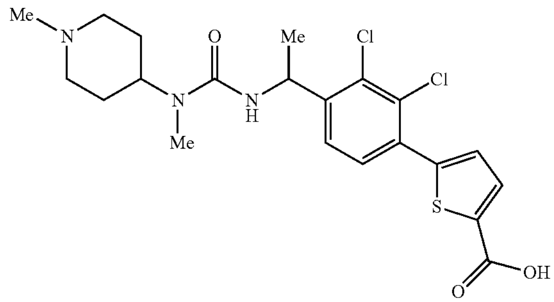 [SMILES: CC(NC(=O)N(C)C1CCN(C)CC1)c1ccc(-c2ccc(C(=O)O)s2)c(Cl)c1Cl] | $IC_{50}$ > 1 μM $EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0692 | *(structure)* | $IC_{50}$ = 550 nM<br>$EC_{50}$ > 1 μM | Not Done | Not Done |
| H0656 | *(structure)* | $IC_{50}$ = 7 nM<br>$EC_{50}$ = 15 nM<br>$E_{max}$ = 1350 | Medium H<br>Medium M | Not Done |
| H0652 | *(structure)* | $IC_{50}$ = 7 nM<br>$EC_{50}$ = 5 nM<br>$E_{max}$ = 1500 | Not Done | Not Done |
| H0713 | *(structure)* | $IC_{50}$ = 187 nM<br>$EC_{50}$ = 29 nM<br>$E_{max}$ = 3424 | Not Done | Not Done |
| H0688 | *(structure)* | $IC_{50}$ = 3 nM<br>$EC_{50}$ = 12 nM<br>$E_{max}$ = 3100 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0774 | 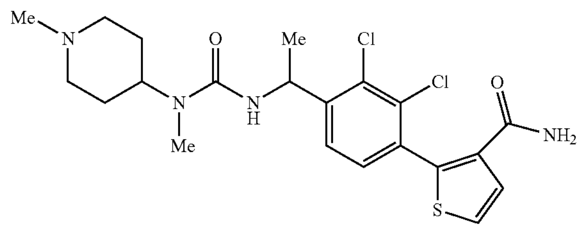 [SMILES: CC(NC(=O)N(C)C1CCN(C)CC1)c1ccc(-c2sccc2C(N)=O)c(Cl)c1Cl] | IC$_{50}$ = 3.4 μM<br>EC$_{50}$ > 30 μM | Not Done | Not Done |
| H0664 | 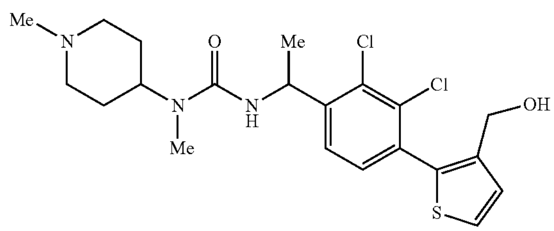 [SMILES: CC(NC(=O)N(C)C1CCN(C)CC1)c1ccc(-c2sccc2CO)c(Cl)c1Cl] | IC$_{50}$ = 261 nM<br>EC$_{50}$ > 30 μM | Not Done | Not Done |
| H0535 | 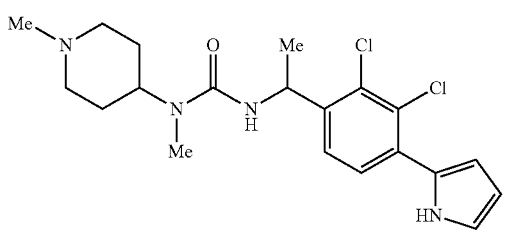 [SMILES: CC(NC(=O)N(C)C1CCN(C)CC1)c1ccc(-c2ccc[nH]2)c(Cl)c1Cl] | IC$_{50}$ = 34 nM<br>EC$_{50}$ = 4 nM | Not Done | Not Done |
| H0499 | 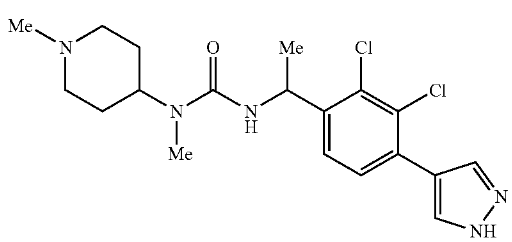 | IC$_{50}$ = 12 nM<br>EC$_{50}$ > 30 μM | Medium H<br>Medium M | NSE (30 mg/kg) |
| H0693 | 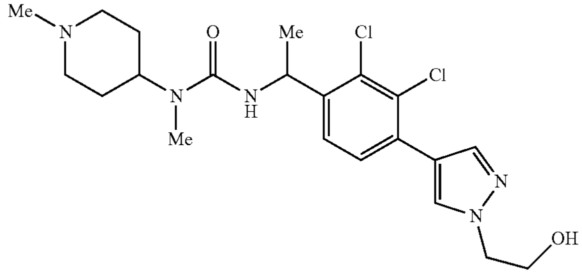 [SMILES: CC(NC(=O)N(C)C1CCN(C)CC1)c1ccc(-c2cnn(CCO)c2)c(Cl)c1Cl] | IC$_{50}$ = 197 nM<br>EC$_{50}$ = 100 nM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0694 | 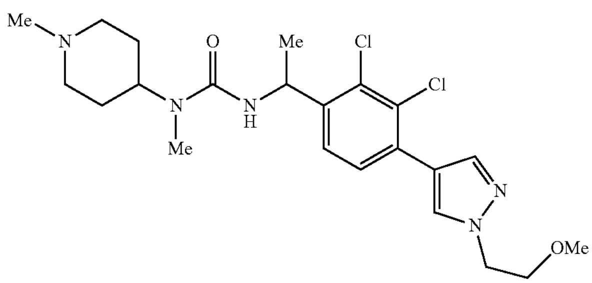 [SMILES: COCCn1cc(-c2ccc(C(C)NC(=O)N(C)C3CCN(C)CC3)c(Cl)c2Cl)cn1] | $IC_{50}$ = 309 nM<br>$EC_{50}$ > 30 μM | Not Done | Not Done |
| H0657 | 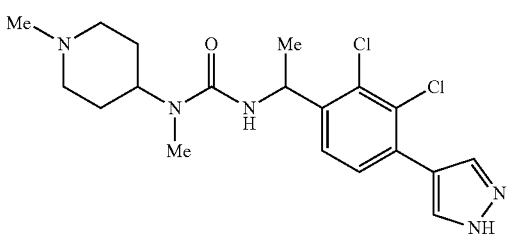 | $IC_{50}$ = 48 nM<br>$EC_{50}$ > 30 μM | Medium H<br>Poor M | 57% inhibition at 1 h, activity up to 8 h (10 mg/kg) |
| H0553 | 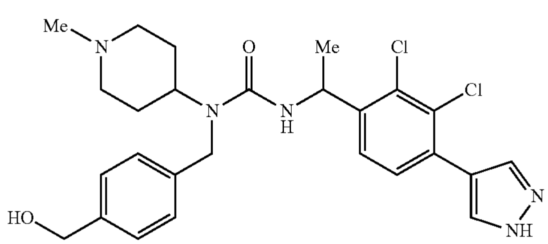 [SMILES: CC(NC(=O)N(Cc1ccc(CO)cc1)C1CCN(C)CC1)c1ccc(-c2cn[nH]c2)c(Cl)c1Cl] | $IC_{50}$ = 7 nM<br>$EC_{50}$ > 30 μM | Medium H<br>Poor M | 57% inhibition at 1 h, activity up to 4 h (10 mg/kg) |
| H0842 | 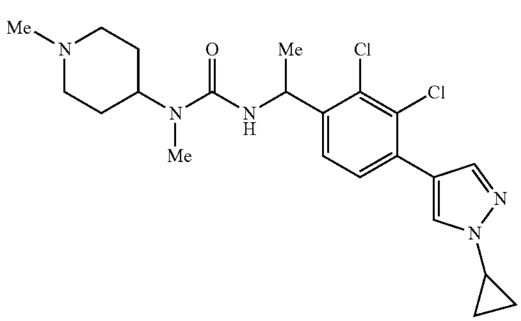 [SMILES: CC(NC(=O)N(C)C1CCN(C)CC1)c1ccc(-c2cnn(C3CC3)c2)c(Cl)c1Cl] | $IC_{50}$ = 64 nM<br>$EC_{50}$ = 67 nM<br>$E_{max}$ = 1411 | Not Done | Not Done |
| H0542 | 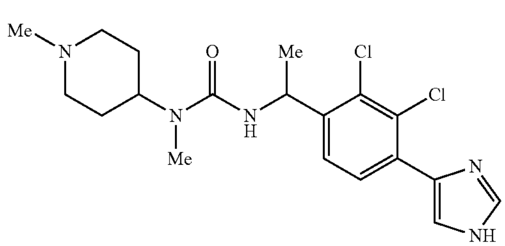 | $IC_{50}$ = 18 nM<br>$EC_{50}$ = 15 nM | High H<br>High M | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0568 | 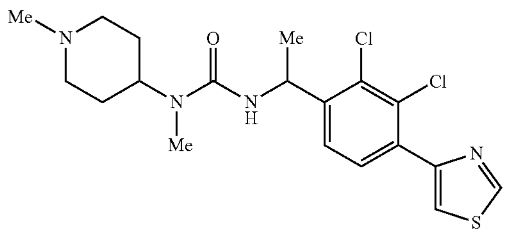 | $IC_{50}$ = 9 nM<br>$EC_{50}$ = 4 nM | High H<br>High M | Not Done |
| H0794 | 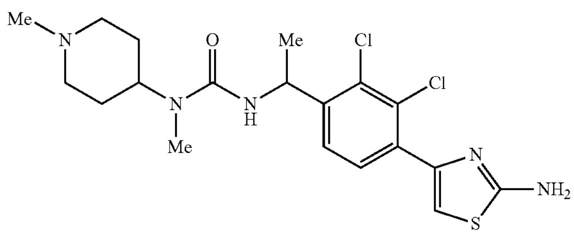 [SMILES: CC(NC(=O)N(C)C1CCN(C)CC1)c1ccc(-c2csc(N)n2)c(Cl)c1Cl] | $IC_{50}$ = 3 nM<br>$EC_{50}$ = 10 nM<br>$E_{max}$ = 4435 | Not Done | Not Done |
| H0841 | 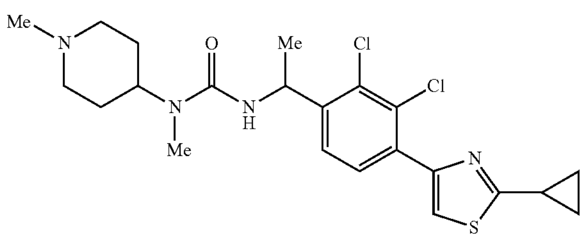 [SMILES: CC(NC(=O)N(C)C1CCN(C)CC1)c1ccc(-c2csc(C3CC3)n2)c(Cl)c1Cl] | $IC_{50}$ = 118 nM<br>$EC_{50}$ > 30 µM | Not Done | PO 10 mg/kg + ANAM 30 mg/kg mice: NSE |
| H0792 | 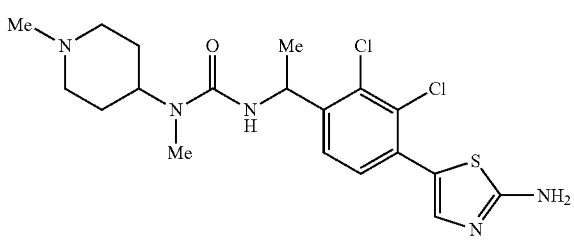 | $IC_{50}$ = 16 nM<br>$EC_{50}$ = 7 nM<br>$E_{max}$ = 1096 | Not Done | Not Done |
| H0569 | 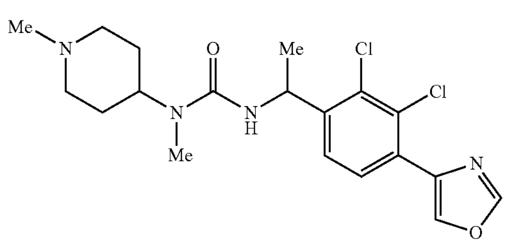 | $IC_{50}$ = 87 nM<br>$EC_{50}$ > 30 µM | Medium H<br>Medium M | Not Done |
| H0565 | 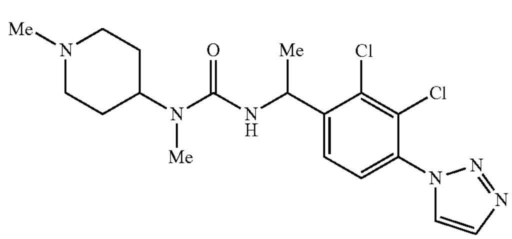 [SMILES: CC(NC(=O)N(C)C1CCN(C)CC1)c1ccc(-n2ccnn2)c(Cl)c1Cl] | $IC_{50}$ = 28 nM<br>$EC_{50}$ = 30 nM | High H<br>High M | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0604 | 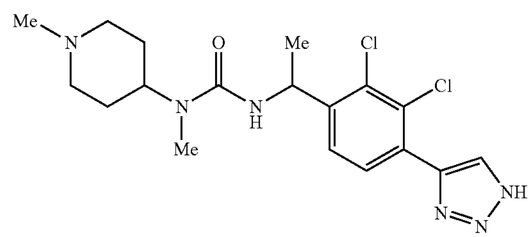 [SMILES: CC(NC(=O)N(C)C1CCN(C)CC1)c1ccc(-c2c[nH]nn2)c(Cl)c1Cl] | $IC_{50}$ = 12 nM<br>$EC_{50}$ = 25 nM | High H<br>High M | Not Done |
| H0595 | 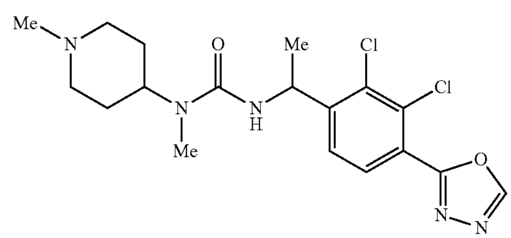 [SMILES: CC(NC(=O)N(C)C1CCN(C)CC1)c1ccc(-c2nnco2)c(Cl)c1Cl] | $IC_{50}$ = 28 nM<br>$EC_{50}$ = 43 nM | Not Done | Not Done |
| H0596 | 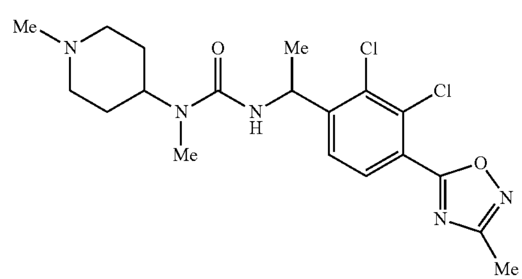 [SMILES: Cc1noc(-c2ccc(C(C)NC(=O)N(C)C3CCN(C)CC3)c(Cl)c2Cl)n1] | $IC_{50}$ = 9 nM<br>$EC_{50}$ = 3 nM | High H<br>High M | NSE (10 mg/kg) |
| H0851 | 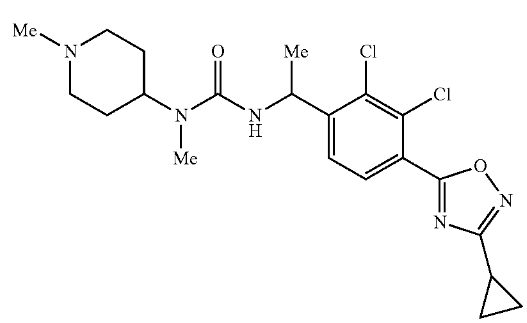 [SMILES: CC(NC(=O)N(C)C1CCN(C)CC1)c1ccc(-c2nc(C3CC3)no2)c(Cl)c1Cl] | $IC_{50}$ = 11 nM<br>$EC_{50}$ = 6 nM<br>$E_{max}$ = 3320 | Not Done | Not Done |
| H0537 | 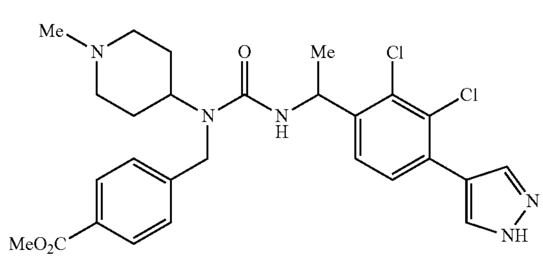 [SMILES: COC(=O)c1ccc(CN(C(=O)NC(C)c2ccc(-c3cn[nH]c3)c(Cl)c2Cl)C2CCN(C)CC2)cc1] | $IC_{50}$ = 13 nM<br>$EC_{50}$ > 30 μM | Poor H<br>Poor M | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0529 | 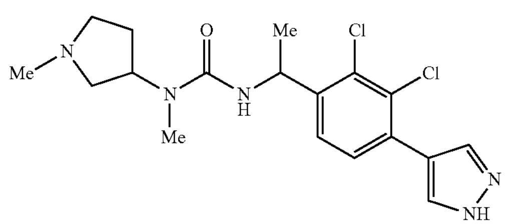 [SMILES: CC(NC(=O)N(C)C1CCN(C)C1)c1ccc(-c2cn[nH]c2)c(Cl)c1Cl] | $IC_{50}$ = 12 nM $EC_{50}$ > 30 μM | Medium H Poor M | Not Done |
| H0528 | 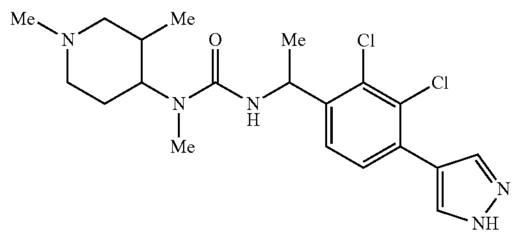 [SMILES: CC(NC(=O)N(C)C1CCN(C)CC1C)c1ccc(-c2cn[nH]c2)c(Cl)c1Cl] | $IC_{50}$ = 34 nM $EC_{50}$ > 30 μM | Medium H Medium M | Not Done |
| H0501 | 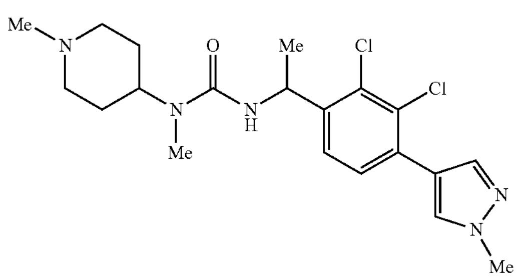 [SMILES: CC(NC(=O)N(C)C1CCN(C)CC1)c1ccc(-c2cnn(C)c2)c(Cl)c1Cl] | $IC_{50}$ = 13 nM $EC_{50}$ = 22 nM | High H High M | Not Done |
| H0507 | 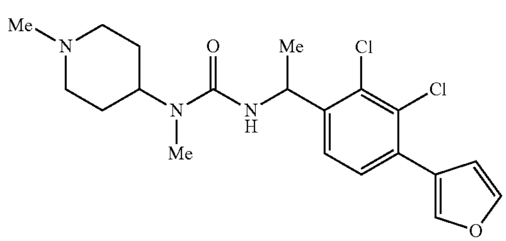 | $IC_{50}$ = 8 nM $EC_{50}$ = 12 nM | High H High M | Not Done |
| H0665 | 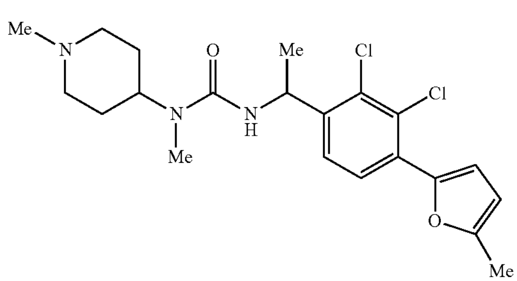 | $IC_{50}$ = 4 nM $EC_{50}$ = 8 nM | High H Medium M | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0508 | 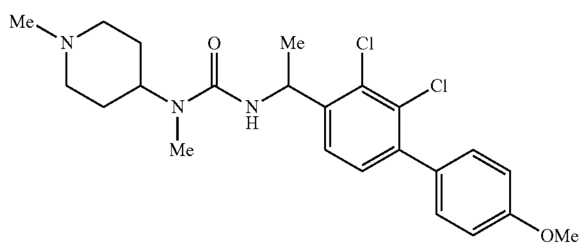 [SMILES: COc1ccc(-c2ccc(C(C)NC(=O)N(C)C3CCN(C)CC3)c(Cl)c2Cl)cc1] | $IC_{50}$ = 76 nM<br>$EC_{50}$ > 30 μM | Medium H<br>High M | Not Done |
| H0509 | 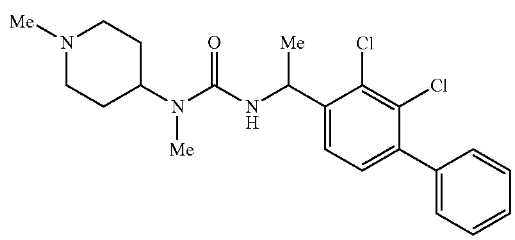 | $IC_{50}$ = 29 nM<br>$EC_{50}$ = 2 μM<br>$E_{max}$ = 1790 | High H<br>High M | 66% inhib 1 h; activity up to 2 h (10 mg/kg) |
| H0510 | 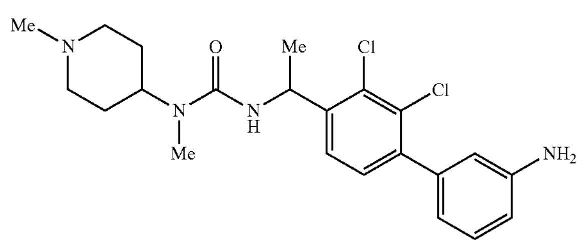 [SMILES: CC(NC(=O)N(C)C1CCN(C)CC1)c1ccc(-c2cccc(N)c2)c(Cl)c1Cl] | $IC_{50}$ = 14 nM<br>$EC_{50}$ > 30 μM | High H<br>High M | 35% inhibition at 4 h, activity up to 24 h (30 mg/kg) |
| H0606 | 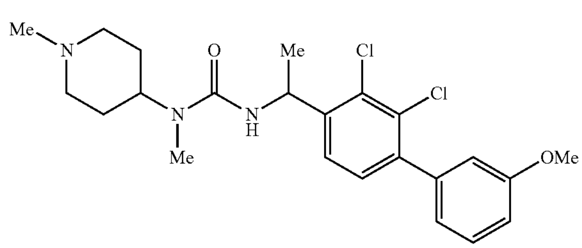 [SMILES: COc1cccc(-c2ccc(C(C)NC(=O)N(C)C3CCN(C)CC3)c(Cl)c2Cl)c1] | $IC_{50}$ = 24 nM<br>$EC_{50}$ = 31 nM<br>$E_{max}$ = 2336 | Not Done | Not Done |
| H0810 | 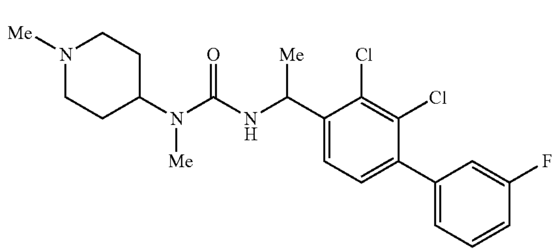 [SMILES: CC(NC(=O)N(C)C1CCN(C)CC1)c1ccc(-c2cccc(F)c2)c(Cl)c1Cl] | $IC_{50}$ = 20 nM<br>$EC_{50}$ = 22 nM<br>$E_{max}$ = 2339 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0696 | 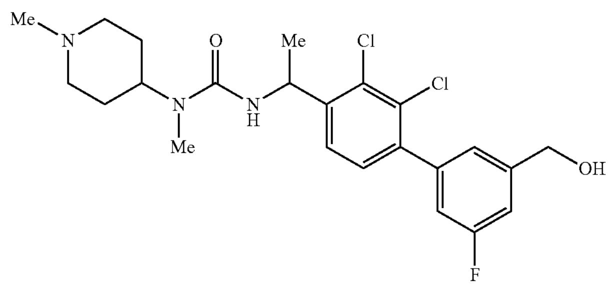 [SMILES: CC(NC(=O)N(C)C1CCN(C)CC1)c1ccc(-c2cc(F)cc(CO)c2)c(Cl)c1Cl] | $IC_{50}$ = 120 nM $EC_{50}$ > 30 μM | Not Done | Not Done |
| H0611 | 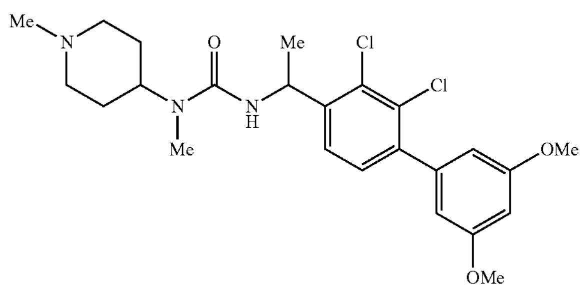 [SMILES: COc1cc(OC)cc(-c2ccc(C(C)NC(=O)N(C)C3CCN(C)CC3)c(Cl)c2Cl)c1] | $IC_{50}$ = 2.3 μM $EC_{50}$ > 30 μM | Not Done | Not Done |
| H0612 | 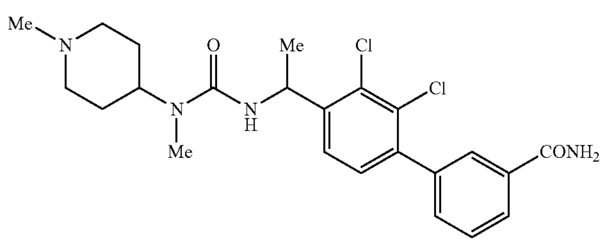 [SMILES: CC(NC(=O)N(C)C1CCN(C)CC1)c1ccc(-c2cccc(C(N)=O)c2)c(Cl)c1Cl] | $IC_{50}$ = 1.6 μM $EC_{50}$ > 30 μM | Not Done | Not Done |
| H0615 | 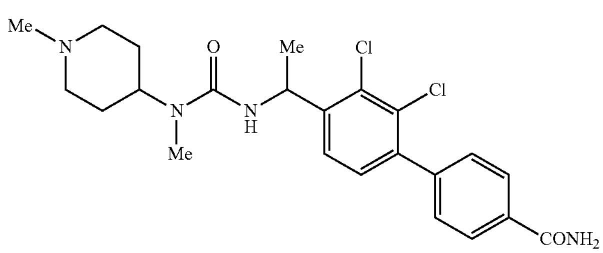 [SMILES: CC(NC(=O)N(C)C1CCN(C)CC1)c1ccc(-c2ccc(C(N)=O)cc2)c(Cl)c1Cl] | $IC_{50}$ = 107 nM $EC_{50}$ > 30 μM | High H Medium M | Not Done |
| H0809 | 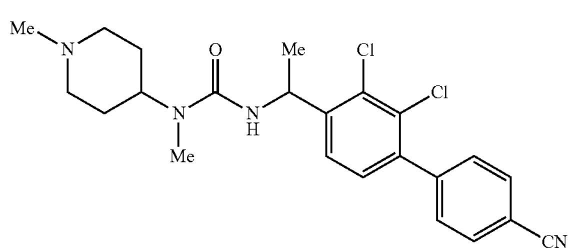 | $IC_{50}$ = 149 nM $EC_{50}$ = 217 nM $E_{max}$ = 2339 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0699 | 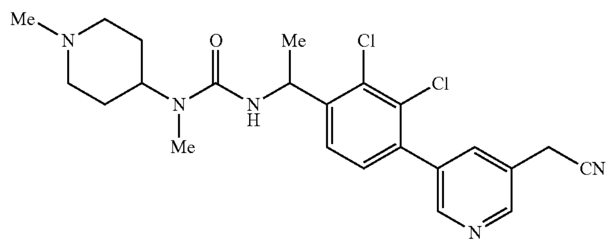 [SMILES: CC(NC(=O)N(C)C1CCN(C)CC1)c1ccc(-c2cncc(CC#N)c2)c(Cl)c1Cl] | $IC_{50}$ = 171 nM<br>$EC_{50}$ > 30 μM | Not Done | Not Done |
| H0607 | 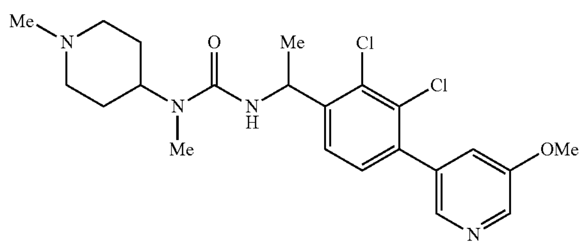 [SMILES: COc1cncc(-c2ccc(C(C)NC(=O)N(C)C3CCN(C)CC3)c(Cl)c2Cl)c1] | $IC_{50}$ = 6 nM<br>$EC_{50}$ = 31 nM<br>$E_{max}$ = 3000 | Medium H<br>Medium M | NSE (10 mg/kg) |
| H0695 | 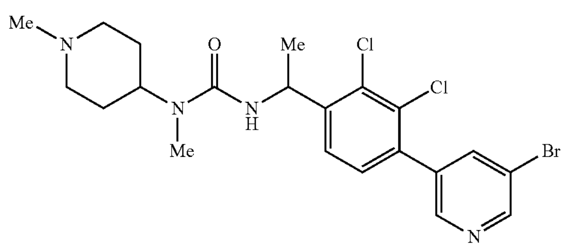 [SMILES: CC(NC(=O)N(C)C1CCN(C)CC1)c1ccc(-c2cncc(Br)c2)c(Cl)c1Cl] | $IC_{50}$ = 78 nM<br>$EC_{50}$ = 5 nM | Not Done | Not Done |
| H0635 | 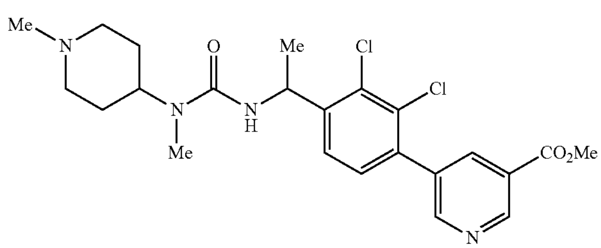 [SMILES: COC(=O)c1cncc(-c2ccc(C(C)NC(=O)N(C)C3CCN(C)CC3)c(Cl)c2Cl)c1] | $IC_{50}$ = 1 μM<br>$EC_{50}$ > 30 μM | Not Done | Not Done |
| H0690 | 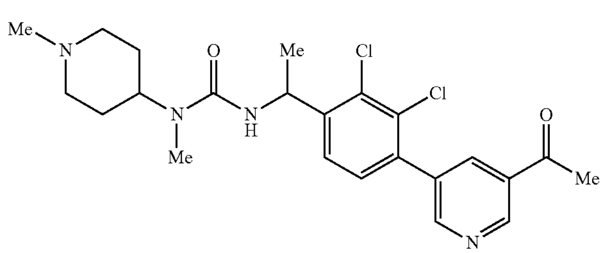 [SMILES: CC(=O)c1cncc(-c2ccc(C(C)NC(=O)N(C)C3CCN(C)CC3)c(Cl)c2Cl)c1] | $IC_{50}$ = 980 nM<br>$EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0735 | 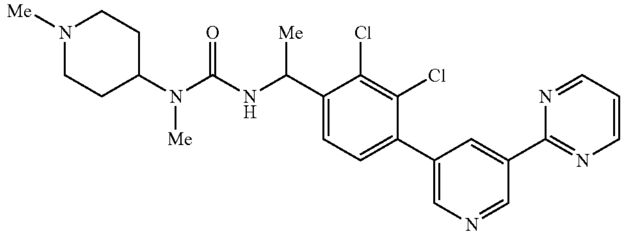 [SMILES: CC(NC(=O)N(C)C1CCN(C)CC1)c1ccc(-c2cncc(-c3ncccn3)c2)c(Cl)c1Cl] | $IC_{50}$ = 209 nM $EC_{50}$ > 30 μM | Not Done | Not Done |
| H0746 | 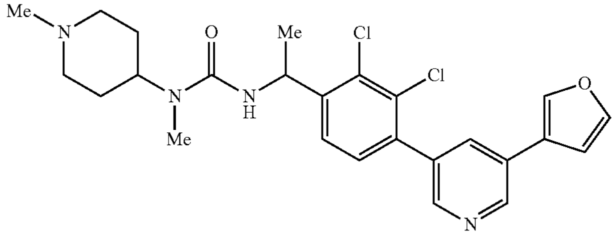 [SMILES: CC(NC(=O)N(C)C1CCN(C)CC1)c1ccc(-c2cncc(-c3ccoc3)c2)c(Cl)c1Cl] | $IC_{50}$ = 216 nM $EC_{50}$ > 30 μM | Not Done | Not Done |
| H0747 | 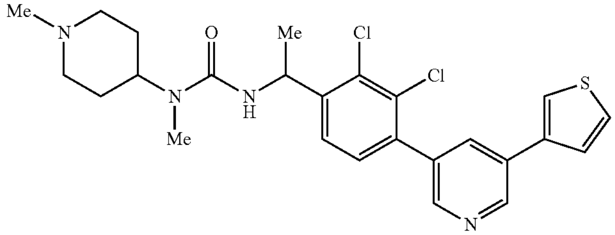 [SMILES: CC(NC(=O)N(C)C1CCN(C)CC1)c1ccc(-c2cncc(-c3ccsc3)c2)c(Cl)c1Cl] | $IC_{50}$ = 84 nM $EC_{50}$ > 30 μM | Not Done | Not Done |
| H0748 | 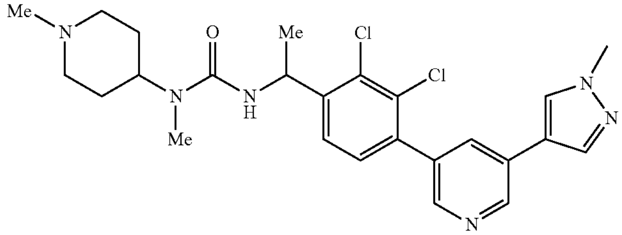 [SMILES: CC(NC(=O)N(C)C1CCN(C)CC1)c1ccc(-c2cncc(-c3cnn(C)c3)c2)c(Cl)c1Cl] | $IC_{50}$ = 554 nM $EC_{50}$ > 30 μM | Not Done | Not Done |
| H0765 | 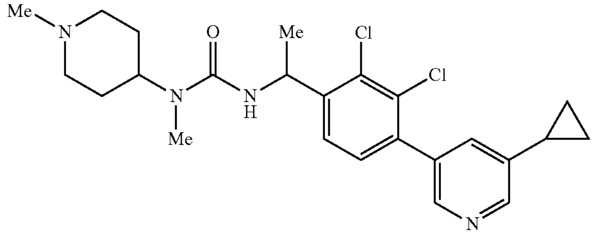 [SMILES: CC(NC(=O)N(C)C1CCN(C)CC1)c1ccc(-c2cncc(C3CC3)c2)c(Cl)c1Cl] | $IC_{50}$ = 61 nM $EC_{50}$ = 137 nM $E_{max}$ = 2810 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0766 | 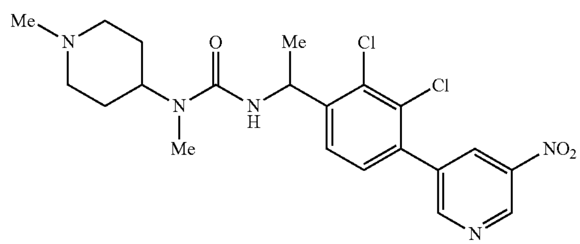 | $IC_{50}$ = 171 nM $EC_{50}$ > 30 μM | Not Done | Not Done |
| H0608 | 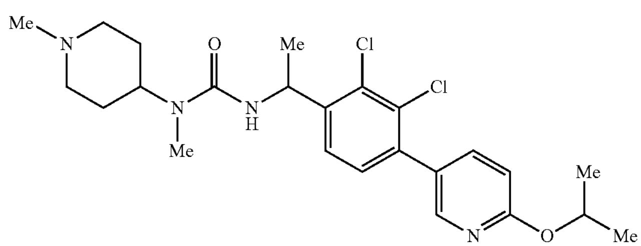 [SMILES: CC(C)Oc1ccc(-c2ccc(C(C)NC(=O)N(C)C3CCN(C)CC3)c(Cl)c2Cl)cn1] | $IC_{50}$ = 69 nM $EC_{50}$ = 422 nM | Not Done | Not Done |
| H0616 | 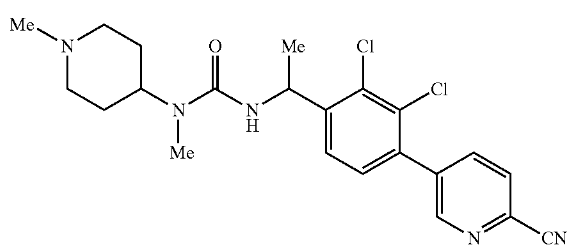 | $IC_{50}$ = 132 nM $EC_{50}$ = 580 nM | Not Done | Not Done |
| H0618 | 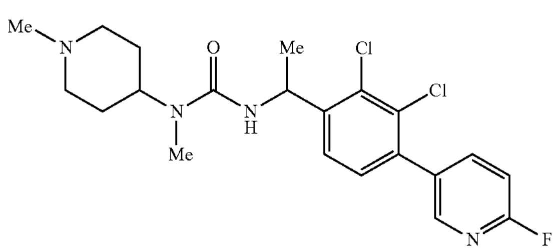 | $IC_{50}$ = 40 nM $EC_{50}$ = 130 nM | Not Done | Not Done |
| H0623 | 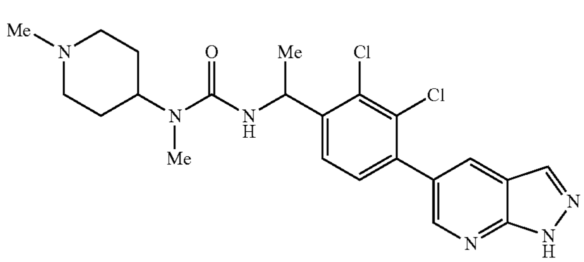 [SMILES: CC(NC(=O)N(C)C1CCN(C)CC1)c1ccc(-c2cnc3[nH]ncc3c2)c(Cl)c1Cl] | $IC_{50}$ = 71 nM $EC_{50}$ > 30 μM | Medium H Poor M | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0610 | 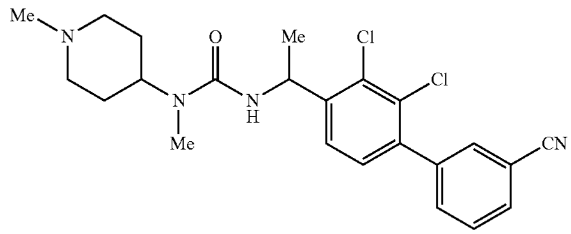 [SMILES: CC(NC(=O)N(C)C1CCN(C)CC1)c1ccc(-c2cccc(C#N)c2)c(Cl)c1Cl] | $IC_{50}$ = 101 nM<br>$EC_{50}$ > 30 μM | Medium H<br>Medium M | Not Done |
| H0517 | 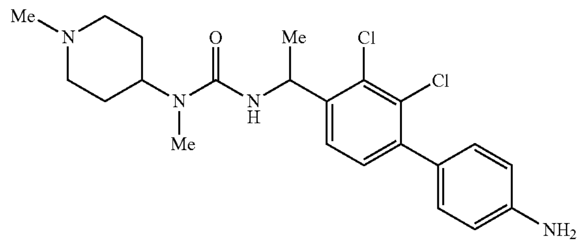 | $IC_{50}$ = 19 nM<br>$EC_{50}$ > 30 μM | Not Done | Not Done |
| H0518 | 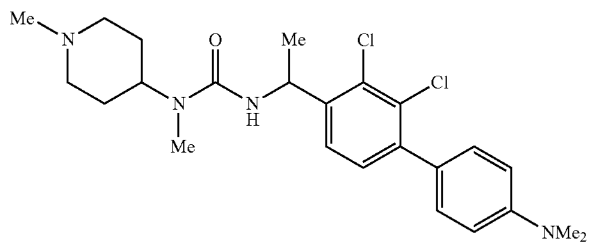 [SMILES: CC(NC(=O)N(C)C1CCN(C)CC1)c1ccc(-c2ccc(N(C)C)cc2)c(Cl)c1Cl] | $IC_{50}$ = 841 nM<br>$EC_{50}$ > 30 μM | Not Done | Not Done |
| H0512 | 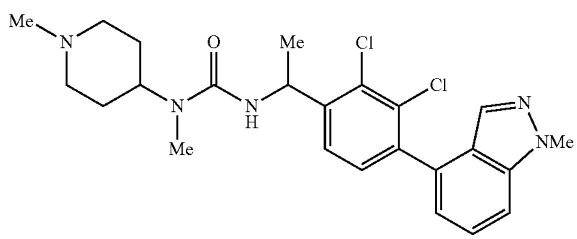 [SMILES: CC(NC(=O)N(C)C1CCN(C)CC1)c1ccc(-c2cccc3c2cnn3C)c(Cl)c1Cl] | $IC_{50}$ = 495 nM<br>$EC_{50}$ > 30 μM | Not Done | Not Done |
| H0513 | 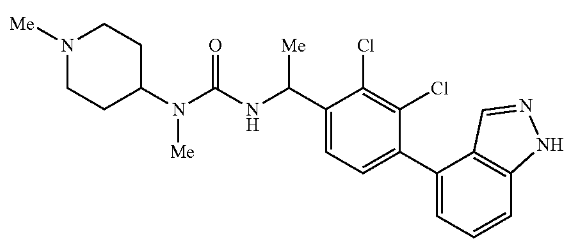 [SMILES: CC(NC(=O)N(C)C1CCN(C)CC1)c1ccc(-c2cccc3[nH]ncc23)c(Cl)c1Cl] | $IC_{50}$ = 544 nM<br>$EC_{50}$ > 30 μM | Not Done | Not Done |

245

246

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0514 | 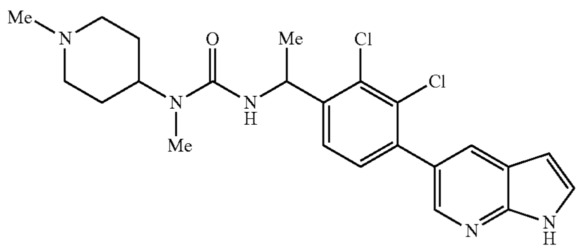 [SMILES: CC(NC(=O)N(C)C1CCN(C)CC1)c1ccc(-c2cnc3[nH]ccc3c2)c(Cl)c1Cl] | $IC_{50}$ = 16 nM<br>$EC_{50}$ = 38 nM | Medium H<br>Medium M | Not Done |
| H0515 | 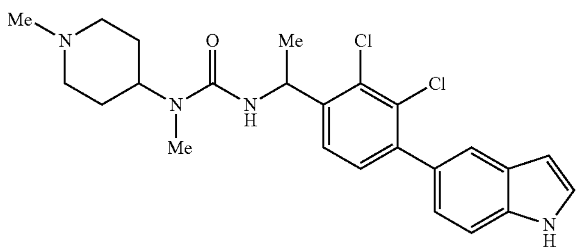 | $IC_{50}$ = 40 nM<br>$EC_{50}$ = 885 nM | Not Done | |
| H0520 | 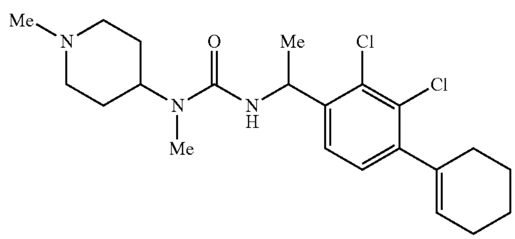 [SMILES: CC(NC(=O)N(C)C1CCN(C)CC1)c1ccc(C2=CCCCC2)c(Cl)c1Cl] | $IC_{50}$ = 202 nM<br>$EC_{50}$ = 394 nM | Not Done | Not Done |
| H0787 | 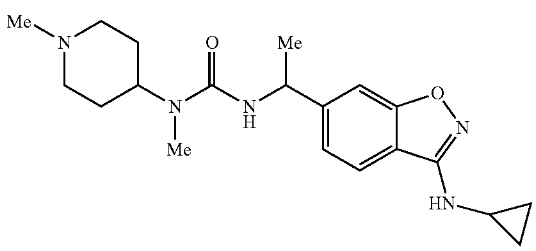 [SMILES: CC(NC(=O)N(C)C1CCN(C)CC1)c1ccc2c(NC3CC3)noc2c1] | $IC_{50}$ = 12 μM<br>$EC_{50}$ = 3 μM | Not Done | Not Done |
| H0582 | 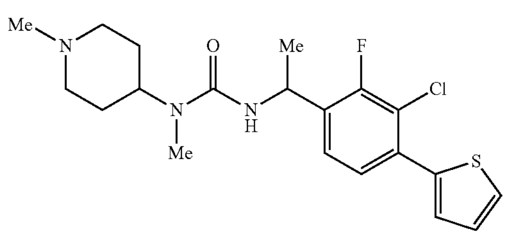 [SMILES: CC(NC(=O)N(C)C1CCN(C)CC1)c1ccc(-c2cccs2)c(Cl)c1F] | $IC_{50}$ = 15 nM<br>$EC_{50}$ = 20 nM<br>$E_{max}$ = 2069 | Medium H<br>Medium M | |
| H0571 | 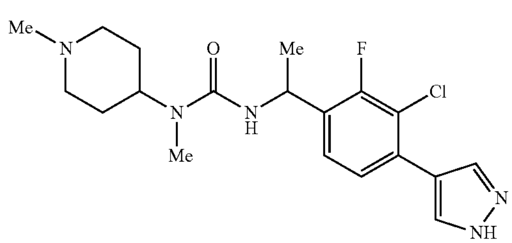 | $IC_{50}$ = 154 nM<br>$EC_{50}$ > 30 μM | Not Done | |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0605 | 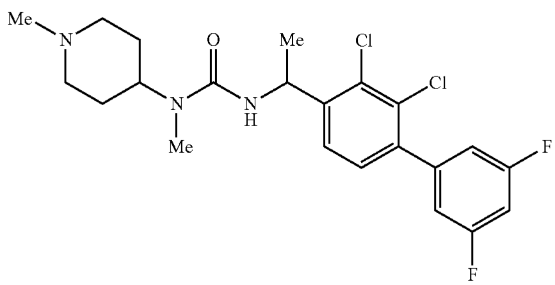 [SMILES: CC(NC(=O)N(C)C1CCN(C)CC1)c1ccc(-c2cc(F)cc(F)c2)c(Cl)c1Cl] | $IC_{50}$ = 31 nM<br>$EC_{50}$ = 96 nM<br>$E_{max}$ = 1833 | Not Done | Not Done |
| H0573 | 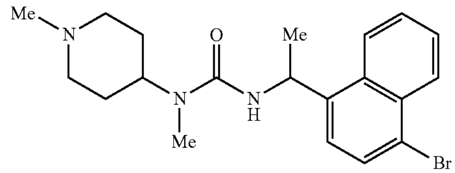 [SMILES: CC(NC(=O)N(C)C1CCN(C)CC1)c1ccc(Br)c2ccccc12] | $IC_{50}$ = 36 nM<br>$EC_{50}$ > 30 μM | High H<br>Medium M | PO: NSE (30 mg/kg) |
| H0574 | 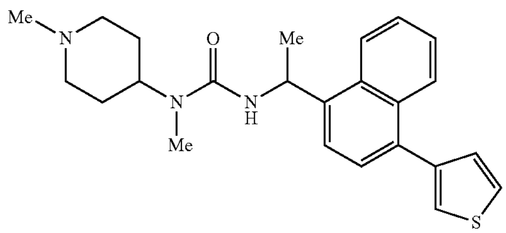 [SMILES: CC(NC(=O)N(C)C1CCN(C)CC1)c1ccc(-c2ccsc2)c2ccccc12] | $IC_{50}$ = 67 nM<br>$EC_{50}$ = 81 nM<br>$E_{max}$ = 2489 | Medium H<br>Medium M | Not Done |
| H0575 | 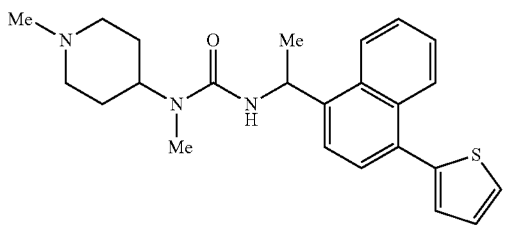 [SMILES: CC(NC(=O)N(C)C1CCN(C)CC1)c1ccc(-c2cccs2)c2ccccc12] | $IC_{50}$ = 32 nM<br>$EC_{50}$ = 28 nM<br>$E_{max}$ = 3533 | Medium H<br>Medium M | Not Done |
| H0576 | 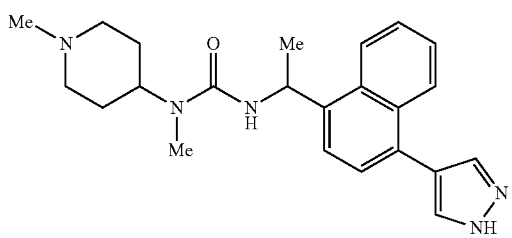 [SMILES: CC(NC(=O)N(C)C1CCN(C)CC1)c1ccc(-c2cn[nH]c2)c2ccccc12] | $IC_{50}$ = 180 nM<br>$EC_{50}$ > 30 μM | Not Done | Not Done |
| H0577 | 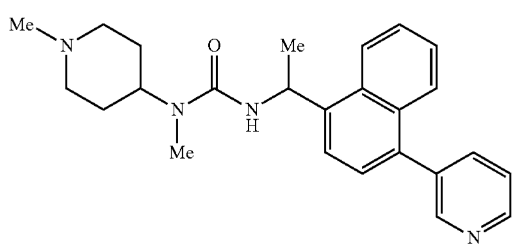 [SMILES: CC(NC(=O)N(C)C1CCN(C)CC1)c1ccc(-c2cccnc2)c2ccccc12] | $IC_{50}$ = 233 nM<br>$EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0591 | 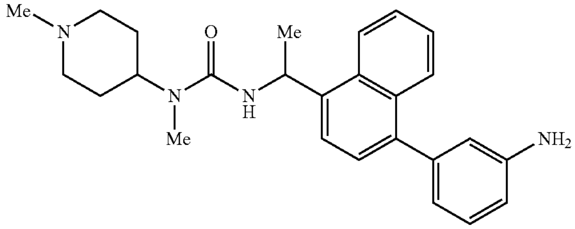 [SMILES: CC(NC(=O)N(C)C1CCN(C)CC1)c1ccc(-c2cccc(N)c2)c2ccccc12] | $IC_{50}$ = 11 nM $EC_{50}$ = 126 nM | Medium H Medium M | Not Done |
| H0597 | 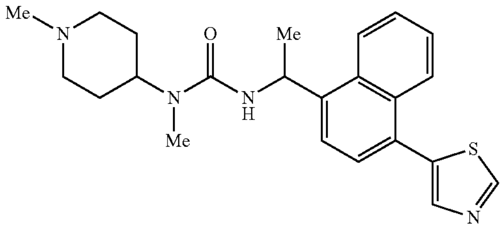 [SMILES: CC(NC(=O)N(C)C1CCN(C)CC1)c1ccc(-c2cncs2)c2ccccc12] | $IC_{50}$ = 24 nM $EC_{50}$ > 30 μM | Poor H Poor M | Not Done |
| H0598 | 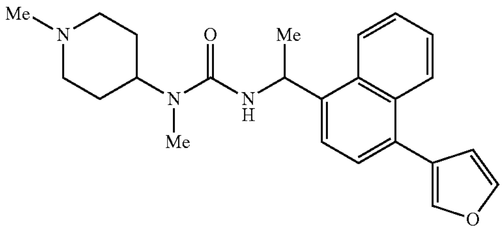 [SMILES: CC(NC(=O)N(C)C1CCN(C)CC1)c1ccc(-c2ccoc2)c2ccccc12] | $IC_{50}$ = 63 nM $EC_{50}$ = 271 nM | Not Done | Not Done |
| H0599 | 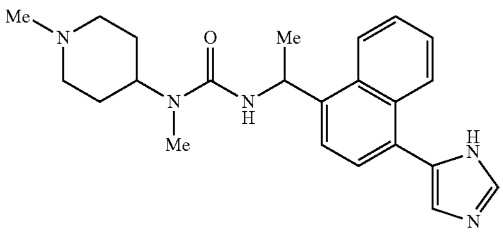 [SMILES: CC(NC(=O)N(C)C1CCN(C)CC1)c1ccc(-c2cnc[nH]2)c2ccccc12] | $IC_{50}$ = 212 nM $EC_{50}$ = 478 nM | Not Done | Not Done |
| H0790 | 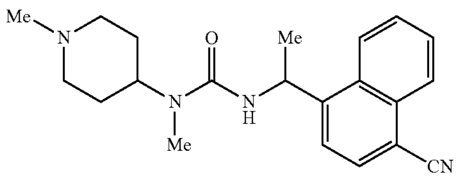 [SMILES: CC(NC(=O)N(C)C1CCN(C)CC1)c1ccc(C#N)c2ccccc12] | $IC_{50}$ = 35 nM $EC_{50}$ = 32 nM $E_{max}$ = 2810 | Not Done | Not Done |
| H0381 | 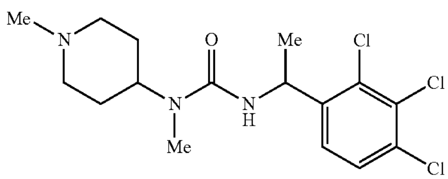 | $IC_{50}$ = 12 nM $EC_{50}$ > 30 μM | Medium H Meidum M | IP: No effect |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0519 | 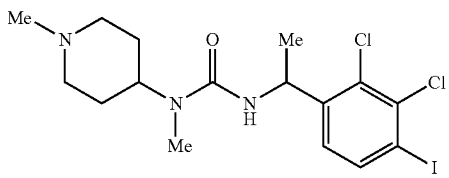 [SMILES: CC(NC(=O)N(C)C1CCN(C)CC1)c1ccc(I)c(Br)c1Cl] | $IC_{50}$ = 3 nM<br>$EC_{50}$ = 6 nM | Medium H<br>Medium M | |
| H0629 | 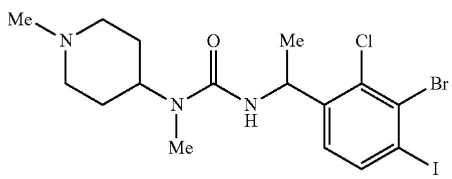 | $IC_{50}$ = 3 nM<br>$EC_{50}$ = 1 nM<br>$E_{max}$ = 5075 | Not Done | Not Done |
| H0658 | 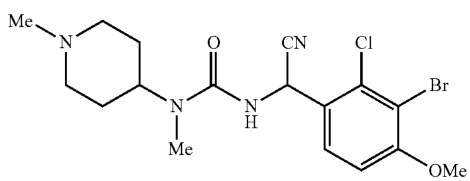 [SMILES: COc1ccc(C(C#N)NC(=O)N(C)C2CCN(C)CC2)c(Cl)c1Br] | $IC_{50}$ = 6 nM<br>$EC_{50}$ = 9 nM<br>$E_{max}$ = 2400 | Not Done | Not Done |
| H0669 | 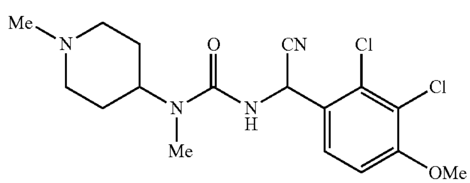 | $IC_{50}$ = 1 nM<br>$EC_{50}$ = 5 nM<br>$E_{max}$ = 4961 | Not Done | Not Done |
| H0671 | 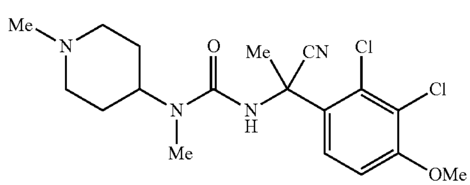 [SMILES: COc1ccc(C(C)(C#N)NC(=O)N(C)C2CCN(C)CC2)c(Cl)c1Cl] | $IC_{50}$ = 34 nM<br>$EC_{50}$ = 60 nM<br>$E_{max}$ = 3748 | Not Done | Not Done |
| H0659 | 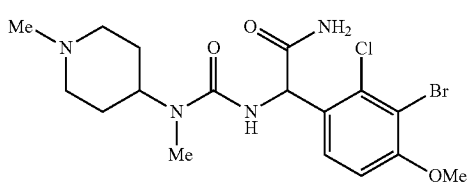 [SMILES: COc1ccc(C(NC(=O)N(C)C2CCN(C)CC2)C(N)=O)c(Cl)c1Br] | $IC_{50}$ = 390 nM<br>$EC_{50}$ = 353 nM<br>$E_{max}$ = 200 | Not Done | Not Done |
| H0521 | 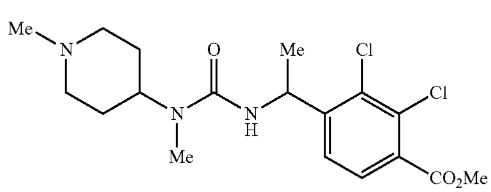 [SMILES: COC(=O)c1ccc(C(C)NC(=O)N(C)C2CCN(C)CC2)c(Cl)c1Cl] | $IC_{50}$ = 20 nM<br>$EC_{50}$ = 19 nM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0602 | (1-methylpiperidin-4-yl)-N-methyl urea linked to 1-(2,3-dichloro-4-((trimethylsilyl)ethynyl)phenyl)ethyl | $IC_{50}$ = 8 nM<br>$EC_{50}$ > 30 μM | Not Done | Not Done |
| H0603 | (1-methylpiperidin-4-yl)-N-methyl urea linked to 1-(2,3-dichloro-4-ethynylphenyl)ethyl | $IC_{50}$ = 2 nM<br>$EC_{50}$ > 30 μM | High H<br>High M | 71% inhibition at 1 h, activity up to 24 h (0.1 mpk), 65% inhibition at 1 h; activity up to 24 hrs (1 mpk), 34% inhibition at 1 h, activity up to 4 h (10 mpk); Inhibition in fed mice after ANAM PO-SC NSE |
| H0677 | (1-methylpiperidin-4-yl)-N-methyl urea linked to 1-(2,3-dichloro-4-ethynylphenyl)ethyl R/S (single enantiomer) | $IC_{50}$ = 5 nM<br>$EC_{50}$ > 30 μM | High H<br>Medium M | Inhib up to 2 h (10 mg/kg) PO: NSE |
| H0678 | (1-methylpiperidin-4-yl)-N-methyl urea linked to 1-(2,3-dichloro-4-ethynylphenyl)ethyl R/S (single enantiomer) | $IC_{50}$ = 55 nM<br>$EC_{50}$ > 30 μM | Medium H<br>Medium M | 78% inhibition at 1 h, activity up to 24 h (10 mg/kg). PO: no effect |
| H0832 | (1-methylpiperidin-4-yl)-N-methyl urea linked to 1-(2,3-dichloro-4-(prop-1-ynyl)phenyl)ethyl | $IC_{50}$ = 11 nM<br>$EC_{50}$ > 30 μM | | |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0852 | 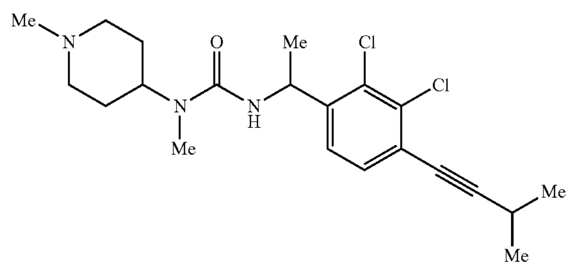 [SMILES: CC(C)C#Cc1ccc(C(C)NC(=O)N(C)C2CCN(C)CC2)c(Cl)c1Cl] | $IC_{50}$ = 22 nM<br>$EC_{50}$ = 18 nM<br>$E_{max}$ = 1683 | Not Done | Not Done |
| H0701 | 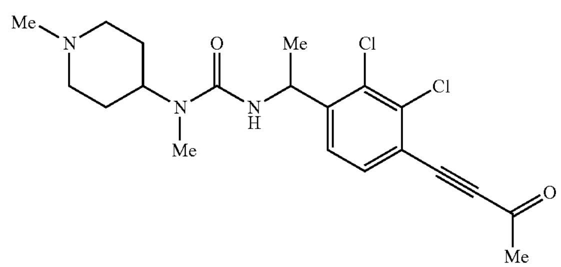 [SMILES: CC(=O)C#Cc1ccc(C(C)NC(=O)N(C)C2CCN(C)CC2)c(Cl)c1Cl] | $IC_{50}$ = 20 nM<br>$EC_{50}$ > 30 μM | Low H<br>Low M | Not Done |
| H0733 | 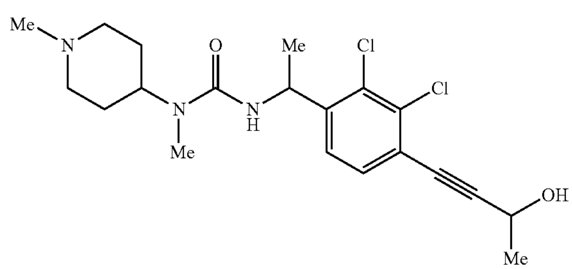 [SMILES: CC(O)C#Cc1ccc(C(C)NC(=O)N(C)C2CCN(C)CC2)c(Cl)c1Cl] | $IC_{50}$ = 95 nM<br>$EC_{50}$ > 30 μM | Not Done | Not Done |
| H0755 | 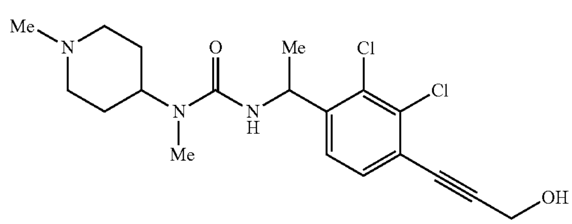 [SMILES: CC(NC(=O)N(C)C1CCN(C)CC1)c1ccc(C#CCO)c(Cl)c1Cl] | $IC_{50}$ = 12 nM<br>$EC_{50}$ = 10 nM<br>$E_{max}$ = 2196 | Not Done | Not Done |
| H0757 | 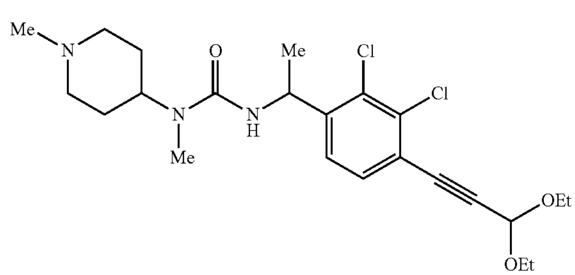 [SMILES: CCOC(C#Cc1ccc(C(C)NC(=O)N(C)C2CCN(C)CC2)c(Cl)c1Cl)OCC] | $IC_{50}$ = 159 nM<br>$EC_{50}$ = 654 nM<br>$E_{max}$ = 2704 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0734 | 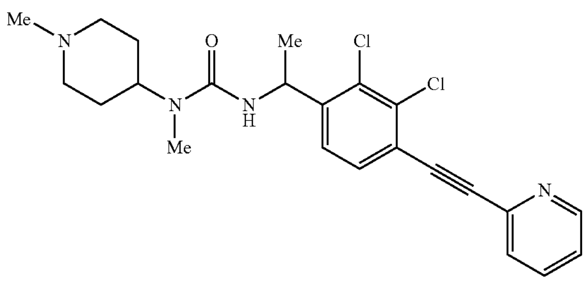 | $IC_{50}$ = 202 nM $EC_{50}$ > 30 μM | Not Done | Not Done |
| H0737 | 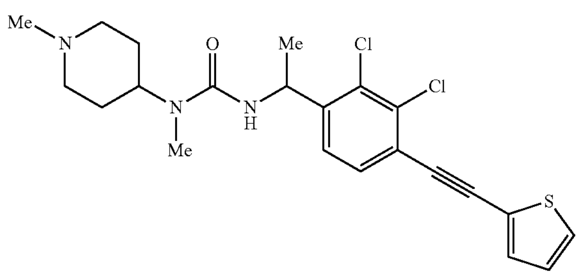 | $IC_{50}$ = 13 nM $EC_{50}$ > 30 μM | High H High M | 75% inhibition at 1 h, activity up to 4 h (10 mg/kg) PO: NSE |
| H0775 | 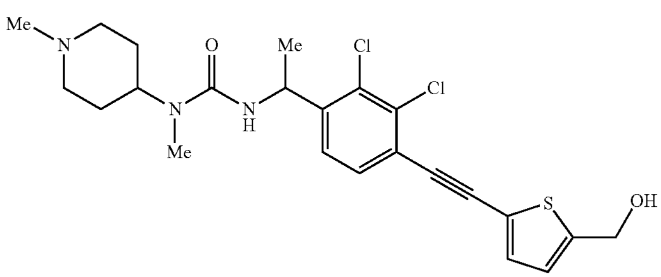 [SMILES: CC(NC(=O)N(C)C1CCN(C)CC1)c1ccc(C#Cc2ccc(CO)s2)c(Cl)c1Cl] | $IC_{50}$ = 74 nM $EC_{50}$ > 5 μM | Not Done | Not Done |
| H0776 | 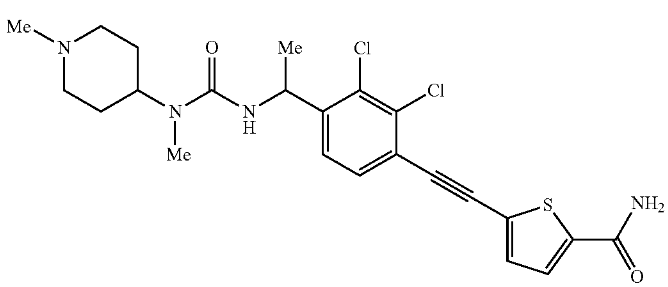 [SMILES: CC(NC(=O)N(C)C1CCN(C)CC1)c1ccc(C#Cc2ccc(C(N)=O)s2)c(Cl)c1Cl] | $IC_{50}$ = 120 nM $EC_{50}$ > 4 μM | Not Done | Not Done |
| H0779 | 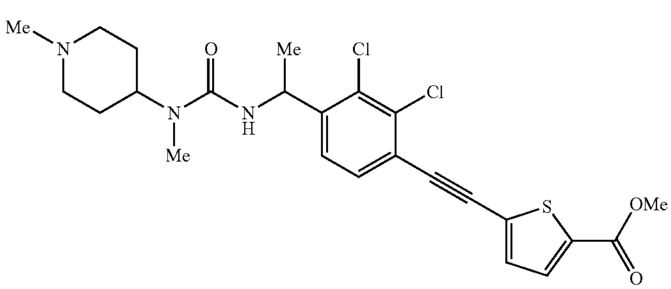 [SMILES: COC(=O)c1ccc(C#Cc2ccc(C(C)NC(=O)N(C)C3CCN(C)CC3)c(Cl)c2Cl)s1] | $IC_{50}$ = 429 nM $EC_{50}$ = 4 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0762 | 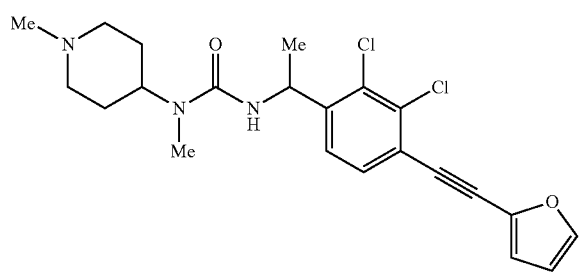 | $IC_{50}$ = 5 nM $EC_{50}$ > 30 μM | High H High M | 93% inhibition at 1 h, activity up to 4 h (10 mg/kg) PO mice and rat: NSEt |
| H0751 | 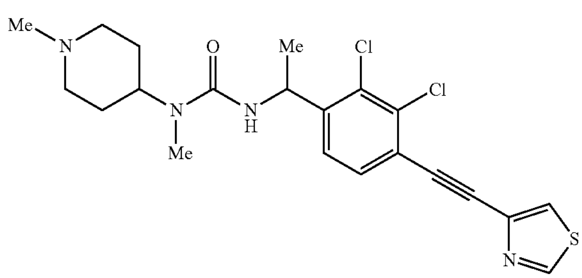 | $IC_{50}$ = 6 nM $EC_{50}$ = 62 nM $E_{max}$ = 1267 | High H High M | 91% inhibition at 1 h, activity up to 24 h (10 mg/kg) PO mice and rat (+ANA): no effect |
| H0763 | 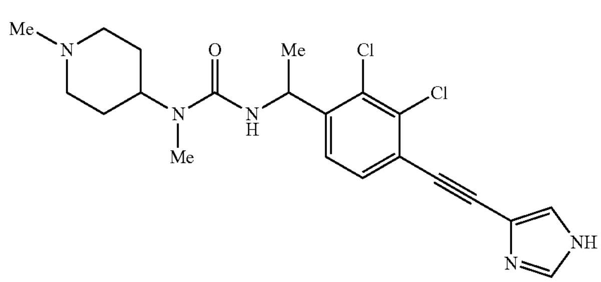 [SMILES: CC(NC(=O)N(C)C1CCN(C)CC1)c1ccc(C#Cc2c[nH]cn2)c(Cl)c1Cl] | IC50 = 835 nM EC50 > 30 μM | Not Done | Not Done |
| H0759 | 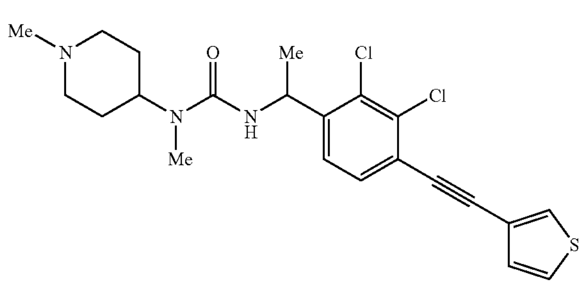 | $IC_{50}$ = 7 nM $EC_{50}$ > 30 μM | High H High M | 85% inhibition at 1 hr, activity up to 8 h (10 mg/kg) PO: no effect |
| H0785 | 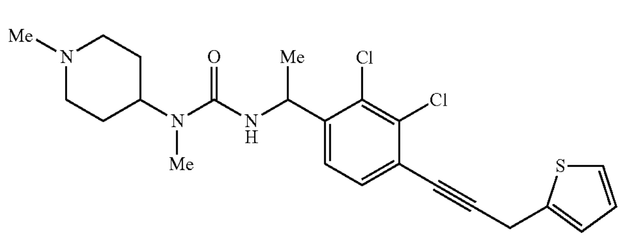 [SMILES: CC(NC(=O)N(C)C1CCN(C)CC1)c1ccc(C#CCc2cccs2)c(Cl)c1Cl] | $IC_{50}$ = 33 nM $EC_{50}$ = 90 nM $E_{max}$ = 2869 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0754 | (structure) | $IC_{50}$ = 11 nM<br>$EC_{50}$ > 30 μM | High H<br>High M | 74% inhibition at 1 h; activity up to 24 h (10 mg/kg)<br>PO and PO + ANAM: no effect |
| H0753 | (structure) | $IC_{50}$ = 60 nM<br>$EC_{50}$ > 30 μM | Not Done | Not Done |
| H0609 | (structure) | $IC_{50}$ = 517 nM<br>$EC_{50}$ > 30 μM | Not Done | Not Done |
| H0764 | (structure) | $IC_{50}$ = 10 nM<br>$EC_{50}$ = 14 nM<br>$E_{max}$ = 1352 | High H<br>High M | 91% inhibition at 1 h, activity up to 24 h (10 mg/kg)<br>PO: 70% inhibition at 2 h (30 mg/kg), activity up to 24 h<br>PO + ANAM: inhib up to 24 h<br>SC: 53% inhibition at 1 h; (30 mg/kg) |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0818 | 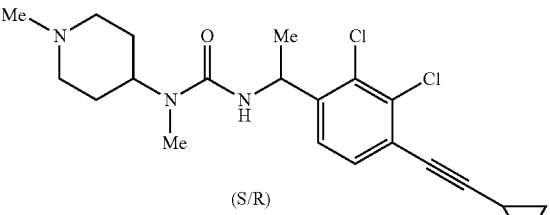 (S/R) (single enantiomer) | $IC_{50}$ = 1.7 nM $EC_{50}$ = 3.5 nM $E_{max}$ = 1915 | Not Done | 22% inhib at 4 h, 30 mg/kg PO fasted mice |
| H0819 | 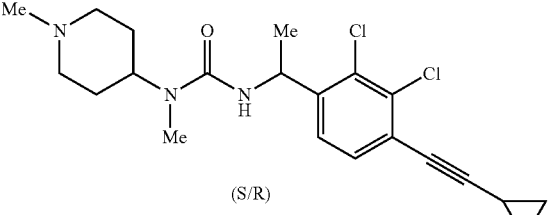 (S/R) (single enantiomer) | $IC_{50}$ = 65 nM $EC_{50}$ = 140 nM $E_{max}$ = 1419 | Not Done | 30 mg/kg PO fasted mice NSE |
| H0838 | 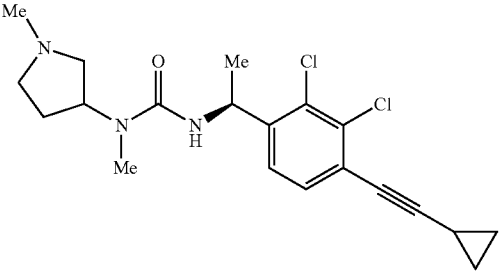 (diastereoisomer mixture) | $IC_{50}$ = 4 nM $EC_{50}$ = 21 nM $E_{max}$ = 1340 | Not Done | 205% increase at 2 h, activity up to 8 h, 30 mg/kg PO mice |
| H0855 | 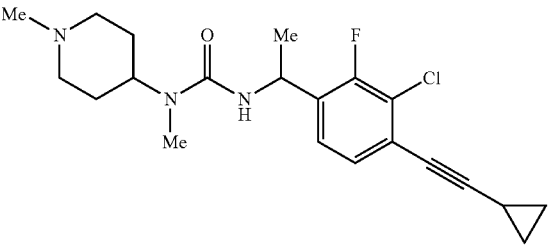 [SMILES: CC(NC(=O)N(C)C1CCN(C)CC1)c1ccc(C#CC2CC2)c(Cl)c1F] | $IC_{50}$ = 256 nM $EC_{50}$ > 30 μM | Not Done | Not Done |
| H0884 | 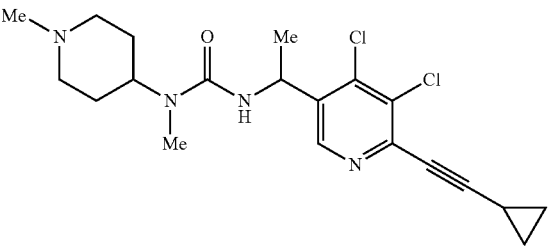 [SMILES: CC(NC(=O)N(C)C1CCN(C)CC1)c1cnc(C#CC2CC2)c(Cl)c1Cl] | $IC_{50}$ = 197 nM $EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0811 | 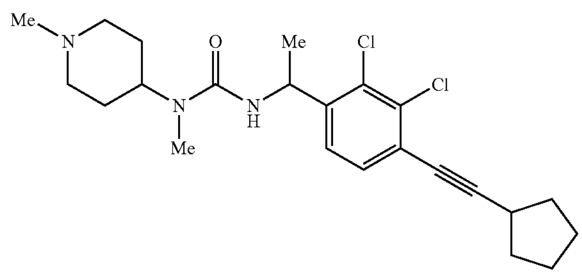 [SMILES: CC(NC(=O)N(C)C1CCN(C)CC1)c1ccc(C#CC2CCCC2)c(Cl)c1Cl] | $IC_{50}$ = 36 nM<br>$EC_{50}$ = 95 nM<br>$E_{max}$ = 1320 | Not Done | Not Done |
| H0812 | 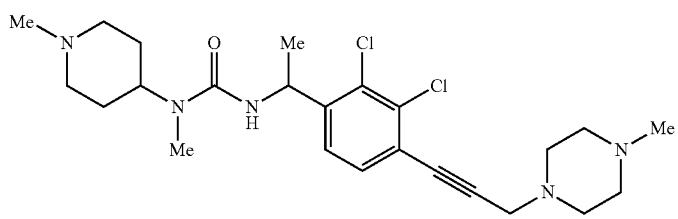 [SMILES: CC(NC(=O)N(C)C1CCN(C)CC1)c1ccc(C#CCN2CCN(C)CC2)c(Cl)c1Cl] | $IC_{50}$ = 1.2 μM<br>$EC_{50}$ = 1.5 μM<br>$E_{max}$ = 871 | Not Done | Not Done |
| H0740 | 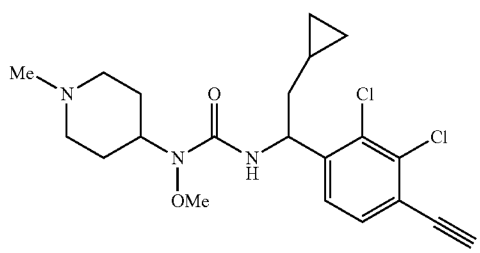 | $IC_{50}$ = 7 nM<br>$EC_{50}$ = 1.5 nM<br>$E_{max}$ = 3620 | Not Done | Not Done |
| H0742 | 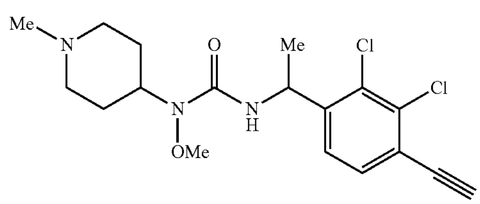 | $IC_{50}$ = 54 nM<br>$EC_{50}$ > 30 μM | Not Done | Not Done |
| H0745 | 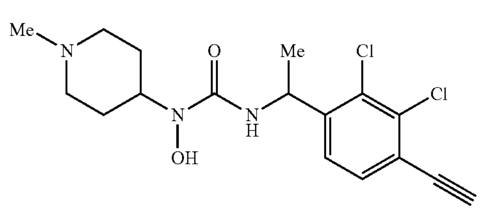 | $IC_{50}$ = 57 nM<br>$EC_{50}$ = 97 nM<br>$E_{max}$ = 2391 | Not Done | Not Done |
| H0749 | 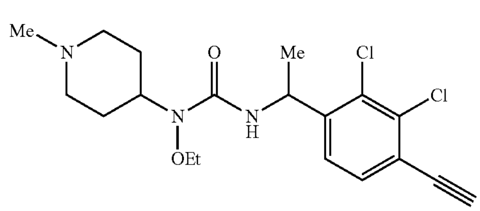 | $IC_{50}$ = 111 nM<br>$EC_{50}$ = 397 nM<br>$E_{max}$ = 1554 | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0744 | 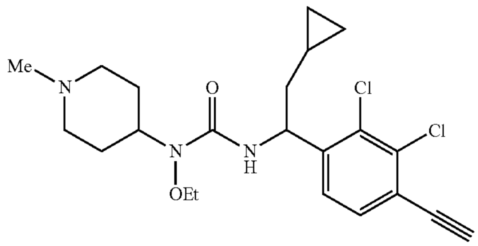 | $IC_{50}$ = 33 nM<br>$EC_{50}$ = 45 nM<br>$E_{max}$ = 3536 | Not Done | Not Done |
| H0626 | 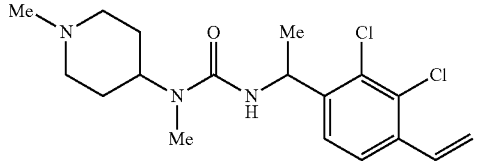 [SMILES: C=Cc1ccc(C(C)NC(=O)N(C)C2CCN(C)CC2)c(Cl)c1Cl] | $IC_{50}$ = 4 nM<br>$EC_{50}$ = 15 nM<br>$E_{max}$ = 3835 | Not Done | Not Done |
| H0767 | 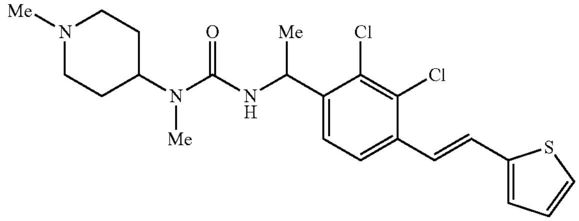 [SMILES: CC(NC(=O)N(C)C1CCN(C)CC1)c1ccc(/C=C/c2cccs2)c(Cl)c1Cl] | $IC_{50}$ = 37 nM<br>$EC_{50}$ > 30 μM | High H<br>High M | 88% inhibition at 1 h, activity up to 4 h (10 mg/kg) PO: NSE |
| H0772 | 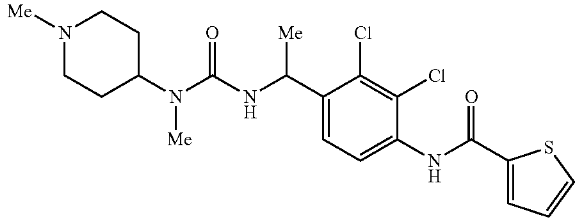 [SMILES: CC(NC(=O)N(C)C1CCN(C)CC1)c1ccc(NC(=O)c2cccs2)c(Cl)c1Cl] | $IC_{50}$ = 3 nM<br>$EC_{50}$ = 7 nM<br>$E_{max}$ = 3569 | Not Done | Not Done |
| H0773 | 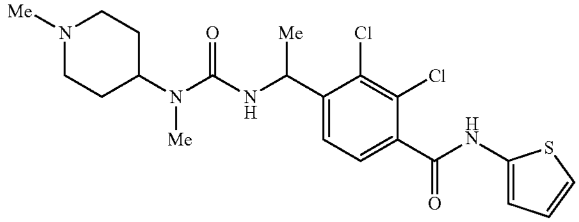 [SMILES: CC(NC(=O)N(C)C1CCN(C)CC1)c1ccc(C(=O)Nc2cccs2)c(Cl)c1Cl] | $IC_{50}$ = 608 nM<br>$EC_{50}$ > 30 μM | Not Done | Not Done |
| H0784 | 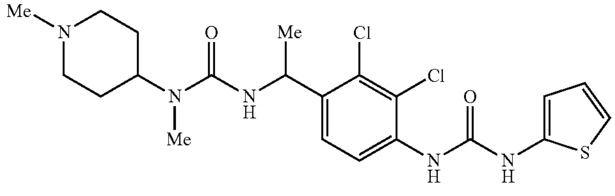 [SMILES: CC(NC(=O)N(C)C1CCN(C)CC1)c1ccc(NC(=O)Nc2cccs2)c(Cl)c1Cl] | $IC_{50}$ = 529 nM<br>$EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0777 | 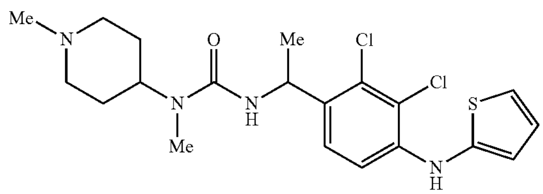 [SMILES: CC(NC(=O)N(C)C1CCN(C)CC1)c1ccc(Nc2cccs2)c(Cl)c1Cl] | $IC_{50}$ = 715 nM<br>$EC_{50}$ = 600 nM<br>$E_{max}$ = 2288 | Not Done | Not Done |
| H0846 | 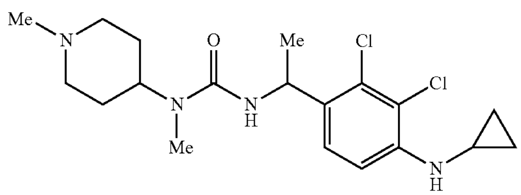 [SMILES: CC(NC(=O)N(C)C1CCN(C)CC1)c1ccc(NC2CC2)c(Cl)c1Cl] | $IC_{50}$ = 170 nM<br>$EC_{50}$ = 130 nM<br>$E_{max}$ = 3815 | Not Done | Not Done |
| H0875 | 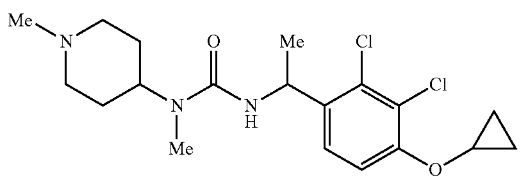 [SMILES: CC(NC(=O)N(C)C1CCN(C)CC1)c1ccc(OC2CC2)c(Cl)c1Cl] | $IC_{50}$ = 91 nM<br>$EC_{50}$ = 50 nM<br>$E_{max}$ = 3751 | Not Done | Not Done |
| H0628 | 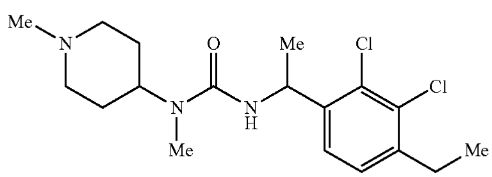 [SMILES: CCc1ccc(C(C)NC(=O)N(C)C2CCN(C)CC2)c(Cl)c1Cl] | $IC_{50}$ = 59 nM<br>$EC_{50}$ = 101 nM<br>$E_{max}$ = 4433 | Not Done | Not Done |
| H0630 | 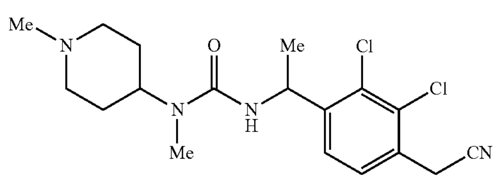 | $IC_{50}$ = 3 nM<br>$EC_{50}$ = 9 nM<br>$E_{max}$ = 4714 | High H<br>High M | Not Done |
| H0633 | 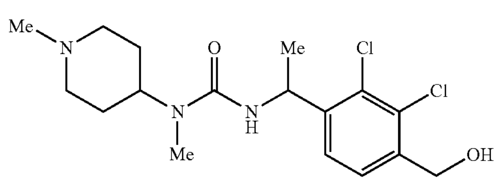 | $IC_{50}$ = 3 nM<br>$EC_{50}$ = 15 nM | High H<br>High M | Not Done |
| H0634 | 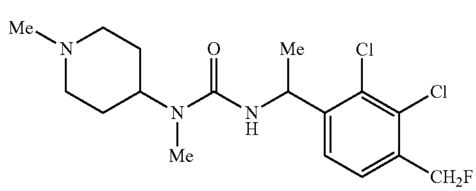 | $IC_{50}$ = 13 nM<br>$EC_{50}$ = 37 nM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0640 | 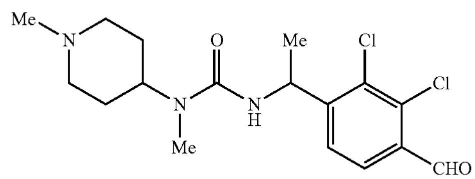 [SMILES: CC(NC(=O)N(C)C1CCN(C)CC1)c1ccc(C=O)c(Cl)c1Cl] | $IC_{50}$ = 103 nM $EC_{50}$ > 30 μM | Not done | Not done |
| H0645 | 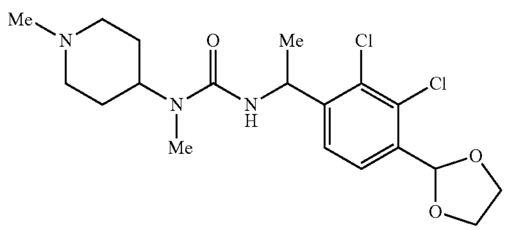 [SMILES: CC(NC(=O)N(C)C1CCN(C)CC1)c1ccc(C2OCCO2)c(Cl)c1Cl] | $IC_{50}$ = 133 nM $EC_{50}$ = 287 nM $E_{max}$ = 2761 | Not done | Not done |
| H0641 | 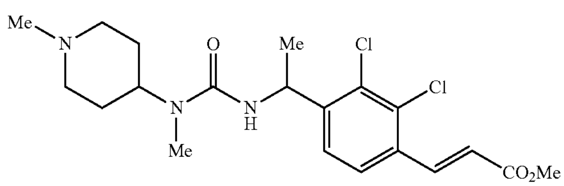 [SMILES: COC(=O)/C=C/c1ccc(C(C)NC(=O)N(C)C2CCN(C)CC2)c(Cl)c1Cl] | $IC_{50}$ = 18 nM $EC_{50}$ = 35 nM $E_{max}$ = 1690 | Not Done | Not Done |
| H0702 | 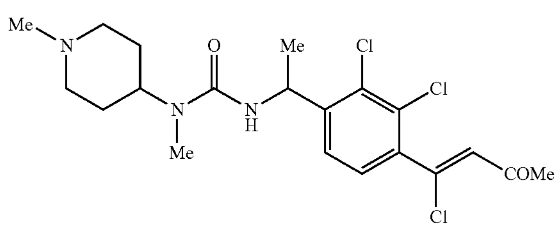 | $IC_{50}$ = 96 nM $EC_{50}$ = 1.1 μM $E_{max}$ = 1940 | Not Done | Not Done |
| H0643 | 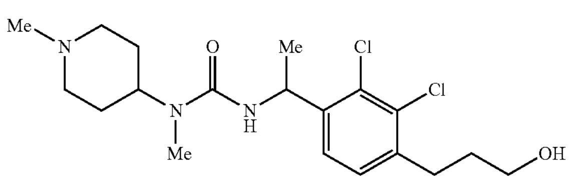 [SMILES: CC(NC(=O)N(C)C1CCN(C)CC1)c1ccc(CCCO)c(Cl)c1Cl] | $IC_{50}$ = 22 nM $EC_{50}$ = 83 nM $E_{max}$ = 2660 | Not done | Not Done |
| H0522 | 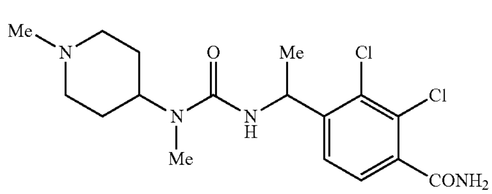 | $IC_{50}$ = 201 nM $EC_{50}$ = 200 nM | Not Done | Not Done |
| H0523 | 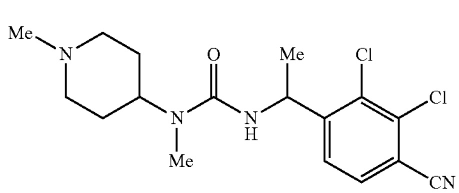 [SMILES: CC(NC(=O)N(C)C1CCN(C)CC1)c1ccc(C#N)c(Cl)c1Cl] | $IC_{50}$ = 668 nM $EC_{50}$ > 30 μM | Not Done | Not Done |

TABLE 1-continued

| Compound No. | Chemical Structure | Activity | Metabolic Stability (H = Human; M = Mouse) | Mouse Food Intake (% Inhibition; Doses as mg/kg i.p.)* |
|---|---|---|---|---|
| H0876 | (structure) | $IC_{50} = 130$ nM $EC_{50} > 30$ μM | Not Done | Not Done |

*NSE: No significant effect.

Example C

Effect of Ghrelin Antagonists of Formula I on Binge Eating in Non-Estrous Female Rats In this Example, the therapeutic potential of compounds were tested for their ability to inhibit binge eating. The animal model used was developed to explore the combination of food restriction and stress. Results disclosed below show that female rats submitted to cycles of food restriction and exposure, the day of the test, to Highly Palatable Food (HPF) for 15 minutes without getting access to it, showed a pronounced and statistically significant increase in HPF intake. Considering the reliability and the robustness of this model, it was adopted to test the inventive compounds. Topiramate, used as reference compound, confirmed its inhibitory effect in this procedure. Moreover, results show that, after acute administration, H0900, H0816, and H0847, reduced binge eating episodes showed in R+S group. H0860, at the considered doses, did not significantly reduce HPF intake in animals exposed to the same procedure.

Animals and Housing:

A total of N=117, 52-day-old female Sprague-Dawley rats (175-200 g) were used. Rats were acclimated in individual cages with metallic walls; the floor and the front wall made of metallic grid. The dimensions of the cage floor being 30 cm×30 cm; the cage is 30 cm high. A front door (30 cm×20 cm) made of metallic grid was positioned in the anterior wall of the cage to gain access to the inside of the cage; the remaining part of the front wall was equipped with a drinking burette.

Rats were kept in a room at constant temperature (20-22° C.) and humidity (45-55%) under a 12-h light/dark cycle (lights on at 08:00 am) with ad lib chow and water. All procedures were conducted in adherence to the European Community Directive for Care and Use of Laboratory Animals.

Diets:

Rats were offered food pellets, 4RF18, Mucedola, Settimo Milanese, Italy (2.6 kcal/g). The Highly Palatable Food (HPF) was prepared by mixing:

a) Nutella Ferrero chocolate cream (5.33 kcal/g; 56%, 31% and 7%, respectively, from carbohydrate, fat and protein): 52% b) grounded food pellets 4RF18, Mucedola, Settimo Milanese, Italy: 33% c) water: 15%

Experimental Design:

The rats were weight-matched into one of two groups so there was no significant difference in mean body weight between the groups:

Group 1: non-restricted and not exposed to stress (NR+NS): N=9

Group 2: restricted and exposed to stress (R+S): N=108

Once assigned to one of these groups, the rats remained in that group throughout the study. The rats exposed to stress were acclimated in different rooms than the group not exposed to stress.

Rats were exposed to 3 consecutive 8-day cycles followed by the final test on day 25:

a) the control group (NR+NS) had chow ad libitum for 4 days, on days 5-6 it received chow+HPF for 2 h; on days 7-8 it had chow ad libitum; on day 25 it was not exposed to stress;

b) the second group (R+S) had chow restricted to 66% of the normal intake for 4 days, was offered chow and HPF (2 h) on days 5-6 and only chow on days 7-8; on day 25 it was not exposed to stress.

The 8-day cycle was repeated three times, but in the third cycle the animals did not have access to HPF.

By the last day of re-feeding, the body weight and food intake of restricted rats were not statistically different from those of non-restricted rats, thus precluding the potentially confounding effect of hunger or energy deficit.

Body weights and food intake were recorded daily. Food intake is expressed as mean kilocalories per kilogram ingested±SEM.

On the test day (day 25) the animals were divided in the following groups as shown in Table 2:

TABLE 2

| No. of Animals | Procedure | Treatment |
|---|---|---|
| 8 | NR NS | Vehicle |
| 9 | R S | Vehicle |
| 9 | R S | H0816 3 mg/kg |
| 9 | R S | H0816 30 mg/kg |
| 9 | R S | H0860 3 mg/kg |
| 9 | R S | H0860 30 mg/kg |
| 9 | R S | H0847 3 mg/kg |
| 9 | R S | H0847 30 mg/kg |
| 9 | R S | H0900 3 mg/kg |
| 9 | R S | H0900 30 mg/kg |
| 9 | R S | Topiramate 60 mg/kg |

It has been reported by Applicants (Micioni Di B et al. 2010) that in the estrous phase of the ovarian cycle, female rats do not exhibit BE in the adopted model; while in all the other three phase of the ovarian cycle they exhibit BE without significant differences in intensity. Therefore, immediately after the test on day 25, vaginal smears were collected and analyzed under microscope to assess the ovarian phase, and data from rats in the estrous phase were not included in the statistical analysis. Vaginal smears were analyzed by an experienced experimenter blind to treatment conditions.

The Stress Procedure:

For 15 min, the container (China coffee cup) containing HPF is placed outside the cage; the container handle is hooked to the top wire wall of the cage in the hollow part where food pellets are usually offered. In these conditions, the animal is able to see the cup in which it received HPF on days 5, 6, 13, and 14 of the first two cycles, is able to see in part the HPF itself, and is able to smell its odour. In this 15-min period, the rat engages in repeated movements of the forepaws, head, and trunk aimed at obtaining the HPF, but it is not able to reach it. Rats undergo the stressful procedure between 10.00 and 12.00 am. After 15 min, the cup is placed inside the cage of the rats in the stress group (R+S), so that the HPF became accessible to the rat.

Compound Preparation:

100 mg of each compound (H0816, H0860, H0847 and H0900) was accurately weighed and suspended in 13.33 ml of 0.5% carboxymethyl cellulose sodium salt (CMC, Sigma-Aldrich Cat. C4888, lot 120M0216V) solution. The lower dose solution was prepared by dilution of 30 mg/ml suspension with 0.5% CMC solution. Suspensions were prepared freshly on test day. Vehicle was composed by a solution of 0.5% carboxymethyl cellulose sodium salt and was prepared by dissolving 1 g of CMC in 200 ml of distilled water. 180 mg of Topiramate was accurately weighed and suspended in 12 ml of 0.5% CMC solution. Compounds (vehicle and active principles) were administered by gavage in a volume of 4 ml/kg of body weight one hour before access to HPF.

Data Analysis:

All data are expressed as the mean±s.e.m. and each value reflects the mean number of animals per group as described in the legends. For data evaluation, the analysis of variance (ANOVA) was used followed by post-hoc (Bonferroni's) test when appropriate. Statistical significance was set at $P<0.05$. The Software used for the Graphs was Origin 7.0. The software for the statistical analysis was SYSTAT 13.0

Binge Eating Model:

The ANOVA revealed a highly significant difference in 2-h HPF intake in the 2 groups of rats following vehicle administration [$F(1,12)=18.9$; $P<0.01$]. As shown in FIG. 1, following vehicle administration HPF intake in the R+S group was markedly higher than that of the control (NR+NS) group. HPF intake of R+S rats was very pronounced in the first 15 min of access to HPF; these animals never engaged in competing behaviours, but continuously remained over the cup containing HPF and focused their attention on the intake. Cumulative HPF intake in the R+S group was significantly higher than in controls up to 120 min after access to HPF.

Figure 2:
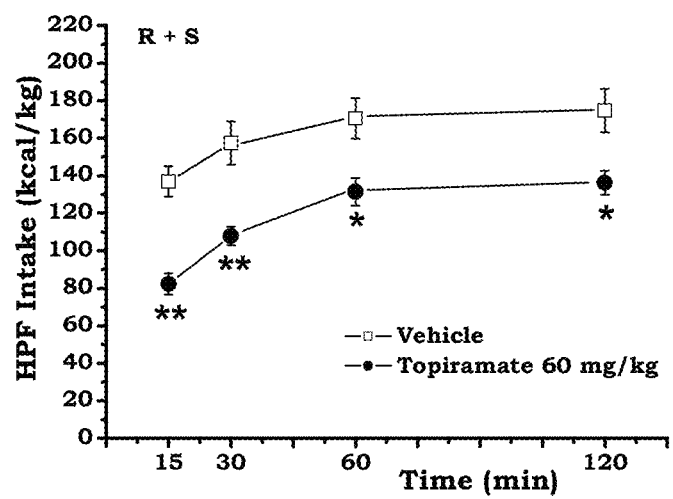
FIG. 2 shows the effect of Topiramate (60 mg/kg) or vehicle in a rat model of binge eating. The values shown are the mean±S.E.M. of HPF intake. Difference between R+S (Restricted and Stressed) vehicle and R+S treated rats: *P<0.05; ** P<0.01.

Effect of Topiramate on Binge Eating:

The ANOVA revealed a significant difference in 2-h HPF intake in the R+S rats treated with Topiramate at the dose of 60 mg/kg [$F(1,11)=16.2$; $P<0.01$]. As shown in FIG. 2, post-hoc comparisons revealed that the effect of Topiramate was statistically significant at all time points for the whole period in which BE was exhibited.

Figure 3:
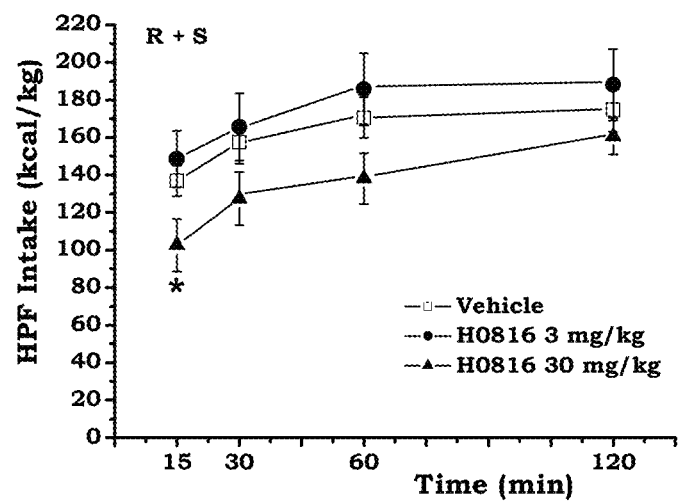
FIG. 3 shows the effect of compound H0816 (3 and 30 mg/kg) or vehicle in a rat model of binge eating. The values shown are the mean±S.E.M. of HPF intake. Difference between R+S vehicle and R+S treated rats: *P<0.05.

Effect of H0816 on Binge Eating:

The ANOVA revealed a significant difference in 2-h HPF intake in the R+S rats treated with H0816 at the doses of 3 and 30 mg/kg [$F(2,19)=3.9$; $P<0.05$]. As shown in FIG. 3, post-hoc comparisons revealed that the effect of H0816 (30 mg/kg) was statistically significant ($P<0.05$) at 15 min time point. H0816 treatment (both doses) did not affect animals' gross behaviour during the 2-h test.

Figure 4:
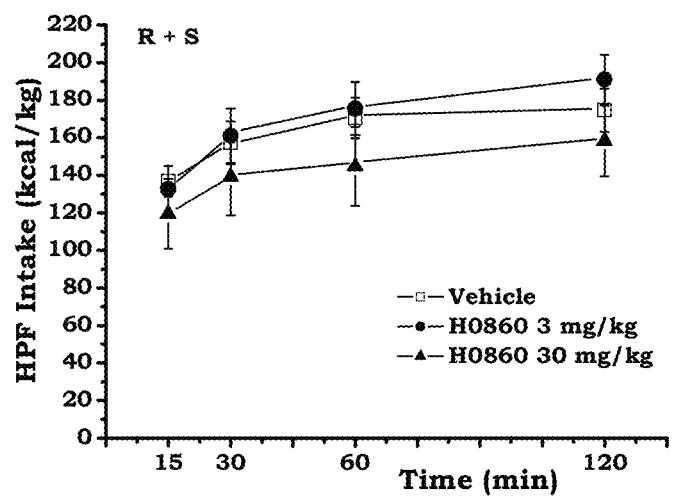
FIG. 4 shows the effect of compound H0860 (3 and 30 mg/kg) or vehicle in a rat model of binge eating. The values shown are the mean±S.E.M. of HPF intake. Statistical difference from vehicle-treated rats was not statistically significant.

Effect of H0860 on Binge Eating:

As shown in FIG. 4, H0860 at the doses of 3 and 30 mg/kg did not affect HPF intake in the R+S group [$F(2,19)=0.6$; $P>0.05$].

Figure 5:
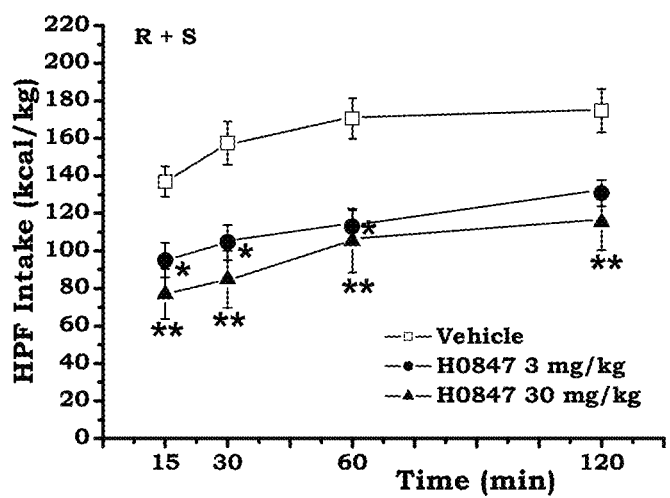
FIG. 5 shows the effect of compound H0847 (3 and 30 mg/kg) or vehicle in a rat model of binge eating. The values shown are the mean±S.E.M. of HPF intake. Difference between R+S vehicle and R+S treated rats: ** P<0.01; * P<0.05.

Effect of H0847 on Binge Eating:

The ANOVA revealed a significant difference in 2-h HPF intake in the R+S rats treated with H0847 at the doses of 3 and 30 mg/kg [$F(2,19)=8.7$; $P<0.01$]. As shown in FIG. 5, post-hoc comparisons revealed that the effect of H0847 (3 mg/kg) was statistically significant at 15, 30 and 60 min after HPF access. At the dose of 30 mg/kg, H0847 significantly ($P<0.01$) reduced HPF intake at all time points for the whole period in which BE was exhibited. Two animals treated with H0847 (3 mg/kg) and one animal treated with the dose of 30 mg/kg showed a mild sedation during the 2-h test.

Figure 6:
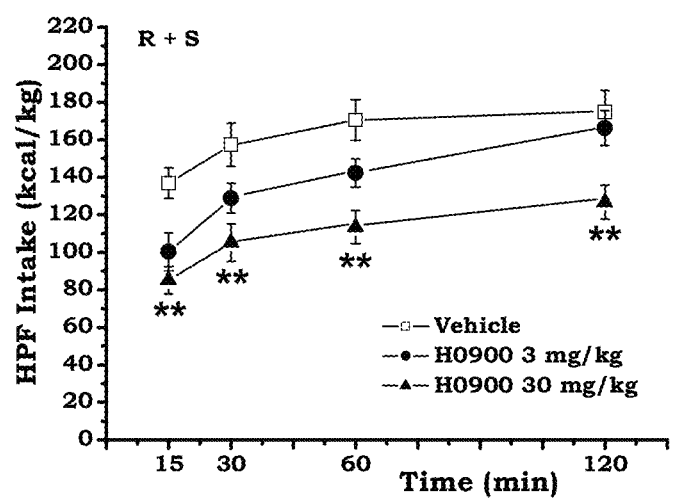
FIG. 6 shows the effect of compound H0900 (3 and 30 mg/kg) or vehicle in a rat model of binge eating. The values shown are the mean±S.E.M. of HPF intake. Difference between R+S vehicle and R+S treated rats: ** P<0.01; *P<0.05.

Effect of H0900 on Binge Eating:

The ANOVA revealed a significant difference in 2-h HPF intake in the R+S rats treated with H0900 at the doses of 3 and 30 mg/kg [$F(2,18)=12.2$; $P<0.01$]. As shown in FIG. 6, post-hoc comparisons revealed that the effect of H0900 (30 mg/kg) was statistically significant ($P<0.01$) at all time points for the whole period in which BE was exhibited. H0900 treatment (both doses) did not affect animals' gross behaviour during the 2-h test.

Effect of Topiramate, H0816, H0860, H0847 H0900 and Vehicle on 2-h Chow Food Intake During Binge Eating Test:

Statistical analysis indicated that acute administration of Topiramate [$F(1,11)=0.9$; $P>0.05$] or H0816 [$F(2,19)=0.3$; $P>0.05$] or H0900 [$F(2,18)=2.2$; $P>0.05$] did not modify 2-h chow intake. As shown in FIG. 7A, the acute administration of H0860 [$F(2,19)=22.9$; $P<0.01$] and H0847 [$F(2,19)=3.9$; $P<0.05$] significantly increased 2-h chow food intake.

Statistical analysis indicated that acute administration of Topiramate [$F(1,11)=0.00$; $P>0.05$] or H0816 [$F(2,19)=1.2$; $P>0.05$] or H0900 [$F(2,18)=2.7$; $P>0.05$] did not modify 24-h chow intake.

Figure 7:
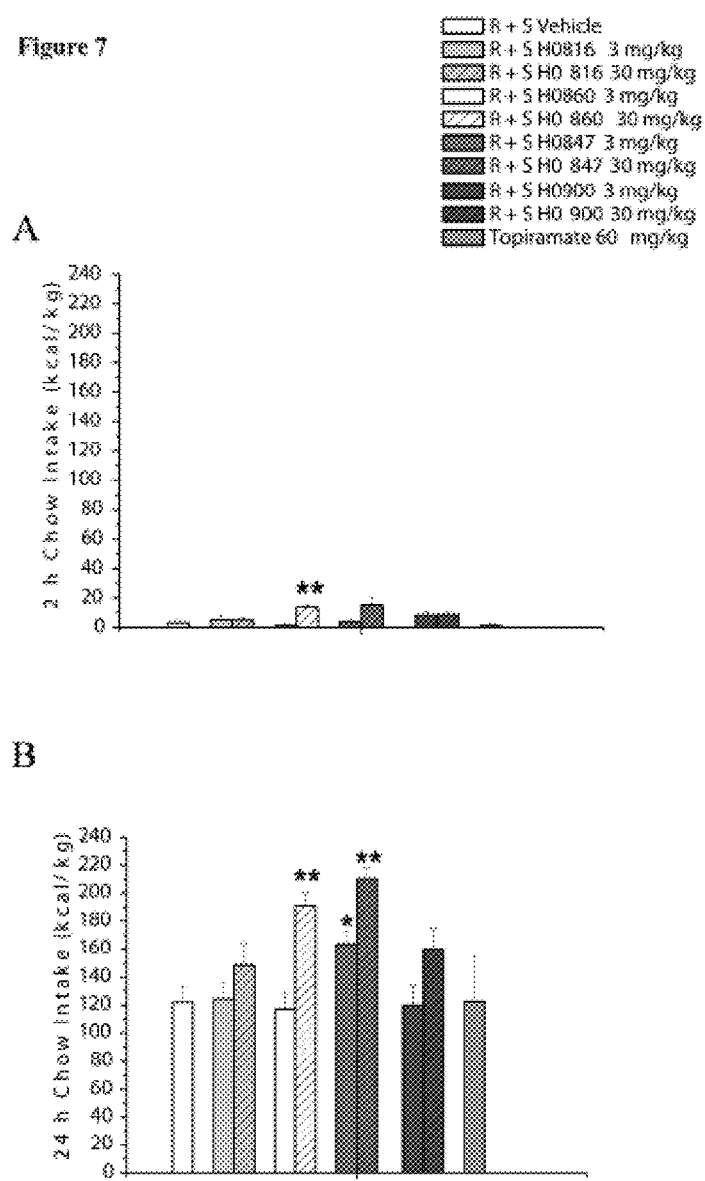
FIG. 7 shows the effect of Topiramate, compounds H0816, H0860, H0847H0900 and vehicle on 2 h (A) and 24 h (B) chow food intake during and after a binge eating test. The values shown are the mean±S.E.M. of HPF intake. Difference between R+S vehicle and R+S treated rats: * P<0.05,** P<0.01.

As shown in FIG. 7, the acute administration of H0860 [$F(2,19)=14.2$; $P<0.01$] and H0847 [$F(2,19)=24.3$; $P<0.01$] significantly increased 24-h chow food intake.

Effect of H0816 on Binge Eating (Second Test):

To confirm the effect of H0816 on BE, a second test was performed after ten days. Of 117 animals used in this study, 53 (the same 8 rats NR+NS and 45 rats R+S) were used for the second test. After one day off at the end of the first test, these groups of rats received an additional 8-day cycle: NR+NS group had 8 days of chow ad libitum, whereas R+S group had 4 days chow restricted to 66% of the normal intake followed by 4 days of chow ad libitum. In this additional cycle, all groups did not have access to HPF. The following day, R+S group was exposed to stress, while NR+NS group was not. On this day, H0816 (3, 10 and 30 mg/kg) and topiramate (60 mg/kg) or vehicle were administered by gavage 1-h before access to HPF. The ANOVA revealed a highly significant difference in 2-h HPF intake in the 2 groups of rats following vehicle administration [$F(1,12)=28.1$; $P<0.01$]. Cumulative HPF intake in the R+S group was significantly higher than in controls up to 120 min after access to it (data not shown). Statistical analysis showed a significant difference in 2-h HPF intake in the R+S rats treated with Topiramate at the dose of 60 mg/kg [$F(1,12)=47.1$; $P<0.01$]. Post-hoc comparisons revealed that the effect of Topiramate was statistically significant at all time points, that is for the whole period in which BE was exhibited (data not shown).

Figure 8:
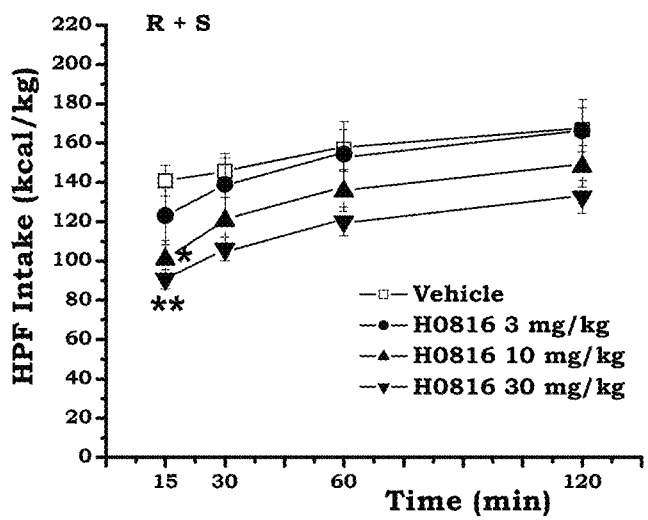
FIG. 8 shows the effect of H0816 (3, 10 and 30 mg/kg) or vehicle in a rat model of binge eating. The values shown are the mean±S.E.M. of HPF intake. Difference between R+S vehicle and R+S treated rats: *P<0.05; **P<0.05.

The ANOVA revealed a significant difference in 2-h HPF intake in the R+S rats treated with H0816 at the doses of 3, 10 and 30 mg/kg [$F(3,25)=3.3$; $P<0.05$]. As shown in FIG. 8, post-hoc comparisons revealed that the effect of H0816 (10 mg/kg) was statistically significant ($P<0.05$) at 15 min time point and the dose of 30 mg/kg completely blocked ($P<0.01$) the BE episode at 15 min. H0816 treatment (both doses) did not affect animals' gross behaviour during the 2-h test. Statistical analysis indicated that acute administration of Topiramate [$F(1,12)=2.3$; $P>0.05$] or H0816 [$F(3,25)=0.2$; $P>0.05$] did not modify 2-h and 24-h ([$F(1,12)=0.03$; $P>0.05$]; [$F(3,25)=0.5$; $P>0.05$]) chow intake (data not shown).

Topiramate, included in the experimental design as positive control, completely abolished BE episode at the dose of 60 mg/kg. In the same experiment, H0900, H0816, and H0847 significantly reduced BE behaviour in the R+S group, after acute administration, confirming the therapeutic potential of selective GHS-R1a antagonism in binge eaters.

In a second experiment, H0816 confirmed, dose dependently, its selective inhibitory effect on BE, with no effect on physiological feeding. Surprisingly, H0847 and H0860 significantly increased 2-h and 24-h chow food intake in the same animals, suggesting a not clean profile as GHS-R1a antagonist.

Example D

Characterizing the Effect of Compounds of Formula (I) on Operant Ethanol Self-Administration in Marchigian Sardinian Alcohol-Preferring (msP) Rats In this experiment, msP-rats (N=24) were trained to self-administer 10% (v/v) ethanol solution in 30-min daily sessions under a fixed-ratio 1 schedule of reinforcement in which each response resulted in delivery of 0.1 mL of fluids. Training continued until stable baseline of alcohol responding was achieved. At this point, before initiation of treatments, rats were trained to gavage administration procedures for three consecutive days (pre-treatment phase) during which they received drug vehicle. At this point animals were tested for the effect of ghrelin antagonists on 10% (v/v) ethanol self-administration. Using a within-subject Latin square design, the first group of msP rats (N=12) was tested for the effect of H0847 (0.0, 1.0 and 3.0 mg/kg), while the second (N=12) was treated with H0816 (0.0, 3.0 and 10.0 mg/kg).

Once the experiment was finished, animals were left in their home cages for several days, in order to wash out the drugs. Then, the same rats were employed to test the remaining ghrelin antagonists compounds H0900 (0.0, 3.0 and 30.0 mg/kg) and H0860 (0.0, 3.0 and 30.0 mg/kg). Once a stable self-administration baseline was reached, treatments begun according to the same experimental procedures described for the previous drugs tested.

All the drugs (or vehicles) were administered orally 1 hour before the beginning of the operant session. Responses at the lever activated the delivery mechanism but did not result in the delivery of alcohol.

Animals and Housing:
Male genetically selected alcohol-preferring Marchigian Sardinian (msP) rats were used (N=24). At the time of the experiments their body weight ranged between 350 and 400 g. They were housed 4 per cages in a room with a reverse 12:12 h light/dark cycle (lights off at 9:30 a.m.), temperature of 20-22° C. and humidity of 45-55%. Rats were offered free access to tap water and food pellets (4RF18, Mucedola, Settimo Milanese, Italy). All the procedures were conducted in adherence with the European Community Council Directive for Care and Use of Laboratory Animals and the National Institutes of Health Guide for the Care and Use of Laboratory Animals.

Compound Preparation:
75 mg of each H0900 and H0860 were accurately weighed and suspended in 10 ml of 0.5% carboxymethyl cellulose sodium salt solution (CMC, Sigma-Aldrich Cat. C4888, lot 120M0216V). The lower dose solution was prepared by dilution of 30 mg/ml suspension with 0.5% CMC solution.

37.5 mg of H0816 were accurately weighed and suspended in 15 ml of 0.5% carboxymethyl cellulose sodium salt solution (CMC, Sigma-Aldrich Cat. C4888, lot 120M0216V). The lower dose solution was prepared by dilution of mg/ml suspension with 0.5% CMC solution.

11.25 mg of H0847 were accurately weighed and suspended in 15 ml of 0.5% carboxymethyl cellulose sodium salt solution (CMC, Sigma-Aldrich Cat. C4888, lot 120M0216V). The lower dose solution was prepared by dilution of mg/ml suspension with 0.5% CMC solution.

Suspensions were prepared freshly on test day. Vehicle was composed of a solution of 0.5% carboxymethyl cellulose sodium salt and was prepared by dissolving 1 g of CMC in 200 ml of distilled water. Vehicle and drugs were administered by gavage in a volume of 4 ml/kg of body weight 1 hour before the access to 10% alcohol solution. 10% (v/v) ethanol solution was prepared every two days by diluting 95% (v/v) ethanol solution (F.L. CARSETTI s.n.c-CAMERINO) in drinkable water.

Equipment:
The self-administration stations consisted of operant conditioning chambers (Med Associate, Inc) enclosed in sound-attenuating, ventilated environmental cubicles. Each chamber was equipped with a drinking reservoir (volume capacity: 0.2) positioned 4 cm above the grid floor in the centre of the front panel of the chamber, two retractable levers located 3 cm (one to the right and the other to the left) of the drinking receptacle and a white cue light located 6 cm above the lever. An infusion pump was activated by responses on the right, or active lever, while responses on the left or inactive lever were recorded but did not result in activation of the pump. Activation of the pump resulted in a delivery of 0.1 ml of fluid. If a time out was programmed, lever presses during this period were counted but did not lead to further infusions. An IBM-compatible computer controlled the delivery of fluids (activation of syringe pump), presentation of visual stimuli and recording of the behavioral data.

Experimental Procedures:
Using operant self-administration chambers (Med Associates), msP rats were trained to lever press for 10% alcohol (v/v) until stable baseline of responding were achieved. 16 self-administration training sessions were carried out to train the animals. Operant sessions lasted 30 minutes and were conducted once a day during the dark phase of the light dark cycle. Active and inactive (control) lever responding were monitored.

After stable baseline of alcohol self-administration was established, msP rats were administered with vehicle or the inventive compounds at 2 different doses using a within subject design. Active and inactive lever responding was monitored: drugs were injected prior to the beginning of the self-administration session, according to indication.

The reinforcement program was FR1-LITO (Fixed Ratio-1 Light Time Out). During the 5 seconds time out (following the reinforced RR) a house light was switched on. The tests were conducted according to a within subject design where drug treatment (doses) was treated as repeated factors. Total number of active and inactive lever responding were subjected to statistical evaluation. Drug testing was carried out every four days. For 2 days before each drug test rats were not subjected to alcohol self-administration sessions.

Statistical Analysis:

Data were analyzed by means of a one-factor (treatment) ANOVA for repeated measures. Analysis of variance was followed by the Newman-Keuls test when appropriate. Statistical significance was set at $p<0.05$.

Figure 9:
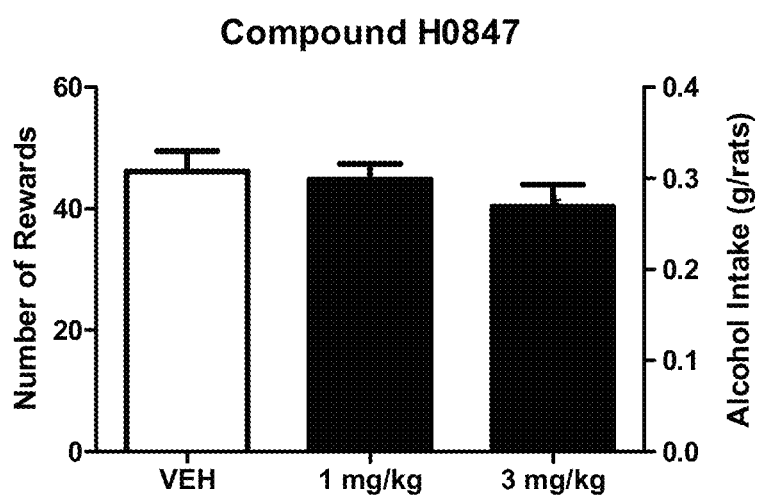
FIG. 9 shows the effect of compound H0847 on alcohol self-administration in msP rats.

As shown in FIG. 9, H0847 had no effect on operant responding for alcohol [$F(2,11)=0.53; p>0.05$]. Responses at the inactive control lever were not modified [$F(2,11)=0.53; p>0.05$].

Figure 10:
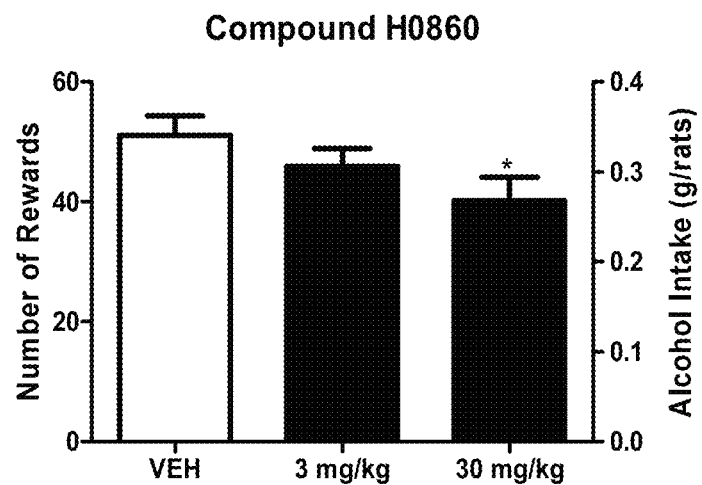
FIG. 10 shows the effect of compound H0860 on alcohol self-administration in msP rats.

As shown in FIG. 10, H0860 significantly reduced operant responding for alcohol [$F(2,11)=4.19; p<0.05$]. Post hoc analysis revealed a significant reduction of alcohol self-administration following treatment with the higher dose (30 mg/kg) (*$p<0.05$). Responses at the inactive control lever were not modified [$F(2,11)=0.15; p>0.05$].

Figure 11:
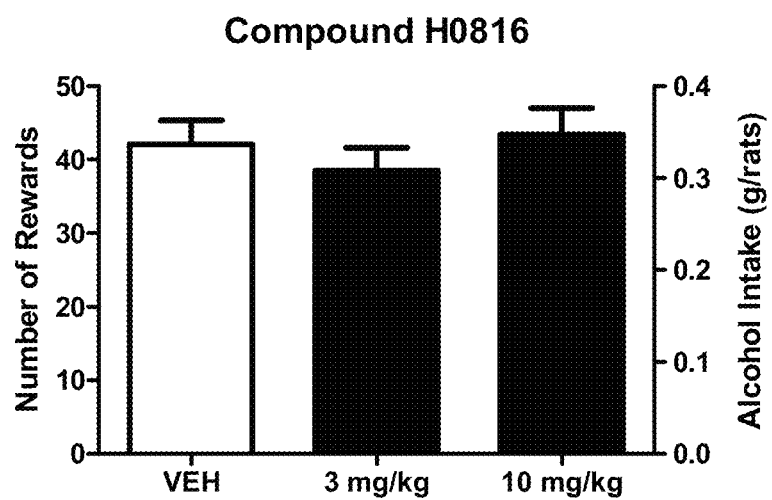
FIG. 11 shows the effect of compound H0816 on alcohol self-administration in msP rats.

As shown in FIG. 11, H0816 had no effect on operant responding for alcohol [$F(2,11)=0.75; p>0.05$]. Responses at the inactive control lever were not modified [$F(2,11)=0.30; p>0.05$].

Figure 12:
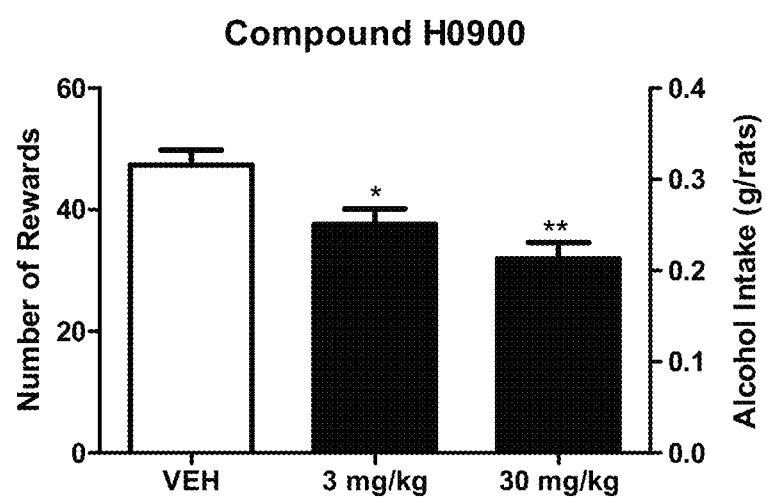
FIG. 12 shows the effect of compound H0900 on alcohol self-administration in msP rats.

As shown in FIG. 12, H0900 significantly reduced operant responding for alcohol [$F(2,11)=8.62; p<0.01$]. Post hoc analysis revealed a significant reduction of alcohol self-administration following treatment with both 3 mg/kg (*$p<0.05$) and 30 mg/kg (**$p<0.01$). Responses at the inactive control lever were not modified [$F(2,11)=1.03; p>0.05$].

In summary, the data shows that, in msP rats, acute oral administration of both H0900 and H0860 induced a statistically significant decrease in ethanol self-administration. For H0900, the effect was seen for both the doses tested (3 and 30 mg/kg). For H0860, only the higher dose (30 mg/kg) reduced ethanol self-administration. On the contrary, in the same experimental conditions, H0847 (1 or 3 mg/kg) and H0816 (3 or 10 mg/kg) had no effect on ethanol responses.

What is claimed is:

1. A compound of Formula I:

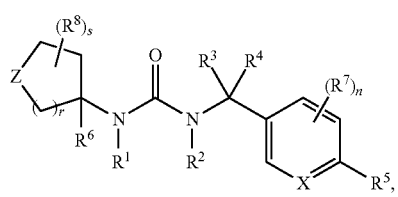

I or a pharmaceutically acceptable salt thereof, wherein:
X is CH or N;
Z is $NR^9$;
$R^1$ is H, $C_{1-6}$ alkyl, benzyl, OH, or $C_{1-6}$ alkoxy, wherein said $C_{1-6}$ alkyl, benzyl, or $C_{1-6}$ alkoxy is optionally substituted with 1-3 substituents selected from halo, OH, $C_{1-6}$ alkyl, $C_{1-6}$ alkoxy, $C_{1-6}$ hydroxyalkyl, $CO(C_{1-6}$ alkyl), CHO, $CO_2H$, $CO_2(C_{1-6}$ alkyl), and $C_{1-6}$ haloalkyl;
$R^2$ is H or $C_{1-6}$ alkyl;
$R^3$ and $R^4$ are each independently H, CN, halo, CHO, $CO_2H$, $C_{1-6}$ alkylcycloalkyl, $C_{1-6}$ alkoxy, $CO(C_{1-6}$ alkyl), $CO_2(C_{1-6}$ alkyl), $CONR^{12}R^{13}$, $C_{1-6}$ alkyl optionally substituted with halo, or $C_{1-6}$ hydroxyalkyl optionally substituted with aryl, wherein aryl is optionally substituted with $C_{1-3}$ hydroxyalkyl;
or $R^3$ and $R^4$ taken together with the carbon atom to which they are attached form a 3-6-membered ring;
$R^5$ is pyridinyl or pyrimidinyl, each optionally substituted with 1-3 substituents selected from halo, CN, OH, $NO_2$, $Si(CH_3)_3$, CHO, $CO_2H$, $CO(C_{1-6}$ alkyl), $CO_2(C_{1-6}$ alkyl), $NR^{14}R^{15}$, $NHCONR^{14}R^{15}$, $CONR^{14}R^{15}$, CH=NOH, $C_{1-6}$ alkyl, $C_{1-6}$ alkoxy, $C_{1-6}$ haloalkyl, $C_{1-6}$ hydroxyalkyl, $C_{2-6}$ alkenyl, $C_{2-6}$ alkynyl, aryl, cycloalkyl, heteroaryl, and heterocycloalkyl;
$R^6$ is H;
$R^7$ is H, CN, or halo;
$R^8$ is H or $C_{1-6}$ alkyl;
$R^9$ is H, $C_{1-6}$ alkyl, $CO(C_{1-6}$ alkyl), CHO, $CO_2H$, or $CO_2(C_{1-6}$ alkyl);
$R^{12}$ and $R^{13}$ are each independently H or $C_{1-6}$ alkyl;
$R^{14}$ and $R^{15}$ are each independently H, $C_{1-6}$ alkyl, $CO(C_{1-6}$ alkyl), CO(heteroaryl), heteroaryl, or cycloalkyl;
r is 2;
s is 0, 1, 2, 3, or 4; and
n is 0, 1, 2, or 3.

2. The compound of claim 1, wherein X is CH.
3. The compound of claim 1, wherein X is N.
4. The compound of claim 1, wherein Z is $N(C_{1-6}$ alkyl).
5. The compound of claim 1, wherein Z is $NCH_3$.
6. The compound of claim 1, wherein $R^1$ is $C_{1-6}$ alkyl.
7. The compound of claim 1, wherein $R^1$ is $CH_3$.
8. The compound of claim 1, wherein $R^1$ is benzyl.
9. The compound of claim 8, wherein said benzyl is optionally substituted with $CO_2(C_{1-6}$ alkyl) or $C_{1-6}$ hydroxyalkyl.
10. The compound of claim 1, wherein $R^1$ is OH.
11. The compound of claim 1, wherein $R^1$ is $C_{1-6}$ alkoxy.
12. The compound of claim 11, wherein said $C_{1-6}$ alkoxy is $OCH_3$, $OCH_2CH_3$ or $O(CH_2)_2CH_3$.
13. The compound of claim 1, wherein $R^2$ is H.
14. The compound of claim 1, wherein $R^3$ and $R^4$ are each independently CN, $C_{1-6}$ alkylcycloalkyl, $CO_2(C_{1-6}$ alkyl), $CONH_2$, $C_{1-6}$ alkyl optionally substituted with halo, or $C_{1-6}$ hydroxyalkyl optionally substituted with aryl.
15. The compound of claim 14, wherein said $C_{1-6}$ alkyl is $CH_3$ or $CH_2CH_3$.
16. The compound of claim 14, wherein said $C_{1-6}$ alkylcycloalkyl is $CH_2$-cyclopropyl.
17. The compound of claim 14, wherein said $C_{1-6}$ hydroxyalkyl is $CH_2OH$.
18. The compound of claim 14, wherein said $CO_2(C_{1-6}$ alkyl) is $CO_2CH_3$.
19. The compound of claim 14, wherein said $C_{1-6}$ alkyl optionally substituted with halo is $CF_3$.
20. The compound of claim 1, wherein $R^3$ and $R^4$ taken together with the carbon atom to which they are attached form a 3-6-membered ring.

21. The compound of claim 20, wherein $R^3$ and $R^4$ are taken together with the carbon atom to which they are attached to form a cyclopropyl ring.

22. The compound of claim 20, wherein $R^3$ and $R^4$ are taken together with the carbon atom to which they are attached form a tetrahydropyranyl ring.

23. The compound of claim 1, wherein $R^5$ is pyridinyl.

24. The compound of claim 1, wherein $R^7$ is halo.

25. The compound of claim 24, wherein said halo is Cl or F.

26. The compound of claim 1, wherein $R^8$ is H.

27. The compound of claim 1, wherein $R^8$ is $C_{1-6}$ alkyl.

28. The compound of claim 1, wherein $R^8$ is $CH_3$.

29. The compound of claim 1, having Formula II:

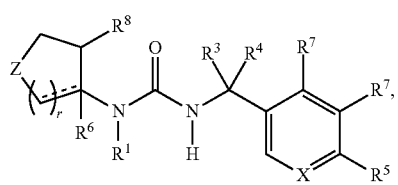

or a pharmaceutically acceptable salt thereof.

30. The compound of claim 1, having Formula III:

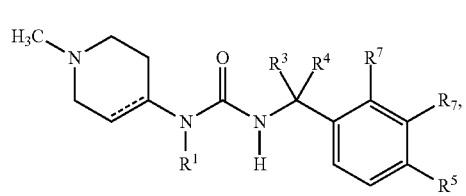

or a pharmaceutically acceptable salt thereof.

31. The compound of claim 1, having formula:

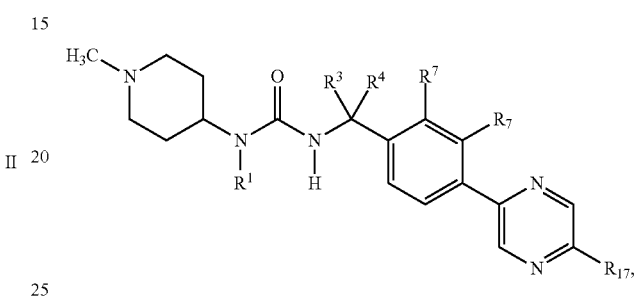

wherein $R^{17}$ is H or halo.

32. A pharmaceutical composition comprising a therapeutically effective amount of a compound of claim 1 and one or more pharmaceutically acceptable excipients.

33. A compound selected from the group consisting of:

| Compound No. | Chemical Structure | Chemical Name |
| --- | --- | --- |
| H0496 | 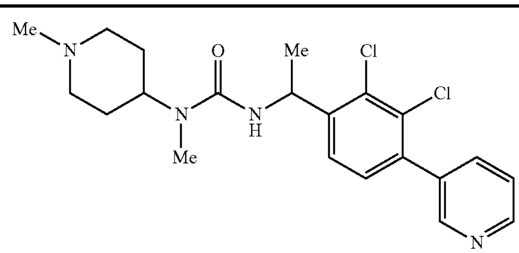 | 3-(1-(2,3-dichloro-4-(pyridin-3-yl)phenyl)ethyl)-1-methyl-1-(1-methylpiperidin-4-yl)urea |
| H0617 | 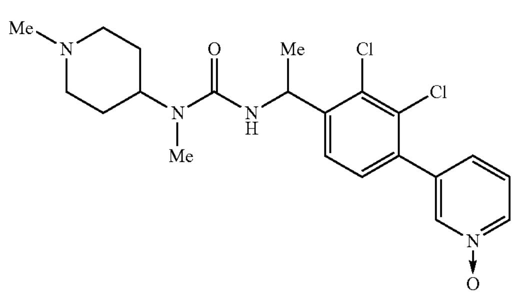 [SMILES: CC(NC(=O)N(C)C1CCN(C)CC1)c1ccc(-c2ccc[n+]([O-])c2)c(Cl)c1Cl] | 3-(1-(2,3-dichloro-4-(pyridin-3-yl)phenyl)ethyl)-1-methyl-1-(1-methylpiperidin-4-yl)urea |
| H0539 | 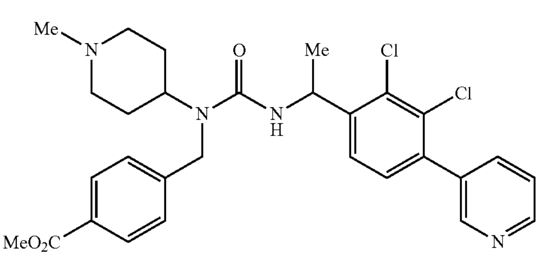 [SMILES: COC(=O)c1ccc(CN(C(=O)NC(C)c2ccc(-c3cccnc3)c(Cl)c2Cl)C2CCN(C)CC2)cc1] | methyl 4-((3-(1-(2,3-dichloro-4-(pyridin-3-yl)phenyl)ethyl)-1-(1-methylpiperidin-4-yl)ureido)methyl)benzoate |

| Compound No. | Chemical Structure | Chemical Name |
|---|---|---|
| H0546 | 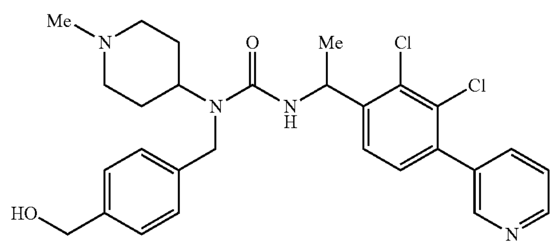 [SMILES: CC(NC(=O)N(Cc1ccc(CO)cc1)C1CCN(C)CC1)c1ccc(-c2cccnc2)c(Cl)c1Cl] | 3-(1-(2,3-dichloro-4-(pyridin-3-yl)phenyl)ethyl)-1-(4-(hydroxymethyl)benzyl)-1-(1-methylpiperidin-4-yl)urea |
| H0527 | 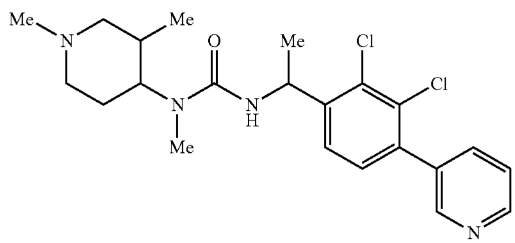 [SMILES: CC(NC(=O)N(C)C1CCN(C)CC1C)c1ccc(-c2cccnc2)c(Cl)c1Cl] | 3-(1-(2,3-dichloro-4-(pyridin-3-yl)phenyl)ethyl)-1-(1,3-dimethylpiperidin-4-yl)-1-methylurea |
| H0497 | 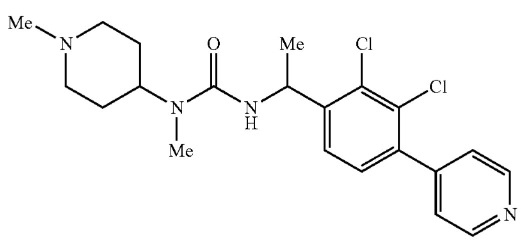 [SMILES: CC(NC(=O)N(C)C1CCN(C)CC1)c1ccc(-c2ccncc2)c(Cl)c1Cl] | 3-(1-(2,3-dichloro-4-(pyridin-4-yl)phenyl)ethyl)-1-methyl-1-(1-methylpiperidin-4-yl)urea |
| H0650 | 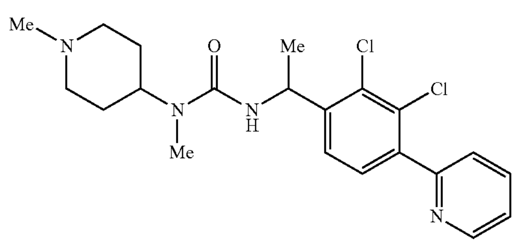 | 3-(1-(2,3-dichloro-4-(pyridin-2-yl)phenyl)ethyl)-1-methyl-1-(1-methylpiperidin-4-yl)urea |
| H0849 | 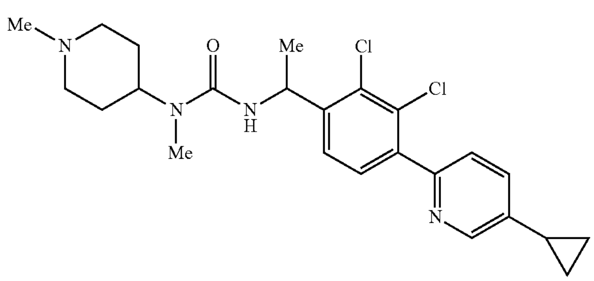 [SMILES: CC(NC(=O)N(C)C1CCN(C)CC1)c1ccc(-c2ccc(C3CC3)cn2)c(Cl)c1Cl] | 3-(1-(2,3-dichloro-4-(5-cyclopropylpyridin-2-yl)phenyl)ethyl)-1-methyl-1-(1-methylpiperidin-4-yl)urea |
| H0511 | 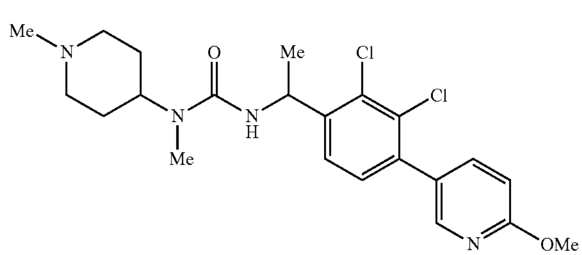 | 3-(1-(2,3-dichloro-4-(6-methoxypyridin-3-yl)phenyl)ethyl)-1-methyl-1-(1-methylpiperidin-4-yl)urea |

| Compound No. | Chemical Structure | Chemical Name |
|---|---|---|
| H0820 | 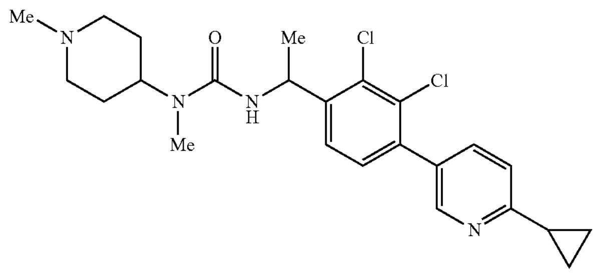 [SMILES: CC(NC(=O)N(C)C1CCN(C)CC1)c1ccc(-c2ccc(C3CC3)nc2)c(Cl)c1Cl] | 3-(1-(2,3-dichloro-4-(6-cyclopropylpyridin-3-yl)phenyl)ethyl)-1-methyl-1-(1-methylpiperidin-4-yl)urea |
| H0613 | 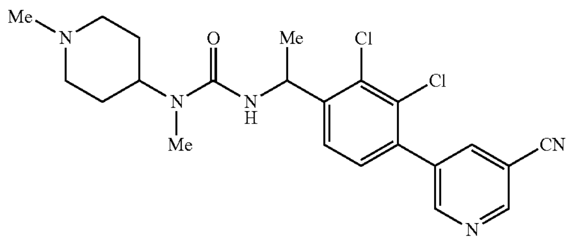 | 3-(1-(2,3-dichloro-4-(5-cyanopyridin-3-yl)phenyl)ethyl)-1-methyl-1-(1-methylpiperidin-4-yl)urea |
| H0614 | 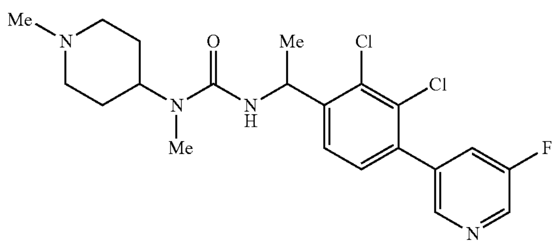 [SMILES: CC(NC(=O)N(C)C1CCN(C)CC1)c1ccc(-c2cncc(F)c2)c(Cl)c1Cl] | 3-(1-(2,3-dichloro-4-(5-fluoropyridin-3-yl)phenyl)ethyl)-1-methyl-1-(1-methylpiperidin-4-yl)urea |
| H0635 | 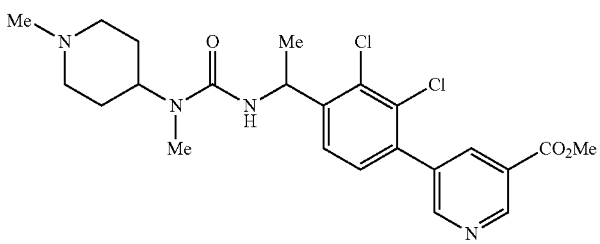 [SMILES: COC(=O)c1cncc(-c2ccc(C(C)NC(=O)N(C)C3CCN(C)CC3)c(Cl)c2Cl)c1] | methyl 5-(2,3-dichloro-4-(1-(3-methyl-3-(1-methylpiperidin-4-yl)ureido)ethyl)phenyl)nicotinate |
| H0636 | 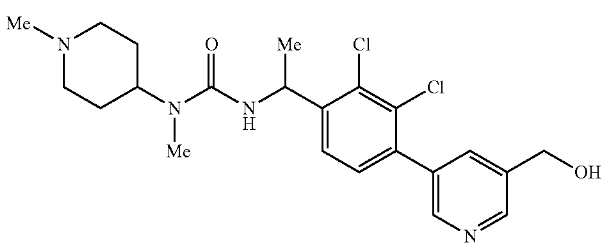 | 3-(1-(2,3-dichloro-4-(5-(hydroxymethyl)pyridin-3-yl)phenyl)ethyl)-1-methyl-1-(1-methylpiperidin-4-yl)urea |
| H0637 | 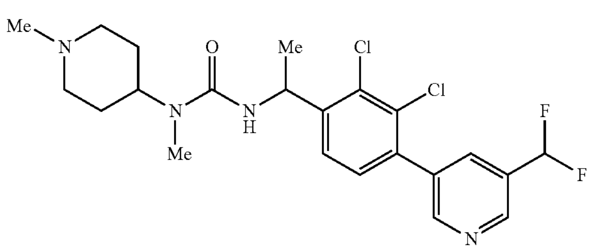 [SMILES: CC(NC(=O)N(C)C1CCN(C)CC1)c1ccc(-c2cncc(C(F)F)c2)c(Cl)c1Cl] | 3-(1-(2,3-dichloro-4-(5-(difluoromethyl)pyridin-3-yl)phenyl)ethyl)-1-methyl-1-(1-methylpiperidin-4-yl)urea |

-continued

| Compound No. | Chemical Structure | Chemical Name |
|---|---|---|
| H0638 | 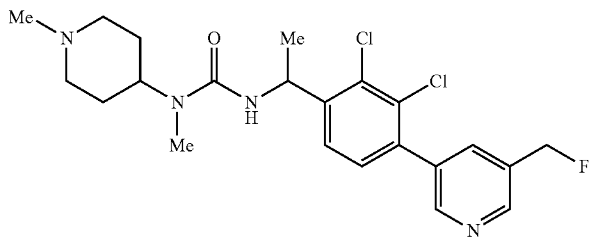 [SMILES: CC(NC(=O)N(C)C1CCN(C)CC1)c1ccc(-c2cncc(CF)c2)c(Cl)c1Cl] | 3-(1-(2,3-dichloro-4-(5-(fluoromethyl)pyridin-3-yl)phenyl)ethyl)-1-methyl-1-(1-methylpiperidin-4-yl)urea |
| H0639 | 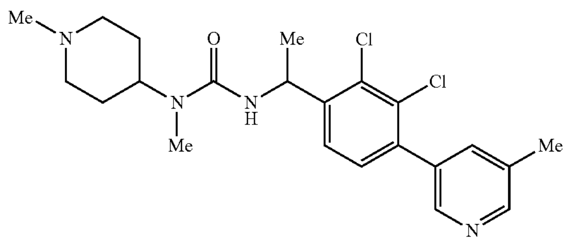 [SMILES: Cc1cncc(-c2ccc(C(C)NC(=O)N(C)C3CCN(C)CC3)c(Cl)c2Cl)c1] | 3-(1-(2,3-dichloro-4-(5-methylpyridin-3-yl)phenyl)ethyl)-1-methyl-1-(1-methylpiperidin-4-yl)urea |
| H0642 | 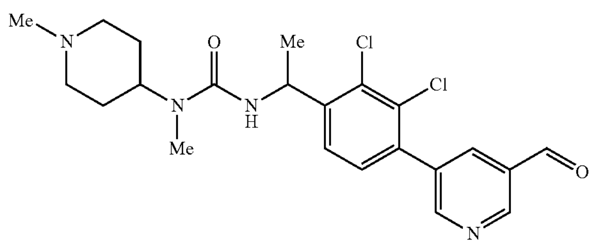 [SMILES: CC(NC(=O)N(C)C1CCN(C)CC1)c1ccc(-c2cncc(C=O)c2)c(Cl)c1Cl] | 3-(1-(2,3-dichloro-4-(5-formylpyridin-3-yl)phenyl)ethyl)-1-methyl-1-(1-methylpiperidin-4-yl)urea |
| H0704 | 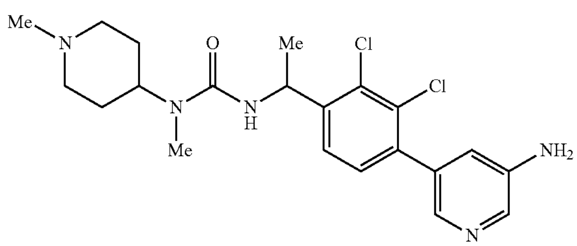 | 3-(1-(4-(5-aminopyridin-3-yl)-2,3-dichlorophenyl)ethyl)-1-methyl-1-(1-methylpiperidin-4-yl)urea |
| H0705 | 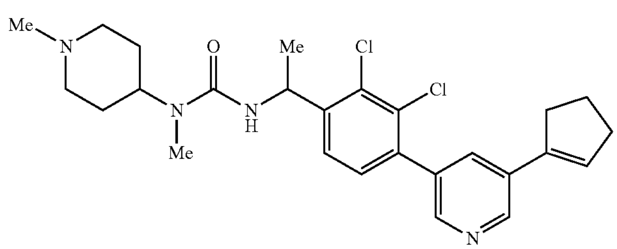 [SMILES: CC(NC(=O)N(C)C1CCN(C)CC1)c1ccc(-c2cncc(C3=CCCC3)c2)c(Cl)c1Cl] | 3-(1-(2,3-dichloro-4-(5-(cyclopent-1-en-1-yl)pyridin-3-yl)phenyl)ethyl)-1-methyl-1-(1-methylpiperidin-4-yl)urea |
| H0707 | 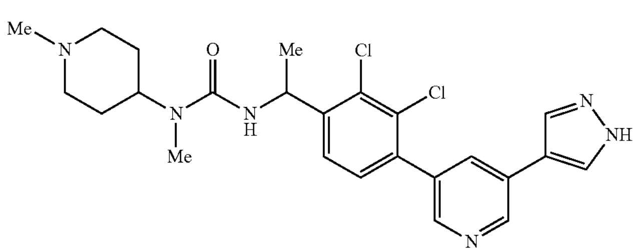 [SMILES: CC(NC(=O)N(C)C1CCN(C)CC1)c1ccc(-c2cncc(-c3cn[nH]c3)c2)c(Cl)c1Cl] | 3-(1-(4-(5-(1H-pyrazol-4-yl)pyridin-3-yl)-2,3-dichlorophenyl)ethyl)-1-methyl-1-(1-methylpiperidin-4-yl)urea |

-continued

| Compound No. | Chemical Structure | Chemical Name |
|---|---|---|
| H0711 | 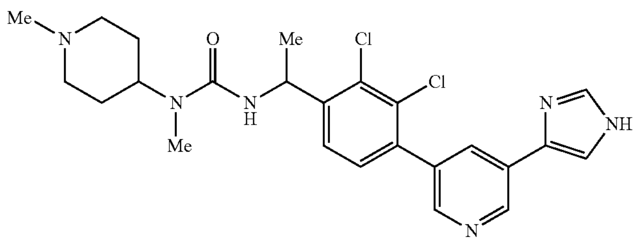 [SMILES: CC(NC(=O)N(C)C1CCN(C)CC1)c1ccc(-c2cncc(-c3c[nH]cn3)c2)c(Cl)c1Cl] | 3-(1-(4-(5-(1H-imidazol-4-yl)pyridin-3-yl)-2,3-dichlorophenyl)ethyl)-1-methyl-1-(1-methylpiperidin-4-yl)urea |
| H0716 | 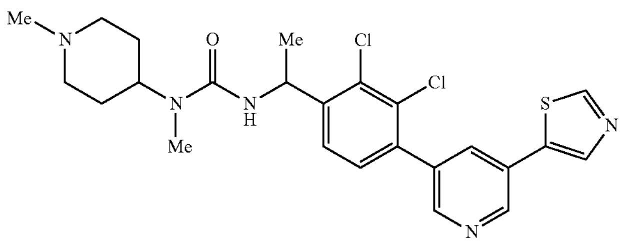 [SMILES: CC(NC(=O)N(C)C1CCN(C)CC1)c1ccc(-c2cncc(-c3cncs3)c2)c(Cl)c1Cl] | 3-(1-(2,3-dichloro-4-(5-(thiazol-5-yl)pyridin-3-yl)phenyl)ethyl)-1-methyl-1-(1-methylpiperidin-4-yl)urea |
| H0717 | 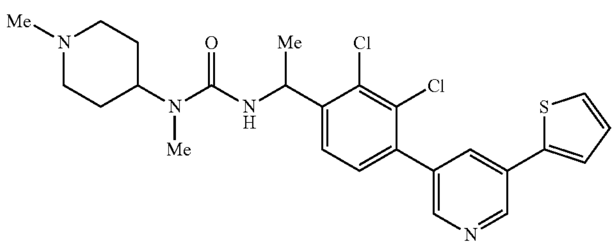 [SMILES: CC(NC(=O)N(C)C1CCN(C)CC1)c1ccc(-c2cncc(-c3cccs3)c2)c(Cl)c1Cl] | 3-(1-(2,3-dichloro-4-(5-(thiophen-2-yl)pyridin-3-yl)phenyl)ethyl)-1-methyl-1-(1-methylpiperidin-4-yl)urea |
| H0718 | 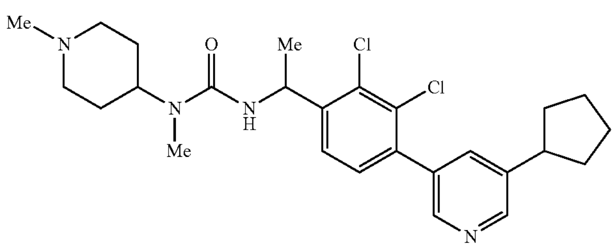 [SMILES: CC(NC(=O)N(C)C1CCN(C)CC1)c1ccc(-c2cncc(C3CCCC3)c2)c(Cl)c1Cl] | 3-(1-(2,3-dichloro-4-(5-cyclopentylpyridin-3-yl)phenyl)ethyl)-1-methyl-1-(1-methylpiperidin-4-yl)urea |
| H0719 | 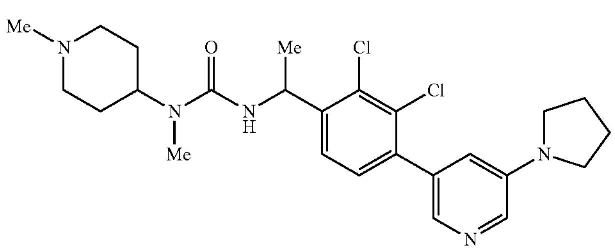 | 3-(1-(2,3-dichloro-4-(5-(pyrrolidin-1-yl)pyridin-3-yl)phenyl)ethyl)-1-methyl-1-(1-methylpiperidin-4-yl)urea |
| H0712 | 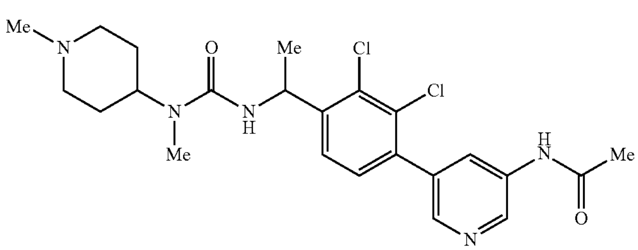 [SMILES: CC(=O)Nc1cncc(-c2ccc(C(C)NC(=O)N(C)C3CCN(C)CC3)c(Cl)c2Cl)c1] | N-(5-(2,3-dichloro-4-(1-(3-methyl-3-(1-methylpiperidin-4-yl)ureido)ethyl)phenyl)pyridin-3-yl)acetamide |

| Compound No. | Chemical Name |
|---|---|
| H0708 | 3-(1-(2,3-dichloro-4-(5-(methoxymethyl)pyridin-3-yl)phenyl)ethyl)-1-methyl-1-(1-methylpiperidin-4-yl)urea |
| H0714 | 3-(1-(2,3-dichloro-4-(5-(2-methoxyethyl)pyridin-3-yl)phenyl)ethyl)-1-methyl-1-(1-methylpiperidin-4-yl)urea |
| H0715 | 3-(1-(2,3-dichloro-4-(5-ethylpyridin-3-yl(phenyl)ethyl)-1-methyl-1-(1-methylpiperidin-4-yl)urea |
| H0706 | 3-(1-(2,3-dichloro-4-(5-vinylpyridin-3-yl)phenyl)ethyl)-1-methyl-1-(1-methylpiperidin-4-yl)urea |
| H0710 | 3-(1-(2,3-dichloro-4-(5-ethynylpyridin-3-yl)phenyl)ethyl)-1-methyl-1-(1-methylpiperidin-4-yl)urea |
| H0666 | 3-(cyano(2,3-dichloro-4-(5-cyanopyridin-3-yl)phenyl)methyl)-1-methyl-1-(1-methylpiperidin-4-yl)urea |

-continued

| Compound No. | Chemical Structure | Chemical Name |
|---|---|---|
| H0739 | 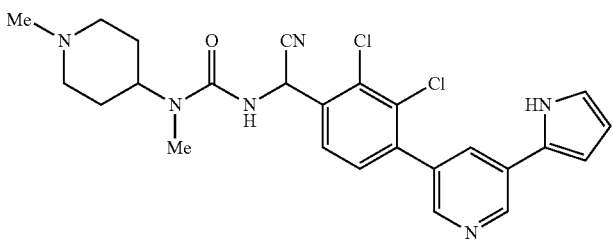 [SMILES: CN1CCC(N(C)C(=O)NC(C#N)c2ccc(-c3cncc(-c4ccc[nH]4)c3)c(Cl)c2Cl)CC1] | 3-((4-(5-(1H-pyrrol-2-yl)pyridin-3-yl)-2,3-dichlorophenyl)(cyano)methyl)-1-methyl-1-(1-methylpiperidin-4-yl)urea |
| H0667 | 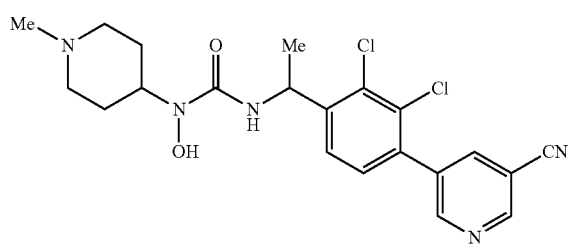 | 3-(1-(2,3-dichloro-4-(5-cyanopyridin-3-yl)phenyl)ethyl)-1-hydroxy-1-(1-methylpiperidin-4-yl)urea |
| H0821 | 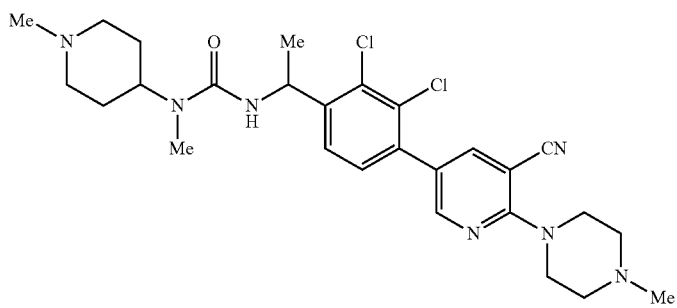 [SMILES: CC(NC(=O)N(C)C1CCN(C)CC1)c1ccc(-c2cnc(N3CCN(C)CC3)c(C#N)c2)c(Cl)c1Cl] | 3-(1-(2,3-dichloro-4-(5-cyano-6-(4-methylpiperazin-1-yl)pyridin-3-yl)phenyl)ethyl)-1-methyl-1-(1-methylpiperidin-4-yl)urea |
| H0646 | 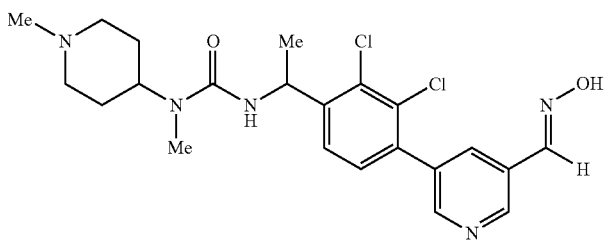 [SMILES: CC(NC(=O)N(C)C1CCN(C)CC1)c1ccc(-c2cncc(/C=N/O)c2)c(Cl)c1Cl] | (E)-3-(1-(2,3-dichloro-4-(5-((hydroxyimino)methyl)pyridin-3-yl)phenyl)ethyl)-1-methyl-1-(1-methylpiperidin-4-yl)urea |
| H0720 | 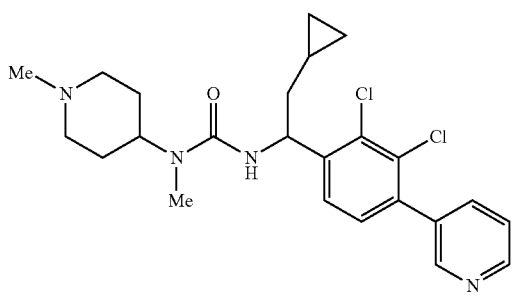 [SMILES: CN1CCC(N(C)C(=O)NC(CC2CC2)c2ccc(-c3cccnc3)c(Cl)c2Cl)CC1] | 3-(2-cyclopropyl-1-(2,3-dichloro-4-(pyridin-3-yl)phenyl)ethyl)-1-methyl-1-(1-methylpiperidin-4-yl)urea |

-continued

| Compound No. | Chemical Structure | Chemical Name |
|---|---|---|
| H0721 | 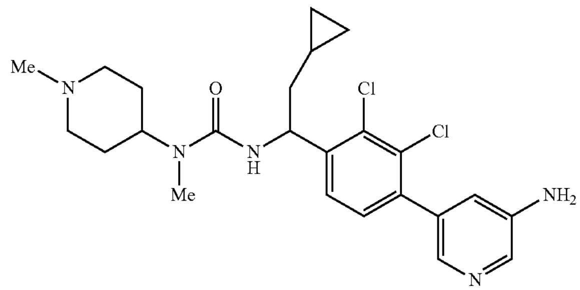 [SMILES: CN1CCC(N(C)C(=O)NC(CC2CC2)c2ccc(-c3cncc(N)c3)c(Cl)c2Cl)CC1] | 3-(1-(4-(5-aminopyridin-3-yl)-2,3-dichlorophenyl)-2-cyclopropylethyl)-1-methyl-1-(1-methylpiperidin-4-yl)urea |
| H0516 | 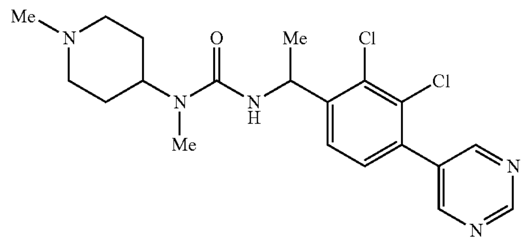 [SMILES: CC(NC(=O)N(C)C1CCN(C)CC1)c1ccc(-c2cncnc2)c(Cl)c1Cl] | 3-(1-(2,3-dichloro-4-(pyrimidin-5-yl)phenyl)ethyl)-1-methyl-1-(1-methylpiperidin-4-yl)urea |
| H0649 | 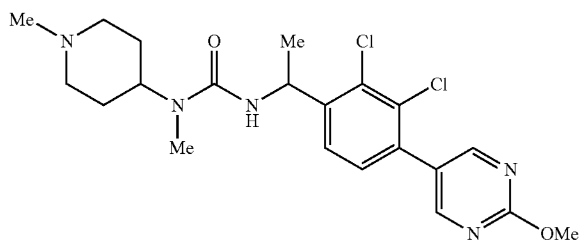 | 3-(1-(2,3-dichloro-4-(2-methoxypyrimidin-5-yl)phenyl)ethyl)-1-methyl-1-(1-methylpiperidin-4-yl)urea |
| H0797 | 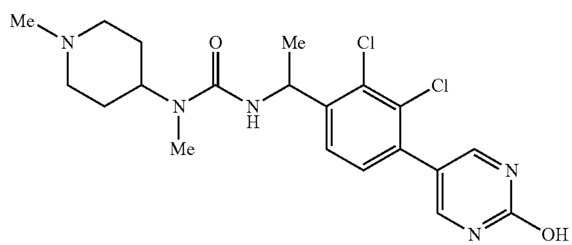 | 3-(1-(2,3-dichloro-4-(2-hydroxypyrimidin-5-yl)phenyl)ethyl)-1-methyl-1-(1-methylpiperidin-4-yl)urea |
| H0798 | 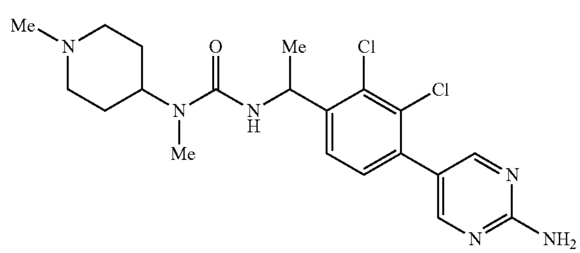 [SMILES: CC(NC(=O)N(C)C1CCN(C)CC1)c1ccc(-c2cnc(N)nc2)c(Cl)c1Cl] | 3-(1-(4-(2-aminopyrimidin-5-yl)-2,3-dichlorophenyl)ethyl)-1-methyl-1-(1-methylpiperidin-4-yl)urea |
| H0799 | 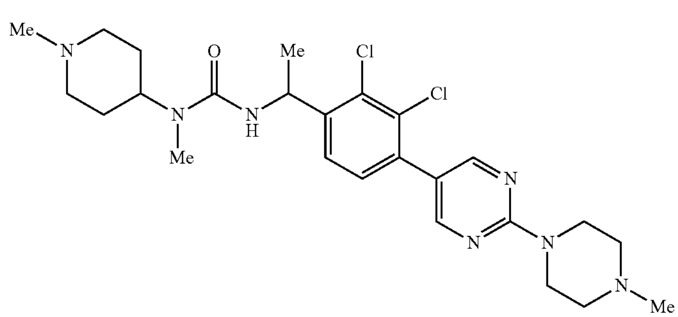 [SMILES: CC(NC(=O)N(C)C1CCN(C)CC1)c1ccc(-c2cnc(N3CCN(C)CC3)nc2)c(Cl)c1Cl] | 3-(1-(2,3-dichloro-4-(2-(4-methylpiperdzin-1-yl)pyrimidin-5-yl)phenyl)ethyl)-1-methyl-1-(1-methylpiperidin-4-yl)urea |

| Compound No. | Chemical Structure | Chemical Name |
|---|---|---|
| H0800 | 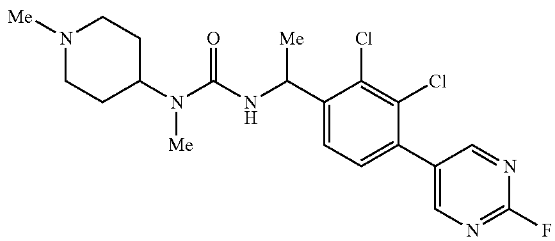 | 3-(1-(2,3-dichloro-4-(2-fluoropyrimidin-5-yl)phenyl)ethyl)-1-methyl-1-(1-methylpiperidin-4-yl)urea |
| H0801 | 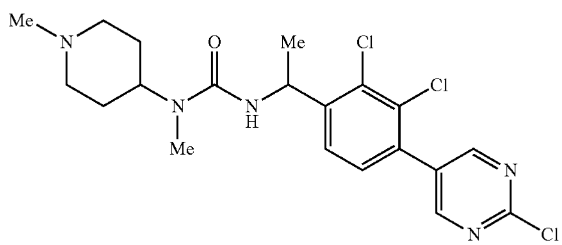 [SMILES: CC(NC(=O)N(C)C1CCN(C)CC1)c1ccc(-c2cnc(Cl)nc2)c(Cl)c1Cl] | 3-(1-(2,3-dichloro-4-(2-chloropyrimidin-5-yl)phenyl)ethyl)-1-methyl-1-(1-methylpiperidin-4-yl)urea |
| H0802 | 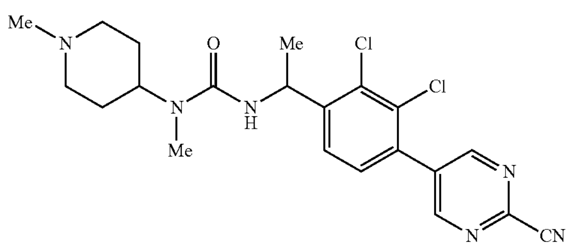 | 3-(1-(2,3-dichloro-4-(2-cyanopyrimidin-5-yl)phenyl)ethyl)-1-methyl-1-(1-methylpiperidin-4-yl)urea |
| H0803 | 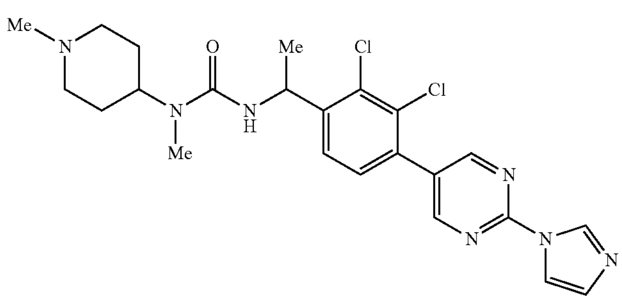 [SMILES: CC(NC(=O)N(C)C1CCN(C)CC1)c1ccc(-c2cnc(-n3ccnc3)nc2)c(Cl)c1Cl] | 3-(1-(4-(2-(1H-imidazol-1-yl)pyrimidin-5-yl)-2,3-dichlorophenyl)ethyl)-1-methyl-1-(1-methylpiperidin-4-yl)urea |
| H0804 | 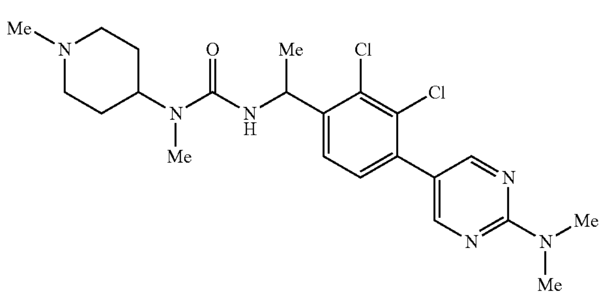 [SMILES: CC(NC(=O)N(C)C1CCN(C)CC1)c1ccc(-c2cnc(N(C)C)nc2)c(Cl)c1Cl] | 3-(1-(2,3-dichloro-4-(2-(dimethylamino)pyrimidin-5-yl)phenyl)ethyl)-1-methyl-1-(1-methylpiperidin-4-yl)urea |

-continued

| Compound No. | Chemical Structure | Chemical Name |
|---|---|---|
| H0805 | 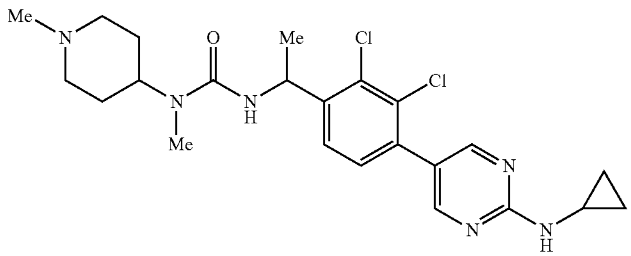 [SMILES: CC(NC(=O)N(C)C1CCN(C)CC1)c1ccc(-c2cnc(NC3CC3)nc2)c(Cl)c1Cl] | 3-(1-(2,3-dichloro-4-(2-(cyclopropylamino)pyrimidin-5-yl)phenyl)ethyl)-1-methyl-1-(1-methylpiperidin-4-yl)urea |
| H0806 | 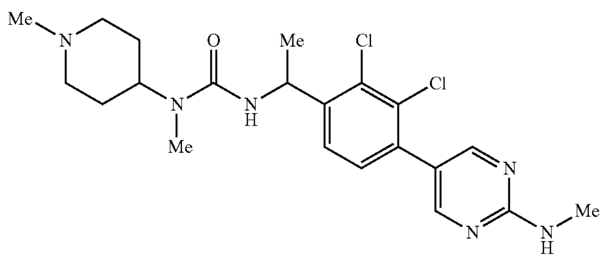 [SMILES: CNc1ncc(-c2ccc(C(C)NC(=O)N(C)C3CCN(C)CC3)c(Cl)c2Cl)cn1] | 3-(1-(2,3-dichloro-4-(2-(methylamino)pyrimidin-5-yl)phenyl)ethyl)-1-methyl-1-(1-methylpiperidin-4-yl)urea |
| H0807 | 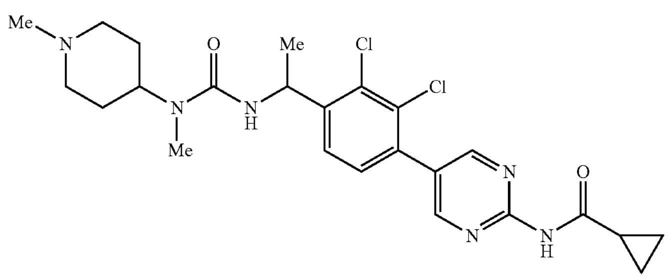 [SMILES: CC(NC(=O)N(C)C1CCN(C)CC1)c1ccc(-c2cnc(NC(=O)C3CC3)nc2)c(Cl)c1Cl] | N-(5-(2,3-dichloro-4-(1-(3-methyl-3-(1-methylpiperidin-4-yl)ureido)ethyl)phenyl)pyrimidin-2-yl)cyclopropanecarboxamide |
| H0854 | 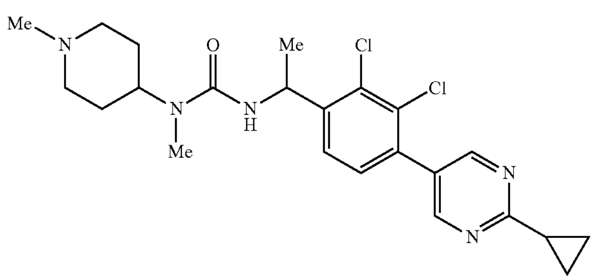 [SMILES: CC(NC(=O)N(C)C1CCN(C)CC1)c1ccc(-c2cnc(C3CC3)nc2)c(Cl)c1Cl] | 3-(1-(2,3-dichloro-4-(2-cyclopropylpyrimidin-5-yl)phenyl)ethyl)-1-methyl-1-(1-methylpiperidin-4-yl)urea |
| H0813 | 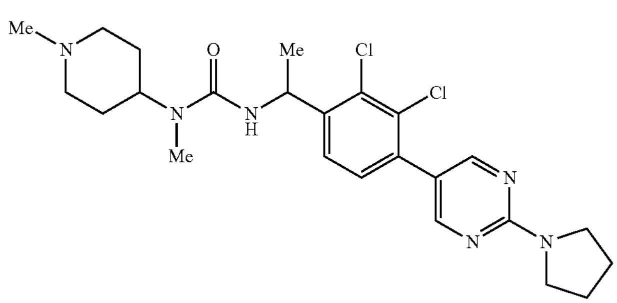 [SMILES: CC(NC(=O)N(C)C1CCN(C)CC1)c1ccc(-c2cnc(N3CCCC3)nc2)c(Cl)c1Cl] | 3-(1-(2,3-dichloro-4-(2-(pyrrolidin-1-yl)pyrimidin-5-yl)phenyl)ethyl)-1-methyl-1-(1-methylpiperidin-4-yl)urea |

-continued

| Compound No. | Chemical Structure | Chemical Name |
|---|---|---|
| H0814 | 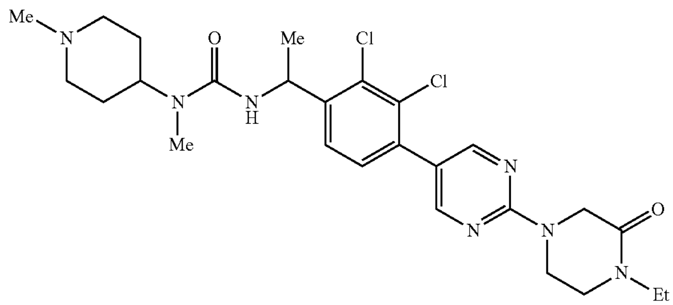 [SMILES: CCN1CCN(c2ncc(-c3ccc(C(C)NC(=O)N(C)C4CCN(C)CC4)c(Cl)c3Cl)cn2)CC1=O] | 3-(1-(2,3-dichloro-4-(2-(4-ethyl-3-oxopiperazin-1-yl)pyrimidin-5-yl)phenyl)ethyl)-1-methyl-1-(1-methylpiperidin-4-yl)urea |
| H0703 | 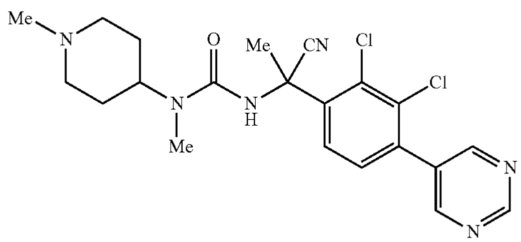 [SMILES: CN1CCC(N(C)C(=O)NC(C)(C#N)c2ccc(-c3cncnc3)c(Cl)c2Cl)CC1] | 3-(1-cyano-1-(2,3-dichloro-4-(pyrimidin-5-yl)phenyl)ethyl)-1-methyl-1-(1-methylpiperidin-4-yl)urea |
| H0709 | 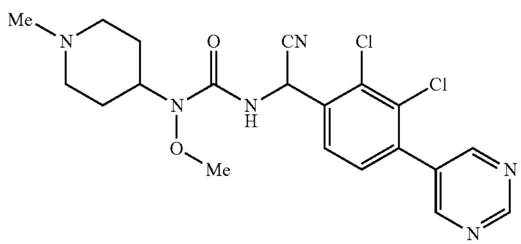 [SMILES: CON(C(=O)NC(C#N)c1ccc(-c2cncnc2)c(Cl)c1Cl)C1CCN(C)CC1] | 3-(cyano(2,3-dichloro-4-(pyrimidin-5-yl)phenyl)methyl)-1-methoxy-1-(1-methylpiperidin-4-yl)urea |
| H0588 | 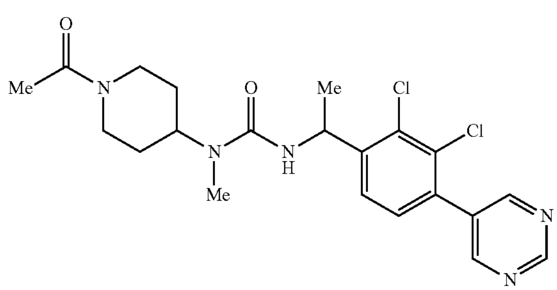 [SMILES: CC(=O)N1CCC(N(C)C(=O)NC(C)c2ccc(-c3cncnc3)c(Cl)c2Cl)CC1] | 1-(1-acetylpiperidin-4-yl)-3-(1-(2,3-dichloro-4-(pyrimidin-5-yl)phenyl)ethyl)-1-methylurea |
| H0663 | 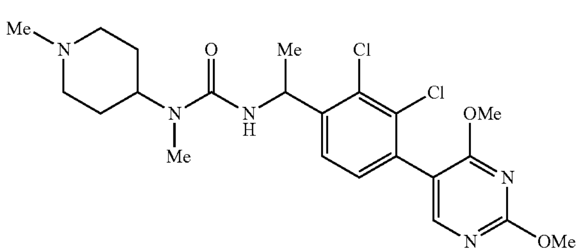 [SMILES: COc1ncc(-c2ccc(C(C)NC(=O)N(C)C3CCN(C)CC3)c(Cl)c2Cl)c(OC)n1] | 3-(1-(2,3-dichloro-4-(2,4-dimethoxypyrimidin-5-yl)phenyl)ethyl)-1-methyl-1-(1-methylpiperidin-4-yl)urea |

-continued

| Compound No. | Chemical Name |
|---|---|
| H0620 | 3-(1-(2,3-dichloro-4-(pyrimidin-5-yl)phenyl)-2-((3-(hydroxymethyl)benzyl)oxy)ethyl)-1-methyl-1-(1-methylpiperidin-4-yl)urea |
| H0624 | 3-(1-(2,3-dichloro-4-(pyrimidin-5-yl)phenyl)ethyl)-1-hydroxy-1-(1-methylpiperidin-4-yl)urea |
| H0662 | methyl 2-(2,3-dichloro-4-(pyrimidin-5-yl)phenyl)-2-(3-methyl-3-(1-methylpiperidin-4-yl)ureido)acetate |
| H0670 | 3-(1-(2,3-dichloro-4-(pyrimidin-5-yl)phenyl)-2-hydroxyethyl)-1-methyl-1-(1-methylpiperidin-4-yl)urea |
| H0673 | 3-(1-(2,3-dichloro-4-(pyrimidin-5-yl)phenyl)cyclopropyl)-1-methyl-1-(1-methylpiperidin-4-yl)urea |

-continued

| Compound No. | Chemical Structure | Chemical Name |
|---|---|---|
| H0727 | 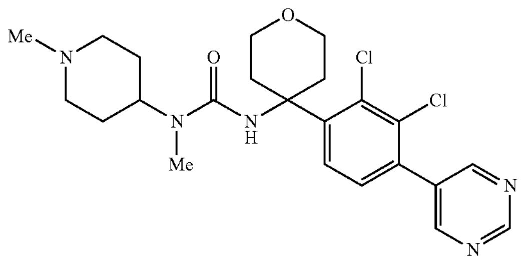 [SMILES: CN1CCC(N(C)C(=O)NC2(c3ccc(-c4cncnc4)c(Cl)c3Cl)CCOCC2)CC1] | 3-(4-(2,3-dichloro-4-(pyrimidin-5-yl)phenyl)tetrahydro-2H-pyran-4-yl)-1-methyl-1-(1-methylpiperidin-4-yl)urea |
| H0631 | 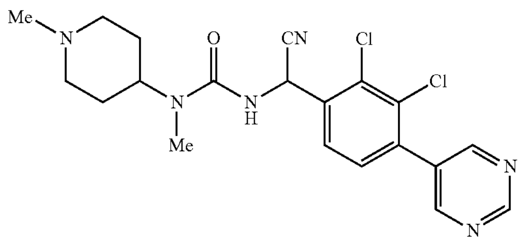 [SMILES: CN1CCC(N(C)C(=O)NC(C#N)c2ccc(-c3cncnc3)c(Cl)c2Cl)CC1] | 3-(cyano(2,3-dichloro-4-(pyrimidin-5-yl)phenyl)methyl)-1-methyl-1-(1-methylpiperidin-4-yl)urea |
| H0686 | 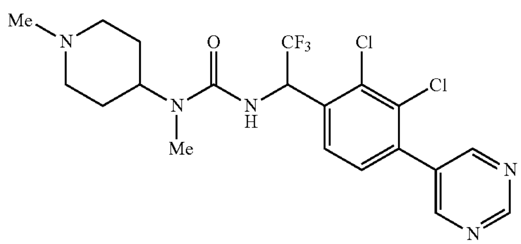 | 3-(1-(2,3-dichloro-4-(pyrimidin-5-yl)phenyl)-2,2,2-trifluoroethyl)-1-methyl-1-(1-methylpiperidin-4-yl)urea |
| H0619 | 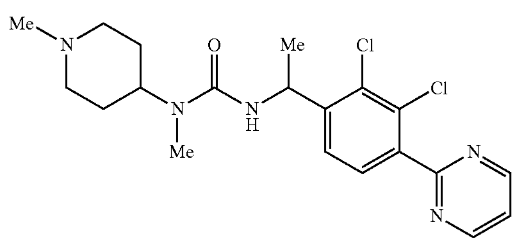 | 3-(1-(2,3-dichloro-4-(pyrimidin-2-yl)phenyl)ethyl)-1-methyl-1-(1-methylpiperidin-4-yl)urea |
| H0768 | 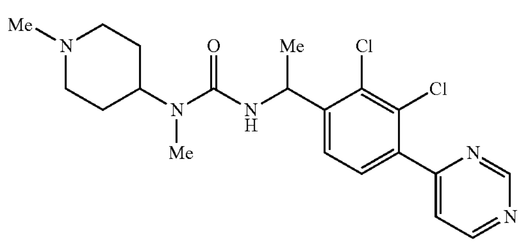 [SMILES: CC(NC(=O)N(C)C1CCN(C)CC1)c1ccc(-c2ccncn2)c(Cl)c1Cl] | 3-(1-(2,3-dichloro-4-(pyrimidin-4-yl)phenyl)ethyl)-1-methyl-1-(1-methylpiperidin-4-yl)urea |
| H0808 | 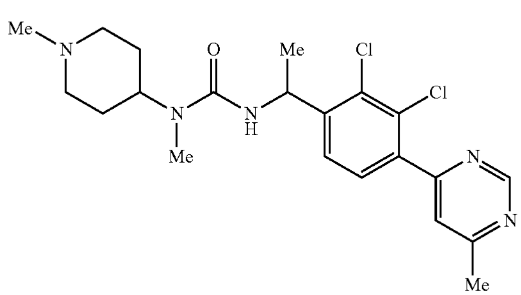 [SMILES: Cc1cc(-c2ccc(C(C)NC(=O)N(C)C3CCN(C)CC3)c(Cl)c2Cl)ncn1] | 3-(1-(2,3-dichloro-4-(6-methylpyrimidin-4-yl)phenyl)ethyl)-1-methyl-1-(1-methylpiperidin-4-yl)urea |

| Compound No. | Chemical Structure | Chemical Name |
|---|---|---|
| H0700 | 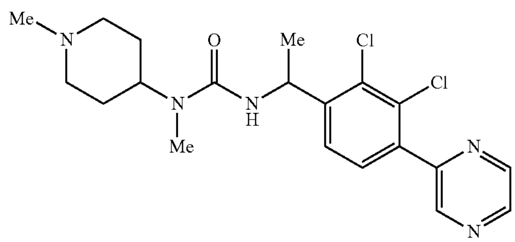 | 3-(1-(2,3-dichloro-4-(pyrazin-2-yl)phenyl)ethyl)-1-methyl-1-(1-methylpiperidin-4-yl)urea |
| H0816 | 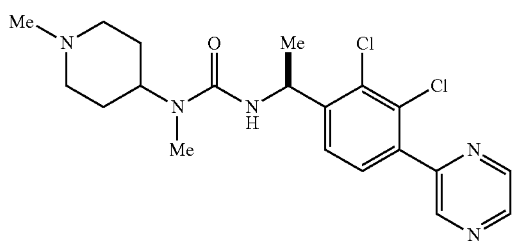 | (S)-3-(1-(2,3-dichloro-4-(pyrazin-2-yl)phenyl)ethyl)-1-methyl-1-(1-methylpiperidin-4-yl)urea |
| H0817 | 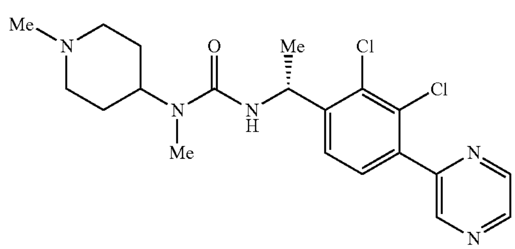 | (R)-3-(1-(2,3-dichloro-4-(pyrazin-2-yl)phenyl)ethyl)-1-methyl-1-(1-methylpiperidin-4-yl)urea |
| H0722 | 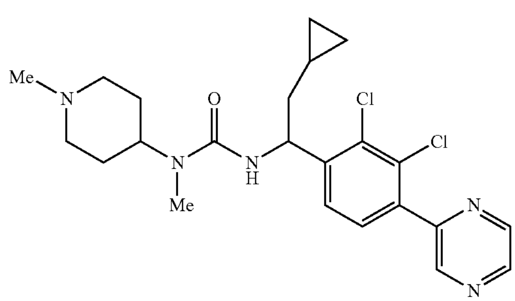 [SMILES: CN1CCC(N(C)C(=O)NC(CC2CC2)c2ccc(-c3cnccn3)c(Cl)c2Cl)CC1] | 3-(2-cyclopropyl-1-(2,3-dichloro-4-(pyrazin-2-yl)phenyl)ethyl)-1-methyl-1-(1-methylpiperidin-4-yl)urea |
| H0741 | 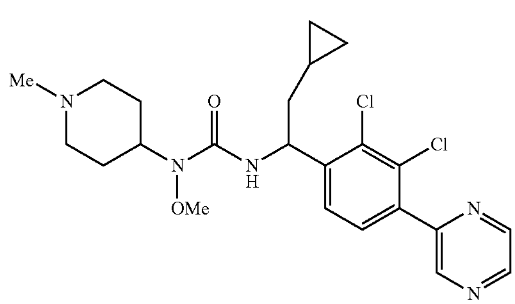 [SMILES: CON(C(=O)NC(CC1CC1)c1ccc(-c2cnccn2)c(Cl)c1Cl)C1CCN(C)CC1] | 3-(2-cyclopropyl-1-(2,3-dichloro-4-(pyrazin-2-yl)phenyl)ethyl)-1-methoxy-1-(1-methylpiperidin-4-yl)urea |

-continued

| Compound No. | Chemical Structure | Chemical Name |
|---|---|---|
| H0752 | 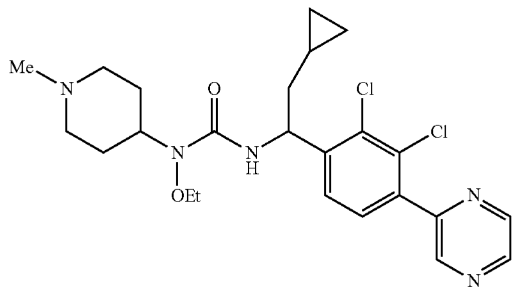 | 3-(2-cyclopropyl-1-(2,3-dichloro-4-(pyrazin-2-yl)phenyl)ethyl)-1-ethoxy-1-(1-methylpiperidin-4-yl)urea |
| H0743 | 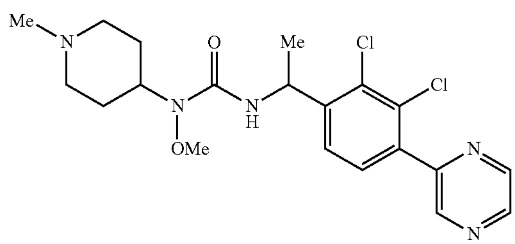 | 3-(1-(2,3-dichloro-4-(pyrazin-2-yl)phenyl)ethyl)-1-methoxy-1-(1-methylpiperidin-4-yl)urea |
| H0750 | 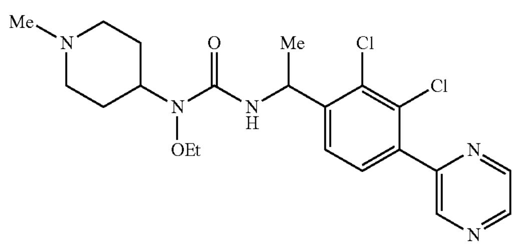 | 3-(1-(2,3-dichloro-4-(pyrazin-2-yl)phenyl)ethyl)-1-ethoxy-1-(1-methylpiperidin-4-yl)urea |
| H0756 | 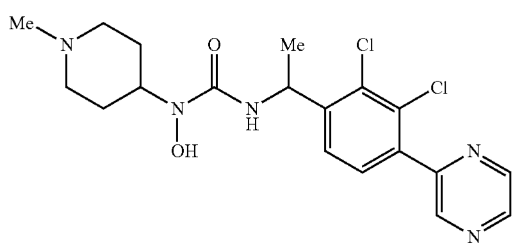 | 3-(1-(2,3-dichloro-4-(pyrazin-2-yl)phenyl)ethyl)-1-hydroxy-1-(1-methylpiperidin-4-yl)urea |
| H0761 | 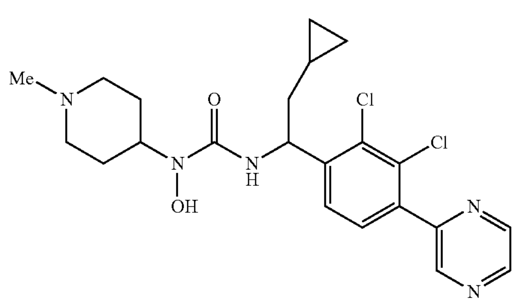 | 3-(2-cyclopropyl-1-(2,3-dichloro-4-(pyrazin-2-yl)phenyl)ethyl)-1-hydroxy-1-(1-methylpiperidin-4-yl)urea |

| Compound No. | Chemical Structure | Chemical Name |
|---|---|---|
| H0781 | 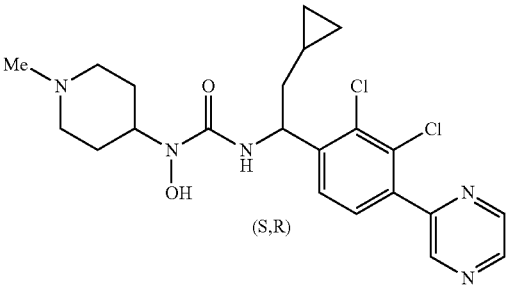 (S,R) | 3-(2-cyclopropyl-1-(2,3-dichloro-4-(pyrazin-2-yl)phenyl)ethyl)-1-hydroxy-1-(1-methylpiperidin-4-yl)urea (single enantiomer) |
| H0782 | 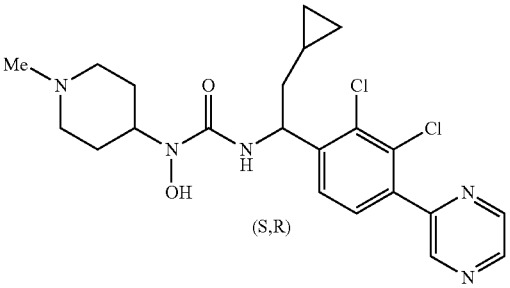 (S,R) | 3-(2-cyclopropyl-1-(2,3-dichloro-4-(pyrazin-2-yl)phenyl)ethyl)-1-hydroxy-1-(1-methylpiperidin-4-yl)urea (single enantiomer) |
| H0824 | 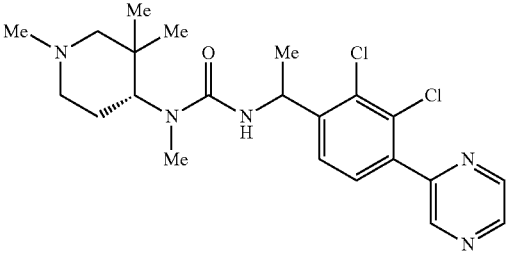 | 3-(1-(2,3-dichloro-4-(pyrazin-2-yl)phenyl)ethyl)-1-methyl-1-((R)-1,3,3-trimethylpiperidin-4-yl)urea |
| H0890 | 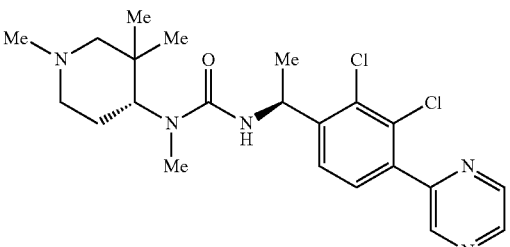 | 3-((S)-1-(2,3-dichloro-4-(pyrazin-2-yl)phenyl)ethyl)-1-methyl-1-((R)-1,3,3-trimethylpiperidin-4-yl)urea |
| H0858 | 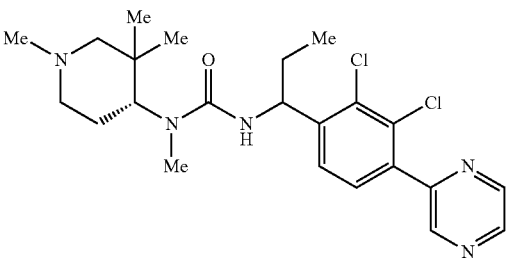 | 3-(1-(2,3-dichloro-4-(pyrazin-2-yl)phenyl)propyl)-1-methyl-1-((R)-1,3,3-trimethylpiperidin-4-yl)urea |

| Compound No. | Chemical Structure | Chemical Name |
|---|---|---|
| H0865 | 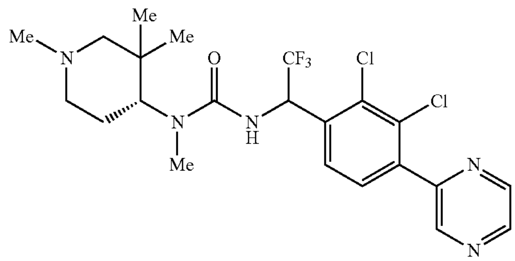 [SMILES: CN1CC[C@@H](N(C)C(=O)NC(c2ccc(-c3cnccn3)c(Cl)c2Cl)C(F)(F)F)C(C)(C)C1] | 3-(1-(2,3-dichloro-4-(pyrazin-2-yl)phenyl)-2,2,2-trifluoroethyl)-1-methyl-1-((R)-1,3,3-trimethylpiperidin-4-yl)urea |
| H0825 | 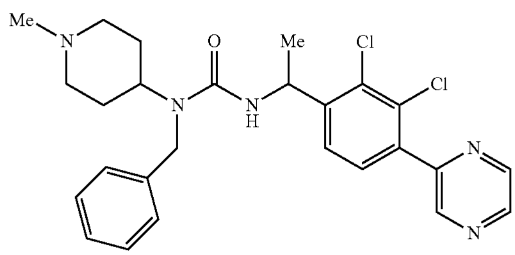 [SMILES: CC(NC(=O)N(Cc1ccccc1)C1CCN(C)CC1)c1ccc(-c2cnccn2)c(Cl)c1Cl] | 1-benzyl-3-(1-(2,3-dichloro-4-(pyrazin-2-yl)phenyl)ethyl)-1-(1-methylpiperidin-4-yl)urea |
| H0826 | 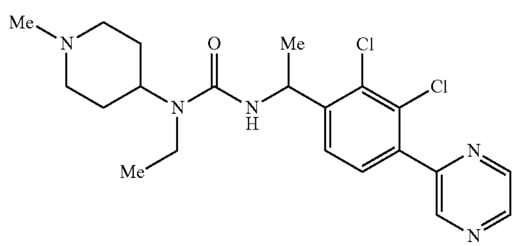 [SMILES: CCN(C(=O)NC(C)c1ccc(-c2cnccn2)c(Cl)c1Cl)C1CCN(C)CC1] | 3-(1-(2,3-dichloro-4-(pyrazin-2-yl)phenyl)ethyl)-1-ethyl-1-(1-methylpiperidin-4-yl)urea |
| H0889 | 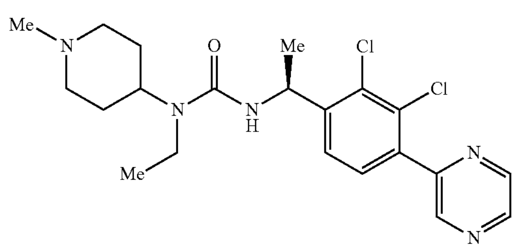 [SMILES: CCN(C(=O)N[C@@H](C)c1ccc(-c2cnccn2)c(Cl)c1Cl)C1CCN(C)CC1] | (S)-3-(1-(2,3-dichloro-4-(pyrazin-2-yl)phenyl)ethyl)-1-ethyl-1-(1-methylpiperidin-4-yl)urea |
| H0896 | 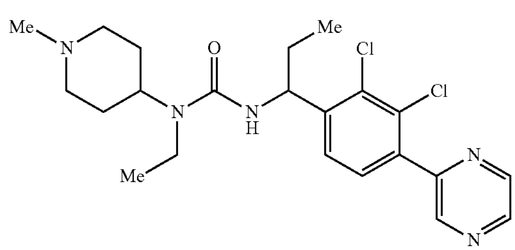 [SMILES: CCC(NC(=O)N(CC)C1CCN(C)CC1)c1ccc(-c2cnccn2)c(Cl)c1Cl] | 3-(1-(2,3-dichloro-4-(pyrazin-2-yl)phenyl)propyl)-1-ethyl-1-(1-methylpiperidin-4-yl)urea |
| H0827 | 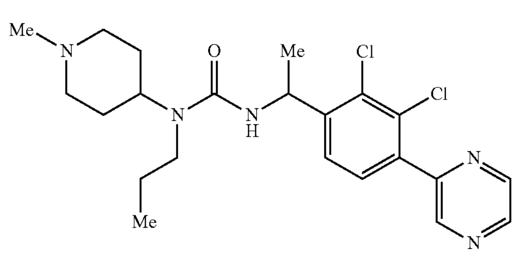 [SMILES: CCCN(C(=O)NC(C)c1ccc(-c2cnccn2)c(Cl)c1Cl)C1CCN(C)CC1] | 3-(1-(2,3-dichloro-4-(pyrazin-2-yl)phenyl)ethyl)-1-(1-methylpiperidin-4-yl)-1-propylurea |

-continued

| Compound No. | Chemical Name |
|---|---|
| H0829 | 3-(1-(2,3-dichloro-4-(pyrazin-2-yl)phenyl)propyl)-1-methyl-1-(1-methylpiperidin-4-yl)urea |
| H0859 | (R)-3-(1-(2,3-dichloro-4-(pyrazin-2-yl)phenyl)propyl)-1-methyl-1-(1-methylpiperidin-4-yl)urea (single enantiomer) |
| H0860 | (S)-3-(1-(2,3-dichloro-4-(pyrazin-2-yl)phenyl)propyl)-1-methyl-1-(1-methylpiperidin-4-yl)urea (single enantiomer) |
| H0922 | methyl 2-(2,3-dichloro-4-(pyrazin-2-yl)phenyl)-2-(3-methyl-3-(1-methylpiperidin-4-yl)ureido)acetate |
| H0924 | 3-(1-(2,3-dichloro-4-(pyrazin-2-yl)phenyl)-2-hydroxyethyl)-1-methyl-1-(1-methylpiperidin-4-yl)urea |
| H0830 | 3-(1-(2,3-dichloro-4-(pyrazin-2-yl)phenyl)-2,2,2-trifluoroethyl)-1-methyl-1-(1-methylpiperidin-4-yl)urea |

-continued

| Compound No. | Chemical Structure | Chemical Name |
|---|---|---|
| H0899 | 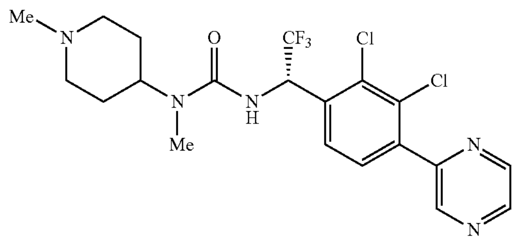 | (S)-3-(1-(2,3-dichloro-4-(pyrazin-2-yl)phenyl)-2,2,2-trifluoroethyl)-1-methyl-1-(1-methylpiperidin-4-yl)urea |
| H0900 | 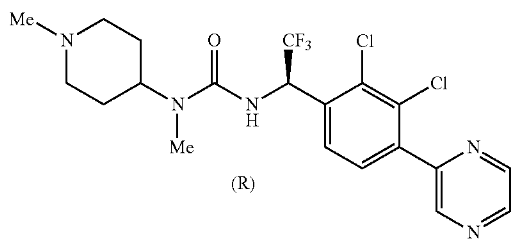 | (R)-3-(1-(2,3-dichloro-4-(pyrazin-2-yl)phenyl)-2,2,2-trifluoroethyl)-1-methyl-1-(1-methylpiperidin-4-yl)urea |
| H0909 | 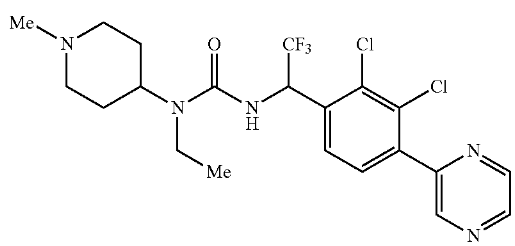 [SMILES: CCN(C(=O)NC(c1ccc(-c2cnccn2)c(Cl)c1Cl)C(F)(F)F)C1CCN(C)CC1] | 3-(1-(2,3-dichloro-4-(pyrazin-2-yl)phenyl)-2,2,2-trifluoroethyl)-1-ethyl-1-(1-methylpiperidin-4-yl)urea |
| H0856 | 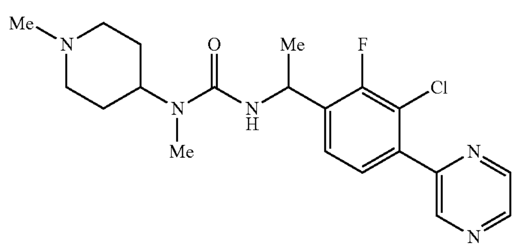 | 3-(1-(3-chloro-2-fluoro-4-(pyrazin-2-yl)phenyl)ethyl)-1-methyl-1-(1-methylpiperidin-4-yl)urea |
| H0815 | 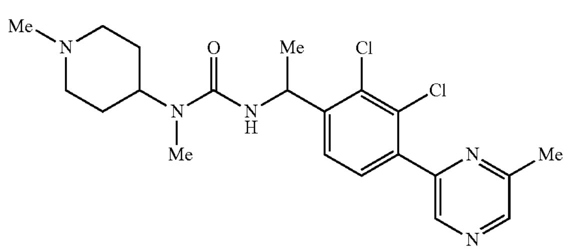 | 3-(1-(2,3-dichloro-4-(6-methylpyrazin-2-yl)phenyl)ethyl)-1-methyl-1-(1-methylpiperidin-4-yl)urea |
| H0831 | 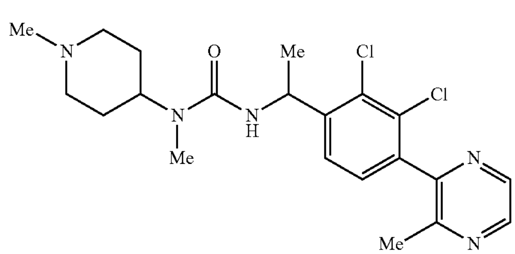 [SMILES: Cc1nccnc1-c1ccc(C(C)NC(=O)N(C)C2CCN(C)CC2)c(Cl)c1Cl] | 3-(1-(2,3-dichloro-4-(3-methylpyrazin-2-yl)phenyl)ethyl)-1-methyl-1-(1-methylpiperidin-4-yl)urea |

-continued

| Compound No. | Chemical Structure | Chemical Name |
|---|---|---|
| H0843 | 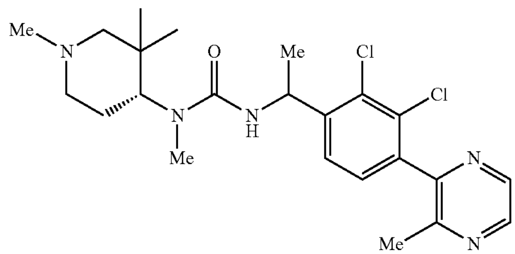 [SMILES: Cc1nccnc1-c1ccc(C(C)NC(=O)N(C)[C@@H]2CCN(C)CC2(C)C)c(Cl)c1Cl] | 3-(1-(2,3-dichloro-4-(3-methylpyrazin-2-yl)phenyl)ethyl)-1-methyl-1-((R)-1,3,3-trimethylpiperidin-4-yl)urea |
| H0844 | 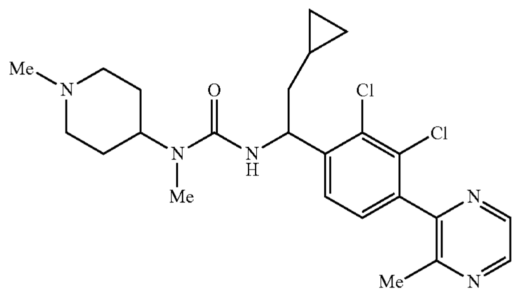 [SMILES: Cc1nccnc1-c1ccc(C(CC2CC2)NC(=O)N(C)C2CCN(C)CC2)c(Cl)c1Cl] | 3-(2-cyclopropyl-1-(2,3-dichloro-4-(3-methylpyrazin-2-yl)phenyl)ethyl)-1-methyl-1-(1-methylpiperidin-4-yl)urea |
| H0738 | 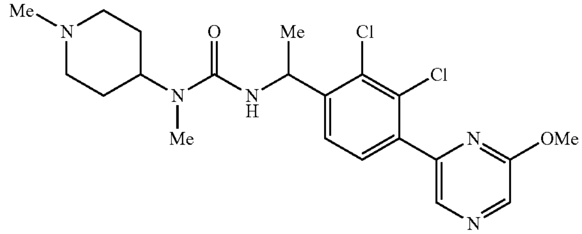 [SMILES: COc1cncc(-c2ccc(C(C)NC(=O)N(C)C3CCN(C)CC3)c(Cl)c2Cl)n1] | 3-(1-(2,3-dichloro-4-(6-methoxypyrazin-2-yl)phenyl)ethyl)-1-methyl-1-(1-methylpiperidin-4-yl)urea |
| H0780 | 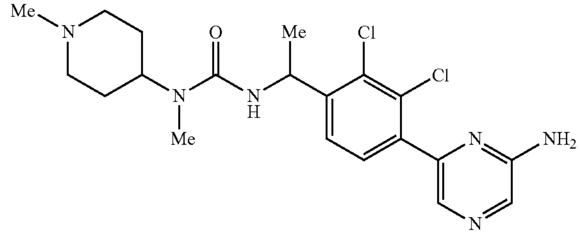 [SMILES: CC(NC(=O)N(C)C1CCN(C)CC1)c1ccc(-c2cncc(N)n2)c(Cl)c1Cl] | 3-(1-(4-(6-aminopyrazin-2-yl)-2,3-dichlorophenyl)ethyl)-1-methyl-1-(1-methylpiperidin-4-yl)urea |
| H0786 | 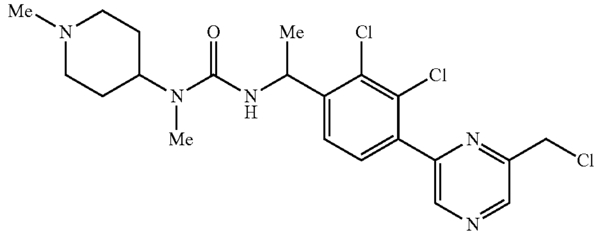 [SMILES: CC(NC(=O)N(C)C1CCN(C)CC1)c1ccc(-c2cncc(CCl)n2)c(Cl)c1Cl] | 3-(1-(2,3-dichloro-4-(6-(chloromethyl)pyrazin-2-yl)phenyl)ethyl)-1-methyl-1-(1-methylpiperidin-4-yl)urea |
| H0791 | 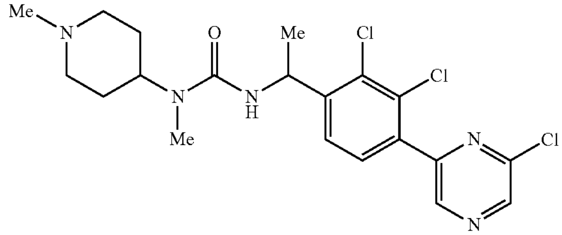 | 3-(1-(2,3-dichloro-4-(6-chloropyrazin-2-yl)phenyl)ethyl)-1-methyl-1-(1-methylpiperidin-4-yl)urea |

-continued

| Compound No. | Chemical Structure | Chemical Name |
|---|---|---|
| H0795 | 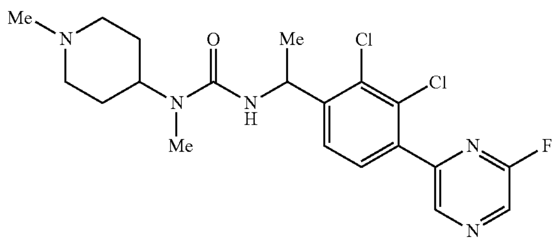 [SMILES: CC(NC(=O)N(C)C1CCN(C)CC1)c1ccc(-c2cncc(F)n2)c(Cl)c1Cl] | 3-(1-(2,3-dichloro-4-(6-fluoropyrazin-2-yl)phenyl)ethyl)-1-methyl-1-(1-methylpiperidin-4-yl)urea |
| H0847 | 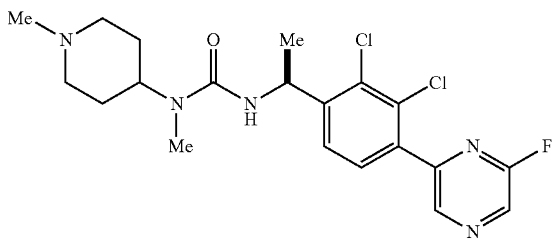 [SMILES: C[C@H](NC(=O)N(C)C1CCN(C)CC1)c1ccc(-c2cncc(F)n2)c(Cl)c1Cl] | (S)-3-(1-(2,3-dichloro-4-(6-fluoropyrazin-2-yl)phenyl)ethyl)-1-methyl-1-(1-methylpiperidin-4-yl)urea |
| H0848 | 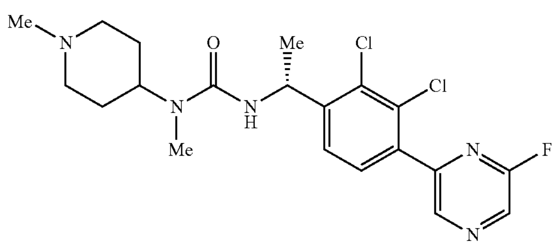 | (R)-3-(1-(2,3-dichloro-4-(6-fluoropyrazin-2-yl)phenyl)ethyl)-1-methyl-1-(1-methylpiperidin-4-yl)urea |
| H0863 | 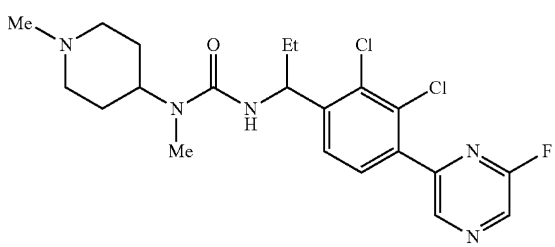 | 3-(1-(2,3-dichloro-4-(6-fluoropyrazin-2-yl)phenyl)propyl)-1-methyl-1-(1-methylpiperidin-4-yl)urea |
| H0908 | 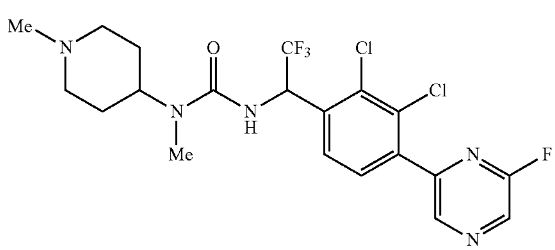 | 3-(1-(2,3-dichloro-4-(6-fluoropyrazin-2-yl)phenyl)-2,2,2-trifluoroethyl)-1-methyl-1-(1-methylpiperidin-4-yl)urea |
| H0840 | 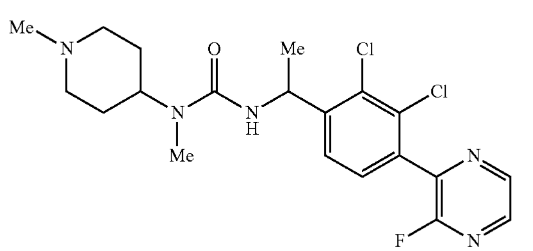 [SMILES: CC(NC(=O)N(C)C1CCN(C)CC1)c1ccc(-c2nccnc2F)c(Cl)c1Cl] | 3-(1-(2,3-dichloro-4-(3-fluoropyrazin-2-yl)phenyl)ethyl)-1-methyl-1-(1-methylpiperidin-4-yl)urea |

-continued

| Compound No. | Chemical Structure | Chemical Name |
|---|---|---|
| H0910 | 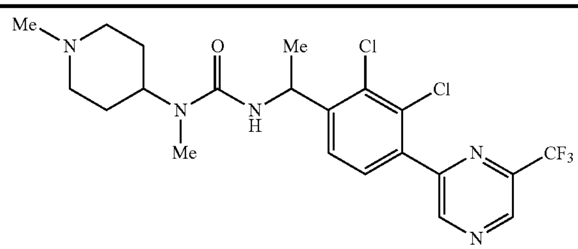 | 3-(1-(2,3-dichloro-4-(6-(trifluoromethyl)pyrazin-2-yl)phenyl)ethyl)-1-methyl-1-(1-methylpiperidin-4-yl)urea |
| H0788 | 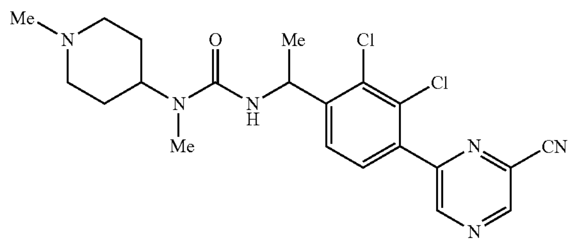 [SMILES: CC(NC(=O)N(C)C1CCN(C)CC1)c1ccc(-c2cncc(C#N)n2)c(Cl)c1Cl] | 3-(1-(2,3-dichloro-4-(6-cyanopyrazin-2-yl)phenyl)ethyl)-1-methyl-1-(1-methylpiperidin-4-yl)urea |
| H0789 | 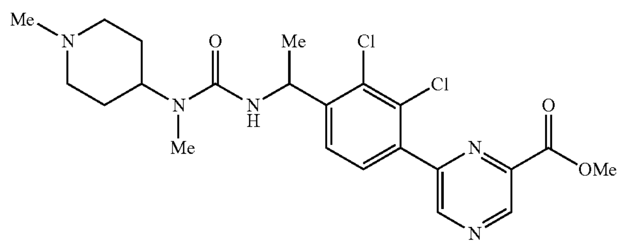 [SMILES: COC(=O)c1cncc(-c2ccc(C(C)NC(=O)N(C)C3CCN(C)CC3)c(Cl)c2Cl)n1] | methyl 6-(2,3-dichloro-4-(1-(3-methyl-3-(1-methylpiperidin-4-yl)ureido)ethyl)phenyl)pyrazine-2-carboxylate |
| H0760 | 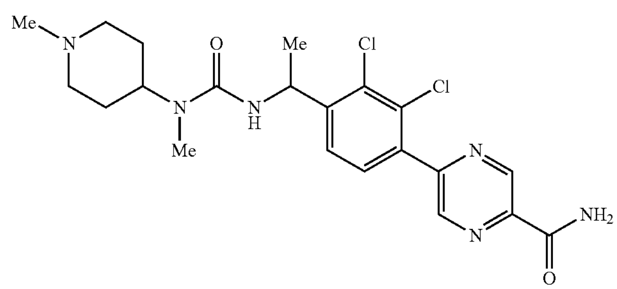 [SMILES: CC(NC(=O)N(C)C1CCN(C)CC1)c1ccc(-c2cnc(C(N)=O)cn2)c(Cl)c1Cl] | 5-(2,3-dichloro-4-(1-(3-methyl-3-(1-methylpiperidin-4-yl)ureido)ethyl)phenyl)pyrazine-2-carboxamide |
| H0769 | 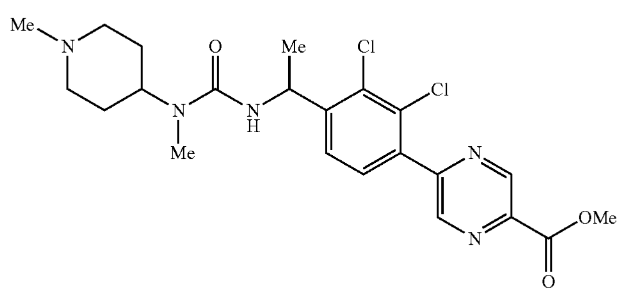 [SMILES: COC(=O)c1cnc(-c2ccc(C(C)NC(=O)N(C)C3CCN(C)CC3)c(Cl)c2Cl)cn1] | methyl 5-(2,3-dichloro-4-(1-(3-methyl-3-(1-methylpiperidin-4-yl)ureido)ethyl)phenyl)pyrazine-2-carboxylate |
| H0771 | 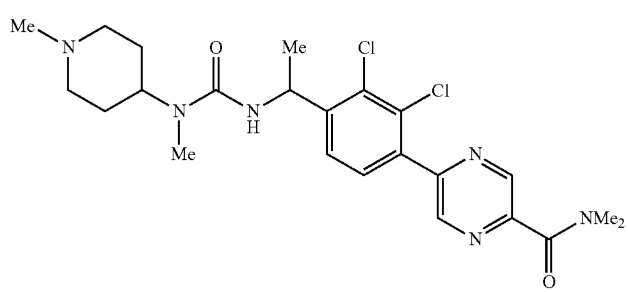 [SMILES: CC(NC(=O)N(C)C1CCN(C)CC1)c1ccc(-c2cnc(C(=O)N(C)C)cn2)c(Cl)c1Cl] | 5-(2,3-dichloro-4-(1-(3-methyl-3-(1-methylpiperidin-4-yl)ureido)ethyl)phenyl)-N,N-dimethylpyrazine-2-carboxamide |

-continued

| Compound No. | Chemical Structure | Chemical Name |
|---|---|---|
| H0770 | 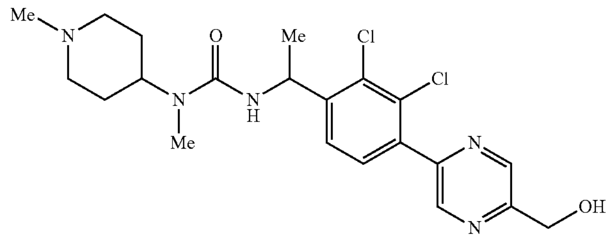 [SMILES: CC(NC(=O)N(C)C1CCN(C)CC1)c1ccc(-c2cnc(CO)cn2)c(Cl)c1Cl] | 3-(1-(2,3-dichloro-4-(5-(hydroxymethyl)pyrazin-2-yl)phenyl)ethyl)-1-methyl-1-(1-methylpiperidin-4-yl)urea |
| H0828 | 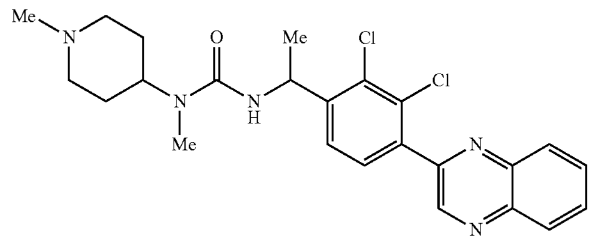 [SMILES: CC(NC(=O)N(C)C1CCN(C)CC1)c1ccc(-c2cnc3ccccc3n2)c(Cl)c1Cl] | 3-(1-(2,3-dichloro-4-(quinoxalin-2-yl)phenyl)ethyl)-1-methyl-1-(1-methylpiperidin-4-yl)urea |
| H0822 | TFA | 3-(1-(2,3-dichloro-4-(5-(4-methylpiperazin-1-yl)pyrazin-2-yl)phenyl)ethyl)-1-methyl-1-(1-methylpiperidin-4-yl)urea |
| H0881 | 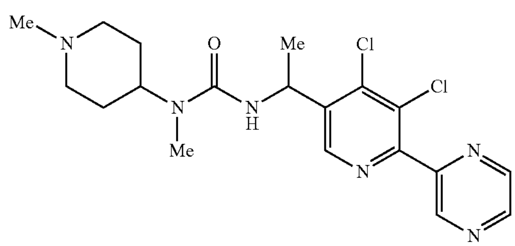 | 3-(1-(4,5-dichloro-6-(pyrazin-2-yl)pyridin-3-yl)ethyl)-1-methyl-1-(1-methylpiperidin-4-yl)urea |
| H0729 | 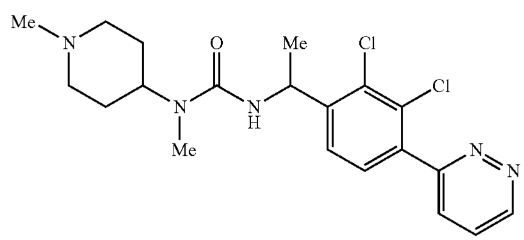 [SMILES: CC(NC(=O)N(C)C1CCN(C)CC1)c1ccc(-c2cccnn2)c(Cl)c1Cl] | 3-(1-(2,3-dichloro-4-(pyridazin-3-yl)phenyl)ethyl)-1-methyl-1-(1-methylpiperidin-4-yl)urea |
| H0783 | 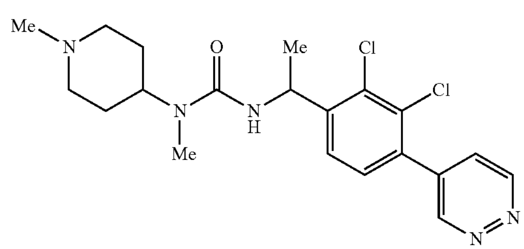 [SMILES: CC(NC(=O)N(C)C1CCN(C)CC1)c1ccc(-c2ccnnc2)c(Cl)c1Cl] | 3-(1-(2,3-dichloro-4-(pyridazin-4-yl)phenyl)ethyl)-1-methyl-1-(1-methylpiperidin-4-yl)urea |

-continued

| Compound No. | Chemical Structure | Chemical Name |
| --- | --- | --- |
| H0793 | 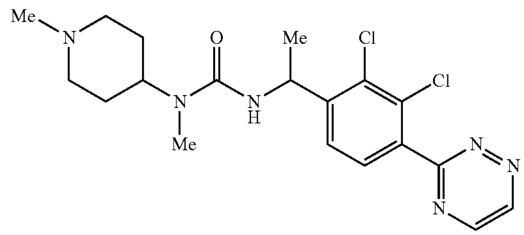 [SMILES: CC(NC(=O)N(C)C1CCN(C)CC1)c1ccc(-c2nccnn2)c(Cl)c1Cl] | 3-(1-(2,3-dichloro-4-(1,2,4-triazin-3-yl)phenyl)ethyl)-1-methyl-1-(1-methylpiperidin-4-yl)urea |
| H0796 | 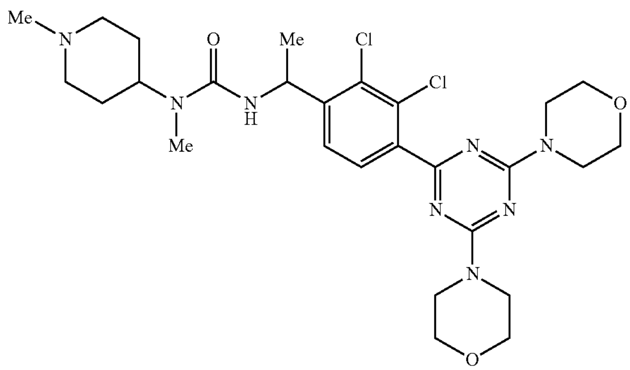 [SMILES: CC(NC(=O)N(C)C1CCN(C)CC1)c1ccc(-c2nc(N3CCOCC3)nc(N3CCOCC3)n2)c(Cl)c1Cl] | 3-(1-(2,3-dichloro-4-(4,6-dimorpholino-1,3,5-triazin-2-yl)phenyl)ethyl)-1-methyl-1-(1-methylpiperidin-4-yl)urea |
| H0498 | 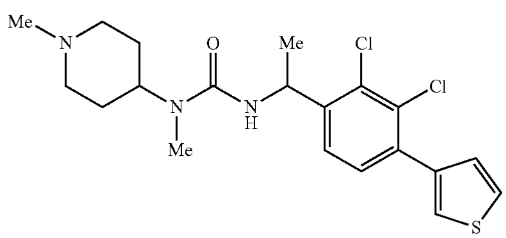 | 3-(1-(2,3-dichloro-4-(thiophen-3-yl)phenyl)ethyl)-1-methyl-1-(1-methylpiperidin-4-yl)urea |
| H0594 | 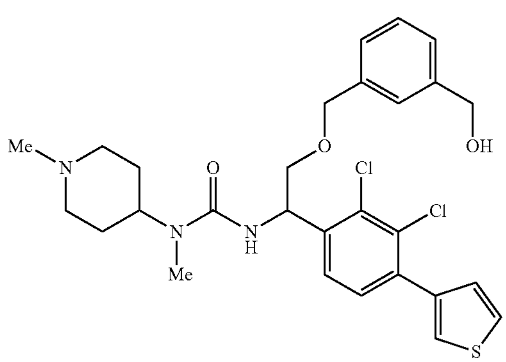 [SMILES: CN1CCC(N(C)C(=O)NC(COCc2cccc(CO)c2)c2ccc(-c3ccsc3)c(Cl)c2Cl)CC1] | 3-(1-(2,3-dichloro-4-(thiophen-3-yl)phenyl)-2-((3-(hydroxymethyl)benzyl)oxy)ethyl)-1-methyl-1-(1-methylpiperidin-4-yl)urea |
| H0644 | 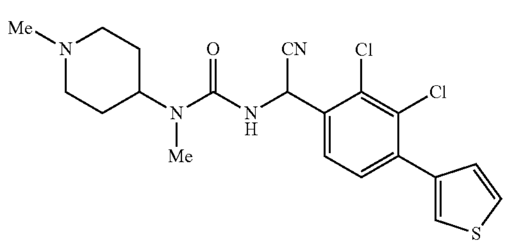 [SMILES: CN1CCC(N(C)C(=O)NC(C#N)c2ccc(-c3ccsc3)c(Cl)c2Cl)CC1] | 3-(cyano(2,3-dichloro-4-(thiophen-3-yl)phenyl)methyl)-1-methyl-1-(1-methylpiperidin-4-yl)urea |

-continued

| Compound No. | Chemical Structure | Chemical Name |
|---|---|---|
| H0536 | 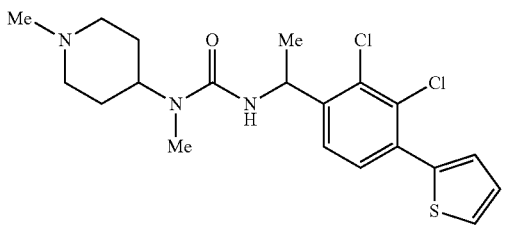 | 3-(1-(2,3-dichloro-4-(thiophen-2-yl)phenyl)ethyl)-1-methyl-1-(1-methylpiperidin-4-yl)urea |
| H0563 | 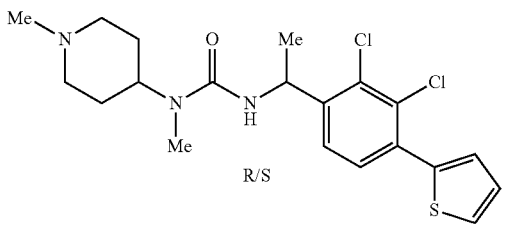 [SMILES: CC(NC(=O)N(C)C1CCN(C)CC1)c1ccc(-c2cccs2)c(Cl)c1Cl] | 3-(1-(2,3-dichloro-4-(thiophen-2-yl)phenyl)ethyl)-1-methyl-1-(1-methylpiperidin-4-yl)urea (single enantiomer) |
| H0564 | 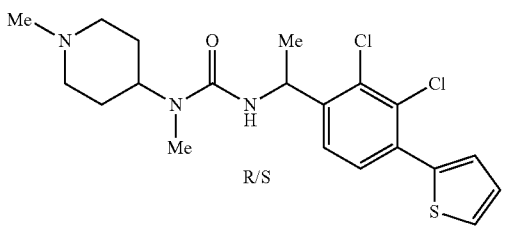 [SMILES: CC(NC(=O)N(C)C1CCN(C)CC1)c1ccc(-c2cccs2)c(Cl)c1Cl] | 3-(1-(2,3-dichloro-4-(thiophen-2-yl)phenyl)ethyl)-1-methyl-1-(1-methylpiperidin-4-yl)urea (single enantiomer) |
| H0627 | 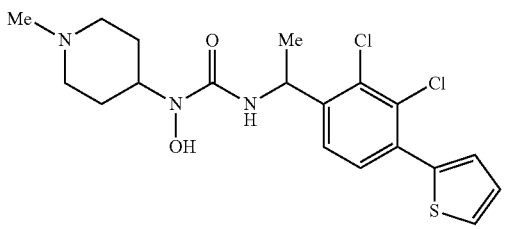 [SMILES: CC(NC(=O)N(O)C1CCN(C)CC1)c1ccc(-c2cccs2)c(Cl)c1Cl] | 3-(1-(2,3-dichloro-4-(thiophen-2-yl)phenyl)ethyl)-1-hydroxy-1-(1-methylpiperidin-4-yl)urea |
| H0660 | 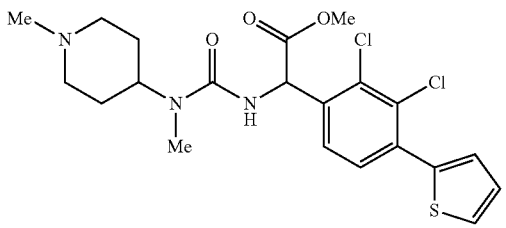 [SMILES: COC(=O)C(NC(=O)N(C)C1CCN(C)CC1)c1ccc(-c2cccs2)c(Cl)c1Cl] | methyl 2-(2,3-dichloro-4-(thiophen-2-yl)phenyl)-2-(3-methyl-3-(1-methylpiperidin-4-yl)ureido)acetate |
| H0661 | 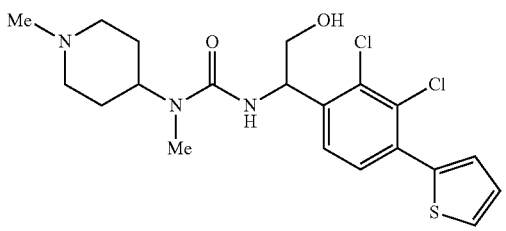 [SMILES: CN1CCC(N(C)C(=O)NC(CO)c2ccc(-c3cccs3)c(Cl)c2Cl)CC1] | 3-(1-(2,3-dichloro-4-(thiophen-2-yl)phenyl)-2-hydroxyethyl)-1-methyl-1-(1-methylpiperidin-4-yl)urea |

-continued

| Compound No. | Chemical Structure | Chemical Name |
|---|---|---|
| H0672 | 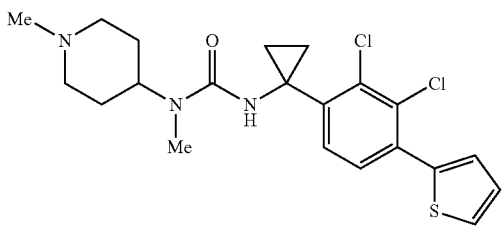 [SMILES: CN1CCC(N(C)C(=O)NC2(c3ccc(-c4cccs4)c(Cl)c3Cl)CC2)CC1] | 3-(1-(2,3-dichloro-4-(thiophen-2-yl)phenyl)cyclopropyl)-1-methyl-1-(1-methylpiperidin-4-yl)urea |
| H0651 | 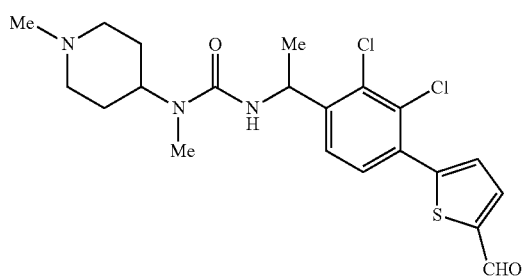 [SMILES: CC(NC(=O)N(C)C1CCN(C)CC1)c1ccc(-c2ccc(C=O)s2)c(Cl)c1Cl] | 3-(1-(2,3-dichloro-4-(5-formylthiophen-2-yl)phenyl)ethyl)-1-methyl-1-(1-methylpiperidin-4-yl)urea |
| H0653 | 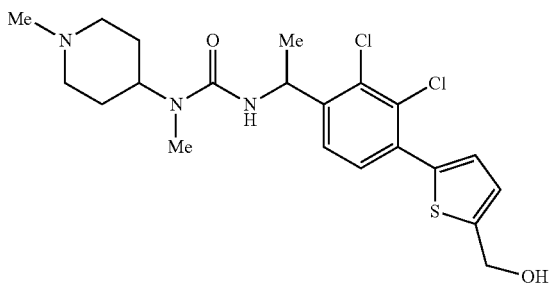 [SMILES: CC(NC(=O)N(C)C1CCN(C)CC1)c1ccc(-c2ccc(CO)s2)c(Cl)c1Cl] | 3-(1-(2,3-dichloro-4-(5-(hydroxymethyl)thiophen-2-yl)phenyl)ethyl)-1-methyl-1-(1-methylpiperidin-4-yl)urea |
| H0668 | 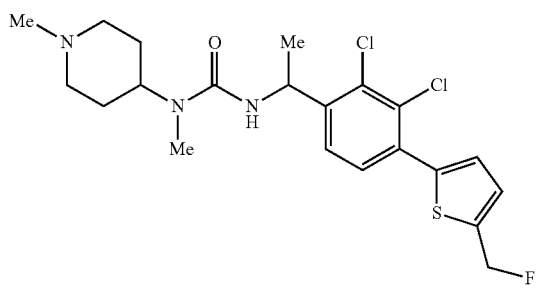 [SMILES: CC(NC(=O)N(C)C1CCN(C)CC1)c1ccc(-c2ccc(CF)s2)c(Cl)c1Cl] | 3-(1-(2,3-dichloro-4-(5-(fluoromethyl)thiophen-2-yl)phenyl)ethyl)-1-methyl-1-(1-methylpiperidin-4-yl)urea |
| H0654 | 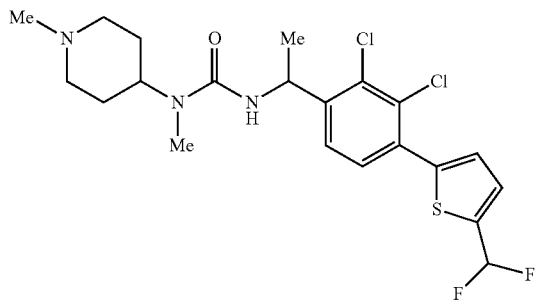 [SMILES: CC(NC(=O)N(C)C1CCN(C)CC1)c1ccc(-c2ccc(C(F)F)s2)c(Cl)c1Cl] | 3-(1-(2,3-dichloro-4-(5-(difluoromethyl)thiophen-2-yl)phenyl)ethyl)-1-methyl-1-(1-methylpiperidin-4-yl)urea |

-continued

| Compound No. | Chemical Structure | Chemical Name |
|---|---|---|
| H0655 | 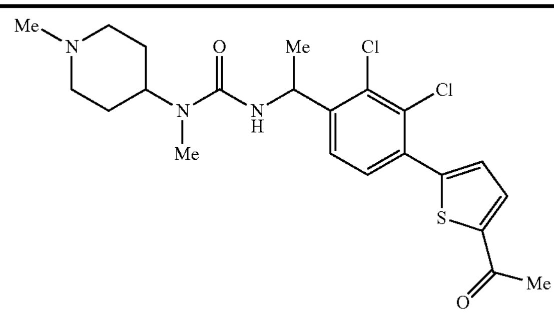 | 3-(1-(4-(5-acetylthiophen-2-yl)-2,3-dichlorophenyl)ethyl)-1-methyl-1-(1-methylpiperidin-4-yl)urea |
| H0691 | 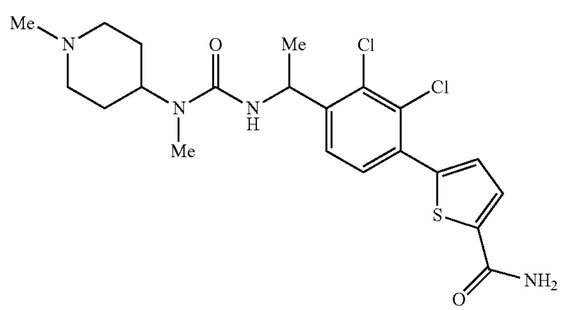 [SMILES: CC(NC(=O)N(C)C1CCN(C)CC1)c1ccc(-c2ccc(C(N)=O)s2)c(Cl)c1Cl] | 5-(2,3-dichloro-4-(1-(3-methyl-3-(1-methylpiperidin-4-yl)ureido)ethyl)phenyl)thiophene-2-carboxamide |
| H0728 | 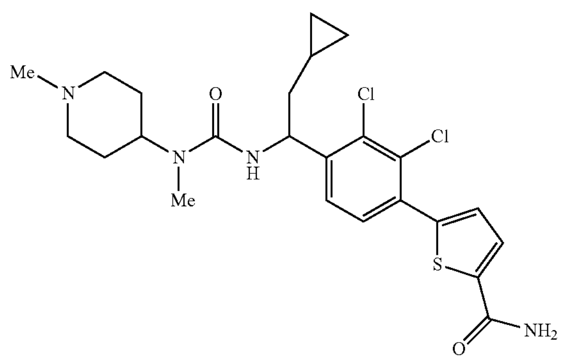 [SMILES: CN1CCC(N(C)C(=O)NC(CC2CC2)c2ccc(-c3ccc(C(N)=O)s3)c(Cl)c2Cl)CC1] | 5-(2,3-dichloro-4-(2-cyclopropyl-1-(3-methyl-3-(1-methylpiperidin-4-yl)ureido)ethyl)phenyl)thiophene-2-carboxamide |
| H0726 | 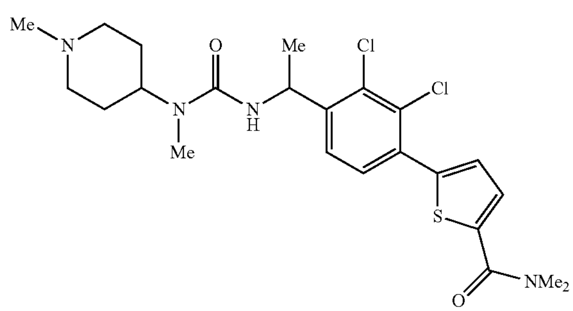 [SMILES: CC(NC(=O)N(C)C1CCN(C)CC1)c1ccc(-c2ccc(C(=O)N(C)C)s2)c(Cl)c1Cl] | 5-(2,3-dichloro-4-(1-(3-methyl-3-(1-methylpiperidin-4-yl)ureido)ethyl)phenyl)-N,N-dimethylthiophene-2-carboxamide |
| H0689 | 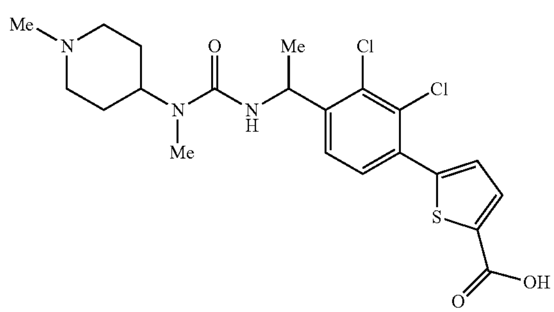 [SMILES: CC(NC(=O)N(C)C1CCN(C)CC1)c1ccc(-c2ccc(C(=O)O)s2)c(Cl)c1Cl] | 5-(2,3-dichloro-4-(1-(3-methyl-3-(1-methylpiperidin-4-yl)ureido)ethyl)phenyl)thiophene-2-carboxylic acid |

-continued

| Compound No. | Chemical Structure | Chemical Name |
| --- | --- | --- |
| H0692 | 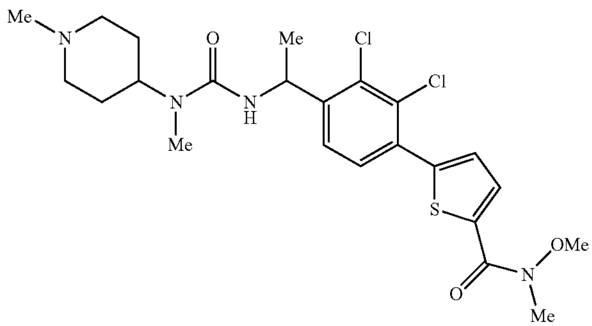 [SMILES: CON(C)C(=O)c1ccc(-c2ccc(C(C)NC(=O)N(C)C3CCN(C)CC3)c(Cl)c2Cl)s1] | 5-(2,3-dichloro-4-(1-(3-methyl-3-(1-methylpiperidin-4-yl)ureido)ethyl)phenyl)-N-methoxy-N-methylthiophene-2-carboxamide |
| H0656 | 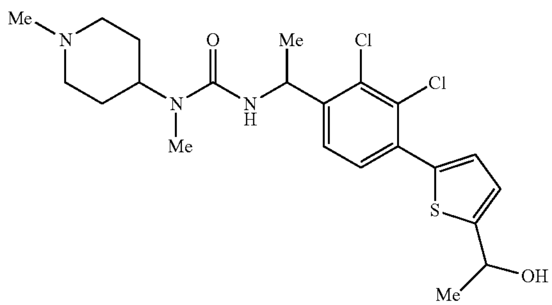 [SMILES: CC(O)c1ccc(-c2ccc(C(C)NC(=O)N(C)C3CCN(C)CC3)c(Cl)c2Cl)s1] | 3-(1-(2,3-dichloro-4-(5-(1-hydroxyethyl)thiophen-2-yl)phenyl)ethyl)-1-methyl-1-(1-methylpiperidin-4-yl)urea |
| H0652 | 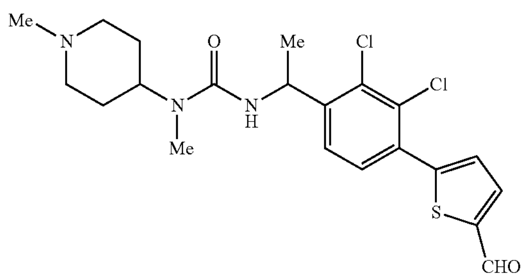 [SMILES: CC(NC(=O)N(C)C1CCN(C)CC1)c1ccc(-c2ccc(C=O)s2)c(Cl)c1Cl] | 3-(1-(2,3-dichloro-4-(5-formylthiophen-2-yl)phenyl)ethyl)-1-methyl-1-(1-methylpiperidin-4-yl)urea |
| H0713 | 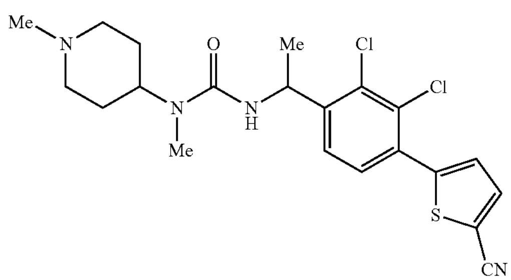 [SMILES: CC(NC(=O)N(C)C1CCN(C)CC1)c1ccc(-c2ccc(C#N)s2)c(Cl)c1Cl] | 3-(1-(2,3-dichloro-4-(5-cyanothiophen-2-yl)phenyl)ethyl)-1-methyl-1-(1-methylpiperidin-4-yl)urea |
| H0688 | 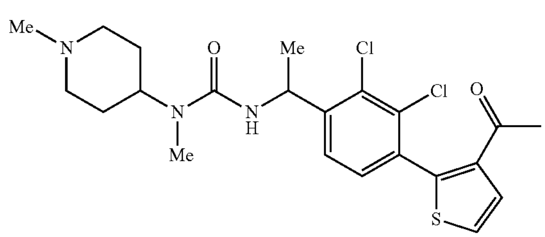 [SMILES: CC(=O)c1ccsc1-c1ccc(C(C)NC(=O)N(C)C2CCN(C)CC2)c(Cl)c1Cl] | 3-(1-(4-(3-acetylthiophen-2-yl)-2,3-dichlorophenyl)ethyl)-1-methyl-1-(1-methylpiperidin-4-yl)urea |

-continued

| Compound No. | Chemical Structure | Chemical Name |
| --- | --- | --- |
| H0774 | 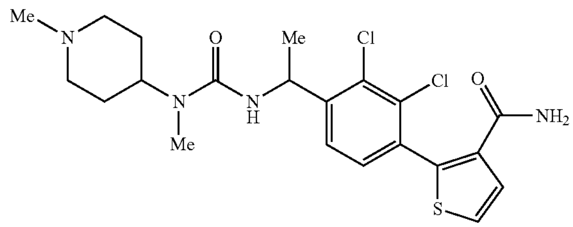 [SMILES: CC(NC(=O)N(C)C1CCN(C)CC1)c1ccc(-c2sccc2C(N)=O)c(Cl)c1Cl] | 2-(2,3-dichloro-4-(1-(3-methyl-3-(1-methylpiperidin-4-yl)ureido)ethyl)phenyl)thiophene-3-carboxamide |
| H0664 | 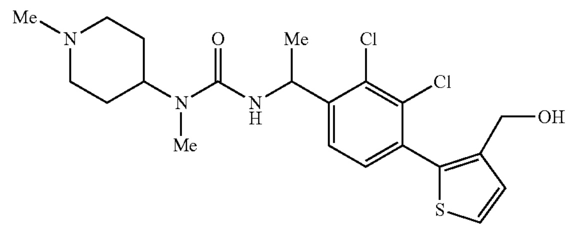 [SMILES: CC(NC(=O)N(C)C1CCN(C)CC1)c1ccc(-c2sccc2CO)c(Cl)c1Cl] | 3-(1-(2,3-dichloro-4-(3-(hydroxymethyl)thiophen-2-yl)phenyl)ethyl)-1-methyl-1-(1-methylpiperidin-4-yl)urea |
| H0535 | 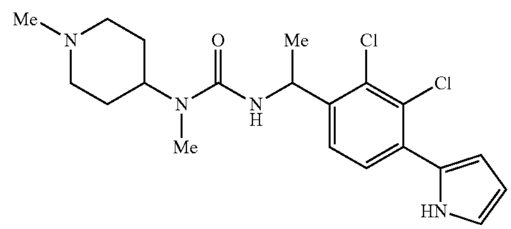 [SMILES: CC(NC(=O)N(C)C1CCN(C)CC1)c1ccc(-c2ccc[nH]2)c(Cl)c1Cl] | 3-(1-(2,3-dichloro-4-(1H-pyrrol-2-yl)phenyl)ethyl)-1-methyl-1-(1-methylpiperidin-4-yl)urea |
| H0499 | 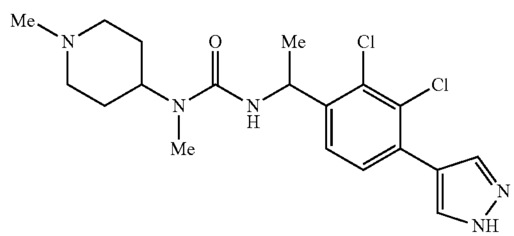 [SMILES: CC(NC(=O)N(C)C1CCN(C)CC1)c1ccc(-c2cn[nH]c2)c(Cl)c1Cl] | 3-(1-(2,3-dichloro-4-(1H-pyrazol-4-yl)phenyl)ethyl)-1-methyl-1-(1-methylpiperidin-4-yl)urea |
| H0693 | 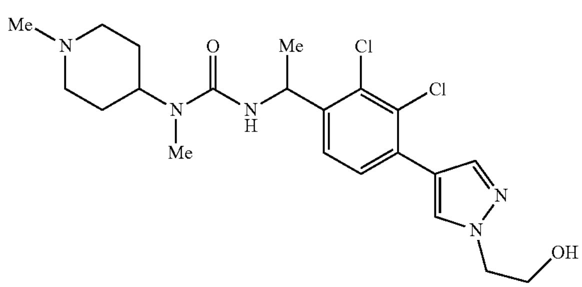 [SMILES: CC(NC(=O)N(C)C1CCN(C)CC1)c1ccc(-c2cnn(CCO)c2)c(Cl)c1Cl] | 3-(1-(2,3-dichloro-4-(1-(2-hydroxyethyl)-1H-pyrazol-4-yl)phenyl)ethyl)-1-methyl-1-(1-methylpiperidin-4-yl)urea |
| H0694 | 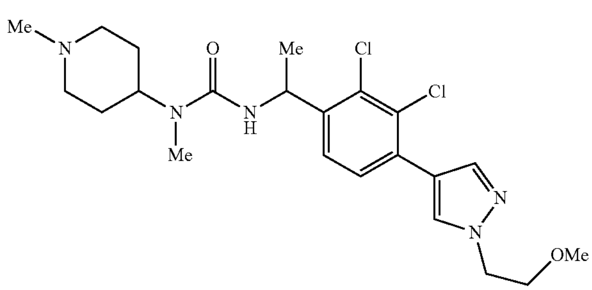 [SMILES: COCCn1cc(-c2ccc(C(C)NC(=O)N(C)C3CCN(C)CC3)c(Cl)c2Cl)cn1] | 3-(1-(2,3-dichloro-4-(1-(2-methoxyethyl)-1H-pyrazol-4-yl)phenyl)ethyl)-1-methyl-1-(1-methylpiperidin-4-yl)urea |

| Compound No. | Chemical Structure | Chemical Name |
|---|---|---|
| H0657 | 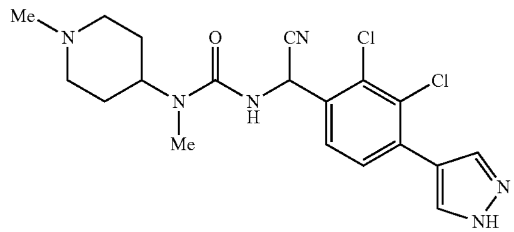 [SMILES: CN1CCC(N(C)C(=O)NC(C#N)c2ccc(-c3cn[nH]c3)c(Cl)c2Cl)CC1] | 3-(cyano(2,3-dichloro-4-(1H-pyrazol-4-yl)phenyl)methyl)-1-methyl-1-(1-methylpiperidin-4-yl)urea |
| H0553 | 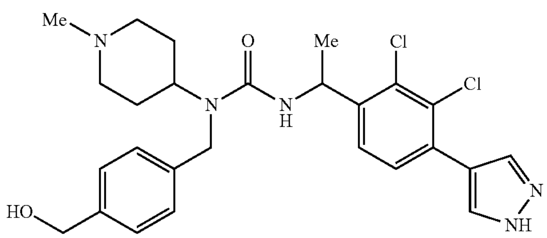 [SMILES: CC(NC(=O)N(Cc1ccc(CO)cc1)C1CCN(C)CC1)c1ccc(-c2cn[nH]c2)c(Cl)c1Cl] | 3-(1-(2,3-dichloro-4-(1H-pyrazol-4-yl)phenyl)ethyl)-1-(4-(hydroxymethyl)benzyl)-1-(1-methylpiperidin-4-yl)urea |
| H0842 | 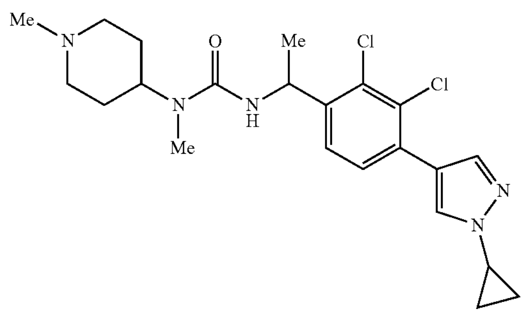 [SMILES: CC(NC(=O)N(C)C1CCN(C)CC1)c1ccc(-c2cnn(C3CC3)c2)c(Cl)c1Cl] | 3-(1-(2,3-dichloro-4-(1-cyclopropyl-1H-pyrazol-4-yl)phenyl)ethyl)-1-methyl-1-(1-methylpiperidin-4-yl)urea |
| H0542 | 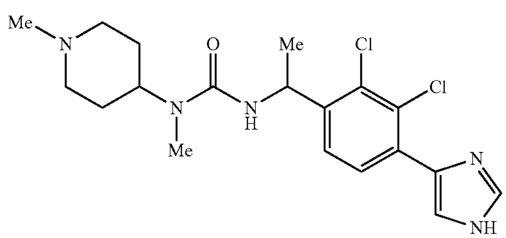 [SMILES: CC(NC(=O)N(C)C1CCN(C)CC1)c1ccc(-c2c[nH]cn2)c(Cl)c1Cl] | 3-(1-(2,3-dichloro-4-(1H-imidazol-4-yl)phenyl)ethyl)-1-methyl-1-(1-methylpiperidin-4-yl)urea |
| H0568 | 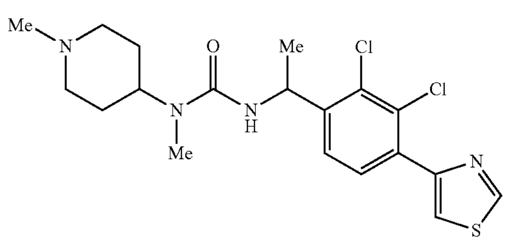 [SMILES: CC(NC(=O)N(C)C1CCN(C)CC1)c1ccc(-c2cscn2)c(Cl)c1Cl] | 3-(1-(2,3-dichloro-4-(thiazol-4-yl)phenyl)ethyl)-1-methyl-1-(1-methylpiperidin-4-yl)urea |
| H0794 | 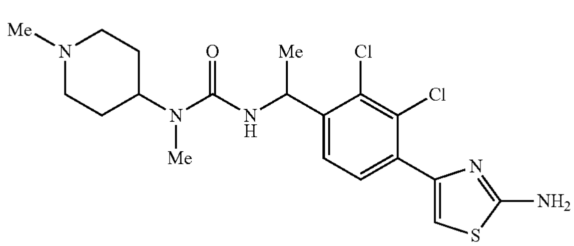 [SMILES: CC(NC(=O)N(C)C1CCN(C)CC1)c1ccc(-c2csc(N)n2)c(Cl)c1Cl] | 3-(1-(4-(2-aminothiazol-4-yl)-2,3-dichlorophenyl)ethyl)-1-methyl-1-(1-methylpiperidin-4-yl)urea |

-continued

| Compound No. | Chemical Structure | Chemical Name |
|---|---|---|
| H0841 | 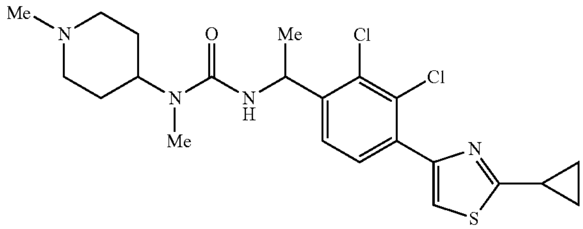 [SMILES: CC(NC(=O)N(C)C1CCN(C)CC1)c1ccc(-c2csc(C3CC3)n2)c(Cl)c1Cl] | 3-(1-(2,3-dichloro-4-(2-cyclopropylthiazol-4-yl)phenyl)ethyl)-1-methyl-1-(1-methylpiperidin-4-yl)urea |
| H0792 | 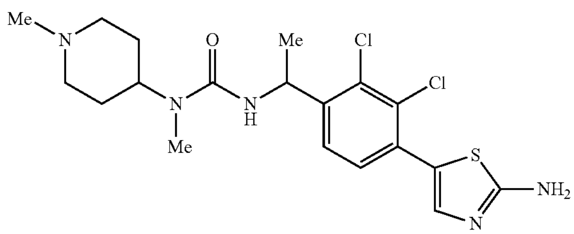 [SMILES: CC(NC(=O)N(C)C1CCN(C)CC1)c1ccc(-c2cnc(N)s2)c(Cl)c1Cl] | 3-(1-(4-(2-aminothiazol-5-yl)-2,3-dichlorophenyl)ethyl)-1-methyl-1-(1-methylpiperidin-4-yl)urea |
| H0569 | 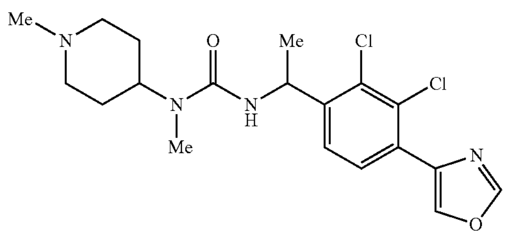 [SMILES: CC(NC(=O)N(C)C1CCN(C)CC1)c1ccc(-c2cocn2)c(Cl)c1Cl] | 3-(1-(2,3-dichloro-4-(oxazol-4-yl)phenyl)ethyl)-1-methyl-1-(1-methylpiperidin-4-yl)urea |
| H0565 | 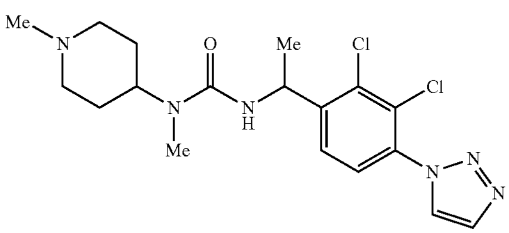 [SMILES: CC(NC(=O)N(C)C1CCN(C)CC1)c1ccc(-n2ccnn2)c(Cl)c1Cl] | 3-(1-(2,3-dichloro-4-(1H-1,2,3-triazol-1-yl)phenyl)ethyl)-1-methyl-1-(1-methylpiperidin-4-yl)urea |
| H0604 | 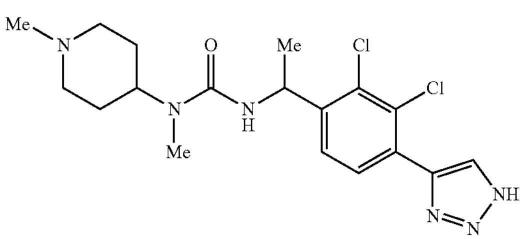 [SMILES: CC(NC(=O)N(C)C1CCN(C)CC1)c1ccc(-c2c[nH]nn2)c(Cl)c1Cl] | 3-(1-(2,3-dichloro-4-(1H-1,2,3-triazol-4-yl)phenyl)ethyl)-1-methyl-1-(1-methylpiperidin-4-yl)urea |
| H0595 | 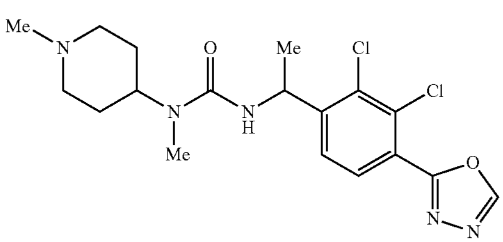 [SMILES: CC(NC(=O)N(C)C1CCN(C)CC1)c1ccc(-c2nnco2)c(Cl)c1Cl] | 3-(1-(2,3-dichloro-4-(1,3,4-oxadiazol-2-yl)phenyl)ethyl)-1-methyl-1-(1-methylpiperidin-4-yl)urea |

| Compound No. | Chemical Structure | Chemical Name |
| --- | --- | --- |
| H0596 | 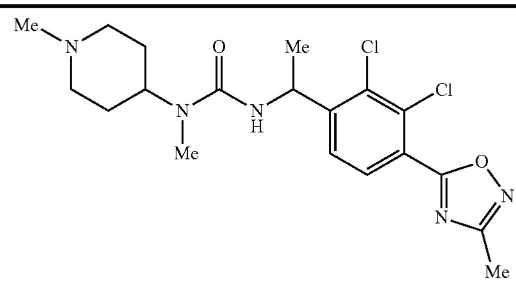 | 3-(1-(2,3-dichloro-4-(3-methyl-1,2,4-oxadiazol-5-yl)phenyl)ethyl)-1-methyl-1-(1-methylpiperidin-4-yl)urea |
| H0851 | 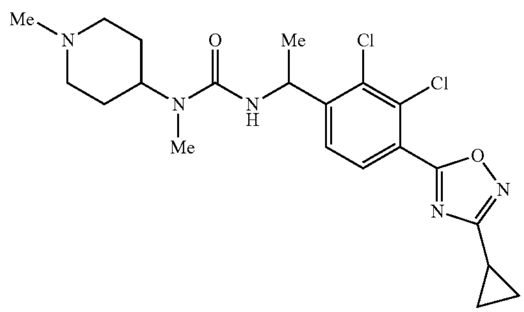 [SMILES: CC(NC(=O)N(C)C1CCN(C)CC1)c1ccc(-c2nc(C3CC3)no2)c(Cl)c1Cl] | 3-(1-(2,3-dichloro-4-(3-cyclopropyl-1,2,4-oxadiazol-5-yl)phenyl)ethyl)-1-methyl-1-(1-methylpiperidin-4-yl)urea |
| H0537 | 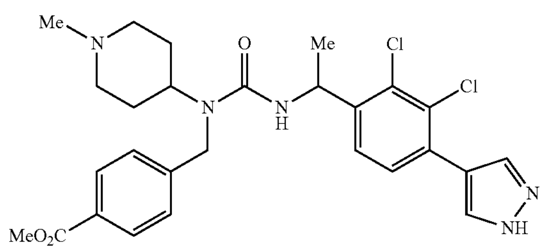 [SMILES: COC(=O)c1ccc(CN(C(=O)NC(C)c2ccc(-c3cn[nH]c3)c(Cl)c2Cl)C2CCN(C)CC2)cc1] | methyl 4-((3-(1-(2,3-dichloro-4-(1H-pyrazol-4-yl)phenyl)ethyl)-1-(1-methylpiperidin-4-yl)ureido)methyl)benzoate |
| H0528 | 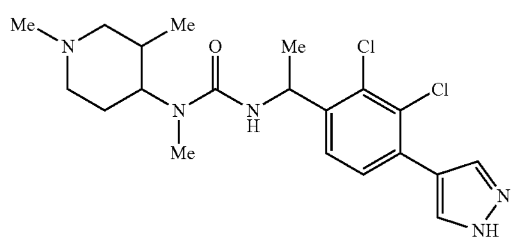 [SMILES: CC(NC(=O)N(C)C1CCN(C)CC1C)c1ccc(-c2cn[nH]c2)c(Cl)c1Cl] | 3-(1-(2,3-dichloro-4-(1H-pyrazol-4-yl)phenyl)ethyl)-1-(1,3-dimethylpiperidin-4-yl)-1-methylurea |
| H0501 | 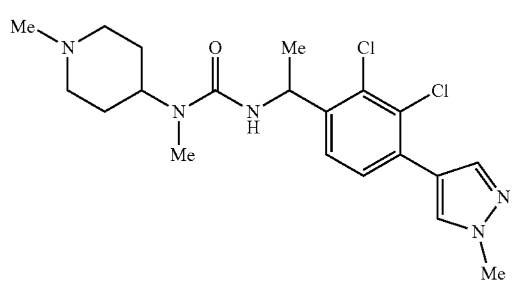 [SMILES: CC(NC(=O)N(C)C1CCN(C)CC1)c1ccc(-c2cnn(C)c2)c(Cl)c1Cl] | 3-(1-(2,3-dichloro-4-(1-methyl-1H-pyrazol-4-yl)phenyl)ethyl)-1-methyl-1-(1-methylpiperidin-4-yl)urea |
| H0507 | 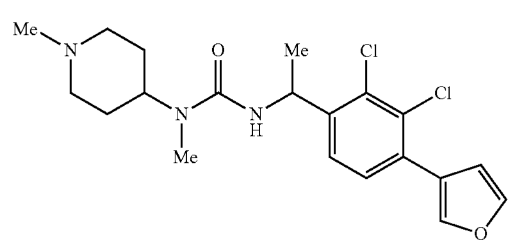 | 3-(1-(2,3-dichloro-4-(furan-3-yl)phenyl)ethyl)-1-methyl-1-(1-methylpiperidin-4-yl)urea |

| Compound No. | Chemical Name |
|---|---|
| H0665 | 3-(1-(2,3-dichloro-4-(5-methylfuran-2-yl)phenyl)ethyl)-1-methyl-1-(1-methylpiperidin-4-yl)urea |
| H0699 | 3-(1-(2,3-dichloro-4-(5-(cyanomethyl)pyridin-3-yl)phenyl)ethyl)-1-methyl-1-(1-methylpiperidin-4-yl)urea |
| H0607 | 3-(1-(2,3-dichloro-4-(5-methoxypyridin-3-yl)phenyl)ethyl)-1-methyl-1-(1-methylpiperidin-4-yl)urea |
| H0695 | 3-(1-(4-(5-bromopyridin-3-yl)-2,3-dichlorophenyl)ethyl)-1-methyl-1-(1-methylpiperidin-4-yl)urea |
| H0635 | methyl 5-(2,3-dichloro-4-(1-(3-methyl-3-(1-methylpiperidin-4-yl)ureido)ethyl)phenyl)nicotinate |
| H0690 | 3-(1-(4-(5-acetylpyridin-3-yl)-2,3-dichlorophenyl)ethyl)-1-methyl-1-(1-methylpiperidin-4-yl)urea |

-continued

| Compound No. | Chemical Structure | Chemical Name |
|---|---|---|
| H0735 | 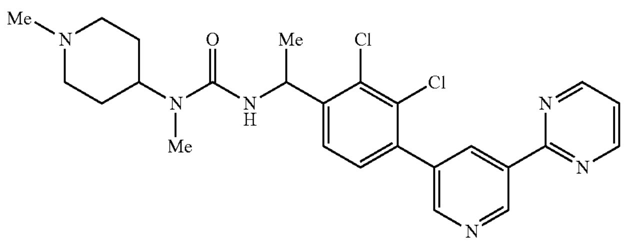 [SMILES: CC(NC(=O)N(C)C1CCN(C)CC1)c1ccc(-c2cncc(-c3ncccn3)c2)c(Cl)c1Cl] | 3-(1-(2,3-dichloro-4-(5-(pyrimidin-2-yl)pyridin-3-yl)phenyl)ethyl)-1-methyl-1-(1-methylpiperidin-4-yl)urea |
| H0746 | 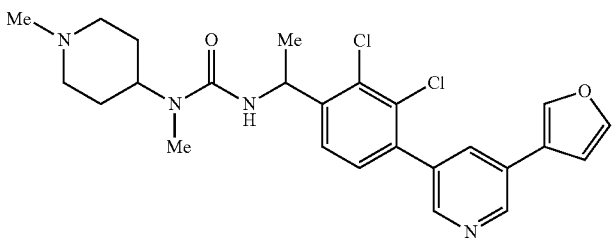 | 3-(1-(2,3-dichloro-4-(5-(furan-3-yl)pyridin-3-yl)phenyl)ethyl)-1-methyl-1-(1-methylpiperidin-4-yl)urea |
| H0747 | 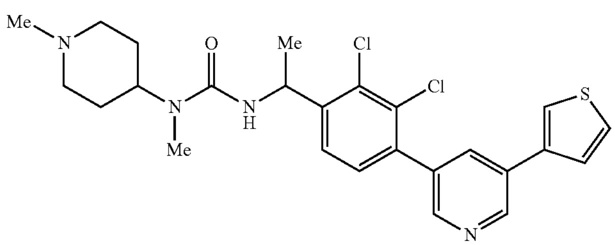 | 3-(1-(2,3-dichloro-4-(5-(thiophen-3-yl)pyridin-3-yl)phenyl)ethyl)-1-methyl-1-(1-methylpiperidin-4-yl)urea |
| H0748 | 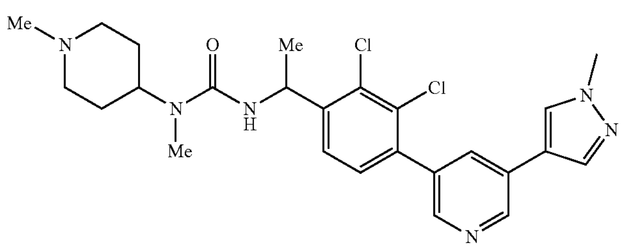 [SMILES: CC(NC(=O)N(C)C1CCN(C)CC1)c1ccc(-c2cncc(-c3cnn(C)c3)c2)c(Cl)c1Cl] | 3-(1-(2,3-dichloro-4-(5-(1-methyl-1H-pyrazol-4-yl)pyridin-3-yl)phenyl)ethyl)-1-methyl-1-(1-methylpiperidin-4-yl)urea |
| H0765 | 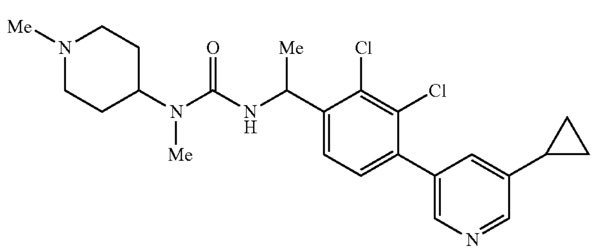 [SMILES: CC(NC(=O)N(C)C1CCN(C)CC1)c1ccc(-c2cncc(C3CC3)c2)c(Cl)c1Cl] | 3-(1-(2,3-dichloro-4-(5-cyclopropylpyridin-3-yl)phenyl)ethyl)-1-methyl-1-(1-methylpiperidin-4-yl)urea |
| H0766 | 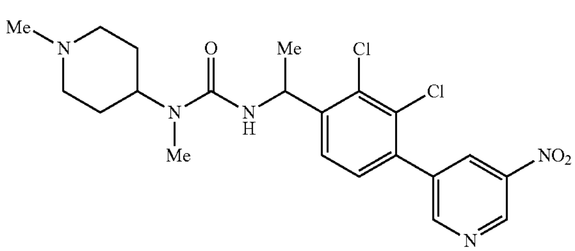 | 3-(1-(2,3-dichloro-4-(5-nitropyridin-3-yl)phenyl)ethyl)-1-methyl-1-(1-methylpiperidin-4-yl)urea |

-continued

| Compound No. | Chemical Structure | Chemical Name |
|---|---|---|
| H0608 | 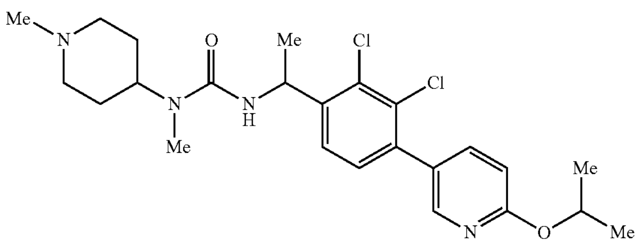 [SMILES: CC(C)Oc1ccc(-c2ccc(C(C)NC(=O)N(C)C3CCN(C)CC3)c(Cl)c2Cl)cn1] | 3-(1-(2,3-dichloro-4-(6-isopropoxypyridin-3-yl)phenyl)ethyl)-1-methyl-1-(1-methylpiperidin-4-yl)urea |
| H0616 | 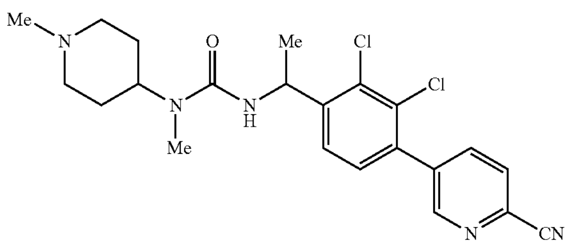 | 3-(1-(2,3-dichloro-4-(6-cyanopyridin-3-yl)phenyl)ethyl)-1-methyl-1-(1-methylpiperidin-4-yl)urea |
| H0618 | 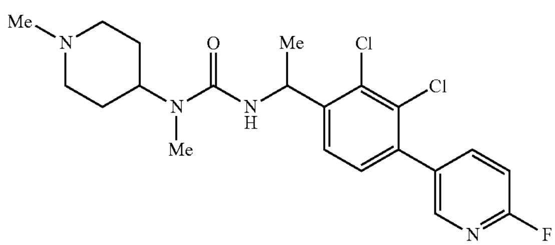 [SMILES: CC(NC(=O)N(C)C1CCN(C)CC1)c1ccc(-c2ccc(F)nc2)c(Cl)c1Cl] | 3-(1-(2,3-dichloro-4-(6-fluoropyridin-3-yl)phenyl)ethyl)-1-methyl-1-(1-methylpiperidin-4-yl)urea |
| H0623 | 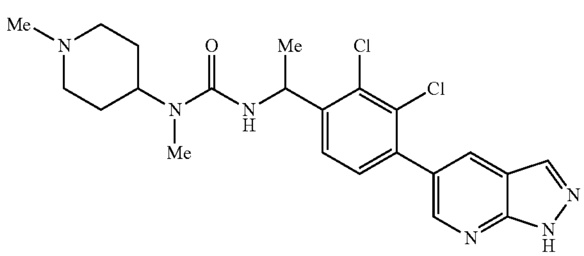 [SMILES: CC(NC(=O)N(C)C1CCN(C)CC1)c1ccc(-c2cnc3[nH]ncc3c2)c(Cl)c1Cl] | 3-(1-(2,3-dichloro-4-(1H-pyrazolo[3,4-b]pyridin-5-yl)phenyl)ethyl)-1-methyl-1-(1-methylpiperidin-4-yl)urea |
| H0512 | 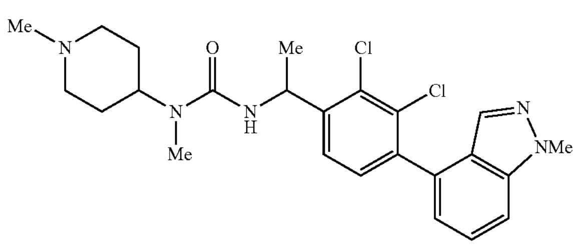 [SMILES: CC(NC(=O)N(C)C1CCN(C)CC1)c1ccc(-c2cccc3c2cnn3C)c(Cl)c1Cl] | 3-(1-(2,3-dichloro-4-(1-methyl-1H-indazol-4-yl)phenyl)ethyl)-1-methyl-1-(1-methylpiperidin-4-yl)urea |
| H0513 | 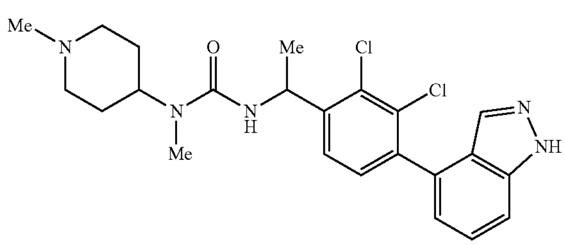 [SMILES: CC(NC(=O)N(C)C1CCN(C)CC1)c1ccc(-c2cccc3[nH]ncc23)c(Cl)c1Cl] | 3-(1-(2,3-dichloro-4-(1H-indazol-4-yl)phenyl)ethyl)-1-methyl-1-(1-methylpiperidin-4-yl)urea |

| Compound No. | Chemical Structure | Chemical Name |
|---|---|---|
| H0514 | 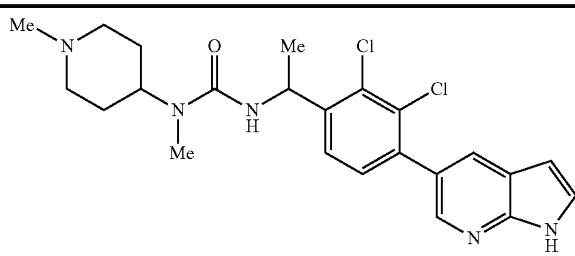 | 3-(1-(2,3-dichloro-4-(1H-pyrrolo[2,3-b]pyridin-5-yl)phenyl)ethyl)-1-methyl-1-(1-methylpiperidin-4-yl)urea |
| H0515 | 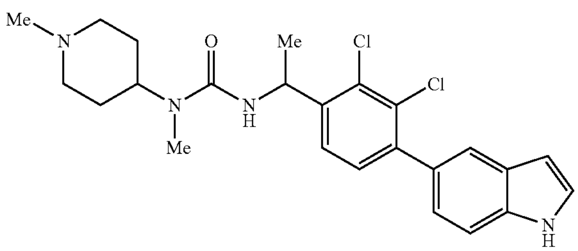 [SMILES: CC(NC(=O)N(C)C1CCN(C)CC1)c1ccc(-c2ccc3[nH]ccc3c2)c(Cl)c1Cl] | 3-(1-(2,3-dichloro-4-(1H-indol-5-yl)phenyl)ethyl)-1-methyl-1-(1-methylpiperidin-4-yl)urea |
| H0582 | 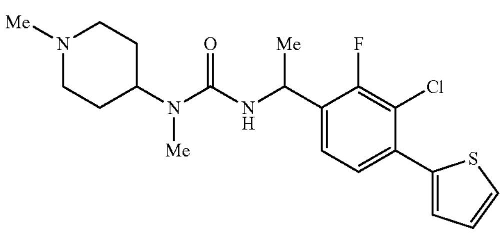 [SMILES: CC(NC(=O)N(C)C1CCN(C)CC1)c1ccc(-c2cccs2)c(Cl)c1F] | 3-(1-(3-chloro-2-fluoro-4-(thiophen-2-yl)phenyl)ethyl)-1-methyl-1-(1-methylpiperidin-4-yl)urea |
| H0571 | | 3-(1-(3-chloro-2-fluoro-4-(1H-pyrazol-4-yl)phenyl)ethyl)-1-methyl-1-(1-methylpiperidin-4-yl)urea | or a pharmaceutically acceptable salt thereof.

34. A compound selected from the group consisting of:

| | | |
|---|---|---|
| H0816 | | (S)-3-(1-(2,3-dichloro-4-(pyrazin-2-yl)phenyl)ethyl)-1-methyl-1-(1-methylpiperidin-4-yl)urea |
| H0900 | | (R)-3-(1-(2,3-dichloro-4-(pyrazin-2-yl)phenyl)-2,2,2-trifluoroethyl)-1-methyl-1-(1-methylpiperidin-4-yl)urea |

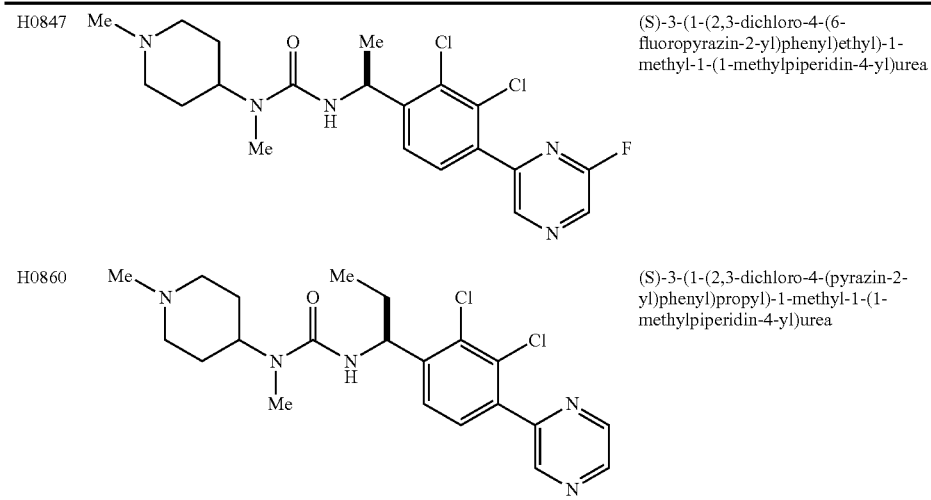

| | | |
|---|---|---|
| H0847 | [structure] | (S)-3-(1-(2,3-dichloro-4-(6-fluoropyrazin-2-yl)phenyl)ethyl)-1-methyl-1-(1-methylpiperidin-4-yl)urea |
| H0860 | [structure] | (S)-3-(1-(2,3-dichloro-4-(pyrazin-2-yl)phenyl)propyl)-1-methyl-1-(1-methylpiperidin-4-yl)urea | or a pharmaceutically acceptable salt thereof.

35. The compound of claim 34, which is (S)-3-(1-(2,3-dichloro-4-(pyrazin-2-yl)phenyl)ethyl)-1-methyl-1-(1-methylpiperidin-4-yl)urea (H0816) or a pharmaceutically acceptable salt thereof.

36. The compound of claim 34, which is (R)-3-(1-(2,3-dichloro-4-(pyrazin-2-yl)phenyl)-2,2,2-trifluoroethyl)-1-methyl-1-(1-methylpiperidin-4-yl)urea (H0900) or a pharmaceutically acceptable salt thereof.

37. The compound of claim 34, which is (S)-3-(1-(2,3-dichloro-4-(6-fluoropyrazin-2-yl)phenyl)ethyl)-1-methyl-1-(1-methylpiperidin-4-yl)urea (H0847) or a pharmaceutically acceptable salt thereof.

38. The compound of claim 34, which is (S)-3-(1-(2,3-dichloro-4-(pyrazin-2-yl)phenyl)propyl)-1-methyl-1-(1-methylpiperidin-4-yl)urea (H0860) or a pharmaceutically acceptable salt thereof.

* * * * *